US010053428B2

(12) United States Patent
Hahn et al.

(10) Patent No.: US 10,053,428 B2
(45) Date of Patent: *Aug. 21, 2018

(54) 5-AMINOTETRAHYDROQUINOLINE-2-CARBOXYLIC ACIDS AND THEIR USE

(71) Applicant: BAYER PHARMA AKTIENGESELLSCHAFT, Berlin (DE)

(72) Inventors: Michael Hahn, Langenfeld (DE); Markus Follmann, Köln (DE); Eva-Maria Becker, Wuppertal (DE); Johannes-Peter Stasch, Solingen (DE); Joerg Keldenich, Wuppertal (DE); Martina Delbeck, Heiligenhaus (DE); Hanna Tinel, Wuppertal (DE); Frank Wunder, Wuppertal (DE); Joachim Mittendorf, Wuppertal (DE); Ildiko Terebesi, Berlin (DE); Dieter Lang, Velbert (DE); René Martin, Leipzig (DE); Walter Hübsch, Wuppertal (DE)

(73) Assignee: BAYER PHARMA AKTIENGESELLSCHAFT, Berlin (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/600,132

(22) Filed: May 19, 2017

(65) Prior Publication Data
US 2017/0260139 A1 Sep. 14, 2017

Related U.S. Application Data

(63) Continuation of application No. 14/609,122, filed on Jan. 29, 2015, now Pat. No. 9,688,636, which is a continuation of application No. 13/945,675, filed on Jul. 18, 2013, now Pat. No. 8,981,104.

(30) Foreign Application Priority Data

Jul. 20, 2012 (EP) ..................... 12177284
May 16, 2013 (EP) ..................... 13167967

(51) Int. Cl.
A61K 31/4706 (2006.01)
C07D 215/48 (2006.01)
C07D 217/26 (2006.01)
C07D 401/12 (2006.01)
C07D 413/12 (2006.01)
A61K 31/4709 (2006.01)
A61K 45/06 (2006.01)
A61K 31/47 (2006.01)

(52) U.S. Cl.
CPC ............ C07D 215/48 (2013.01); A61K 31/47 (2013.01); A61K 31/4706 (2013.01); A61K 31/4709 (2013.01); A61K 45/06 (2013.01); C07D 217/26 (2013.01); C07D 401/12 (2013.01); C07D 413/12 (2013.01)

(58) Field of Classification Search
CPC .. C07D 215/48; C07D 217/26; C07D 401/12; C07D 413/12; A61K 31/4706; A61K 31/4709; A61K 31/47; A61K 31/06; A61K 45/06
See application file for complete search history.

(56) References Cited

U.S. PATENT DOCUMENTS

| | | | |
|---|---|---|---|
| 4,873,262 A | 10/1989 | Junge et al. | |
| 4,880,802 A | 11/1989 | Schohe et al. | |
| 5,047,422 A | 9/1991 | Junge et al. | |
| 6,693,102 B2 | 2/2004 | Stasch et al. | |
| 6,743,798 B1 | 6/2004 | Straub et al. | |
| 6,833,364 B1 | 12/2004 | Straub et al. | |
| 6,939,989 B2 | 9/2005 | Harter et al. | |
| 6,939,990 B2 | 9/2005 | Harter et al. | |
| 7,087,644 B1 | 8/2006 | Alonso-Alija et al. | |
| 7,173,037 B2 | 2/2007 | Alsonso-Alija et al. | |
| 7,705,043 B2 | 4/2010 | Alonso-Alija et al. | |
| 8,420,656 B2 | 4/2013 | Follmann et al. | |
| 8,653,099 B2 | 2/2014 | Colburn et al. | |
| 8,673,903 B2 | 3/2014 | Hubsch et al. | |
| 8,921,377 B2 | 12/2014 | Follmann et al. | |
| 8,981,104 B2* | 3/2015 | Hahn .................. | C07D 217/26 546/170 |
| 9,096,592 B2 | 8/2015 | Follmann et al. | |
| 9,688,636 B2 | 6/2017 | Hahn et al. | |
| 2004/0082658 A1 | 4/2004 | Harter et al. | |
| 2004/0082798 A1 | 4/2004 | Alonso-Alija | |
| 2004/0092593 A1 | 5/2004 | Harter et al. | |
| 2004/0110840 A1 | 6/2004 | Harter et al. | |
| 2004/0176446 A1 | 9/2004 | Alonso-Alija | |
| 2006/0052397 A1 | 3/2006 | Alonso-Alija | |
| 2009/0227640 A1 | 9/2009 | Bartel et al. | |
| 2013/0237551 A1 | 9/2013 | Follmann et al. | |
| 2013/0267548 A1 | 10/2013 | Follmann et al. | |
| 2014/0350020 A1 | 11/2014 | Follmann et al. | |
| 2015/0080414 A1 | 3/2015 | Follmann et al. | |
| 2015/0148376 A1* | 5/2015 | Hahn .................. | C07D 217/26 514/311 |
| 2015/0174113 A1 | 6/2015 | Hubsch et al. | |

FOREIGN PATENT DOCUMENTS

CA 2804470 A1 1/2012
CA 2809911 A1 3/2012
(Continued)

OTHER PUBLICATIONS

Beyer C. et al., "Stimulation of soluble guanylate cyclase reduces experimental dermal fibrosis," Ann Rheum Dis 2012;71:1019-1026.
(Continued)

Primary Examiner — D Margaret M Seaman
(74) Attorney, Agent, or Firm — Buchanan Ingersoll & Rooney PC

(57) ABSTRACT

The present application relates to novel 5-amino-5,6,7,8-tetrahydroquinoline-2-carboxylic acids, to processes for their preparation, to their use for the treatment and/or prevention of diseases, and to their use for producing medicaments for the treatment and/or prevention of diseases, especially for the treatment and/or prevention of cardiovascular and cardiopulmonary disorders.

34 Claims, No Drawings

(56) References Cited

FOREIGN PATENT DOCUMENTS

| | | | |
|---|---|---|---|
| CA | 2816671 A1 | 5/2012 | |
| EP | 0041488 A1 | 9/1981 | |
| EP | 0064964 A1 | 11/1982 | |
| EP | 0270947 B1 | 6/1988 | |
| FR | 2659853 A1 | 3/1990 | |
| WO | 1990/15047 A1 | 12/1990 | |
| WO | 199518617 A1 | 7/1995 | |
| WO | 1999/62505 A1 | 12/1999 | |
| WO | 00/6568 A1 | 2/2000 | |
| WO | 00/06569 A1 | 2/2000 | |
| WO | 2000/35882 A1 | 6/2000 | |
| WO | 200119780 A2 | 3/2001 | |
| WO | 02/070461 A1 | 9/2002 | |
| WO | 02/070462 A1 | 9/2002 | |
| WO | 02/070510 A2 | 9/2002 | |
| WO | 2002070459 A1 | 9/2002 | |
| WO | 2002070460 A1 | 9/2002 | |
| WO | 03/095451 A1 | 11/2003 | |
| WO | 2005012291 A1 | 2/2005 | |
| WO | 2006104826 A2 | 10/2006 | |
| WO | 2009023669 A1 | 2/2009 | |
| WO | 2009032249 A1 | 3/2009 | |
| WO | 2011/141409 A1 | 11/2011 | |
| WO | 2011/147809 A1 | 12/2011 | |
| WO | 2011161099 A1 | 12/2011 | |
| WO | 2012/004258 A1 | 1/2012 | |
| WO | 2012/028647 A1 | 3/2012 | |
| WO | 2012/059549 A1 | 5/2012 | |
| WO | 2012122340 A1 | 9/2012 | |
| WO | 2013157528 A1 | 10/2013 | |

OTHER PUBLICATIONS

Beyer C. et al., "Stimulation of the soluble guanylate cyclase (sGC) inhibits fibrosis by blocking non-canonical TGFβ signalling," Ann Rheum Dis 2015;74:1408-1416.
FDA World Health Organization, "FDA approves Bayer's new class of drug ADEMPAS (riociguat) tablets to treat adults with PAH and persistent, recurrent or inoperable CTEPH," Cision PR Newswire (Oct. 8, 2013), 18:54 ET, 8 pages.
Ghofrani et al., "Acute effects of riociguat in borderline or manifest pulmonary hypertension associated with chronic obstructive pulmonary disease," Pulm Circ. Jun. 2015;5(2):296-304, Abstract.
Jindal N. et al., "Inhalation of nitric oxide in acute respiratory distress syndrome," J Lab Clin Med Jul. 2000; 136:21-28.
Johnson E. et al., "Acute lung injury: epidemiology, pathogenesis, and treatment," J Aer Med and Pulm Drug Delivery 2010, vol. 23, (4) 243-252.
Sandner P. et al., "Anti-fibrotic effects of soluble guanylate cyclase stimulators and activators: a review of the preclinical evidence," Resp Med (2017) 122:S1-S9.
Stasch et al., "Renal effects of soluble guanylate cyclase stimulators and activators: a review of the preclinical evidence," Current Opinions in Pharmacology (2015) 21:95-104.
Stasch J. et al., "Soluble guanylate cyclase as an emerging therapeutic target in cardiopulmonary disease," Circulation May 24, 2011, 123:2263-2273.
Evgenov, "NO-Independent Stimulators and Activators of Soluble Guanylate Cyclase: Discovery and Therapeutic Potential," Nature Reviews: Drug Discovery, Sep. 2006, 5(9):755-768.
Evgenov, "Inhaled Agonists of Soluble Guanylate Cyclase Induce Selective Pulmonary Vasodilation," AM. J. Respir. Crit. Care Med., 2007, 176:1138-1145.
Becker, "Desaturation" Effects in a Model of Secondary Pulmonary Hypertension—Riociguat in Comparison, Pneumologie, 2011, 65(Suppl. 2):S122-S123 (in German).
Bice, "NO-independent stimulation or activation of soluble guanylyl cyclase during early reperfusion limits infarct size," Cardiovascular Research, Oxford Journal of Medicine, 2014, 101:220-228.
Bitler, "The Preparation and Properties of Crystalline Firefly Luciferin," Archives of Biochemistry and Biophysics, 1957, 72:358-368.
Blanco, "Hemodynamic and Gas Exchange Effects of Sildenafil in Patients with Chronic Obstructive Pulmonary Disease and Pulmonary Hypertension," Am. J. Respir. Crit. Care Med., 2010, 181:270-278.
Ghofrani, "Neue Therapieoptionen in der Behandlung der pulmonalarteriellen Hypertonie," Herz, 2005, 30 (4):296-302.
Ghosh, "Studies on Oxygen heterocycles Part-1: Acid Catalysed and Photochemical Reactions of Some Aryldiazoketones," Tetrahedron, 1989, 45(5):1441-1446.
Greene, "The Role of Protective Groups in Organic Synthesis," Fourth Edition, Wiley, New York, 2007, 1-15.
Hönicka, "Purified soluble guanylyl cyclase expressed in a baculovirus/Sf9 system: stimulation by YC-1, nitric oxide, and carbon monoxide," Journal Mol. Med., 1999, 77:14-23.
Hörig, "From bench to clinic and back: Perspective on the 1st IQPC Translational Research conference," Journal of Translational Med, Dec. 2004, 2:44.
Humbert, "Cellular and Molecular Pathobiology of Pulmonary Arterial Hypertension," Journal of the Am. College of Cardiology, 2004, 43(12):S13-S24.
Humbert et al, "The 4th World Symposium on Pulmonary Hypertension," Journal of the Am. College of Cardiology, 2009, 54(1):S1-S2.
Ito, "Current Drug Targets and Future Therapy of Pulmonary Arterial Hypertension," Current Med. Chemistry, 2007, 14:719-733.
Liu, "(R)- and (S)-5,6,7,8-Tetrahydro-1-hydroxy-N,N-dipropyl-9H-benzocyclohepten-8-ylamine. Stereoselective Interactions with 5-HT1A Receptors in the Brain," J. Med. Chem., 1989, 32:2311-2318.
Hoeper, "Diagnosis, Assessment, and Treatment of Non-Pulmonary Arterial Hypertension Pulmonary Hypertension," Journal of the Am. College of Cardiology, 2009, 54(1):S85-S96.
Martin, "Structure of Cinaciguat (BAY 58-2667) Bound to Nostoc H-NOX Domain Reveals Insights into Heme-mimetic Activation of the Soluble Guanylyl Cyclase," Journal of Biol. Chem., Jul. 16, 2010, 285(29):22651-22657.
Montani et al., "Updated clinical classification of pulmonary hypertension," Pulmonary Circulation, Disease and their treatment, Third Edition, Hodder Arnold Pub., Peacock et al (Eds.), 2011, 197-206.
Nossaman et al., "Stimulators and Activators of Soluble Guanylate Cyclase: Review and Potential Therapeutic Indications," Critical Care Research and Practice, 2012, 290805: 1-12.
Pettit et al., "Synthesis of the 6- and 7-Hydroxy-5,8-dioxocarbostyrils," Journal of Organic Chemistry, Mar. 1968, 33(3):1089-1092.
Rosenzweig, E. B., "Emerging treatments for pulmonary arterial hypertension," Expert Opinion Emerging Drugs, 2006, 11(4):609-619.
Schäfer, et al.: "Failure is an option: learning from unsuccessful proof-of-concept trials," Drug Discovery Today, 2008, 13(21/22): 913-916.
Schmidt, et al.: NO- and Haem-Independent Soluble Guanylate Cyclase Activators, Handbook of Experimental Pharmacology, 2009, 191:309-339.
Stachel et al., "Discovery of pyrrolidine-based b-secretase inhibitors: Lead advancement through conformational design for maintenance of ligand binding efficiency," Bioorganic Med. Chem. Letters, 2012, 22:240-244.
Stasch et al., "NO-and Haem-independent Activation of Soluble Guanylyl Cyclase: Molecular Basis and Cardiovascular Implications of a New Pharmacological Principle," British Journal of Pharmacology, 2002, Bd. 136 (5):773-783.
Stasch et al., "Targeting the Heme-Oxidized Nitric Oxide Receptor for Selective Vasodilation of Diseased Blood Vessels," J. Clin. Invest., Sep. 2006, 116(9): 2552-2561.
Stolz et al., "A randomised, controlled trial of bosentan in severe COPD," European Resp. Journal, 2008 32 (3):619-628.
Vanejevs et al., "Positive and Negative Modulation of Group I Metabotropic Glutamate Receptors," Journal Med. Chem., 2008, 51:634-647.

(56) References Cited

OTHER PUBLICATIONS

Witte et al., "Experimental heart failure in rats: effects on cardiovascular circadian rhythms and on myocardial β-adrenergic signaling," 2000, 47:350-358.

Wunder et al., "A cell-based cGMP assay useful for ultra-high-throughput screening and dentiWcation of modulators of the nitric oxide/cGMP pathway," Analytical Biochemistry, 2005, 339:104-112.

Gerlach et al., Synthesis of Benzoic and Tetralone Carboxylic Acid Esters from Phenols by Palladium Catalyzed Alkoxy/Aryloxy Carbonylation, Tetrahedron Letters, vol. 33, No. 38, pp. 5499-5502 (1992).

Takeuchi et al., Rhodium Complex-Catalyzed Desilylative Cyclocarbonylation of 1-Aryl-2-(trimethylsilyl)acetylenes: A New Route to 2,3,-Dihydro-1H-inden-1-ones, 58 J. Org. Chem. 5386, 5386-5392 (1993).

Erlanson et al., "Fragment-Based Drug Discovery", Journal of Medicinal Chemistry, Jul. 2004; 20 pages.

Gur, S. et al., "Exploring the Potential of NO-Independent Stimulators and Activators of Soluble Guanylate Cyclase for the Medical Treatment of Erectile Dysfunction", Current Pharmaceutical Design, 2010. 16:1619-1633.

\* cited by examiner

5-AMINOTETRAHYDROQUINOLINE-2-CARBOXYLIC ACIDS AND THEIR USE

The present application relates to novel 5-amino-5,6,7,8-tetrahydroquinoline-2-carboxylic acids, to processes for their preparation, to their use for the treatment and/or prevention of diseases, and to their use for producing medicaments for the treatment and/or prevention of diseases, especially for the treatment and/or prevention of cardiovascular and cardiopulmonary disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and contain one haem per heterodimer, which is part of the regulatory site. The latter is of central importance for the mechanism of activation. NO is able to bind to the iron atom of haem and thus markedly increase the activity of the enzyme. Haem-free preparations cannot, by contrast, be stimulated by NO. Carbon monoxide (CO) is also able to attach to the central iron atom of haem, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to pulmonary hypertension, high blood pressure, platelet activation, increased cellular proliferation, endothelial dysfunction, atherosclerosis, angina pectoris, heart failure, thromboses, stroke and myocardial infarction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of haem. Besides the side effects, the development of tolerance is one of the crucial disadvantages of this mode of treatment [O. V. Evgenov et al., *Nature Rev. Drug Disc.* 5 (2006), 755].

Substances which directly stimulate soluble guanylate cyclase, i.e. without previous release of NO, have been identified in recent years. The indazole derivative YC-1 was the first NO-independent but haem-dependent sGC stimulator described [Evgenov et al., ibid.]. Based on YC-1, further substances were discovered which are more potent than YC-1 and show no relevant inhibition of phosphodiesterases (PDE). This led to the identification of the pyrazolopyridine derivatives BAY 41-2272, BAY 41-8543 and BAY 63-2521 (riociguat). Together with the recently published structurally different substances CMF-1571 and A-350619, these compounds form the new class of the sGC stimulators [Evgenov et al., ibid.]. A common characteristic of this substance class is an NO-independent and selective activation of the haem-containing sGC. In addition, sGC stimulators in combination with NO have a synergistic effect on sGC activation based on a stabilization of the nitrosyl-haem complex. If the haem group is removed from the soluble guanylate cyclase, the enzyme still has a detectable catalytic basal activity, i.e. cGMP is still being formed. The remaining catalytic basal activity of the haem-free enzyme cannot be stimulated by any of the stimulators mentioned above [Evgenov et al., ibid.].

In addition, NO- and haem-independent sGC activators, with BAY 58-2667 (cinaciguat) as proto-type of this class, have been identified. Common characteristics of these substances are that in combination with NO they only have an additive effect on enzyme activation, and that the activation of the oxidized or haem-free enzyme is markedly higher than that of the haem-containing enzyme [Evgenov et al., ibid.; J. P. Stasch et al., *Br. J. Pharmacol.* 136 (2002), 773; J. P. Stasch et al., *J. Clin. Invest.* 116 (2006), 2552]. Spectroscopic studies show that BAY 58-2667 displaces the oxidized haem group which, as a result of the weakening of the iron-histidine bond, is attached only weakly to the sGC. It has also been shown that the characteristic sGC haem binding motif Tyr-x-Ser-x-Arg is absolutely essential both for the interaction of the negatively charged propionic acids of the haem group and for the action of BAY 58-2667. Against this background, it is assumed that the binding site of BAY 58-2667 at the sGC is identical to the binding site of the haem group [J. P. Stasch et al., *J. Clin. Invest.* 116 (2006), 2552]. Recently, crystallization studies with the Nostoc H-NOX domain, of a prokaryotic haem binding domain having high sequence homology to sGC, have shown that BAY 58-2667 binds at the haem binding site [F. van den Akker et al., *J. Biol. Chem.* 285 (2010), 22651].

Pulmonary hypertension (PH) is a progressive lung disorder which, untreated, leads to death within a few years after diagnosis. By definition, the mean pulmonary aterial pressure (mPAP) in case of chronic pulmonary hypertension is >25 mmHg at rest or >30 mmHg during exertion (normal value <20 mmHg). The pathophysiology of pulmonary hypertension is characterized by vasoconstriction and remodeling of the pulmonary vessels. In chronic PH there is neomuscularization primarily of unmuscularized pulmonary vessels, and the vascular muscles of the already muscularized vessels increase in circumference. This increasing obliteration of the pulmonary circulation results in progressive stress on the right heart, which leads to a reduced output from the right heart and eventually ends in right heart failure [M. Humbert et al., *J. Am. Coll. Cardiol.* 2004, 43, 13S-24S]. Idiopathic (or primary) pulmonary arterial hypertension (IPAH) is a very rare disorder, whereas secondary pulmonary hypertension (non-PAH PH) is very common, and it is thought that the latter is currently the third most common group of cardiovascular disorders after coronary heart disease and systemic hypertension. Since 2008, pulmonary hypertension is classified in accordance with the Dana Point classification into various sub-groups according to the respective etiology [M. Humbert and V. V. McLaughlin, *J. Am. Coll. Cardiol.* 2009, 54 (1), S1-S2; D. Montana and G. Simonneau, in: A. J. Peacock et al. (Eds.), *Pulmonary Circulation. Diseases and their treatment*, 3$^{rd}$ edition, Hodder Arnold Publ., 2011, pp. 197-206].

Despite all the advances in the therapy of PH there is as yet no prospect of cure of this serious disorder. Standard therapies available on the market (for example prostacyclin analogs, endothelin receptor antagonists, phosphodiesterase inhibitors) are able to improve the quality of life, the exercise tolerance and the prognosis of the patients. These are therapeutic principles which are administered systemically and act primarily hemodynamically by modulating vessel tone. The applicability of these medicaments is limited owing to side effects, some of which are serious, and/or complicated administration forms. The period over which the clinical situation of the patients can be improved or stabilized by specific monotherapy is limited (for example owing to the development of tolerance). Eventually the therapy escalates and thus a combination therapy is applied, where a plurality of medicaments must be given concurrently. Currently, these standard therapeutics are approved only for the treatment of pulmonary arterial hypertension (PAH). In the case of secondary forms of PH such as PH-COPD, these therapeutic principles (for example sildenafil, bosentan) fail in clinical studies since, as a result of non-selective vasodilatation, they lead to a reduction (desaturation) of the arterial oxygen content in the patients. The probable reason for this is an unfavourable effect on the ventilations-perfusion adaptation in the lung in hetero-genous lung disorders owing to the systemic administration of non-selective vasodilatators [I. Blanco et al., *Am. J. Respir. Crit. Care Med.* 2010, 181, 270-278; D. Stolz et al., *Eur. Respir. J.* 2008, 32, 619-628].

Novel combination therapies are one of the most promising future therapeutic options for the treatment of pulmonary hypertension. In this connection, the finding of novel pharmacological mechanisms for the treatment of PH is of particular interest [Ghofrani et al., *Herz* 2005, 30, 296-302; E. B. Rosenzweig, *Expert Opin. Emerging Drugs* 2006, 11, 609-619; T. Ito et al., *Curr. Med. Chem.* 2007, 14, 719-733]. In particular novel therapeutic approaches which can be combined with the therapy concepts already on the market may form the basis of a more efficient treatment and thus be of great advantage for the patients. In addition, selective pulmonary applicability of such a novel principle of action could offer the option of not only using it for PAH, but especially also provide a first therapy option for patients suffering from secondary forms of PH.

In an animal model of pulmonary hypertension, it was demonstrated that inhalative administration of the sGC activator BAY 58-2667 (cinaciguat) in the form of microparticles leads to a dose-dependent selective reduction of the pulmonary arterial pressure. In this model, intravenous administration of 1H-1,2,4-oxadiazolo[4,3-a]quinoxalin-1-one (ODQ), which oxidizes the prosthetic haem group of the sGC, reduced the vasodilative effect of inhaled NO (iNO), whereas this was increased by BAY 58-2267. These results led to the hypothesis that inhalative administration of an sGC activator might represent a novel effective treatment method for patients suffering from pulmonary hypertension, in particular if the response of these patients to iNO and/or to PDE5 inhibitors is reduced as a consequence of a lack of NO or an oxidation of sGC [O. V. Evgenov et al., *Am. J. Respir. Crit. Care Med.* 2007, 176, 1138-1145]. However, in this model cinaciguat for its part did not have a sufficient duration of action, and in addition higher dosages led to unwanted systemic side effects.

Accordingly, it was an object of the present invention to provide novel compounds which, in the manner described above, act as activators of soluble guanylate cyclase and as such can be employed in particular for the treatment and prevention of cardiovascular disorders. In addition, these novel compounds should have improved selectivity of pulmonary action and thus be suitable in particular for the treatment of pulmonary hypertension and its secondary forms. To this end, it should be possible to combine the novel compounds with PAH standard therapy, but also with the basic therapeutics in secondary PH forms.

Various aminodicarboxylic acid derivatives for the treatment of cardiovascular disorders are disclosed in the patent applications WO 01/19780-A2, WO 02/070459-A1, WO 02/070460-A1, WO 02/070461-A1, WO 02/070462-A1 and WO 02/070510-A2. WO 2009/023669-A1 describes substituted 5,6,7,8-tetrahydroquinolines as C5a receptor modulators for the treatment of inflammatory and immune disorders. WO 95/18617-A1 and WO 00/35882-A1 described 1-amino-1,2,3,4-tetrahydronaphthalene derivatives for the treatment of neurological disorders. WO 2006/104826-A2 discloses acylated 5-amino-5,6,7,8-tetrahydronaphthalene-2-carboxamides as glucagon receptor antagonists for the treatment of diabetes.

The present invention provides compounds of the general formula (I)

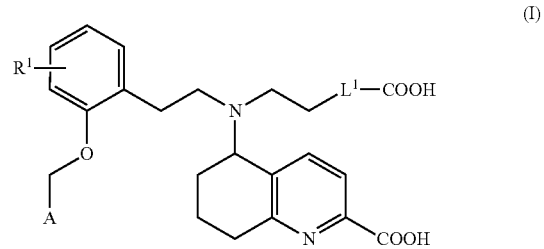

(I)

in which
$R^1$ represents hydrogen or fluorine,
$L^1$ represents ethane-1,2-diyl or 1,4-phenylene,
and
A represents a group of the formula

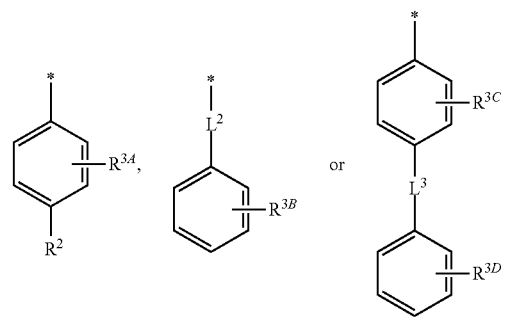

in which
* denotes the respective point of attachment to the remainder of the molecule,
$L^2$ represents straight-chain $(C_1\text{-}C_6)$-alkanediyl,
L represents a bond, —O—, —$CH_2$—, —$CH_2$—$CH_2$— or —CH=CH—,
$R^2$ represents $(C_1\text{-}C_4)$-alkyl which may be substituted up to six times by fluorine,
or
represents $(C_3\text{-}C_6)$-cycloalkyl which may be mono- or disubstituted by identical or different radicals selected from the group consisting of fluorine, difluoromethyl, trifluoromethyl and $(C_1\text{-}C_4)$-alkyl,
or
represents 4- to 6-membered heterocyclyl which contains one or two identical or different hetero ring members selected from the group consisting of N($R^4$), O, S and S(O)$_2$ where $R^4$ represents ($C_1$-$C_4$)-alkyl or ($C_1$-$C_4$)-alkylcarbonyl or, in the case that N($R^4$) represents a ring nitrogen atom by means of which said heterocyclyl is attached to the adjacent phenyl group, is not present, or represents 5-membered heteroaryl which contains one, two or three identical or different ring heteroatoms selected from the group consisting of N, O and S and may optionally be fused to a phenyl ring, where the heteroaryl ring and the optionally fused phenyl ring may each be mono- or disubstituted by identical or different radicals selected from the group consisting of fluorine, chlorine, cyano, difluoromethyl, trifluoromethyl, ($C_1$-$C_4$)-alkyl, difluoromethoxy, trifluoromethoxy and ($C_1$-$C_4$)-alkoxy, or represents chlorine, and $R^{3A}$, $R^{3B}$, $R^{3C}$ and $R^{3D}$ independently of one another represent hydrogen or a substituent selected from the group consisting of fluorine, chlorine, bromine, cyano, ($C_1$-$C_4$)-alkyl, difluoromethyl, trifluoromethyl, ($C_1$-$C_4$)-alkoxy, difluoromethoxy and trifluoromethoxy, and salts, solvates and solvates of the salts thereof.

Compounds according to the invention are the compounds of the formula (I) and the salts, solvates and solvates of the salts thereof, the compounds of the formulae mentioned hereinafter and encompassed by formula (I) and the salts, solvates and solvates of the salts thereof, and the compounds which are mentioned hereinafter as exemplary embodiments and encompassed by formula (I) and the salts, solvates and solvates of the salts thereof, insofar as the compounds encompassed by formula (I) and mentioned hereinafter are not already salts, solvates and solvates of the salts.

Salts which are preferred for the purposes of the present invention are physiologically acceptable salts of the compounds according to the invention. Also encompassed are salts which are themselves unsuitable for pharmaceutical uses but can be used for example for isolating, purifying or storing the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, benzenesulphonic acid, toluenesulphonic acid, naphthalenedisulphonic acid, formic acid, acetic acid, trifluoroacetic acid, propionic acid, succinic acid, fumaric acid, maleic acid, lactic acid, tartaric acid, malic acid, citric acid, gluconic acid, benzoic acid and embonic acid.

Physiologically acceptable salts of the compounds according to the invention also include salts of conventional bases, such as, by way of example and preferably, alkali metal salts (e.g. sodium and potassium salts), alkaline earth metal salts (e.g. calcium and magnesium salts), zinc salts and ammonium salts derived from ammonia or organic amines having 1 to 16 C atoms, such as, by way of example and preferably, ethylamine, diethylamine, triethylamine, N,N-diisopropylethylamine, monoethanolamine, diethanolamine, triethanolamine, tromethamine, dimethylaminoethanol, diethylaminoethanol, choline, procaine, dicyclohexylamine, dibenzylamine, N-methylmorpholine, N-methylpiperidine, arginine, lysine and 1,2-ethylenediamine.

Solvates in the context of the invention are designated as those forms of the compounds according to the invention which form a complex in the solid or liquid state by coordination with solvent molecules. Hydrates are a specific form of solvates, in which the coordination takes place with water. Hydrates are preferred solvates in the context of the present invention.

Depending on their structure, the compounds according to the invention may exist in different stereoisomeric forms, i.e. in the form of configurational isomers or if appropriate also as conformational isomers (enantiomers and/or diastereomers, including those in the case of atropisomers). The present invention therefore encompasses the enantiomers and diastereomers and the respective mixtures thereof. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by generally customary processes known to those skilled in the art, for example by the methods described below and the methods described in the working examples, by using corresponding isotopic modifications of the respective reagents and/or starting materials therein.

The present invention moreover also includes prodrugs of the compounds according to the invention. The term "prodrugs" here designates compounds which themselves can be biologically active or inactive, but are converted (for example metabolically or hydrolytically) into compounds according to the invention during their dwell time in the body.

The present invention comprises in particular hydrolysable ester derivatives of the carboxylic acids of the formula (I) according to the invention as prodrugs. These are to be understood as meaning esters which can be hydrolysed to the free carboxylic acids, as the compounds that are mainly active biologically, in physiological media, under the conditions of the biological tests described later and in particular in vivo by enzymatic or chemical routes. $(C_1-C_4)$-alkyl esters, in which the alkyl group can be straight-chain or branched, are preferred as such esters. Particular preference is given to methyl, ethyl or tert-butyl esters.

In the context of the present invention, the substituents have the following meaning, unless specified otherwise:

$(C_1-C_4)$-Alkyl in the context of the invention represents a straight-chain or branched monovalent alkyl radical having 1 to 4 carbon atoms. The following may be mentioned by way of example and by way of preference: methyl, ethyl, n-propyl, isopropyl, n-butyl, isobutyl, sec-butyl and tert-butyl.

$(C_1-C_6)$-Alkanediyl and $(C_3-C_5)$-alkanediyl in the context of the invention represent a straight-chain, α,ω-divalent alkyl radical having 1 to 6 or 3 to 5 carbon atoms. The following may be mentioned by way of example and by way of preference: methylene, ethane-1,2-diyl (1,2-ethylene), propane-1,3-diyl (1,3-propylene), butane-1,4-diyl (1,4-butylene), pentane-1,5-diyl (1,5-pentylene) and hexane-1,6-diyl (1,6-hexylene).

$(C_1-C_4)$-Alkylcarbonyl in the context of the invention represents a straight-chain or branched alkyl radical having 1 to 4 carbon atoms which is attached via a carbonyl group [—C(=O)—] to the remainder of the molecule. The following may be mentioned by way of example and by way of preference: acetyl, propionyl, n-butyryl, isobutyryl, n-pentanoyl and pivaloyl.

$(C_1-C_4)$-Alkoxy in the context of the invention represents a straight-chain or branched alkoxy radical having 1 to 4 carbon atoms. The following may be mentioned by way of example and by way of preference: methoxy, ethoxy, n-propoxy, isopropoxy, n-butoxy, isobutoxy, sec-butoxy and tert-butoxy.

$(C_3-C_6)$-Cycloalkyl in the context of the invention represents a monocyclic saturated carbocycle having 3 to 6 ring carbon atoms. The following may be mentioned by way of example and by way of preference: cyclopropyl, cyclobutyl, cyclopentyl and cyclohexyl.

4- to 6-membered heterocyclyl in the context of the invention represents a monocyclic saturated heterocycle having a total of 4 to 6 ring atoms which contains one or two identical or different ring heteroatoms from the group consisting of N, O, S and S(O)$_2$ and is attached via a carbon atom or optionally via a ring nitrogen atom. Preference is given to 5- or 6-membered heterocyclyl which contains a ring nitrogen atom and may additionally contain a further ring heteroatom from the group consisting of N and O. Examples which may be mentioned are: azetidinyl, oxetanyl, thietanyl, pyrrolidinyl, pyrazolidinyl, tetrahydrofuranyl, thiolanyl, 1,2-oxazolidinyl, 1,3-oxazolidinyl, 1,3-thiazolidinyl, piperidinyl, piperazinyl, tetrahydropyranyl, tetrahydrothiopyranyl, 1,3-dioxanyl, 1,4-dioxanyl, 1,2-oxazinanyl, morpholinyl and thiomorpholinyl. Preference is given to pyrrolidinyl, piperidinyl, piperazinyl and morpholinyl.

5-membered heteroaryl in the context of the invention represents an aromatic heterocycle (hetero-aromatic ring) which has a total of 5 ring atoms, contains up to three identical or different ring heteroatoms from the group consisting of N, O and S and is attached via a ring carbon atom or optionally via a ring nitrogen atom. Preference is given to 5-membered heteroaryl which contains a ring nitrogen atom and additionally one or two further ring heteroatoms from the group consisting of N, O and S. Examples which may be mentioned are: furyl, pyrrolyl, thienyl, pyrazolyl, imidazolyl, 1,2-oxazolyl (isoxazolyl), 1,3-oxazolyl, 1,2-thiazolyl (isothiazolyl), 1,3-thiazolyl, 1,2,3-triazolyl, 1,2,4-triazolyl, 1,2,4-oxadiazolyl, 1,3,4-oxadiazolyl, 1,2,4-thiadiazolyl and 1,3,4-thiadiazolyl. Preference is given to 1,2-oxazolyl (isoxazolyl), 1,3-oxazolyl, 1,2-thiazolyl (isothiazolyl), 1,3-thiazolyl, 1,2,4-oxadiazolyl, 1,3,4-oxadiazolyl, 1,2,4-thiadiazolyl and 1,3,4-thiadiazolyl.

In the context of the present invention, all radicals which occur more than once are defined independently of one another. If radicals in the compounds according to the invention are substituted, the radicals may be mono- or polysubstituted, unless specified otherwise. Substitution by one, two or three identical or different substituents is preferred. Particular preference is given to substitution by one or two identical or different substituents.

A particular embodiment of the present invention comprises compounds of the formula (I) in which
R$^1$ represents hydrogen,
and salts, solvates and solvates of the salts thereof.

A further particular embodiment of the present invention comprises compounds of the formula (I) in which
R$^1$ represents fluorine which is located in the para-position relative to the ACH$_2$O group, and salts, solvates and solvates of the salts thereof.

A further particular embodiment of the present invention comprises compounds of the formula (I) in which
L$^1$ represents ethane-1,2-diyl,
and salts, solvates and solvates of the salts thereof.

A further particular embodiment of the present invention comprises compounds of the formula (I) in which
L$^1$ represents 1,4-phenylene,
and salts, solvates and solvates of the salts thereof.

Preference in the context of the present invention is given to compounds of the formula (I) in which
R$^1$ represents hydrogen or fluorine,
L$^1$ represents ethane-1,2-diyl or 1,4-phenylene,
and
A represents a group of the formula

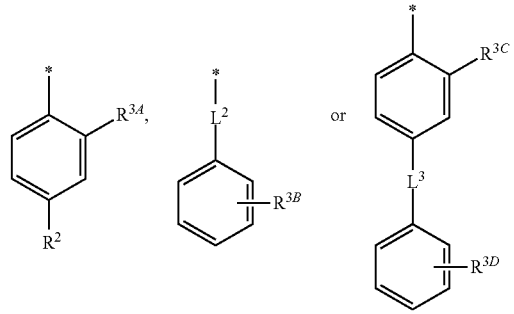

in which
* denotes the respective point of attachment to the remainder of the molecule,
L$^2$ represents straight-chain $(C_3-C_5)$-alkanediyl,
L$^3$ represents a bond, —CH$_2$—CH$_2$— or —CH=CH—,
R$^2$ represents $(C_1-C_4)$-alkyl which may be substituted up to three times by fluorine,
or
represents cyclopentyl or cyclohexyl which may be mono- or disubstituted by identical or different radicals selected from the group consisting of fluorine, methyl and trifluoromethyl,
or
represents 5- or 6-membered heterocyclyl of the formula

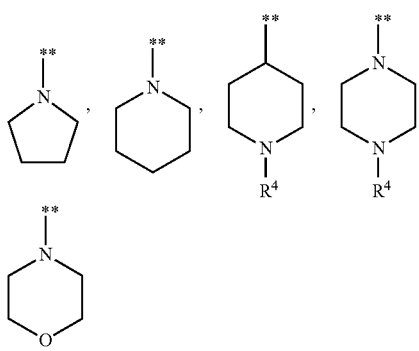

in which
   ** denotes the respective point of attachment to the adjacent phenyl group
   and
   $R^4$ represents methyl, acetyl or propionyl,
   or
   represents 5-membered heteroaryl selected from the group consisting of 1,2-oxazolyl, 1,3-oxazolyl, 1,2-thiazolyl, 1,3-thiazolyl, 1,2,4-oxadiazolyl, 1,3,4-oxadiazolyl, 1,2,4-thiadiazolyl and 1,3,4-thiadiazolyl, where the heteroaryl groups mentioned may each be substituted by methyl or trifluoromethyl
   and
   where 1,2-oxazolyl, 1,3-oxazolyl, 1,2-thiazolyl and 1,3-thiazolyl may be fused with a phenyl ring which for its part may be substituted by fluorine, chlorine, cyano, methyl, trifluoromethyl or trifluoromethoxy,
$R^{3A}$ represents hydrogen, fluorine, chlorine, methyl or trifluoromethyl,
$R^{3B}$ represents hydrogen, fluorine, chlorine, methyl, trifluoromethyl, methoxy or trifluoromethoxy,
$R^{3C}$ represents hydrogen, fluorine, chlorine, methyl or trifluoromethyl,
and
$R^{3D}$ represents hydrogen, fluorine, chlorine, cyano, methyl, trifluoromethyl, methoxy or trifluoromethoxy,
and salts, solvates and solvates of the salts thereof.

Particular preference in the context of the present invention is given to compounds of the formula (I) in which
$R^1$ represents hydrogen or fluorine,
$L^1$ represents ethane-1,2-diyl or 1,4-phenylene,
and
A represents a group of the formula

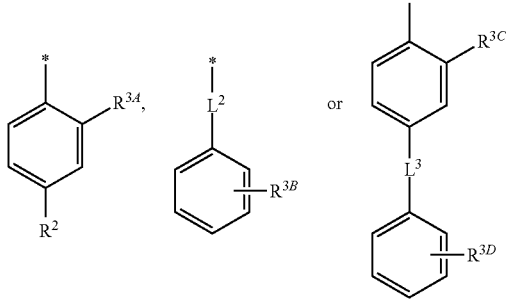

in which
* denotes the respective point of attachment to the remainder of the molecule, $L^2$ represents straight-chain $(C_3$-$C_5)$-alkanediyl,
$L^3$ represents a bond, —$CH_2$—$CH_2$— or —CH=CH—,
$R^2$ represents $(C_1$-$C_4)$-alkyl which may be substituted up to three times by fluorine,
   or
   represents cyclopentyl or cyclohexyl which may be mono- or disubstituted by identical or different radicals selected from the group consisting of fluorine, methyl and trifluoromethyl,
   or
   represents 6-membered heterocyclyl of the formula

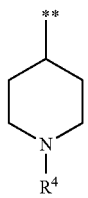

in which
* denotes the point of attachment to the adjacent phenyl group
and
$R^4$ represents methyl, acetyl or propionyl,
   or
   represents 1,3-benzoxazol-2-yl, 1,2-benzoxazol-3-yl or 1,3-benzothiazol-2-yl which may be substituted by a radical selected from the group consisting of fluorine, chlorine, cyano, methyl, trifluoromethyl and trifluoromethoxy,
$R^{3A}$ represents hydrogen, fluorine, chlorine, methyl or trifluoromethyl,
$R^{3B}$ represents hydrogen, fluorine, chlorine, methyl, trifluoromethyl or trifluoromethoxy,
$R^{3C}$ represents hydrogen, fluorine, chlorine, methyl or trifluoromethyl, and
$R^{3D}$ represents hydrogen, fluorine, chlorine, cyano, methyl, trifluoromethyl or trifluoromethoxy,
and salts, solvates and solvates of the salts thereof.

Very particular preference in the context of the present invention is given to compounds of the formula (I) in which
$R^1$ represents hydrogen or fluorine,
$L^1$ represents ethane-1,2-diyl or 1,4-phenylene,
and
A represents a group of the formula

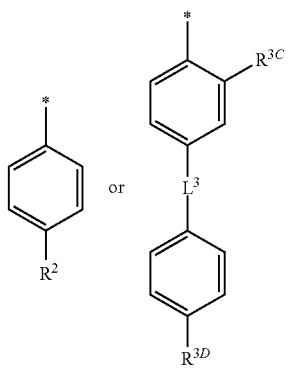

in which
* denotes the respective point of attachment to the remainder of the molecule, L³ represents a bond or —CH₂—CH₂—,
R² represents tert-butyl, cyclohexyl, 4-(trifluoromethyl)cyclohexyl or 1,3-benzoxazol-2-yl which may be substituted by chlorine, cyano, methyl or trifluoromethyl,
R³ᶜ represents hydrogen or chlorine,
and
R³ᴰ represents hydrogen, fluorine or trifluoromethyl,
and salts, solvates and solvates of the salts thereof.

The definitions of radicals indicated specifically in the respective combinations or preferred combinations of radicals are replaced as desired irrespective of the particular combinations indicated for the radicals also by definitions of radicals of other combinations. Combinations of two or more of the abovementioned preferred ranges are very particularly preferred.

The invention furthermore provides a process for preparing the compounds of the formula (I) according to the invention, characterized in that either

[A] a compound of the formula (II)

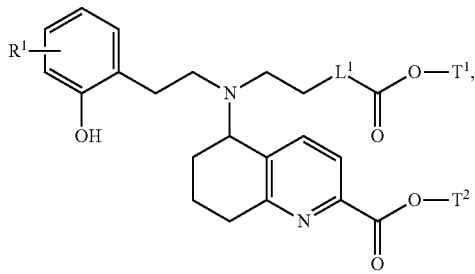

in which R¹ and L¹ have the meanings given above
and
T¹ and T² are identical or different and represent (C₁-C₄)-alkyl,
is reacted in the presence of a base with a compound of the formula (III)

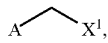

in which A has the meanings given above
and
X¹ represents a leaving group such as, for example, chlorine, bromine, iodine, mesylate, triflate or tosylate,
or

[B] a compound of the formula (IV)

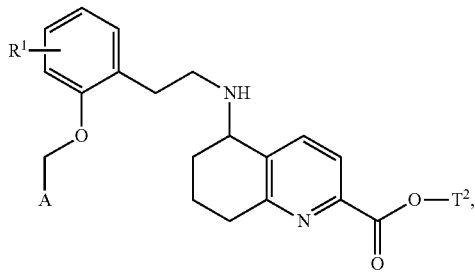

in which R¹ and A have the meanings given above
and
T² represents (C₁-C₄)-alkyl,
is reacted in the presence of a base with a compound of the formula (V)

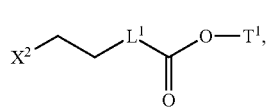

in which L¹ has the meanings given above,
T¹ represents (C₁-C₄)-alkyl,
and
X² represents a leaving group such as, for example, chlorine, bromine, iodine, mesylate, triflate or tosylate,
and the respective resulting compound of the formula (VI)

in which R¹, A, L¹, T¹ and T² have the meanings given above,
is then converted by hydrolysis of the ester groupings —C(O)OT¹ and —C(O)OT² into the corresponding dicarboxylic acid of the formula (I)
and the compounds of the formula (I) obtained in this manner are optionally separated into their enantiomers and/or diastereomers and/or optionally converted with the appropriate (i) solvents and/or (ii) bases or acids into their solvates, salts and/or solvates of the salts.

Suitable inert solvents for process steps (II)+(III)→(VI) and (IV)+(V)→(VI) are, for example, ethers such as diethyl ether, diisopropyl ether, methyl tert-butyl ether, tetrahydrofuran, 1,4-dioxane, 1,2-dimethoxyethane or bis-(2-methoxyethyl) ether, hydrocarbons such as benzene, toluene, xylene, pentane, hexane, heptane, cyclohexane or mineral oil fractions, or dipolar aprotic solvents such as acetone, methyl ethyl ketone, acetonitrile, N,N-dimethylformamide (DMF), N,N-dimethylacetamide (DMA), dimethyl sulphoxide (DMSO), N,N'-dimethylpropyleneurea (DMPU) or N-methylpyrrolidinone (NMP). It is also possible to use mixtures of these solvents. Preference is given to using acetonitrile or dimethylformamide.

Suitable bases for process steps (II)+(III)→(VI) and (IV)+(V)→(VI) are in particular alkali metal carbonates such as sodium carbonate, potassium carbonate or caesium carbonate, alkali metal alkoxides such as sodium methoxide or potassium methoxide, sodium ethoxide or potassium ethoxide or sodium tert-butoxide or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide, or organometallic compounds such as n-butyllithium or phenyllithium. The base used is preferably sodium carbonate, potassium carbonate or caesium carbonate. In certain cases the addition of an alkylation catalyst such as, for example, lithium bromide, sodium iodide or potassium iodide, tetra-n-butylammonium bromide or benzyltriethylammonium chloride may be advantageous.

The reactions (II)+(III)→(VI) and (IV)+(V)→(VI) are generally carried out in a temperature range of from 0° C. to +150° C., preferably at from +50° C. to +100° C.

The hydrolysis of the ester groups —C(O)OT$^1$ and —C(O)OT$^2$ in process step (VI)→(I) is carried out by customary methods by treating the esters in inert solvents with acids or bases, where in the latter variant the salts initially formed are converted by treatment with acid into the free carboxylic acids. In the case of the tert-butyl esters, the ester cleavage is preferably carried out using acids.

If the groups T$^1$ and T$^2$ are different, the hydrolysis may optionally be carried out simultaneously in a one-pot reaction or in two separate reaction steps.

Suitable inert solvents for these reactions are water or the organic solvents customary for an ester cleavage. These preferably include alcohols such as methanol, ethanol, n-propanol, isopropanol, n-butanol or tert-butanol, or ethers such as diethyl ether, tetrahydrofuran, 1,4-dioxane or 1,2-dimethoxyethane, or other solvents such as dichloromethane, acetone, methyl ethyl ketone, N,N-dimethylformamide or dimethyl sulphoxide. It is also possible to use mixtures of these solvents. In the case of a basic ester hydrolysis, preference is given to using mixtures of water with dioxane, tetrahydrofuran, methanol, ethanol, dimethylformamide and/or dimethyl sulphoxide. In the case of the reaction with trifluoroacetic acid, preference is given to using dichloromethane, and in the case of the reaction with hydrogen chloride, preference is given to using tetrahydrofuran, diethyl ether, dioxane or water.

Suitable bases are the customary inorganic bases. These include in particular alkali metal or alkaline earth metal hydroxides such as, for example, lithium hydroxide, sodium hydroxide, potassium hydroxide or barium hydroxide, or alkali metal or alkaline earth metal carbonates such as sodium carbonate, potassium carbonate or calcium carbonate. Preference is given to lithium hydroxide, sodium hydroxide or potassium hydroxide.

Suitable acids for the ester cleavage are, in general, sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesuphonic acid or mixtures thereof, if appropriate with addition of water. Preference is given to hydrogen chloride or trifluoroacetic acid in the case of tert-butyl esters and hydrochloric acid in the case of the methyl esters.

The ester cleavage is generally carried out in a temperature range of from −20° C. to +120° C., preferably at from 0° C. to +80° C.

The process steps described above can be carried out at normal, elevated or reduced pressure (for example in the range from 0.5 to 5 bar); in general, all the reactions are carried out at atmospheric pressure.

For their part, the compounds of the formula (II) can be prepared by converting 5-oxo-5,6,7,8-tetrahydroquinoline-2-carbonitrile (VII)

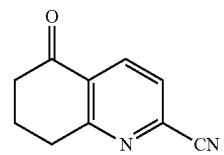

(VII)

via reductive amination with a 2-(2-methoxyphenyl)ethylamine of the formula (VIII)

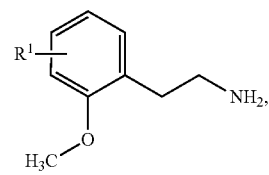

(VIII)

in which R$^1$ has the meanings given above
into a secondary amine of the formula (IX)

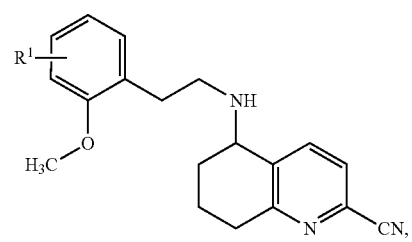

(IX)

in which R$^1$ has the meanings given above,
then alkylating in the presence of a base with a compound of the formula (V)

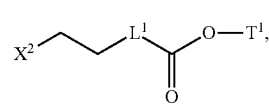

(V)

in which L$^1$, T$^1$ and X$^2$ have the meanings given above
to give a tertiary amine of the formula (X)

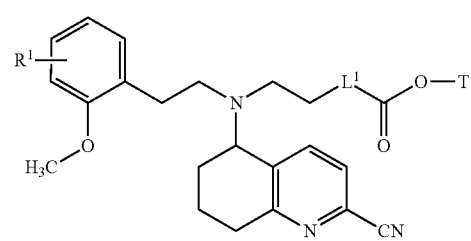

(X)

in which L$^1$, R$^1$ and T$^1$ have the meanings given above,
then removing the phenolic methyl ether grouping by treatment with boron tribromide or hydrogen bromide and finally converting the resulting compound of the formula (XI)

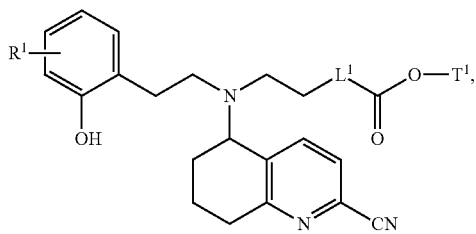

(XI)

in which $L^1$, $R^1$ and $T^1$ have the meanings given above by acid-catalyzed solvolysis of the nitrile group with an alcohol of the formula (XII)

$T^2$-OH (XII), in which $T^2$ has the meaning given above into the dicarboxylic ester of the formula (II).

The reaction (VII)+(VIII)→(IX) is carried out in a solvent which is customary for reductive aminations and inert under the reaction conditions, if appropriate in the presence of an acid and/or a dehydrating agent as catalyst. These solvents include, for example, tetrahydrofuran, toluene, dichloromethane, 1,2-dichloroethane, N,N-dimethylformamide and alcohols such as methanol, ethanol, n-propanol or isopropanol; it is also possible to use mixtures of such solvents. Preference is given to using toluene, methanol and/or ethanol. Suitable catalysts are customary organic acids such as acetic acid or p-toluenesulphonic acid.

Suitable reducing agents for these amination reactions are in particular borohydrides such as, for example, sodium borohydride, sodium cyanoborohydride, sodium triacetoxyborohydride or tetra-n-butylammonium borohydride; preference is given to using sodium borohydride.

The reaction (VII)+(VIII)→(IX) is preferably carried out in a two-step process initially in a temperature range of from +50° C. to +120° C. (for the imine condensation) and then at from 0° C. to +30° C. (for the borohydride reduction).

With respect to solvent, base and temperature, the alkylation in process step (IX)+(V)→(X) is carried out under reaction conditions analogous to those described above for the reaction (IV)+(V)→(VI).

The cleavage of the phenolic methyl ether group in process step (X)→(XI) is carried out by customary methods by treatment with boron tribromide in dichloromethane at from −20° C. to +10° C. or by heating with a solution of hydrogen bromide in glacial acetic acid or water to from +100° C. to +130° C. If under these reaction conditions the ester grouping —C(O)OT$^1$ and/or the nitrile group are—wholly or partially—hydrolyzed at the same time, the dicarboxylic acid of the formula (XIII)

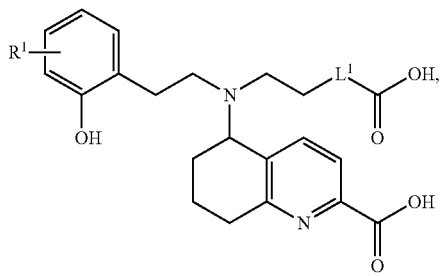

(XIII)

in which $L^1$ and $R^1$ have the meanings given above, formed in this manner can be re-esterified to the dicarboxylic ester of the formula (II), for example by subsequent treatment with methanol or ethanol in the presence of hydrogen chloride or thionyl chloride [$T^1$=$T^2$=methyl or ethyl in (II)].

The compounds of the formula (IV) can be prepared by initially converting the above-described compound of the formula (IX)

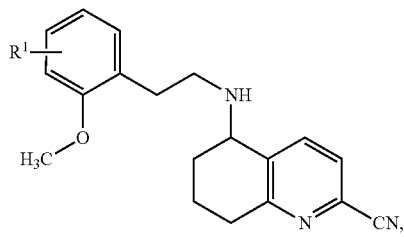

(IX)

in which $R^1$ has the meanings given above with the aid of aqueous hydrobromic acid into the hydroxycarboxylic acid of the formula (XIV)

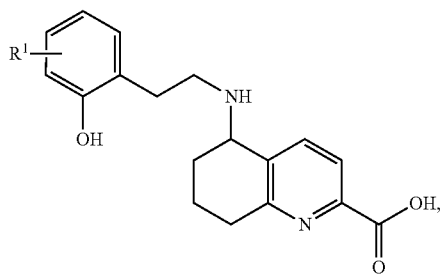

(XIV)

in which $R^1$ has the meanings given above, then esterifying under acid catalysis with an alcohol of the formula (XII)

$T^2$-OH (XII), in which $T^2$ has the meaning given above to give a compound of the formula (XV)

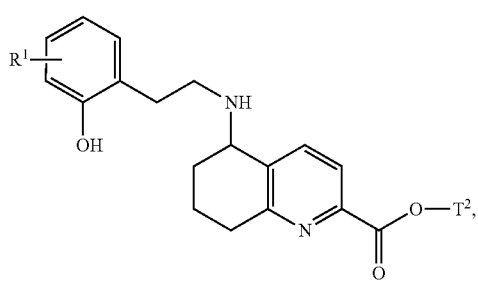

(XV)

in which $R^1$ and $T^2$ have the meanings given above, then converting the amine compound (XV) into a protected derivative of the formula (XVI)

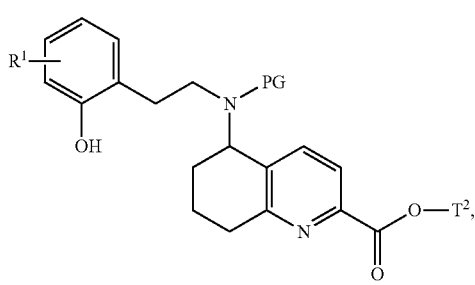

(XVI)

in which $R^1$ and $T^2$ have the meanings given above
and
PG represents a suitable temporary amino protective group such as, for example, tert-butoxycarbonyl,
subsequently alkylating in the presence of a base with a compound of the formula (III)

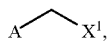

(III)

in which A and $X^1$ have the meanings given above,
to give a compound of the formula (XVII)

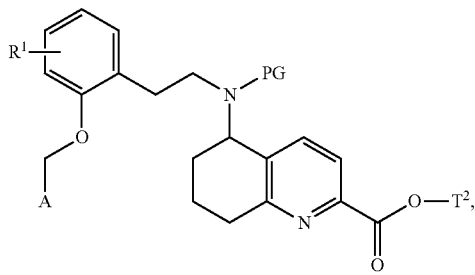

(XVII)

in which A, PG, $R^1$ and $T^2$ have the meanings given above,
and finally removing the temporary protective group PG again.

The transformation (IX)→(XIV)→(XV) is carried out in a manner analogous to that described above for the reaction sequence (X)→(XI) [or (XIII)]→(II).

Suitable protective groups PG in compound (XVI) are customary amino protective groups, in particular those of the non-benzylic carbamate type such as, for example, allyloxycarbonyl (Alloc), tert-butoxycarbonyl (Boc) or 9-fluorenylmethoxycarbonyl (Pmoc). Here, the protective group PG is chosen such that the conditions for its removal in process step (XVII)→(IV) are compatible with the respective ester radical $T^2$ employed. Introduction and removal of the protective group are carried out by customary methods [see, for example, T. W. Greene and P. G. M. Wuts, *Protective Groups in Organic Synthesis*, Wiley, New York, 1999]. Preference is given to using the tert-butoxycarbonyl group (Boc).

With respect to solvent, base and temperature, the alkylation in process step (XVI)+(III)→(XVII) is carried out under reaction conditions analogous to those described above for the reaction (II)+(III)→(VI).

The compound of the formula (VII)

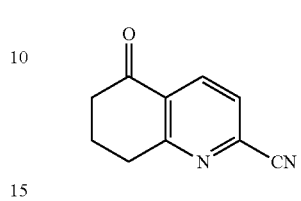

(VII)

shown above is novel as such and can be prepared by palladium-catalyzed halogen/cyanide exchange starting with the chloro compound (XVIII)

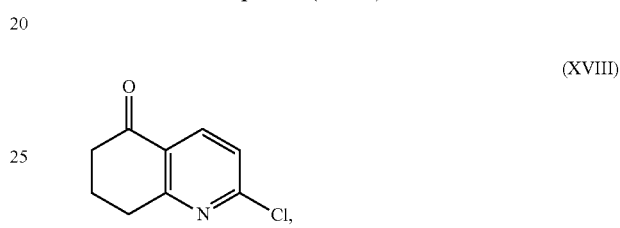

(XVIII)

which is known from the literature (see Reaction Scheme 1 below). The reaction is preferably carried out using zinc cyanide with the aid of tetrakis(triphenylphosphine)palladium as catalyst in a dipolar aprotic solvent such as N,N-dimethylformamide or N,N-dimethylacetamide in a temperature range of from +80° C. to +150° C.

The reactions described above can be carried out at normal, elevated or reduced pressure (for example in the range from 0.5 to 5 bar); in general, all the reactions are carried out at atmospheric pressure.

Separation of the compounds according to the invention into the corresponding enantiomers and/or diastereomers can, if expedient, even be carried out at the stage of the compounds (II), (IV), (VI), (IX), (X), (XI), (XIII), (XIV), (XV), (XVI) or (XVII), which are then reacted further in separated form in accordance with the process sequences described above. Such a separation of the stereoisomers can be carried out by customary methods known to the person skilled in the art. In the context of the present invention, preference is given to using chromatographic processes on achiral or chiral separation phases; in the case of carboxylic acids as intermediates or end products, it may alternatively also be possible to achieve separation via diastereomeric salts using chiral bases.

The compounds of the formulae (III), (V), (VIII), (XII) and (XVIII) are either commercially available or described as such in the literature, or they can be prepared in a manner obvious to the person skilled in the art analogously to methods published in the literature. Numerous detailed procedures and literature references for preparing the starting materials can also be found in the Experimental Part in the section on the preparation of the starting materials and intermediates.

The preparation of the compounds according to the invention can be illustrated in an exemplary manner by the reaction schemes below:

Scheme 1
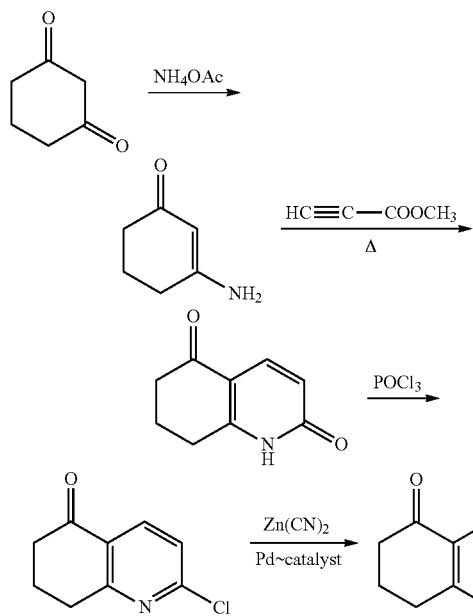
[see also S. J. Stachel et al., *Bioorg. Med. Chem. Lett.* 22, 240-244 (2012); M. Vanejevs et al, *J. Med. Chem.* 51 (3), 634-647 (2008); G. R. Pettit et al., *J. Org. Chem.* 23 (3), 1089-1092 (1968)].
Scheme 2
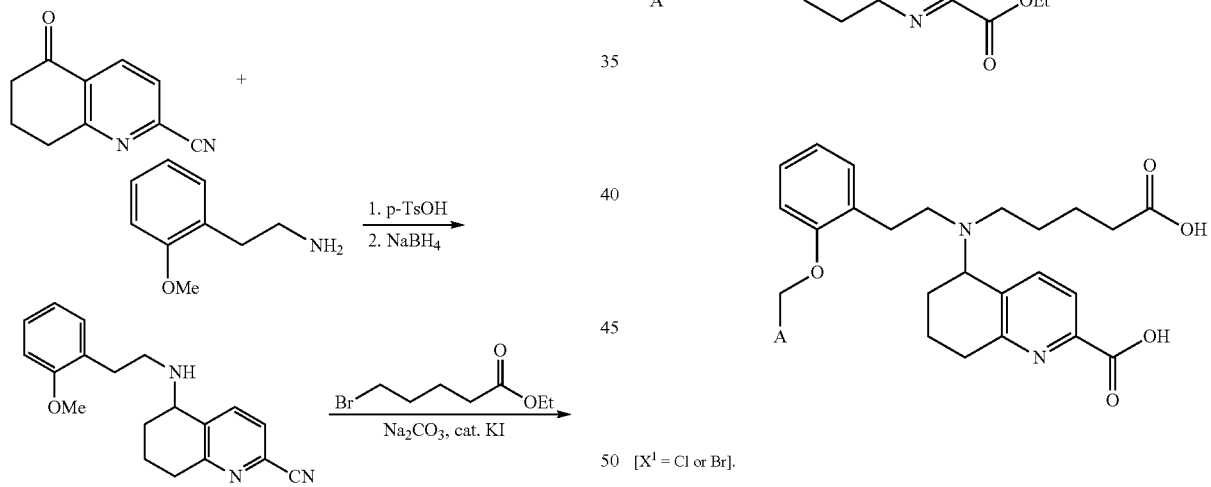
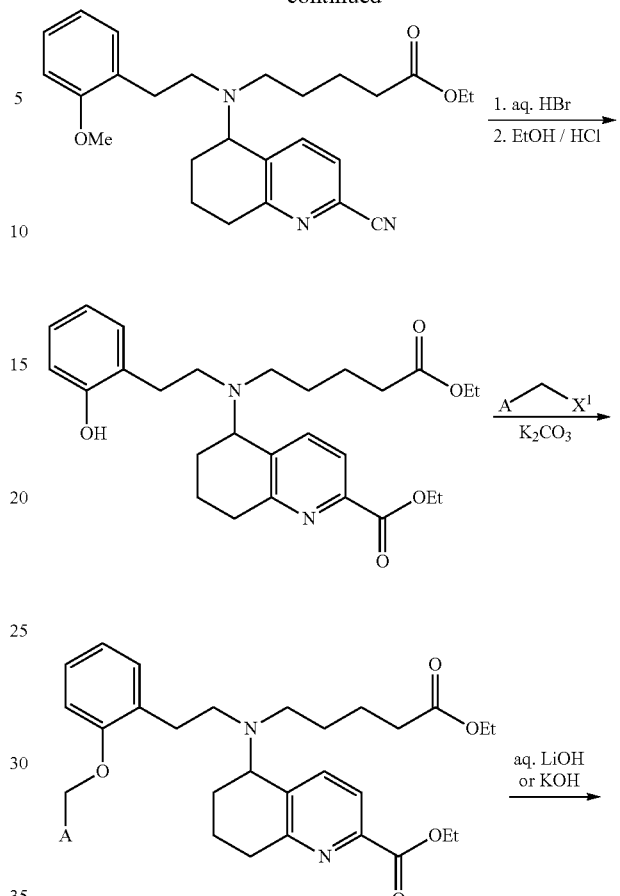
[$X^1$ = Cl or Br].
Scheme 3
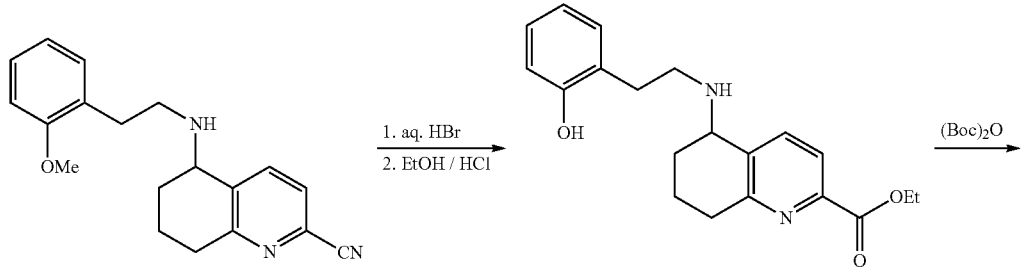

-continued

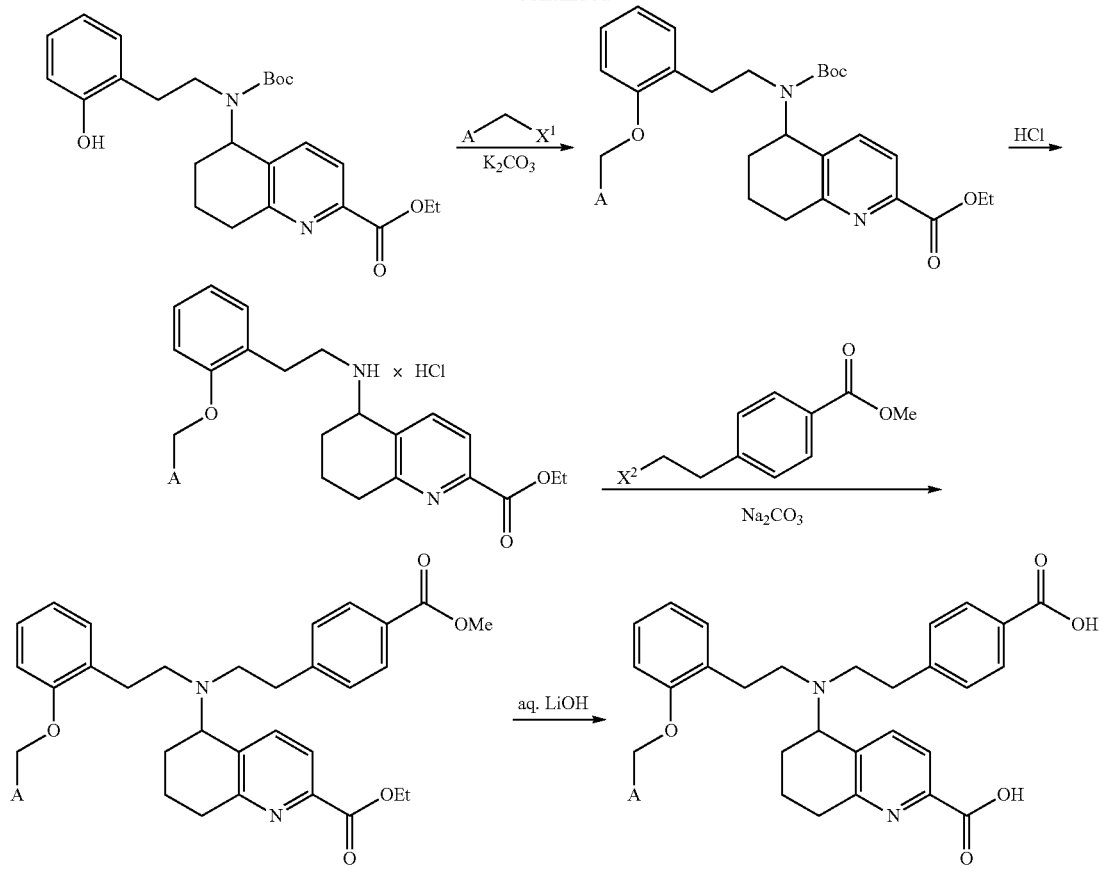

[X¹ = Cl or Br; X² = Cl or I].

The compounds according to the invention have useful pharmacological properties and can be used for prevention and treatment of disorders in humans and animals.

In the context of the present invention, the term "treatment" or "treat" includes the inhibition, delay, arrest, amelioration, attenuation, limitation, reduction, suppression, reversal or cure of a disease, a condition, a disorder, an injury or a health impairment, of the development, course or the progression of such states and/or the symptoms of such states. Here, the term "therapy" is understood to be synonymous with the term "treatment".

In the context of the present invention, the terms "prevention", "prophylaxis" or "precaution" are used synonymously and refer to the avoidance or reduction of the risk to get, to contract, to suffer from or to have a disease, a condition, a disorder, an injury or a health impairment, a development or a progression of such states and/or the symptoms of such states.

The treatment or the prevention of a disease, a condition, a disorder, an injury or a health impairment may take place partially or completely.

The compounds according to the invention are potent activators of soluble guanylate cyclase. They lead to vasorelaxation, inhibition of platelet aggregation and a lowering of the blood pressure, as well as an increased coronary blood flow and microcirculation. These activities are mediated via direct haem-independent activation of soluble guanylate cyclase and an increase in intracellular cGMP levels.

In addition, the compounds according to the invention have further advantageous properties, in particular with respect to their pulmoselective action (in contrast to a systemic action), their lung retention time and/or their duration of action following intrapulmonary administration.

The compounds according to the invention are particularly suitable for the treatment and/or prevention of cardiovascular, cardiopulmonary, thromboembolic, fibrotic and pulmonary disorders.

Accordingly, the compounds according to the invention can be used in medicaments for the treatment and/or prevention of cardiovascular and cardiopulmonary disorders such as, for example high blood pressure (hypertension), heart failure, coronary heart disease, stable and unstable angina pectoris, pulmonary arterial hypertension (PAH) and secondary forms of pulmonary hypertension (PH), renal hypertension, disorders of peripheral and cardial vessels, arrhythmias, atrial and ventricular arrhythmias and impaired conduction such as, for example, grade I-III atrioventricular blocks, supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV nodes reentry tachycardia, Wolff-Parkinson-White syndrome, acute coronary syndrome (ACS), autoimmune heart disorders (pericarditis, endocarditis, valvolitis, aortitis, cardiomyopathies), boxer cardiomyopathy, aneurysms, shock such as cardiogenic shock, septic shock and anaphylactic shock, furthermore for the treatment and/or prevention of thromboembolic disorders and ischaemias such as myocardial ischaemia, myocardial infarction, stroke, cardial hypertrophy, transitory and ischaemic attacks, preeclampsia, inflammatory cardiovascular disorders, spasms of the coronary arteries and the peripheral arteries, formation of oedemas such as, for example, pulmonary oedema, brain oedema, renal oedema or heart failure-induced oedema, impaired peripheral perfusion, reperfusion damage, arterial and venous thromboses, microalbuminuria, heart failure, endothelial dysfunction, micro- and macrovascular damage (vasculitis), and also for preventing restenoses for example after thrombolysis therapies, percutaneous transluminal angioplasties (PTA), percutaneous transluminal coronary angioplasties (PTCA), heart transplants and bypass operations.

In the context of the present invention, the term "pulmonary hypertension" encompasses both primary and secondary subforms thereof, as defined below by the Dana Point classification according to their respective aetiology [see D. Montana and G. Simonneau, in: A. J. Peacock et al. (Eds.), *Pulmonary Circulation. Diseases and their treatment*, $3^{rd}$ edition, Hodder Arnold Publ., 2011, pp. 197-206; M. M. Hoeper et al., *J. Am. Coll. Cardiol.* 2009, 54 (1), S85-S96]. These include in particular in group 1 pulmonary arterial hypertension (PAH), which, among others, embraces the idiopathic and the familial forms (IPAH and FPAH, respectively). Furthermore, PAH also embraces persistent pulmonary hypertension of the newborn and the associated pulmonary arterial hypertension (APAH) associated with collagenoses, congenital systemic pulmonary shunt lesions, portal hypertension, HIV infections, the intake of certain drugs and medicaments (for example of appetite suppressants), with disorders having a significant venous/capillary component such as pulmonary venoocclusive disorder and pulmonary capillary haemangiomatosis, or with other disorders such as disorders of the thyroid, glycogen storage diseases, Gaucher disease, hereditary teleangiectasia, haemoglobinopathies, myeloproliferative disorders and splenectomy. Group 2 of the Dana Point classification comprises PH patients having a causative left heart disorder, such as ventricular, atrial or valvular disorders. Group 3 comprises forms of pulmonary hypertension associated with a lung disorder, for example with chronic obstructive lung disease (COPD), interstitial lung disease (ILD), pulmonary fibrosis (IPF), and/or hypoxaemia (e.g. sleep apnoe syndrome, alveolar hypoventilation, chronic high-altitude sickness, hereditary deformities). Group 4 includes PH patients having chronic thrombotic and/or embolic disorders, for example in the case of thromboembolic obstruction of proximal and distal pulmonary arteries (CTEPH) or non-thrombotic embolisms (e.g. as a result of tumour disorders, parasites, foreign bodies). Less common forms of pulmonary hypertension, such as in patients suffering from sarcoidosis, histiocytosis X or lymphangiomatosis, are summarized in group 5.

In the context of the present invention, the term "heart failure" encompasses both acute and chronic forms of heart failure, and also more specific or related types of disease, such as acute decompensated heart failure, right heart failure, left heart failure, global failure, ischemic cardiomyopathy, dilated cardiomyopathy, hypertrophic cardiomyopathy, idiopathic cardiomyopathy, congenital heart defects, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and also diastolic heart failure and systolic heart failure.

In addition, the compounds according to the invention can also be used for treatment and/or prevention of arteriosclerosis, disturbed lipid metabolism, hypolipoproteinaemias, dyslipidaemias, hypertriglyceridaemias, hyperlipidaemias, combined hyperlipidaemias, hypercholesterolaemias, abetalipoproteinemia, sitosterolemia, xanthomatosis, Tangier disease, adiposity, obesity, and also of metabolic syndrome.

Furthermore, the compounds according to the invention can be used for treatment and/or prevention of primary and secondary Raynaud's phenomenon, of microcirculation disorders, claudication, tinnitus, peripheral and autonomic neuropathies, diabetic microangiopathies, diabetic retinopathy, diabetic ulcers at the extremities, gangrene, CREST syndrome, erythematosis, onychomycosis and rheumatic disorders.

The compounds according to the invention can additionally also be used for preventing ischaemic and/or reperfusion-related damage to organs or tissues and also as additives for perfusion and preservation solutions of organs, organ parts, tissues or tissue parts of human or animal origin, in particular for surgical interventions or in the field of transplantation medicine.

Furthermore, the compounds according to the invention are suitable for treatment and/or prophylaxis of renal disorders, especially of renal insufficiency and kidney failure. In the context of the present invention, the terms renal insufficiency and kidney failure comprise both acute and chronic manifestations thereof, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney graft rejection and immunocomplex-induced kidney diseases, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally raised blood concentrations of urea, nitrogen, potassium and/or creatinine, altered activity of renal enzymes such as, for example, glutamyl synthetase, altered urine osmolarity or urine volume, increased microalbuminuria, macroalbuminuria, lesions on glomerulae and arterioles, tubular dilation, hyperphosphataemia and/or need for dialysis. The present invention also encompasses the use of the compounds according to the invention for treatment and/or prophylaxis of sequelae of renal insufficiency, for example hypertension, pulmonary oedema, heart failure, uremia, anemia, electrolyte disturbances (for example hypercalemia, hyponatremia) and disturbances in bone and carbohydrate metabolism.

In addition, the compounds according to the invention are suitable for treatment and/or prevention of urological disorders, for example benign prostate syndrome (BPS), benign prostate hyperplasia (BPH), benign prostate enlargement (BPE), bladder outlet obstruction (BOO), lower urinary tract syndrome (LUTS), neurogenic overactive bladder (OAB), incontinence, for example mixed, urge, stress or overflow incontinence (MUI, UUI, SUI, OUI), pelvic pain, and also erectile dysfunction and female sexual dysfunction.

The compounds according to the invention are also suitable for treatment and/or prevention of asthmatic disorders, chronic-obstructive pulmonary diseases (COPD), acute respiratory distress syndrome (ARDS) and acute lung injury (ALI), alpha-1 antitrypsin deficiency (AATD), pulmonary fibrosis, pulmonary emphysema (for example pulmonary emphysema induced by cigarette smoke) and cystic fibrosis (CF).

The compounds described in the present invention are also active compounds for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelination, multiple sclerosis, thalamic degeneration, Creutzfeld-Jacob dementia, HIV dementia, schizophrenia with dementia or Korsakoff's psychosis. They are also suitable for the treatment and/or prevention of central nervous system disorders such as states of anxiety, tension and depression, CNS-related sexual dysfunctions and sleep disturbances, and for controlling pathological disturbances of the intake of food, stimulants and addictive substances.

Furthermore, the compounds according to the invention are also suitable for regulation of cerebral blood flow and are thus effective agents for control of migraine. They are also suitable for the prophylaxis and control of sequelae of cerebral infarct (Apoplexia cerebri) such as stroke, cerebral ischaemias and craniocerebral trauma. The compounds according to the invention can likewise be used to control states of pain.

Moreover, the compounds according to the invention have antiinflammatory action and can therefore be used as antiinflammatories for treatment and/or prevention of sepsis (SIRS), multiple organ failure (MODS, MOF), inflammatory disorders of the kidney, chronic bowel inflammations (IBD, Crohn's Disease, UC), pancreatitis, peritonitis, rheumatoid disorders, inflammatory skin disorders and inflammatory eye disorders.

Furthermore, the compounds according to the invention are suitable for the treatment and/or prevention of fibrotic disorders of the internal organs, for example of the lung, of the heart, of the kidneys, of the bone marrow and especially of the liver, and also of dermatological fibroses and fibrotic disorders of the eye. In the context of the present inventions, the term "fibrotic disorders" encompasses especially disorders such as hepatic fibrosis, hepatic cirrhosis, pulmonary fibrosis, endomyocardial fibrosis, nephropathy, glomerulonephritis, interstitial renal fibrosis, fibrotic damage resulting from diabetes, myelofibrosis and similar fibrotic disorders, scleroderma, morphea, keloids, hypertrophic scarring, naevi, diabetic retinopathy, proliferative vitreoretinopathy and disorders of the connective tissue (for example sarcoidosis). The compounds according to the invention can likewise be used for promoting wound healing, for controlling postoperative scarring, for example resulting from glaucoma operations, and cosmetically for ageing and keratinized skin.

By virtue of their activity profile, the compounds according to the invention are particularly suitable for the treatment and/or prevention of cardiovascular and cardiopulmonary disorders such as primary and secondary forms of pulmonary hypertension, heart failure, angina pectoris and hypertension, and also for the treatment and/or prevention of thromboembolic disorders, ischaemias, vascular disorders, impaired microcirculation, renal insufficiency, fibrotic disorders and arteriosclerosis.

The present invention furthermore provides the use of the compounds according to the invention for the treatment and/or prevention of disorders, in particular the disorders mentioned above.

The present invention furthermore provides the use of the compounds according to the invention for preparing a medicament for the treatment and/or prevention of disorders, in particular the disorders mentioned above.

The present invention furthermore provides a medicament comprising at least one of the compounds according to the invention for the treatment and/or prevention of disorders, in particular the disorders mentioned above.

The present invention furthermore provides the use of the compounds according to the invention in a method for the treatment and/or prevention of disorders, in particular the disorders mentioned above.

The present invention furthermore provides a method for the treatment and/or prevention of disorders, in particular the disorders mentioned above, using an effective amount of at least one of the compounds according to the invention.

The compounds according to the invention can be used alone or in combination with other active compounds if necessary. The present invention further relates to medicaments containing at least one of the compounds according to the invention and one or more further active compounds, in particular for the treatment and/or prophylaxis of the aforementioned diseases. As suitable combination active compounds, we may mention for example and preferably:

organic nitrates and NO-donors, for example sodium nitroprusside, nitroglycerin, isosorbide mononitrate, isosorbide dinitrate, molsidomine or SIN-1, and inhalational NO;

compounds that inhibit the degradation of cyclic guanosine monophosphate (cGMP) and/or cyclic adenosine monophosphate (cAMP), for example inhibitors of phosphodiesterases (PDE) 1, 2, 3, 4 and/or 5, in particular PDE 4 inhibitors such as roflumilast or revamilast and PDE 5 inhibitors such as sildenafil, vardenafil, tadalafil, udenafil, dasantafil, avanafil, mirodenafil or lodenafil;

NO-independent but haem-dependent stimulators of guanylate cyclase, in particular riociguat and the compounds described in WO 00/06568, WO 00/06569, WO 02/42301, WO 03/095451, WO 2011/147809, WO 2012/004258, WO 2012/028647 and WO 2012/059549;

prostacyclin analogs and IP receptor agonists, for example and preferably iloprost, beraprost, treprostinil, epoprostenol or NS-304;

endothelin receptor antagonists, for example and preferably bosentan, darusentan, ambrisentan or sitaxsentan;

human neutrophile elastase (HNE) inhibitors, for example and preferably sivelestat or DX-890 (Reltran);

compounds which inhibit the signal transduction cascade, in particular from the group of the tyrosine kinase inhibitors, for example and preferably dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib, masitinib or tandutinib;

Rho kinase inhibitors, for example and preferably fasudil, Y-27632, SLx-2119, BF-66851, BF-66852, BF-66853, KI-23095 or BA-1049;

anti-obstructive agents as used, for example, for the therapy of chronic-obstructive pulmonary disease (COPD) or bronchial asthma, for example and preferably inhalatively or systemically administered beta-receptor mimetics (e.g. bedoradrine) or inhalatively administered anti-muscarinergic substances;

antiinflammatory and/or immunosuppressive agents as used, for example for the therapy of chronic-obstructive pulmonary disease (COPD), of bronchial asthma or pulmonary fibrosis, for example and preferably systemically or inhalatively administered corticosteroides, flutiform, pirfenidone, acetylcysteine, azathioprine or BIBF-1120;

chemotherapeutics as used, for example, for the therapy of neoplasias of the lung or other organs;

active compounds used for the systemic and/or inhalative treatment of pulmonary disorders, for example for cystic fibrosis (alpha-1-antitrypsin, aztreonam, ivacaftor, lumacaftor, ataluren, amikacin, levofloxacin), chronic obstructive pulmonary diseases (COPD) (LAS40464, PT003, SUN-101), acute respiratory distress syndrome (ARDS) and acute lung injury (ALI) (interferon-beta-1a, traumakines), obstructive sleep apnoe (VI-0521), bronchiectasis (mannitol, ciprofloxacin), Bronchiolitis obliterans (cyclosporine, aztreonam) and sepsis (pagibaximab, Voluven, ART-123);

active compounds used for treating muscular dystrophy, for example idebenone;

antithrombotic agents, for example and preferably from the group of platelet aggregation inhibitors, anticoagulants or profibrinolytic substances;

active compounds for lowering blood pressure, for example and preferably from the group of calcium antagonists, angiotensin AII antagonists, ACE inhibitors, endothelin antagonists, renin inhibitors, alpha-blockers, beta-blockers, mineralocorticoid receptor antagonists and diuretics; and/or active compounds that alter fat metabolism, for example and preferably from the group of thyroid receptor agonists, cholesterol synthesis inhibitors such as for example and preferably HMG-CoA-reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists.

Antithrombotic agents are preferably to be understood as compounds from the group of platelet aggregation inhibitors, anticoagulants or profibrinolytic substances.

In a preferred embodiment of the invention, the compounds according to the invention are administered in combination with a platelet aggregation inhibitor, for example and preferably aspirin, clopidogrel, ticlopidine or dipyridamole.

In a preferred embodiment of the invention, the compounds according to the invention are administered in combination with a thrombin inhibitor, for example and preferably ximelagatran, melagatran, dabigatran, bivalirudin or Clexane.

In a preferred embodiment of the invention, the compounds according to the invention are administered in combination with a GPIIb/IIIa antagonist, for example and preferably tirofiban or abciximab.

In a preferred embodiment of the invention, the compounds according to the invention are administered in combination with a factor Xa inhibitor, for example and preferably rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, for example and preferably coumarin.

The agents for lowering blood pressure are preferably to be understood as compounds from the group of calcium antagonists, angiotensin AII antagonists, ACE inhibitors, endothelin antagonists, renin inhibitors, alpha-blockers, beta-blockers, mineralocorticoid-receptor antagonists and diuretics.

In a preferred embodiment of the invention, the compounds according to the invention are administered in combination with a calcium antagonist, for example and preferably nifedipine, amlodipine, verapamil or diltiazem.

In a preferred embodiment of the invention, the compounds according to the invention are administered in combination with an alpha-1-receptor blocker, for example and preferably prazosin.

In a preferred embodiment of the invention, the compounds according to the invention are administered in combination with a beta-blocker, for example and preferably propranolol, atenolol, timolol, pindolol, alprenolol, oxprenolol, penbutolol, bupranolol, metipranolol, nadolol, mepindolol, carazolol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, for example and preferably losartan, candesartan, valsartan, telmisartan or embursatan.

In a preferred embodiment of the invention, the compounds according to the invention are administered in combination with an ACE inhibitor, for example and preferably enalapril, captopril, lisinopril, ramipril, delapril, fosinopril, quinopril, perindopril or trandopril.

In a preferred embodiment of the invention, the compounds according to the invention are administered in combination with an endothelin antagonist, for example and preferably bosentan, darusentan, ambrisentan or sitaxsentan.

In a preferred embodiment of the invention, the compounds according to the invention are administered in combination with a renin inhibitor, for example and preferably aliskiren, SPP-600 or SPP-800.

In a preferred embodiment of the invention, the compounds according to the invention are administered in combination with a mineralocorticoid-receptor antagonist, for example and preferably spironolactone or eplerenone.

In a preferred embodiment of the invention, the compounds according to the invention are administered in combination with a diuretic, for example and preferably furosemide, bumetanide, Torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Agents altering fat metabolism are preferably to be understood as compounds from the group of CETP inhibitors, thyroid receptor agonists, cholesterol synthesis inhibitors such as HMG-CoA-reductase or squalene synthesis inhibitors, the ACAT inhibitors, MTP inhibitors, PPAR-alpha, PPAR-gamma and/or PPAR-delta agonists, cholesterol-absorption inhibitors, polymeric bile acid adsorbers, bile acid reabsorption inhibitors, lipase inhibitors and the lipoprotein (a) antagonists.

In a preferred embodiment of the invention, the compounds according to the invention are administered in combination with a CETP inhibitor, for example and preferably torcetrapib, (CP-5294/4), JJT-705 or CETP-vaccine (Avant).

In a preferred embodiment of the invention, the compounds according to the invention are administered in combination with a thyroid receptor agonist, for example and preferably D-thyroxin, 3,5,3'-triiodothyronin (T3), CGS 23425 or axitirome (CGS 26214).

In a preferred embodiment of the invention, the compounds according to the invention are administered in combination with an HMG-CoA-reductase inhibitor from the class of statins, for example and preferably lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, for example and preferably BMS-188494 or TAK-475.

In a preferred embodiment of the invention, the compounds according to the invention are administered in combination with an ACAT inhibitor, for example and preferably avasimibe, melinamide, pactimibe, eflucimibe or SMP-797.

In a preferred embodiment of the invention, the compounds according to the invention are administered in combination with an MTP inhibitor, for example and preferably implitapide, BMS-201038, R-103757 or JIT-130.

In a preferred embodiment of the invention, the compounds according to the invention are administered in combination with a PPAR-gamma agonist, for example and preferably pioglitazone or rosiglitazone.

In a preferred embodiment of the invention, the compounds according to the invention are administered in combination with a PPAR-delta agonist, for example and preferably GW 501516 or BAY 68-5042.

In a preferred embodiment of the invention, the compounds according to the invention are administered in combination with a cholesterol-absorption inhibitor, for example and preferably ezetimibe, tiqueside or pamaqueside.

In a preferred embodiment of the invention, the compounds according to the invention are administered in combination with a lipase inhibitor, for example and preferably orlistat.

In a preferred embodiment of the invention, the compounds according to the invention are administered in combination with a polymeric bile acid adsorber, for example and preferably cholestyramine, colestipol, colesolvam, CholestaGel or colestimide.

In a preferred embodiment of the invention, the compounds according to the invention are administered in combination with a bile acid reabsorption inhibitor, for example and preferably ASBT (=IBAT) inhibitors, e.g. AZD-7806, S-8921, AK-105, BARI-1741, SC-435 or SC-635.

In a preferred embodiment of the invention, the compounds according to the invention are administered in combination with a lipoprotein(a) antagonist, for example and preferably gemcabene calcium (CI-1027) or nicotinic acid.

The present invention further relates to medicaments that contain at least one compound according to the invention, usually together with one or more inert, non-toxic, pharmaceutically suitable excipients, and use thereof for the aforementioned purposes.

The compounds according to the invention can have systemic and/or local action. For this purpose they can be applied in a suitable way, e.g. by oral, parenteral, intrapulmonary, nasal, sublingual, lingual, buccal, rectal, dermal, transdermal, conjunctival, or otic administration or as implant or stent.

For these routes of application, the compounds according to the invention can be administered in suitable dosage forms.

Dosage forms functioning according to the prior art, for rapid and/or modified release of the compounds according to the invention, which contain the compounds according to the invention in crystalline and/or amorphized and/or dissolved form, e.g. tablets (uncoated or coated tablets, for example with enteric coatings or coatings with delayed dissolution or insoluble coatings, which control the release of the compound according to the invention), tablets or films/wafers that disintegrate rapidly in the oral cavity, films/lyophilizates, capsules (for example hard or soft gelatin capsules), sugar-coated pills, granules, pellets, powders, emulsions, suspensions, aerosols or solutions, are suitable for oral administration.

Parenteral administration can take place with avoidance of an absorption step (e.g. intravenous, intraarterial, intracardiac, intraspinal or intralumbar) or with inclusion of an absorption (e.g intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates or sterile powders.

Suitable for the other routes of administration are, for example, pharmaceutical forms for inhalation (inter alia powder inhalers, nebulizers, aerosols), nasal drops, solutions, sprays; tablets for lingual, sublingual or buccal administration, films/wafers or capsules, suppositories, preparations for the ears and eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

Oral, intrapulmonary (inhalative) and intravenous administration are preferred.

The compounds according to the invention can be converted into the stated administration forms. This can take place in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and masking flavours and/or odours.

It has generally proved to be advantageous on parenteral administration to administer amounts of about 0.001 to 1 mg/kg, preferably about 0.01 to 0.5 mg/kg of body weight to achieve effective results. On oral administration, the dosage is about 0.01 to 100 mg/kg, preferably about 0.01 to 20 mg/kg, and very particularly preferably about 0.1 to 10 mg/kg of body weight. On intrapulmonary administration, the amount is generally about 0.1 to 50 mg per inhalation.

It may nevertheless be necessary where appropriate to deviate from the stated amounts, in particular as a function of body weight, administration route, individual response to the active compound, type of preparation and time or interval over which administration takes place. Thus, in some cases it may be sufficient to make do with less than the aforementioned minimum amount, whereas in other cases the upper limit mentioned must be exceeded. Where relatively large amounts are administered, it may be advisable to distribute these in a plurality of single doses over the day.

The following exemplary embodiments illustrate the invention. The invention is not restricted to the examples.

The percentage data in the following tests and examples are, unless indicated otherwise, percentages by weight; parts are parts by weight Solvent ratios, dilution ratios and concentration data of liquid/liquid solutions are based in each case on the volume.

A. EXAMPLES

Abbreviations and Acronyms abs. absolute
Ac acetyl
aq. aqueous, aqueous solution
Boc tert-butoxycarbonyl
Ex example
Bu butyl
c concentration
cat. catalytic
CI chemical ionization (in MS)
d day(s)
TLC thin-layer chromatography
DCI direct chemical ionization (in MS)
de diastereomeric excess
DMA N,N-dimethylacetamide
DMF N,N-dimethylformamide
DMSO dimethyl sulphoxide
ee enantiomeric excess
EI electron impact ionization (in MS)
ent enantiomerically pure, enantiomer
eq. equivalent(s)
ESI electrospray ionization (in MS)
Et ethyl
GC gas chromatography
sat. saturated
h hour(s)
HPLC high-pressure, high-performance liquid chromatography
iPr isopropyl
conc. concentrated
LC-MS liquid chromatography-coupled mass spectroscopy
Me methyl
min minute(s)
MS mass spectroscopy
NMR nuclear magnetic resonance spectroscopy
p para
Ph phenyl
Pr propyl
rac racemic, racemate
$R_f$ retention index (in TLC)
RP reverse phase (in HPLC)
RT room temperature
$R_t$ retention time (in HPLC or GC)
tBu tert-butyl
TFA trifluoroacetic acid
THP tetrahydrofuran
Ts toluenesulphonyl (tosyl)
UV ultraviolet spectroscopy
v/v ratio by volume (of a solution)

GC-MS and LC-MS Methods:

Method 1 (LC-MS):

Instrument: Waters Acquity SQD UPLC System; column: Waters Acquity UPLC HSS T3 1.8μ, 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; flow rate: 0.40 ml/min; oven: 50° C.; UV detection: 210-400 nm.

Method 2 (LC-MS):

Instrument: Micromass Quattro Premier with Waters UPLC Acquity; column: Thermo Hypersil GOLD 1.9μ, 50 mm×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A; flow rate: 0.3 ml/min; oven: 50° C.; UV detection: 210 nm.

Method 3 (LC-MS):

Instrument: Waters Acquity SQD UPLC System; column: Waters Acquity UPLC HSS T3 1.8μ, 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; flow rate: 0.40 ml/min; oven: 50° C.; UV detection: 208-400 nm.

Method 4 (LC-MS):

Instrument: Waters Acquity SQD UPLC System; column: Waters Acquity UPLC HSS T3 1.8μ, 30 mm×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; flow rate: 0.60 ml/min; oven: 50° C.; UV detection: 208-400 nm.

Method 5 (GC-MS):

Instrument: Thermo DFS, Trace GC Ultra; column: Restek RTX-35, 15 m×200 μm×0.33 μm; constant helium flow: 1.20 ml/min; oven: 60° C.; inlet: 220° C.; gradient: 60° C., 30° C./min→300° C. (maintained for 3.33 min).

Method 6 (LC-MS):

Instrument: Waters Acquity SQD UPLC System; column: Waters Acquity UPLC HSS T3 1.8μ, 50 mm×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5

Starting Materials and Intermediates:

Example 1A

3-Aminocyclohex-2-en-1-one

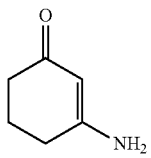

A solution of 250 g (2.2 mol) of cyclohexane-1,3-dione and 180.45 g (2.3 mol) of ammonium acetate in 1.3 liters of toluene was heated under reflux for 2 hours using a water separator with reflux condenser. The reaction was then concentrated to dryness. The residue was taken up in 1.3 liters of ethyl acetate and 100 ml of methanol and heated to 110° C. The solution was then filtered while hot and slowly cooled to room temperature. The solution was then stored overnight at about 4° C. in the fridge. The resulting crystalline precipitate was filtered off and dried under reduced pressure. This gave 66.59 g (0.60 mol) as a first batch of the target product. Under reduced pressure, the recovered filtrate was concentrated to a volume of about 800 ml, seeded with a little crystalline product and then stored at about 4° C. for 12 days. The resulting crystalline precipitate was filtered off and dried under reduced pressure. This gave a further 13.28 g (0.12 mol) of the target product. Under reduced pressure, the recovered filtrate was concentrated to dryness. The residue was dissolved in 100 ml of a mixture of ethyl acetate and methanol (10:1), applied to silica gel and purified chromatographically on silica gel (mobile phase: ethyl acetate/methanol 10:1). This gave a further 113.79 g (1.02 mol) of the desired product as a yellow solid. In this manner, a total of 193.66 g (1.74 mol, 78% of theory) of the target product were obtained.

$^1$H-NMR (400 MHz, DMSO-d$_6$, δ/ppm): 1.71-1.84 (m, 2H), 2.01 (t, 2H), 2.25 (t, 2H), 4.91 (s, 1H), 6.39-6.99 (br. s, 2H).

Example 2A 7,8-Dihydroquinoline-2,5(1H,6H)-dione

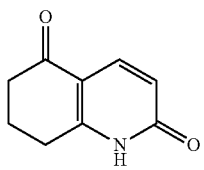 [SMILES: O=C1CCCc2[nH]c(=O)ccc21]

With stirring, 113.79 g (1.02 mol) of 3-aminocyclohex-2-en-1-one and 114.37 ml (1.19 mol) of methyl propionate were heated at 105° C. for 1 hour. The dark homogeneous solution formed was then slowly heated further to 170° C. After 20 min (temperature: 135° C.), a viscous material formed, and there was a marked evolution of gas. After a further 15 min (temperature: 160° C.), the reaction material became even more viscous while the evolution of gas subsided. After a total of 42 min, a temperature of 170° C. had been reached. After a further 13 min at this temperature, the reaction material was cooled to room temperature. 200 ml of dichloromethane were then added, the mixture was heated briefly and placed into an ultrasonic bath and the crystalline residue formed was filtered off. This procedure was repeated once more with a further 200 ml of dichloromethane. The crystalline residues obtained in this manner were combined, taken up in 1.6 liters of methanol and then heated with stirring until the solid had dissolved completely. This solution was then slowly cooled to room temperature and then stored in a fridge at about 4° C. for 2 days. The crystalline precipitate was filtered off and dried under reduced pressure. This gave 47.65 g (0.29 mol, 29% of theory) of the target product.

$^1$H-NMR (400 MHz, DMSO-d$_6$, δ/ppm): 1.90-2.07 (m, 2H), 2.42 (t, 2H), 2.78 (t, 2H), 6.23 (d, 1H), 7.76 (d, 1H), 12.06 (br. s, 1H).

Example 3A

2-Chloro-7,8-dihydroquinolin-5(6H)-one

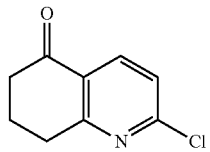 [SMILES: O=C1CCCc2nc(Cl)ccc21]

Under nitrogen, 21.02 g (0.13 mol) of 7,8-dihydroquinoline-2,5(1H,6H)-dione were suspended in 100 ml of acetonitrile (anhydrous, <30 ppm H$_2$O), and 135.28 ml (density 1.46 g/ml, 1.29 mol) of phosphorus oxychloride were added. The yellowish suspension was then heated to 75° C. and stirred at this temperature for 1.25 hours. The yellow clear solution was then cooled to room temperature, and 150 ml of toluene were added. The solution was then concentrated on a rotary evaporator to about 100 ml, and another 150 ml of toluene were added. The solution was then concentrated to dryness on a rotary evaporator. 300 ml of ethyl acetate were then added to the orange oil obtained. Subsequently, the solution was carefully (evolution of gas) added to 500 ml of saturated aqueous sodium bicarbonate solution and stirred for 15 min. The phases were separated and the aqueous phase was extracted with 200 ml of ethyl acetate. The combined organic phases were washed twice with 250 ml of water and once with 100 ml of saturated sodium chloride solution, dried over sodium sulphate, filtered and concentrated to dryness under reduced pressure. This gave 22.58 g (0.12 mmol, 96% of theory) of the target compound as a slightly yellowish solid.

$^1$H-NMR (400 MHz, DMSO-d$_6$, δ/ppm): 2.06-2.17 (m, 2H), 2.61-2.70 (m, 2H), 3.05 (t, 2H), 7.51 (d, 1H), 8.18 (d, 1H).

Example 4A

5-Oxo-5,6,7,8-tetrahydroquinoline-2-carbonitrile

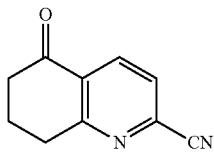 [SMILES: N#Cc1ccc2c(n1)CCCC2=O]

Under nitrogen, 42.25 g (0.23 mol) of 2-chloro-7,8-dihydroquinolin-5(6H)-one, 54.64 g (0.47 mol) of zinc cyanide and 13.44 g (0.01 mol) of tetrakis(triphenylphosphine)palladium were suspended in 200 ml of anhydrous N,N-dimethylacetamide (water content <0.01%, degassed with nitrogen beforehand), heated to 100° C. and stirred at this temperature for 2 hours. After complete conversion (monitored by TLC, mobile phase petroleum ether/ethyl acetate 2:1), the reaction mixture (grey suspension) was cooled to room temperature and filtered through Celite, and the filter cake was washed with 500 ml of ethyl acetate. 200 ml of saturated aqueous sodium chloride solution were then added to the resulting organic solution. A white precipitate was formed, which was filtered off and discarded. The organic phase was separated off, washed three times with in each case 200 ml of saturated sodium chloride solution, dried over sodium sulphate, filtered and concentrated to dryness. The residue obtained was applied to 20 g of silica gel and purified by column chromatography on silica gel (80 g cartridge; flow rate: 60 ml/min; mobile phase: petroleum ether/ethyl acetate 95:5→60:40 over 40 min, then isocratic petroleum ether/ethyl acetate 60:40 for 30 min). This gave 26.35 g (0.15 mmol, 66% of theory) of the target compound.

MS (EI): m/z=172 (M)+.

$^1$H-NMR (400 MHz, CDCl$_3$, δ/ppm): 2.19-2.30 (m, 2H), 2.70-2.79 (m, 2H), 3.20 (t, 2H), 7.67 (d, 1H), 8.39 (d, 1H).

Example 5A rac-5-{[2-(2-Methoxyphenyl)ethyl]amino}-5,6,7,8-tetrahydroquinoline-2-carbonitrile

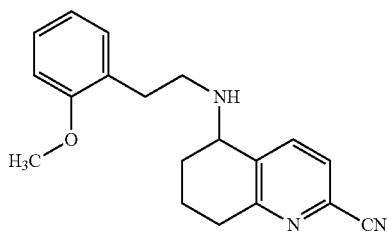 [SMILES: COc1ccccc1CCNC1CCCc2nc(C#N)ccc21]

41.10 g (0.24 mol) of 5-oxo-5,6,7,8-tetrahydroquinoline-2-carbonitrile were dissolved in 500 ml of toluene, and 35.51 ml (0.25 mol) of 2-(2-methoxyphenyl)ethylamine and 4.54 g (0.024 mol) of p-toluenesulphonic acid monohydrate were added. The reaction solution was then stirred under reflux for 5 hours (using a water separator). Subsequently, the reaction solution was evaporated to dryness and the residue was taken up in 500 ml of ethanol (anhydrous) and, with stirring, cooled to 0° C. A little at a time (careful: reaction mixture foams), 18.06 g (0.48 mol) of sodium borohydride were then added to the reaction solution, and the mixture was stirred overnight. Subsequently, the reaction mixture was concentrated on a rotary evaporator to about 100 ml, and 300 ml of water and 300 ml of ethyl acetate were added. The phases were separated and the aqueous phase was extracted twice with in each case 150 ml of ethyl acetate. The combined organic phases were washed twice with in each case 250 ml of saturated sodium chloride solution, dried over sodium sulphate, filtered and concentrated to a volume of about 150 ml on a rotary evaporator. The solution obtained in this manner was applied to 50 g of silica gel and purified by column chromatography on silica gel (80 g cartridge; flow rate: 75 ml/min; mobile phase: petroleum ether/ethyl acetate 85:15→50:50 over 45 min). This gave 39.03 g (0.10 mol, content 80%, 43% of theory) of the target compound.

$^1$H-NMR (400 MHz, CDCl$_3$, δ/ppm): 1.68-1.88 (m, 2H), 1.98-2.10 (m, 2H), 2.76-3.02 (m, 6H), 3.80 (s, 3H), 3.81-3.91 (m, 1H), 6.81-6.93 (m, 2H), 7.15 (dd, 1H), 7.24 (tt, 1H), 7.43 (d, 1H), 7.82 (d, 1H).

Example 6A rac-Ethyl 5-{(2-cyano-5,6,7,8-tetrahydroquinolin-5-yl)[2-(2-methoxyphenyl)ethyl]amino}-pentanoate

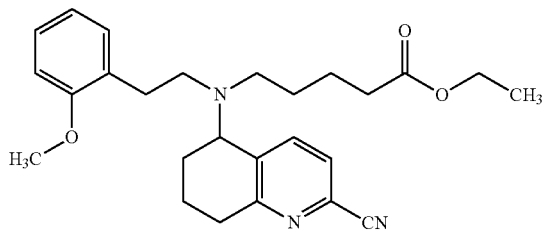 [SMILES: CCOC(=O)CCCCN(CCc1ccccc1OC)C1CCCc2nc(C#N)ccc21]

17.07 ml (0.11 mol) of ethyl 5-bromopentanoate, 8.43 g (0.05 mol) of potassium iodide and 22.61 g (0.21 mol) of anhydrous sodium carbonate were added to a solution of 31.22 g (0.10 mol) of 5-{[2-(2-methoxyphenyl)ethyl]amino}-5,6,7,8-tetrahydroquinoline-2-carbonitrile in 300 ml of dry acetonitrile, and the mixture was heated under reflux for 4 days. The reaction was then concentrated to a volume of about 50 ml on a rotary evaporator. The solution obtained was taken up in 250 ml of ethyl acetate and 400 ml of saturated aqueous sodium chloride solution, and the organic phase was then removed. The aqueous phase was extracted twice with in each case 150 ml of ethyl acetate. The combined organic phases were dried over sodium sulphate, filtered and concentrated to dryness. The residue obtained was applied to 25 g of silica gel and purified by column chromatography on silica gel (80 g cartridge; flow rate: 60 ml/min; mobile phase: petroleum ether/ethyl acetate 95:5→80:20 over 30 min). This gave 28.89 g (0.05 mol, content 80%, 52% of theory) of the target compound as an orange oil.

$^1$H-NMR (400 MHz, DMSO-d$_6$, δ/ppm): 1.11-1.19 (m, 1H), 1.16 (t, 3H), 1.33-1.60 (m, 5H), 1.61-1.79 (m, 1H), 1.93-2.09 (m, 3H), 2.23 (t, 2H), 2.39-2.55 (m, 1H, partially obscured by DMSO signal), 2.56-2.75 (m, 2H), 2.77-2.88 (m, 2H), 3.64 (s, 3H), 3.96-4.09 (m, 4H), 6.84 (t, 1H), 6.88 (d, 1H), 7.07 (d, 1H), 7.17 (t, 1H), 7.65 (d, 1H), 7.84 (d, 1H).

Example 7A rac-Ethyl 5-{(5-ethoxy-5-oxopentyl)[2-(2-hydroxyphenyl)ethyl]amino}-5,6,7,8-tetrahydroquinoline-2-carboxylate

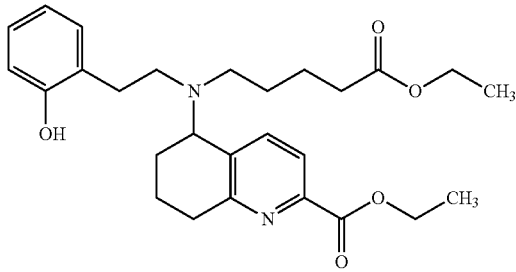 [SMILES: CCOC(=O)CCCCN(CCc1ccccc1O)C1CCCc2nc(C(=O)OCC)ccc21]

Under nitrogen, 23.23 g (0.05 mol) of ethyl 5-{(2-cyano-5,6,7,8-tetrahydroquinolin-5-yl)[2-(2-methoxyphenyl)ethyl]amino}pentanoate were taken up in 175 ml of hydrobromic acid (48% in water). The syrup-like solution was then heated to 120° C. and stirred at this temperature for 5 hours. The clear yellow reaction solution was then cooled to room temperature and concentrated to dryness. Subsequently, 350 ml of anhydrous ethanol and 25 ml of a 4 N solution of hydrogen chloride in dioxane were added to the residue obtained, and the mixture was stirred at 65° C. overnight. The reaction mixture was then concentrated on a rotary evaporator to about 50 ml, 550 ml of saturated aqueous sodium bicarbonate solution were carefully added and the mixture was extracted three times with in each case 150 ml of ethyl acetate. The combined organic phases were dried over sodium sulphate, filtered and concentrated to dryness. The residue obtained (brown oil) was dissolved in 100 ml of ethyl acetate, 65 g of silica gel were added and the mixture was once more concentrated to dryness. The residue was then purified by column chromatography on silica gel (metal column 58×8 cm, 1600 ml of silica gel; mobile phase: ethyl acetate/petroleum ether 1:5, after about 3 liters 1:4, after about 3.5 liters 1:3). This gave 9.43 g (0.02 mol, 38% of theory) of the target compound as a colourless oil.

MS (EI): m/z=468 (M)$^+$.

$^1$H-NMR (400 MHz, DMSO-d$_6$, δ/ppm): 1.12-1.19 (m, 1H), 1.15 (t, 3H), 1.31 (t, 3H), 1.35-1.61 (m, 5H), 1.61-1.79 (m, 1H), 1.93-2.09 (m, 3H), 2.22 (t, 2H), 2.40-2.62 (m, 2H, partially obscured by DMSO signal), 2.62-2.78 (m, 1H), 2.78-2.88 (m, 2H), 3.97-4.09 (m, 4H), 4.32 (q, 2H), 6.62-6.75 (m, 2H), 6.92-7.02 (m, 2H), 7.71 (d, 1H), 7.92 (d, 1H), 9.14 (s, 1H).

Example 8A rac-5-{[2-(2-Hydroxyphenyl)ethyl]amino}-5,6,7,8-tetrahydroquinoline-2-carboxylic acid

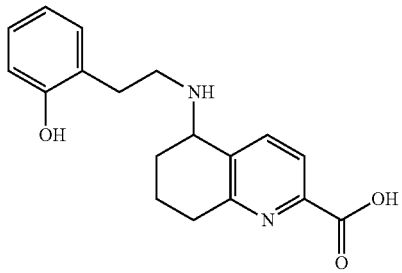 [SMILES: O=C(O)c1ccc2c(n1)CCCC2NCCc1ccccc1O]

14.6 g (47.5 mmol) of 5-{[2-(2-methoxyphenyl)ethyl]amino}-5,6,7,8-tetrahydroquinoline-2-carbonitrile were taken up in 100 ml of hydrobromic acid (48% in water) and stirred at boiling point for 5 hours. The reaction solution was then cooled to room temperature, diluted with water and adjusted to pH 6 with saturated sodium bicarbonate solution. The crystals formed were filtered off with suction, washed with water and air-dried. This gave 14.6 g (46.76 mmol, 98% of theory) of the target compound.

LC-MS (Method 2): R$_t$=1.08 min; m/z=313 (M+H)$^+$.

Example 9A rac-Ethyl 5-{[2-(2-hydroxyphenyl)ethyl]amino}-5,6,7,8-tetrahydroquinoline-2-carboxylate

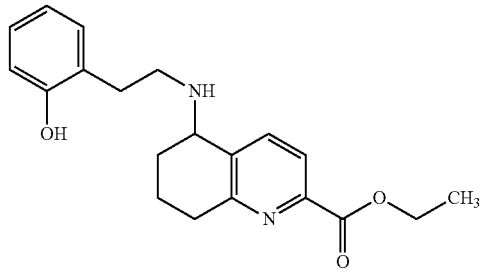 [SMILES: CCOC(=O)c1ccc2c(n1)CCCC2NCCc1ccccc1O]

645 ml of anhydrous ethanol and 52 ml of a 4 N solution of hydrogen chloride in dioxane were added to 25.8 g (82.59 mmol) of 5-{[2-(2-hydroxyphenyl)ethyl]amino}-5,6,7,8-tetrahydroquinoline-2-carboxylic acid, and the mixture was stirred under reflux overnight. The reaction solution was then cooled to room temperature, and first ethyl acetate and then, slowly, saturated aqueous sodium bicarbonate solution were added. Subsequently, the organic phase was separated off, dried over sodium sulphate, filtered and concentrated to dryness. This gave 23.9 g (70.21 mmol, 85% of theory) of the target compound.

LC-MS (Method 4): R$_t$=0.57 min; m/z=341 (M+H)$^+$.

$^1$H-NMR (400 MHz, CDCl$_3$, δ/ppm): 1.42 (t, 3H), 1.85-2.02 (m, 4H), 2.77-2.86 (m, 2H), 2.86-3.05 (m, 2H), 3.06-3.23 (m, 2H), 3.92-4.00 (m, 1H), 4.46 (q, 2H), 6.77 (t, 1H), 6.91 (d, 1H), 7.00 (d, 1H), 7.14 (t, 1H), 7.89 (d, 1H), 7.96 (d, 1H).

Example 10A rac-Ethyl 5-{(tert-butoxycarbonyl)[2-(2-hydroxyphenyl)ethyl]amino)}-5,6,7,8-tetrahydroquinoline-2-carboxylate

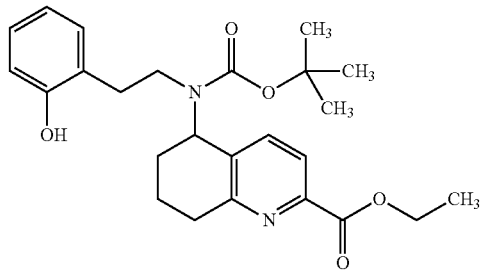 [SMILES: CCOC(=O)c1ccc2c(n1)CCCC2N(CCc1ccccc1O)C(=O)OC(C)(C)C]

23.85 g (70.06 mmol) of ethyl 5-{[2-(2-hydroxyphenyl)ethyl]amino}-5,6,7,8-tetrahydroquinoline-2-carboxylate were dissolved in 530 ml of dichloromethane and, with stirring, cooled to 0° C. A solution of 16.06 g (73.56 mmol) of di-tert-butyl dicarbonate in 30 ml of dichloromethane was then slowly added dropwise, and the reaction mixture was stirred at room temperature overnight. The reaction solution was then concentrated to dryness and the residue was triturated with ethanol. After filtration, the filter cake was washed repeatedly with ethanol and then air-dried. This gave 27.2 g (61.74 mmol, 88% of theory) of the target compound.

LC-MS (Method 4): $R_t$=1.19 min; m/z=441 (M+H)$^+$.

$^1$H-NMR (400 MHz, CDCl$_3$, δ/ppm): 1.01-1.24 (m, 4H), 1.24-1.37 (m, 3H), 1.39-1.58 (m, 5H), 1.65-1.90 (m, 1H), 1.90-2.12 (m, 3H), 2.64-3.00 (m, 5H), 3.14-3.55 (m, 1H, partially obscured by H$_2$O signal), 4.32 (q, 2H), 4.63-4.85 (m, 0.5H), 5.08-5.30 (m, 0.5H), 6.59-6.83 (m, 2H), 6.91-7.14 (m, 2H), 7.40-7.64 (m, 1H), 7.79-7.87 (m, 1H), 9.31 (s, 1H).

Example 11A 4-(Chloromethyl)-N-(2-hydroxy-5-methylphenyl)benzamide

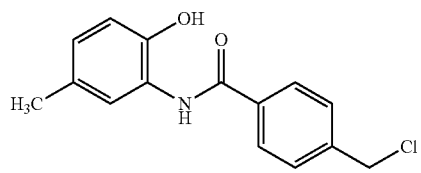 [SMILES: Cc1ccc(O)c(NC(=O)c2ccc(CCl)cc2)c1]

With stirring, 37.52 g (446.6 mmol) of sodium bicarbonate were added to 50 g (406 mmol) of 2-amino-4-methylphenol in 250 ml of 2-methoxyethanol. 84.4 g (446.6 mmol) of 4-chloromethylbenzoyl chloride, dissolved in 250 ml of 2-methoxyethanol, were then added dropwise to the solution over 15 min. During this time, an increase in reaction temperature of from room temperature to 40° C. was observed. After 4 hours of stirring, 1 liter of water and 10 ml of concentrated hydrochloric acid were added to the reaction mixture. The crystals formed were filtered off and dried under reduced pressure. This gave 116 g of the target compound which were reacted further without further purification.

LC-MS (Method 3): $R_t$=1.10 min; m/z=276 (M+H)$^+$.

Example 12A

2-[4-(Chloromethyl)phenyl]-5-methyl-1,3-benzoxazole

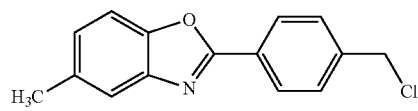 [SMILES: Cc1ccc2oc(-c3ccc(CCl)cc3)nc2c1]

With stirring, 5 g (26.3 mmol) of p-toluenesulphonic acid monohydrate were added to 116 g (about 406 mmol) of 4-(chloromethyl)-N-(2-hydroxy-5-methylphenyl)benzamide in 700 ml of 1,2-dichlorobenzene. The reaction solution was then heated to 175° C. (oil bath temperature) and stirred at this temperature on a water separator for 3 hours. The reaction solution was then cooled to room temperature, 200 ml of hexane were added and the mixture was stirred for about 1 hour. The precipitated solid was filtered off, washed with hexane and air-dried. This gave 56 g (217.29 mmol, 53% of theory) of the target compound.

LC-MS (Method 3): $R_t$=1.29 min; m/z=258 (M+H)$^+$.

$^1$H-NMR (400 MHz, CDCl$_3$, δ/ppm): 2.45 (s, 3H), 4.88 (s, 2H), 7.26 (dd, 1H), 7.61 (s, 1H), 7.67 (dd, 3H), 8.20 (d, 2H).

Example 13A

1-{4-[4-(Chloromethyl)phenyl]piperidin-1-yl}propan-1-one

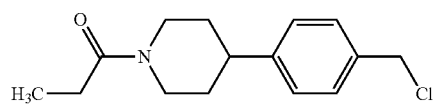

5 g (23 mmol) of 1-(4-phenylpiperidin-1-yl)propan-1-one, 4.84 g (161 mmol) of paraformaldehyde and 4.7 g (34.5 mmol) of zinc chloride were initially charged in 200 ml of dichloromethane. With vigorous stirring, hydrogen chloride gas was then passed through the reaction mixture for 30 min. After the introduction had ended, the reaction mixture was stirred at room temperature overnight. Water was then added to the reaction solution, the organic phase was separated off and the aqueous phase was extracted with ethyl acetate. The combined organic phases were dried over sodium sulphate, filtered and concentrated to dryness on a rotary evaporator. The residue obtained was purified by preparative HPLC. During concentration, some of the product hydrolyzed to the analogous 4-(hydroxymethyl) compound. The product mixture obtained (3.68 g) was then taken up with stirring in 100 ml of THF, and 500 mg of zinc chloride and then 2 ml of thionyl chloride were added. This mixture was then stirred at room temperature for 1 hour. After addition of water and ethyl acetate to the reaction solution, the organic phase was separated off, dried over sodium sulphate, filtered and concentrated to dryness. This gave 3.4 g (12.79 mmol, 56% of theory) of the target compound.

LC-MS (Method 2): $R_t$=2.18 min; m/z=266 (M+H)$^+$.

$^1$H-NMR (400 MHz, DMSO-d$_6$, δ/ppm): 1.00 (t, 3H), 1.36-1.61 (m, 2H), 1.69-1.84 (m, 2H), 2.35 (q, 2H), 2.52-2.63 (m, 1H, partially obscured by DMSO signal), 2.70-2.82 (m, 1H), 3.02-3.14 (m, 1H), 3.91-3.99 (m, 1H), 4.50-4.60 (m, 1H), 4.73 (s, 2H), 7.25 (d, 2H), 7.36 (d, 2H).

Example 14A 1-(Bromomethyl)-4-[trans-4-(trifluoromethyl)cyclohexyl]benzene

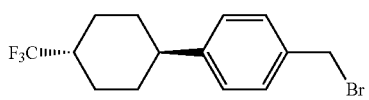 [SMILES: FC(F)(F)[C@H]1CC[C@H](c2ccc(CBr)cc2)CC1]

Under argon, 2 g (7.74 mmol) of (4-[trans-4-(trifluoromethyl)cyclohexyl]phenyl)methanol [for the preparation, see patent application WO 2009/032249-A1, Example 8/Steps C-E] were dissolved in 40 ml of THF, and 2.437 g (9.29 mmol) of triphenylphosphine and 3.081 g (9.29 mmol) of carbon tetrabromide were added in succession. The reaction mixture was stirred at room temperature overnight. Subsequently, first water and then ethyl acetate were added. The organic phase was separated off and then dried over magnesium sulphate, filtered and concentrated to dryness. The residue obtained was purified chromatographically on silica gel (mobile phase: cyclohexane/ethyl acetate 10:1). This gave 2.07 g (6.44 mmol, 83% of theory) of the target compound.

GC-MS (Method 5): $R_t$=6.14 min; m/z=422 (M+H)$^+$.

$^1$H-NMR (400 MHz, CDCl$_3$, δ/ppm): 1.32-1.59 (m, 4H), 1.68-1.78 (m, 1H), 1.81-1.91 (m, 2H), 1.91-2.01 (m, 2H), 2.27-2.42 (m, 1H), 4.68 (s, 2H), 7.22 (d, 2H), 7.37 (d, 2H).

Example 15A rac-Ethyl 5-{(5-ethoxy-5-oxopentyl)[2-(2-{[4-(2-phenylethyl)benzyl]oxy}phenyl)ethyl]amino}-5,6,7,8-tetrahydroquinoline-2-carboxylate

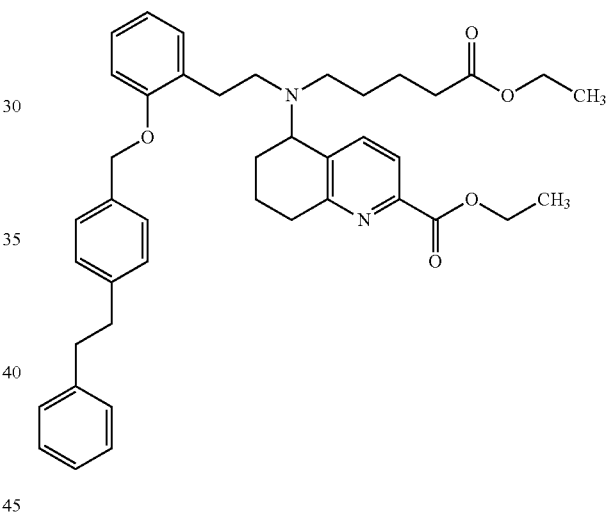

Under argon, 500 mg (1.07 mmol) of ethyl 5-{(5-ethoxy-5-oxopentyl)[2-(2-hydroxyphenyl)-ethyl]amino}-5,6,7,8-tetrahydroquinoline-2-carboxylate, 246 mg (1.07 mmol) of 1-(chloromethyl)-4-(2-phenylethyl)benzene and 295 mg (2.13 mmol) of potassium carbonate in 5 ml of DMF were heated to 80° C. and stirred at this temperature for 6 hours. After cooling, water and ethyl acetate were added to the reaction mixture and the phases were then separated. The organic phase was washed twice with water and once with saturated sodium chloride solution and then concentrated to dryness. This gave 760 mg (1.01 mmol, content 88%, 94% of theory) of the target compound.

LC-MS (Method 1): $R_t$=1.37 min; m/z=663 (M+H)$^+$.

Analogously to Example 15A, the following compounds were prepared from the starting materials stated for each case:

| Example | Name/Structure/Starting materials | Analytical data |
|---|---|---|
| 16A | rac-ethyl 5-[(5-ethoxy-5-oxopentyl){2-[2-({4-[2-(4-fluorophenyl)ethyl]benzyl}oxy)phenyl]ethyl}-amino]-5,6,7,8-tetrahydroquinoline-2-carboxylate 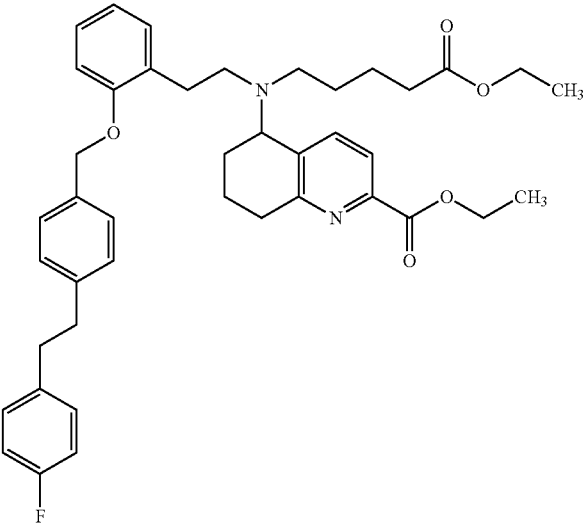 [SMILES: CCOC(=O)CCCCN(CCc1ccccc1OCc1ccc(CCc2ccc(F)cc2)cc1)C1CCCc2nc(C(=O)OCC)ccc21] from ethyl 5-{(5-ethoxy-5-oxopentyl)[2-(2-hydroxyphenyl)ethyl]amino}-5,6,7,8-tetrahydroquinoline-2-carboxylate and 1-(chloromethyl)-4-[2-(4-fluorophenyl)ethyl]benzene | LC-MS (Method 1): $R_t$ = 1.36 min; m/z = 681 $(M + H)^+$. |
| 17A | rac-ethyl 5-{(5-ethoxy-5-oxopentyl)[2-(2-{[4'-(trifluoromethyl)biphenyl-4-yl]methoxy}phenyl)ethyl]-amino}-5,6,7,8-tetrahydroquinoline-2-carboxylate 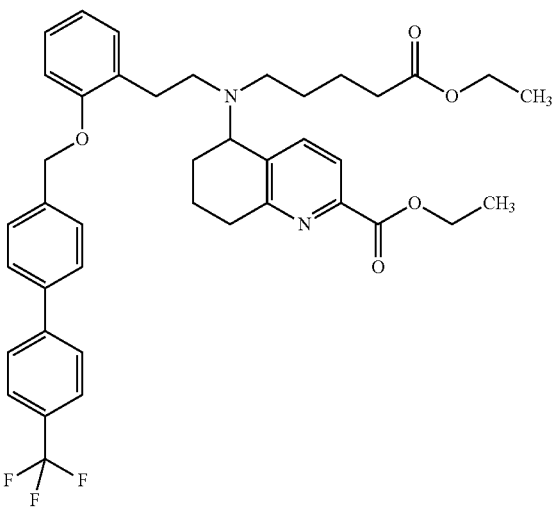 [SMILES: CCOC(=O)CCCCN(CCc1ccccc1OCc1ccc(-c2ccc(C(F)(F)F)cc2)cc1)C1CCCc2nc(C(=O)OCC)ccc21] from ethyl 5-{(5-ethoxy-5-oxopentyl)[2-(2-hydroxyphenyl)ethyl]amino}-5,6,7,8-tetrahydroquinoline-2-carboxylate and 4-(bromomethyl)-4'-(trifluoromethyl)biphenyl | LC-MS (Method 4): $R_t$ = 1.42 min; m/z = 703 $(M + H)^+$. |

Example 18A rac-Ethyl 5-{(tert-butoxycarbonyl)[2-(2-{[4-(5-methyl-1,3-benzoxazol-2-yl)benzyl]oxy}phenyl)-ethyl]amino}-5,6,7,8-tetrahydroquinoline-2-carboxylate

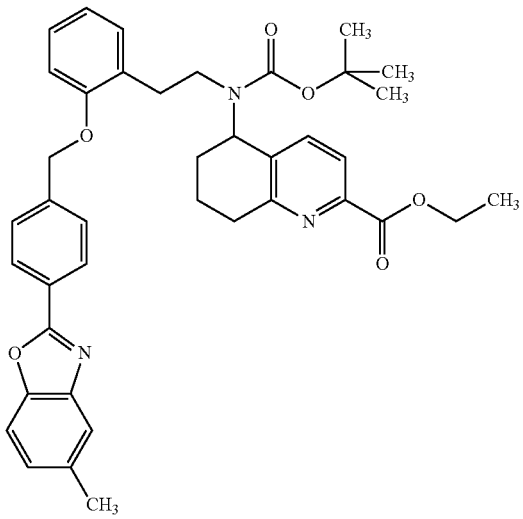

5 g (11.35 mmol) of ethyl 5-{(tert-butoxycarbonyl)[2-(2-hydroxyphenyl)ethyl]amino}-5,6,7,8-tetrahydroquinoline-2-carboxylate, 3.51 g (13.62 mmol) of 2-[4-(chloromethyl)phenyl]-5-methyl-1,3-benzoxazole and 3.92 g (28.37 mmol) of potassium carbonate in 50 ml of acetonitrile were heated to 110° C. and stirred at this temperature overnight. After cooling, the reaction mixture was filtered, the filter cake was washed repeatedly with acetonitrile and the combined filtrates were concentrated to dryness on a rotary evaporator. The residue obtained was purified chromatographically on silica gel (mobile phase: cyclohexane/ethyl acetate 4:1→2:1). This gave 6.59 g (9.96 mmol, 87% of theory) of the target compound.

LC-MS (Method 3): $R_t$=1.62 min; m/z=662 (M+H)$^+$.
$^1$H-NMR (400 MHz, CDCl$_3$, δ/ppm): 1.01-1.21 (m, 4H), 1.22-1.35 (m, 3H), 1.37-1.59 (m, 5.5H), 1.60-1.74 (m, 0.5H), 1.74-1.97 (m, 3H), 2.46 (s, 3H), 2.57-2.79 (m, 2H), 2.79-3.04 (m, 3H), 3.16-3.30 (m, 0.5H), 3.40-3.54 (m, 0.5H), 4.27 (q, 2H), 4.44-4.64 (m, 0.5H), 5.03-5.28 (m, 2.5H), 6.83-6.95 (m, 1H), 6.97-7.04 (m, 0.5H), 7.04-7.14 (m, 1H), 7.14-7.29 (m, 3H), 7.40-7.49 (m, 0.5H), 7.49-7.72 (m, 4H), 7.82 (d, 1H), 8.06 (d, 1H), 8.14 (d, 1H).

Analogously to Example 18A, the following compounds were prepared from the starting materials stated for each case:

| Example | Name/Structure/Starting materials | Analytical data |
|---|---|---|
| 19A | rac-ethyl 5-{(tert-butoxycarbonyl)[2-(2-{[4-(1-propionylpiperidin-4-yl)benzyl]oxy}phenyl)ethyl]-amino}-5,6,7,8-tetrahydroquinoline-2-carboxylate<br><br>from ethyl 5-{(tert-butoxycarbonyl)[2-(2-hydroxy-phenyl)ethyl]amino}-5,6,7,8-tetrahydroquinoline-2-carboxylate and 1-{4-[4-(chloromethyl)phenyl]-piperidin-1-yl}propan-1-one | LC-MS (Method 3): $R_t$ = 1.45 min; m/z = 670 (M + H)$^+$.<br><br>$^1$H-NMR (400 MHz, DMSO-d$_6$): δ [ppm] = 1.02 (t, 3H), 1.07-1.22 (m, 4H), 1.26-1.34 (m, 3H), 1.34-1.62 (m, 7H), 1.64-1.95 (m, 5H), 2.29-2.41 (m, 2H), 2.47-2.98 (m, 7H, partially obscured by DMSO signal), 3.00-3.14 (m, 1H), 3.14-3.33 (m, 1H, partially obscured by H$_2$O signal), 3.37-3.49 (m, 1H), 3.87-4.03 (m, 1H), 4.24-4.38 (m, 2H), 4.45-4.63 (m, 1H), 4.92-5.19 (m, 3H), 6.80-6.93 (m, 1H), 6.95-7.58 (m, 8H), 7.82 (d, 1H). |

-continued

| Example | Name/Structure/Starting materials | Analytical data |
|---------|-----------------------------------|-----------------|
| 20A | rac-ethyl 5-[(tert-butoxycarbonyl)(2-{2-[(4-tert-butylbenzyl)oxy]phenyl}ethyl)amino]-5,6,7,8-tetrahydroquinoline-2-carboxylate<br />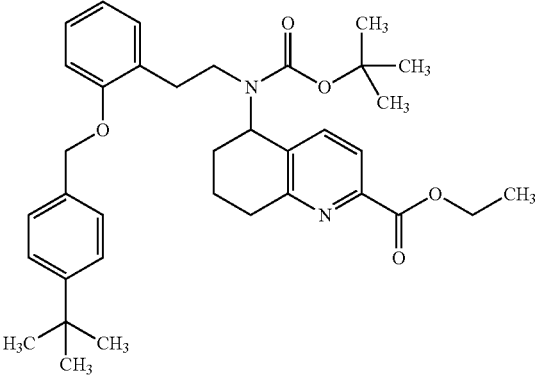 [SMILES: CCOC(=O)c1ccc2c(n1)CCCC2N(CCc1ccccc1OCc1ccc(C(C)(C)C)cc1)C(=O)OC(C)(C)C]<br />from ethyl 5-{(tert-butoxycarbonyl)[2-(2-hydroxyphenyl)ethyl]amino}-5,6,7,8-tetrahydroquinoline-2-carboxylate and 4-tert-butylbenzyl bromide | LC-MS (Method 4):<br />$R_t$ = 1.64 min; m/z = 587 $(M + H)^+$. |
| 21A | rac-ethyl 5-[(tert-butoxycarbonyl)(2-{2-[(4-cyclohexylbenzyl)oxy]phenyl}ethyl)amino]-5,6,7,8-tetrahydroquinoline-2-carboxylate<br />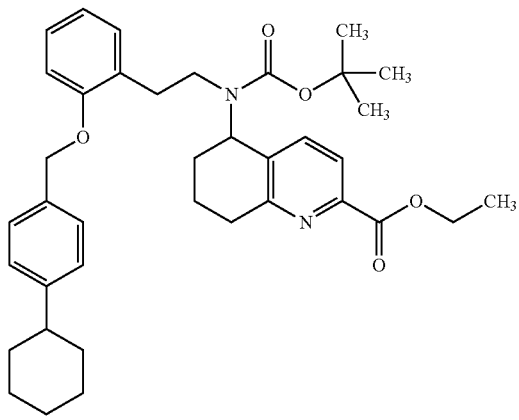 [SMILES: CCOC(=O)c1ccc2c(n1)CCCC2N(CCc1ccccc1OCc1ccc(C2CCCCC2)cc1)C(=O)OC(C)(C)C]<br />from ethyl 5-{(tert-butoxycarbonyl)[2-(2-hydroxyphenyl)ethyl]amino}-5,6,7,8-tetrahydroquinoline-2-carboxylate and 1-(chloromethyl)-4-cyclohexylbenzene | LC-MS (Method 3):<br />$R_t$ = 1.72 min; m/z = 613 $(M + H)^+$. |

Example 22A rac-Ethyl 5-{(tert-butoxycarbonyl)[2-(2-{[3-chloro-4'-(trifluoromethyl)biphenyl-4-yl]methoxy}-phenyl)ethyl]amino}-5,6,7,8-tetrahydroquinoline-2-carboxylate

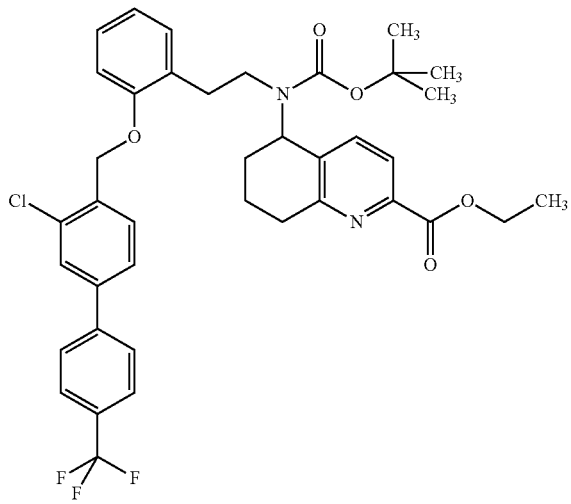 [SMILES: CCOC(=O)c1ccc2c(n1)CCCC2N(CCc1ccccc1OCc1ccc(-c2ccc(C(F)(F)F)cc2)cc1Cl)C(=O)OC(C)(C)C]

250 mg (0.57 mmol) of rac-ethyl 5-{(tert-butoxycarbonyl)[2-(2-hydroxyphenyl)ethyl]amino}-5,6,7,8-tetrahydroquinoline-2-carboxylate (Example 10A), 277 mg (0.68 mmol) of 4-(bromomethyl)-3-chloro-4'-(trifluoromethyl)biphenyl and 118 mg (0.85 mmol) of potassium carbonate in 10 ml of acetonitrile were heated to 110° C. and stirred at this temperature for 4 h. After cooling, the reaction mixture was filtered, the filter cake was washed repeatedly with acetonitrile and the combined filtrates were concentrated to dryness on a rotary evaporator. The residue obtained was purified chromatographically on silica gel (mobile phase: cyclohexane/ethyl acetate 10:1→4:1). The product obtained in this manner was re-purified by preparative HPLC (mobile phase: methanol/water 9:1). This gave 182 mg (0.26 mmol, 45% of theory) of the target compound.

LC-MS (Method 3): $R_t$=1.70 min; m/z=709/711 (M+H)$^+$.

Also analogously to Example 18A, the following compounds were prepared from the starting materials stated for each case:

| Example | Name/Structure/Starting materials | Analytical data |
|---|---|---|
| 23A | rac-ethyl 5-[(tert-butoxycarbonyl)(2-{2-[(5-phenylpentyl)oxy]phenyl}ethyl)amino]-5,6,7,8-tetrahydroquinoline-2-carboxylate | LC-MS (Method 3): $R_t$ = 1.64 min; m/z = 587 (M + H)$^+$. |

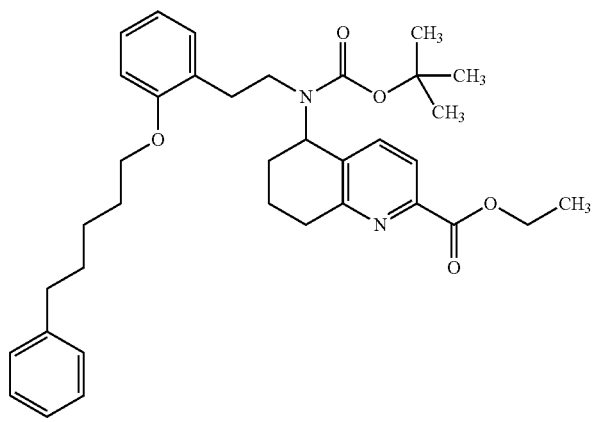 [SMILES: CCOC(=O)c1ccc2c(n1)CCCC2N(CCc1ccccc1OCCCCCc1ccccc1)C(=O)OC(C)(C)C]

from ethyl 5-{(tert-butoxycarbonyl)[2-(2-hydroxyphenyl)ethyl]amino}-5,6,7,8-tetrahydroquinoline-2-carboxylate and (5-bromopentyl)benzene

| Example | Name/Structure/Starting materials | Analytical data |
|---|---|---|
| 24A | rac-ethyl 5-[(tert-butoxycarbonyl){2-[2-({4-[trans-4-(trifluoromethyl)cyclohexyl]benzyl}oxy)phenyl]-ethyl}amino]-5,6,7,8-tetrahydroquinoline-2-carboxylate<br><br>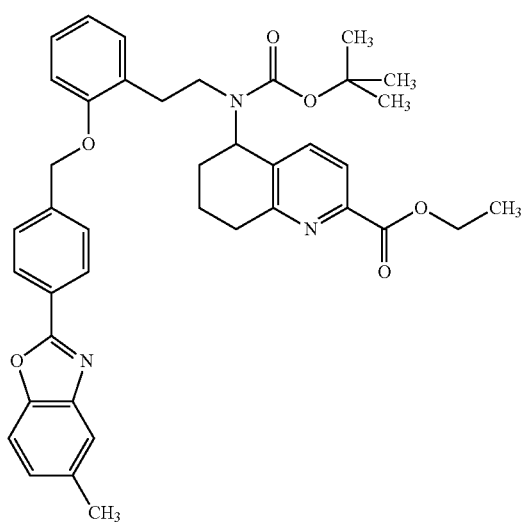<br><br>from ethyl 5-{(tert-butoxycarbonyl)[2-(2-hydroxyphenyl)ethyl]amino}-5,6,7,8-tetrahydroquinoline-2-carboxylate and 1-(bromomethyl)-4-[trans-4-(trifluoromethyl)cyclohexyl]benzene | LC-MS (Method 3):<br>$R_t$ = 1.66 min; m/z = 681 (M + H)$^+$. |

Example 25A and Example 26A

Ethyl 5-{(tert-butoxycarbonyl)[2-(2-{[4-(5-methyl-1,3-benzoxazol-2-yl)benzyl]oxy}phenyl)ethyl]-amino}-5,6,7,8-tetrahydroquinoline-2-carboxylate (Enantiomers 1 and 2)

6.59 g (9.96 mmol) of racemic ethyl 5-{(tert-butoxycarbonyl)[2-(2-{[4-(5-methyl-1,3-benzoxazol-2-yl)benzyl]oxy}phenyl)ethyl]amino}-5,6,7,8-tetrahydroquinoline-2-carboxylate (Example 18A) were separated into the enantiomers by supercritical fluid chromatography (SPC) on a chiral phase [column: Daicel Chiracel OD-H, 5 μm, 250 mm×20 mm; mobile phase: carbon dioxide/ethanol 75:25 (v/v); flow rate: 125 ml/min; pressure: 150 bar; UV detection: 210 nm; temperature: 38° C.]:

Example 25A (Enantiomer 1)

(+)-Ethyl 5-{(tert-butoxycarbonyl)[2-(2-{[4-(5-methyl-1,3-benzoxazol-2-yl)benzyl]oxy}phenyl)-ethyl]amino}-5,6,7,8-tetrahydroquinoline-2-carboxylate Yield: 2864 mg $R_t$=2.92 min; chemical purity >99%; >99.9% ee [column: Chiralpak OD-H, 5 μm, 250 mm×4.6 mm; mobile phase: carbon dioxide/ethanol 75:25 (v/v); flow rate: 4 ml/min; temperature: 34.3° C.; UV detection: 210 nm].

$[\alpha]_D^{20}$=+6.345°, c=0.415, methanol.

LC-MS (Method 3): $R_t$=1.62 min; m/z=662 (M+H)$^+$.

$^1$H-NMR (400 MHz, CDCl$_3$, δ/ppm): 1.01-1.21 (m, 4H), 1.22-1.35 (m, 3H), 1.37-1.59 (m, 5.5H), 1.60-1.74 (m, 0.5H), 1.74-1.97 (m, 3H), 2.46 (s, 3H), 2.57-2.79 (m, 2H), 2.79-3.04 (m, 3H), 3.16-3.30 (m, 0.5H), 3.40-3.54 (m, 0.5H), 4.27 (q, 2H), 4.44-4.64 (m, 0.5H), 5.03-5.28 (m, 2.5H), 6.83-6.95 (m, 1H), 6.97-7.04 (m, 0.5H), 7.04-7.14

(m, 1H), 7.14-7.29 (m, 3H), 7.40-7.49 (m, 0.5H), 7.49-7.72 (m, 4H), 7.82 (d, 1H), 8.06 (d, 1H), 8.14 (d, 1H).

Example 26A (Enantiomer 2)

(−)-Ethyl 5-{(tert-butoxycarbonyl)[2-(2-{[4-(5-methyl-1,3-benzoxazol-2-yl)benzyl]oxy}phenyl)-ethyl]amino}-5,6,7,8-tetrahydroquinoline-2-carboxylate Yield: 2359 mg
$R_t$=4.52 min; chemical purity >99%; >99.9% ee
[column: Chiralpak OD-H, 5 μm, 250 mm×4.6 mm; mobile phase: carbon dioxide/ethanol 75:25 (v/v); flow rate: 4 ml/min; temperature: 34.3° C.; UV detection: 210 nm].
$[\alpha]_D^{20}$=−6.082°, c=0.589, methanol.
LC-MS (Method 3): $R_t$=1.62 min; m/z=662 (M+H)$^+$.
$^1$H-NMR (400 MHz, CDCl$_3$, δ/ppm): 0.98-1.20 (m, 4H), 1.21-1.33 (m, 3H), 1.37-1.59 (m, 5.5H), 1.60-1.74 (m, 0.5H), 1.74-1.98 (m, 3H), 2.46 (s, 3H), 2.58-2.79 (m, 2H), 2.79-3.03 (m, 3H), 3.17-3.30 (m, 0.5H), 3.40-3.54 (m, 0.5H), 4.27 (q, 2H), 4.44-4.64 (m, 0.5H), 5.02-5.27 (m, 2.5H), 6.83-6.96 (m, 1H), 6.96-7.04 (m, 0.5H), 7.04-7.13 (m, 1H), 7.14-7.30 (m, 3H), 7.40-7.49 (m, 0.5H), 7.49-7.72 (m, 4H), 7.82 (d, 1H), 8.06 (d, 1H), 8.14 (d, 1H).

Example 27A

Ethyl 5-{[2-(2-{[4-(5-methyl-1,3-benzoxazol-2-yl)benzyl]oxy}phenyl)ethyl]amino}-5,6,7,8-tetrahydroquinoline-2-carboxylate dihydrochloride (Enantiomer 1)

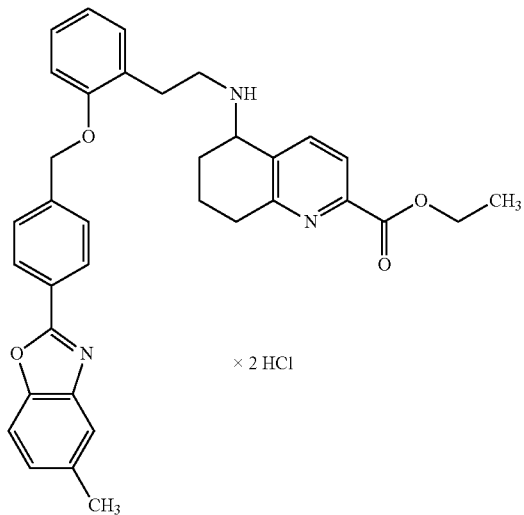 [SMILES: CCOC(=O)c1ccc2c(n1)CCCC2NCCc1ccccc1OCc1ccc(-c2nc3cc(C)ccc3o2)cc1]

5 ml of a 4 N solution of hydrogen chloride in dioxane were added to 581 mg (0.88 mmol) of (+)-ethyl 5-{(tert-butoxycarbonyl)[2-(2-{[4-(5-methyl-1,3-benzoxazol-2-yl)benzyl]oxy}phenyl)-ethyl]amino}-5,6,7,8-tetrahydroquinoline-2-carboxylate (Example 25A), and the mixture was stirred at room temperature for 4 h. The reaction solution was then concentrated to dryness and the residue was dried under high vacuum overnight. This gave 564 mg (0.88 mmol, 100% of theory) of the target product as a beige solid.
LC-MS (Method 3): $R_t$=0.96 min; m/z=562 (M+H)$^+$.
$^1$H-NMR (400 MHz, DMSO-d$_6$, δ/ppm): 1.28 (t, 3H), 1.76-1.89 (m, 1H), 1.97-2.10 (m, 2H), 2.10-2.19 (m, 1H), 2.80-2.92 (m, 1H), 2.92-3.03 (m, 1H), 3.05-3.14 (m, 2H), 3.14-3.72 (m, 2H), 3.54-3.61 (m, 1H), 3.57 (s, 3H), 4.29 (q, 2H), 4.62-4.71 (m, 1H), 5.26 (s, 2H), 6.96 (t, 1H), 7.12 (d, 1H), 7.22-7.32 (m, 3H), 7.62 (s, 1H), 7.65 (m, 3H), 7.84 (d, 1H), 8.20 (d, 3H), 9.29-9.46 (br. s, 2H).

Example 28A

Ethyl 5-{[2-(2-{[4-(5-methyl-1,3-benzoxazol-2-yl)benzyl]oxy}phenyl)ethyl]amino}-5,6,7,8-tetrahydroquinoline-2-carboxylate dihydrochloride (Enantiomer 2)

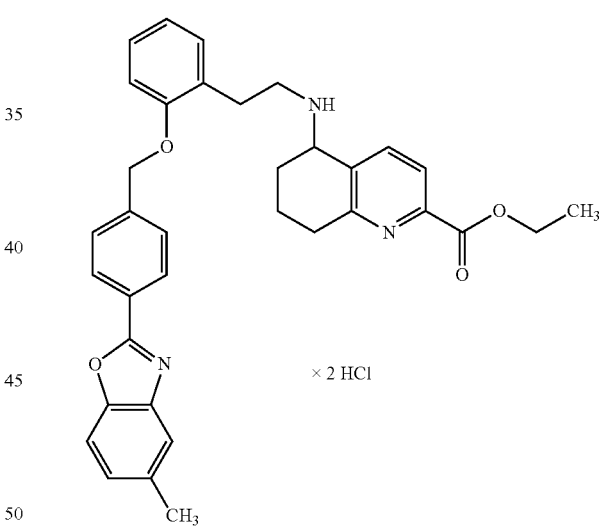

6.1 ml of a 4 N solution of hydrogen chloride in dioxane were added to 620 mg (0.94 mmol) of (−)-ethyl 5-{(tert-butoxycarbonyl)[2-(2-{[4-(5-methyl-1,3-benzoxazol-2-yl)benzyl]oxy}phenyl)-ethyl]amino}-5,6,7,8-tetrahydroquinoline-2-carboxylate (Example 26A), and the mixture was stirred at room temperature for 4 h. The reaction solution was then concentrated to dryness and the residue was dried under high vacuum overnight. This gave 604 mg (about 0.95 mmol, about 100% of theory) of the target product as a beige solid.
LC-MS (Method 3): $R_t$=1.05 min; m/z=562 (M+H)$^+$.
Analogously to Examples 27A and 28A, the following compounds were prepared:

| Example | Name/Structure/Starting material | Analytical data |
|---|---|---|
| 29A | rac-ethyl 5-{[2-(2-{[4-(1-propionylpiperidin-4-yl)-benzyl]oxy}phenyl)ethyl]amino}-5,6,7,8-tetra-hydroquinoline-2-carboxylate dihydrochloride<br>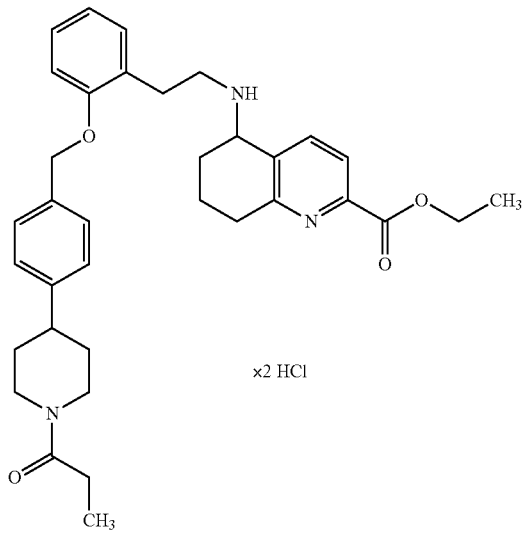 [SMILES: CCOC(=O)c1ccc2c(n1)CCCC2NCCc1ccccc1OCc1ccc(C2CCN(C(=O)CC)CC2)cc1]<br>from ethyl 5-{(tert-butoxycarbonyl)[2-(2-{[4-(1-propionylpiperidin-4-yl)benzyl]oxy}phenyl)ethyl]-amino}-5,6,7,8-tetrahydroquinoline-2-carboxylate | LC-MS (Method 3):<br>$R_t$ = 0.89 min; m/z = 570<br>$(M + H)^+$. |
| 30A | rac-ethyl 5-[(2-{2-[(4-tert-butylbenzyl)oxy]phenyl}-ethyl)amino]-5,6,7,8-tetrahydroquinoline-2-carboxylate dihydrochloride<br>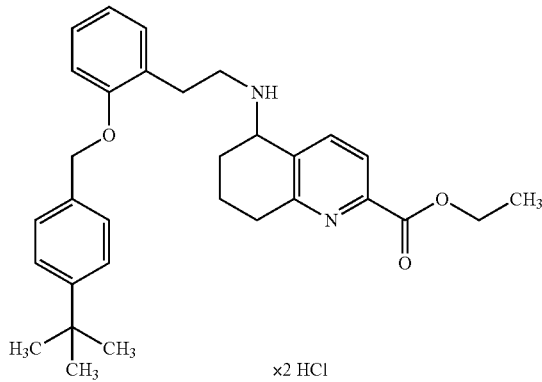 [SMILES: CCOC(=O)c1ccc2c(n1)CCCC2NCCc1ccccc1OCc1ccc(C(C)(C)C)cc1]<br>from ethyl 5-[(tert-butoxycarbonyl)(2-{2-[(4-tert-butylbenzyl)oxy]phenyl}ethyl)amino]-5,6,7,8-tetrahydroquinoline-2-carboxylate | LC-MS (Method 1):<br>$R_t$ = 0.98 min; m/z = 487<br>$(M + H)^+$. |

-continued

| Example | Name/Structure/Starting material | Analytical data |
|---|---|---|
| 31A | rac-ethyl 5-[(2-{2-[(4-cyclohexylbenzyl)oxy]-phenyl}ethyl)amino]-5,6,7,8-tetrahydroquinoline-2-carboxylate dihydrochloride<br />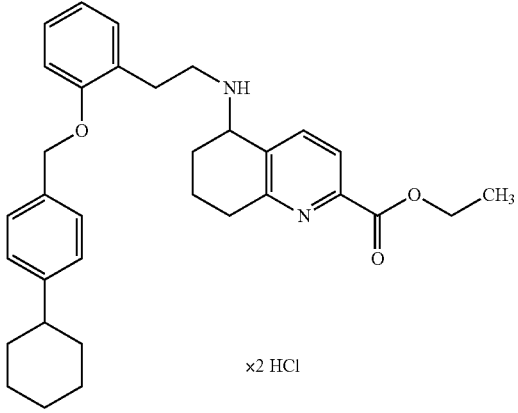 [SMILES: CCOC(=O)c1ccc2c(n1)CCCC2NCCc1ccccc1OCc1ccc(C2CCCCC2)cc1]<br />x2 HCl<br />from ethyl 5-[(tert-butoxycarbonyl)(2-{2-[(4-cyclohexylbenzyl)oxy]phenyl}ethyl)amino]-5,6,7,8-tetrahydroquinoline-2-carboxylate | LC-MS (Method 3):<br />$R_t$ = 1.03 min; m/z = 513<br />$(M + H)^+$. |
| 32A | rac-ethyl 5-{[2-(2-{[3-chloro-4'-(trifluoromethyl)-biphenyl-4-yl]methoxy}phenyl)ethyl]amino}-5,6,7,8-tetrahydroquinoline-2-carboxylate dihydrochloride<br />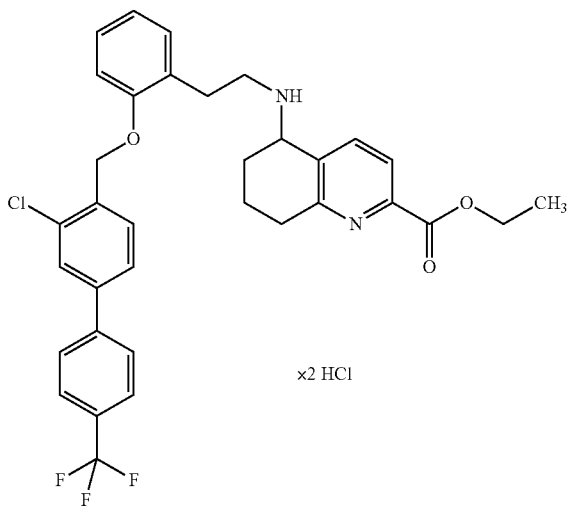 [SMILES: CCOC(=O)c1ccc2c(n1)CCCC2NCCc1ccccc1OCc1ccc(-c2ccc(C(F)(F)F)cc2)cc1Cl]<br />x2 HCl<br />from ethyl 5-{(tert-butoxycarbonyl)[2-(2-{[3-chloro-4'-(trifluoromethyl)biphenyl-4-yl]methoxy}-phenyl)ethyl]amino}-5,6,7,8-tetrahydroquinoline-2-carboxylate | LC-MS (Method 3):<br />$R_t$ = 1.05 min; m/z = 609<br />$(M + H)^+$. |

| Example | Name/Structure/Starting material | Analytical data |
|---|---|---|
| 33A | rac-ethyl 5-[(2-{2-[(5-phenylpentyl)oxy]phenyl}-ethyl)amino]-5,6,7,8-tetrahydroquinoline-2-carboxylate dihydrochloride<br>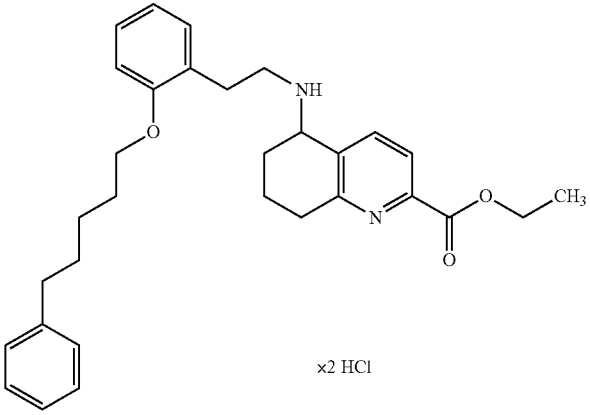 [SMILES: CCOC(=O)c1ccc2c(n1)CCCC2NCCc1ccccc1OCCCCCc1ccccc1]<br>from ethyl 5-[(tert-butoxycarbonyl)(2-{2-[(5-phenylpentyl)oxy]phenyl}ethyl)amino]-5,6,7,8-tetrahydroquinoline-2-carboxylate | LC-MS (Method 3):<br>$R_t$ = 0.97 min; m/z = 487 $(M + H)^+$. |
| 34A | rac-ethyl 5-({2-[2-({4-[trans-4-(trifluoromethyl)-cyclohexyl]benzyl}oxy)phenyl]ethyl}amino)-5,6,7,8-tetrahydroquinoline-2-carboxylate dihydrochloride<br>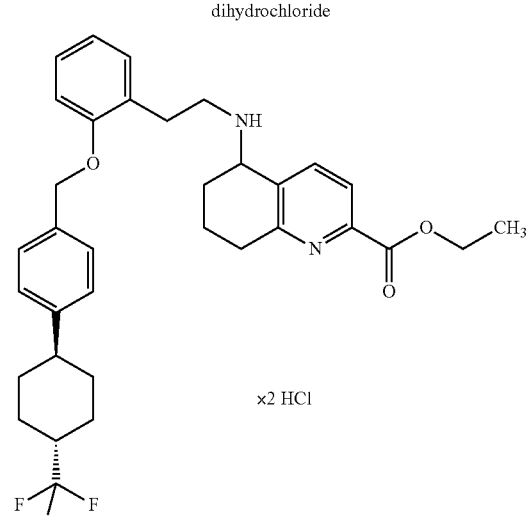<br>from ethyl 5-[(tert-butoxycarbonyl){2-[2-({4-[trans-4-(trifluoromethyl)cyclohexyl]benzyl}oxy)phenyl]-ethyl}amino]-5,6,7,8-tetrahydroquinoline-2-carboxylate | The title compound was reacted further without further characterization. |

Example 35A (−)-Ethyl 5-{(5-ethoxy-5-oxopentyl)[2-(2-{[4-(5-methyl-1,3-benzoxazol-2-yl)benzyl]oxy}phenyl)-ethyl]amino}-5,6,7,8-tetrahydroquinoline-2-carboxylate (Enantiomer 1)

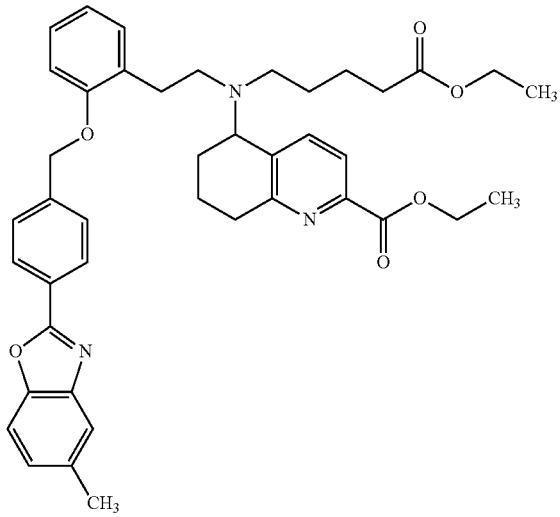 [SMILES: CCOC(=O)CCCCN(CCc1ccccc1OCc1ccc(-c2nc3cc(C)ccc3o2)cc1)C1CCCc2nc(C(=O)OCC)ccc21]

0.27 ml (1.70 mmol) of ethyl 5-bromopentanoate, 14 mg (0.09 mmol) of potassium iodide and 372 mg (2.57 mmol) of anhydrous sodium carbonate were added to a solution of 543 mg (0.86 mmol) of ethyl 5-{[2-(2-{[4-(5-methyl-1,3-benzoxazol-2-yl)benzyl]oxy}phenyl)ethyl]amino}-5,6,7,8-tetrahydroquinoline-2-carboxylate dihydrochloride (Enantiomer 1, Example 27A) in 10 ml of dry acetonitrile, and the mixture was heated under reflux overnight. A further 0.2 ml of ethyl 5-bromopentanoate was then added, and the mixture was stirred under reflux for 8 hours. Another 0.2 ml of ethyl 5-bromopentanoate and about 14 mg of potassium iodide were then added, and the mixture was once more heated under reflux overnight. After addition of a further 0.2 ml of ethyl 5-bromopentanoate, the mixture was stirred under reflux for another 8 hours. Finally, another about 14 mg of potassium iodide were added and the mixture was heated further under reflux overnight. The reaction was then filtered, the filter cake was washed with acetonitrile and the filtrate was concentrated to dryness. The residue obtained was purified chromatographically on silica gel (mobile phase: cyclohexane/ethyl acetate 3:1). This gave 396 mg (0.57 mmol, 67% of theory) of the title compound as a colourless oil.

LC-MS (Method 3): $R_t$=1.36 min; m/z=690 (M+H)$^+$.

$^1$H-NMR (400 MHz, DMSO-d$_6$, δ/ppm): 1.10 (t, 3H), 1.26 (t, 3H), 1.30-1.70 (m, 7H), 1.89-2.04 (m, 2H), 2.09-2.20 (m, 2H), 2.35-2.64 (m, 3H, partially obscured by DMSO signal), 2.45 (s, 3H), 2.65-2.86 (m, 4H), 3.92-4.02 (m, 3H), 4.26 (q, 2H), 5.04-5.15 (m, 2H), 6.87 (t, 1H), 6.99 (d, 1H), 7.09-7.21 (m, 2H), 7.25 (d, 1H), 7.52 (d, 2H), 7.61 (s, 1H), 7.63-7.68 (m, 2H), 7.87 (d, 1H), 8.15 (d, 2H).

$[α]_D^{20}$=−52.70°, c=0.420, methanol.

Example 36A (+)-Ethyl 5-{(5-ethoxy-5-oxopentyl)[2-(2-{[4-(5-methyl-1,3-benzoxazol-2-yl)benzyl]oxy}phenyl)-ethyl]amino}-5,6,7,8-tetrahydroquinoline-2-carboxylate (Enantiomer 2)

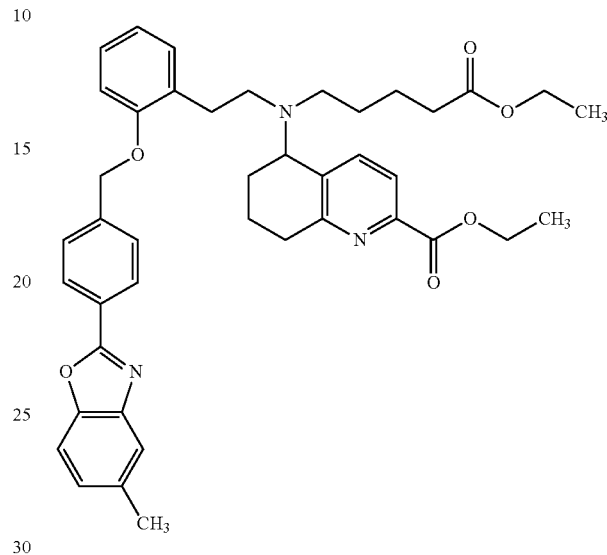

0.28 ml (1.78 mmol) of ethyl 5-bromopentanoate, 15 mg (0.09 mmol) of potassium iodide and 283 mg (2.67 mmol) of anhydrous sodium carbonate were added to a solution of 564 mg (0.89 mmol) of ethyl 5-{[2-(2-{[4-(5-methyl-1,3-benzoxazol-2-yl)benzyl]oxy}phenyl)ethyl]amino}-5,6,7,8-tetrahydroquinoline-2-carboxylate dihydrochloride (Enantiomer 2, Example 28A) in 10 ml of dry acetonitrile, and the mixture was heated under reflux overnight. A further 0.2 ml of ethyl 5-bromopentanoate was then added, and the mixture was stirred under reflux for another 8 hours. Another 0.2 ml of ethyl 5-bromopentanoate and about 14 mg of potassium iodide were then added, and the mixture was once more heated under reflux overnight. After addition of a further 0.2 ml of ethyl 5-bromopentanoate, the mixture was stirred under reflux for another 8 hours. Finally, another about 14 mg of potassium iodide were added and the mixture was heated further under reflux overnight. The reaction was then filtered, the filter cake was washed with acetonitrile and the filtrate was concentrated to dryness. The residue obtained was purified chromatographically on silica gel (mobile phase: cyclohexane/ethyl acetate 3:1). This gave 320 mg (0.46 mmol, 52% of theory) of the title compound as a colourless oil.

LC-MS (Method 3): $R_t$=1.37 min; m/z=690 (M+H)$^+$.

$^1$H-NMR (400 MHz, DMSO-d$_6$, δ/ppm): 1.10 (t, 3H), 1.26 (t, 3H), 1.30-1.70 (m, 7H), 1.89-2.04 (m, 2H), 2.10-2.19 (m, 2H), 2.38-2.64 (m, 3H, partially obscured by DMSO signal), 2.45 (s, 3H), 2.65-2.87 (m, 4H), 3.91-4.03 (m, 3H), 4.26 (q, 2H), 5.04-5.15 (m, 2H), 6.87 (t, 1H), 6.99 (d, 1H), 7.09-7.21 (m, 2H), 7.25 (d, 1H), 7.52 (d, 2H), 7.61 (s, 1H), 7.66 (dd, 2H), 7.87 (d, 1H), 8.15 (d, 2H).

$[α]_D^{20}$=+54.950, c=0.330, methanol.

Analogously to Examples 35A and 36A, the following compounds were prepared:

| Example | Name/Structure/Starting materials | Analytical data |
|---------|-----------------------------------|-----------------|
| 37A | rac-ethyl 5-{(5-ethoxy-5-oxopentyl)[2-(2-{[4-(1-propionylpiperidin-4-yl)benzyl]oxy}phenyl)ethyl]-amino}-5,6,7,8-tetrahydroquinoline-2-carboxylate 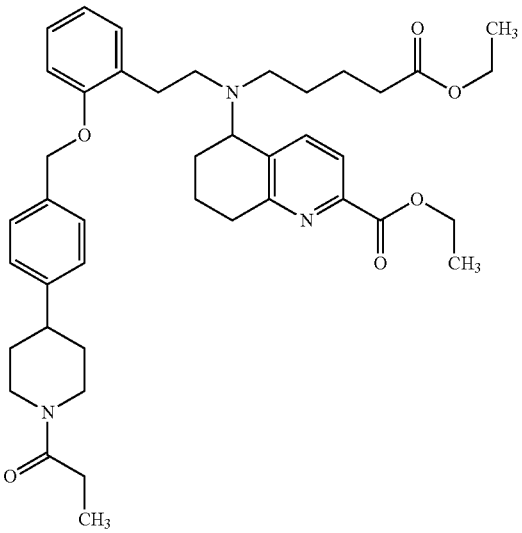 [SMILES: CCOC(=O)CCCCN(CCc1ccccc1OCc1ccc(C2CCN(C(=O)CC)CC2)cc1)C1CCCc2nc(C(=O)OCC)ccc21] from ethyl 5-{[2-(2-{[4-(1-propionylpiperidin-4-yl)-benzyl]oxy}phenyl)ethyl]amino}-5,6,7,8-tetrahydro-quinoline-2-carboxylate dihydrochloride and ethyl 5-bromopentanoate | LC-MS (Method 3): $R_t$ = 1.11 min; m/z = 698 (M + H)⁺. |
| 38A | rac-ethyl 5-[(2-{2-[(4-tert-butylbenzyl)oxy]phenyl}-ethyl)(5-ethoxy-5-oxopentyl)amino]-5,6,7,8-tetra-hydroquinoline-2-carboxylate 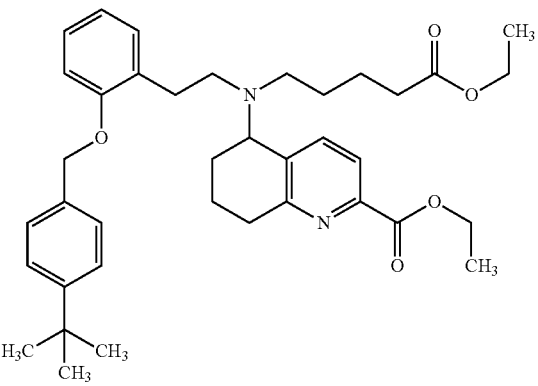 [SMILES: CCOC(=O)CCCCN(CCc1ccccc1OCc1ccc(C(C)(C)C)cc1)C1CCCc2nc(C(=O)OCC)ccc21] from ethyl 5-[(2-{2-[(4-tert-butylbenzyl)oxy]-phenyl}ethyl)amino]-5,6,7,8-tetrahydroquinoline-2-carboxylate dihydrochloride and ethyl 5-bromo-pentanoate | LC-MS (Method 4): $R_t$ = 1.40 min; m/z = 615 (M + H)⁺. |

-continued

| Example | Name/Structure/Starting materials | Analytical data |
|---------|-----------------------------------|-----------------|
| 39A | rac-ethyl 5-[(2-{2-[(4-cyclohexylbenzyl)oxy]-phenyl}ethyl)(5-ethoxy-5-oxopentyl)amino]-5,6,7,8-tetrahydroquinoline-2-carboxylate<br>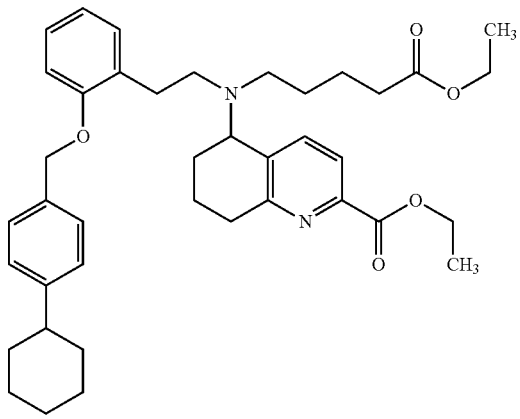 [SMILES: CCOC(=O)CCCCN(CCc1ccccc1OCc1ccc(C2CCCCC2)cc1)C1CCCc2nc(C(=O)OCC)ccc21]<br>from ethyl 5-[(2-{2-[(4-cyclohexylbenzyl)oxy]-phenyl}ethyl)amino]-5,6,7,8-tetrahydroquinoline-2-carboxylate dihydrochloride and ethyl 5-bromo-pentanoate | LC-MS (Method 3):<br>$R_t$ = 1.49 min; m/z = 641<br>$(M + H)^+$. |
| 40A | rac-ethyl 5-{[2-(2-{[3-chloro-4'-(trifluoromethyl)-biphenyl-4-yl]methoxy}phenyl)ethyl](5-ethoxy-5-oxopentyl)amino}-5,6,7,8-tetrahydroquinoline-2-carboxylate<br>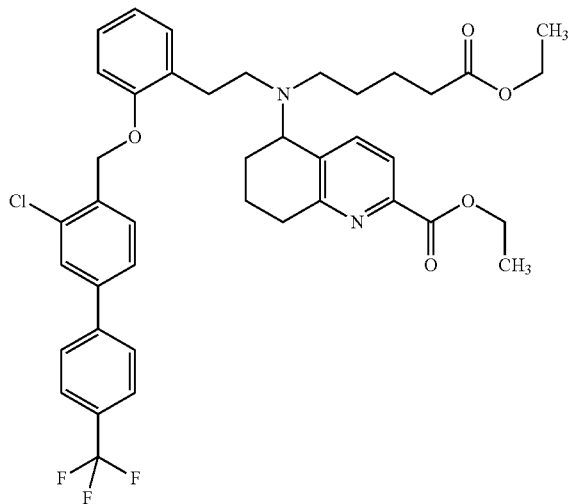 [SMILES: CCOC(=O)CCCCN(CCc1ccccc1OCc1ccc(-c2ccc(C(F)(F)F)cc2)cc1Cl)C1CCCc2nc(C(=O)OCC)ccc21]<br>from ethyl 5-{[2-(2-{[3-chloro-4'-(trifluoromethyl)-biphenyl-4-yl]methoxy}phenyl)ethyl]amino}-5,6,7,8-tetrahydroquinoline-2-carboxylate dihydrochloride and ethyl 5-bromopentanoate | LC-MS (Method 3):<br>$R_t$ = 1.49 min; m/z = 737<br>$(M + H)^+$. |

| Example | Name/Structure/Starting materials | Analytical data |
|---|---|---|
| 41A | rac-ethyl 5-[(5-ethoxy-5-oxopentyl)(2-{2-[(5-phenylpentyl)oxy]phenyl}ethyl)amino]-5,6,7,8-tetrahydroquinoline-2-carboxylate<br>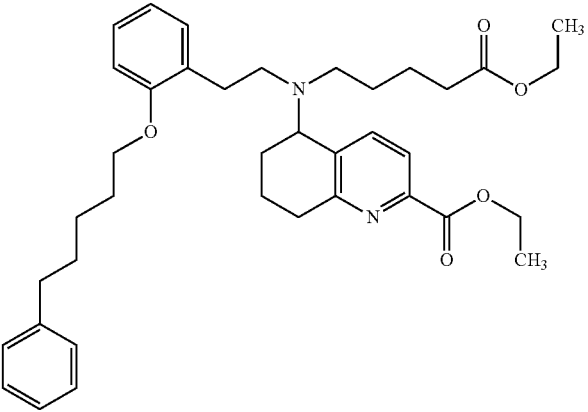 [SMILES: CCOC(=O)CCCCN(CCc1ccccc1OCCCCCc1ccccc1)C1CCCc2nc(C(=O)OCC)ccc21]<br>from ethyl 5-[(2-{2-[(5-phenylpentyl)oxy]phenyl}-ethyl)amino]-5,6,7,8-tetrahydroquinoline-2-carboxylate dihydrochloride and ethyl 5-bromo-pentanoate | LC-MS (Method 3):<br>$R_t$ = 1.35 min; m/z = 615 $(M + H)^+$. |
| 42A | rac-ethyl 5-[(5-ethoxy-5-oxopentyl){2-[2-({4-[trans-4-(trifluoromethyl)cyclohexyl]benzyl}oxy)-phenyl]ethyl}amino]-5,6,7,8-tetrahydroquinoline-2-carboxylate<br>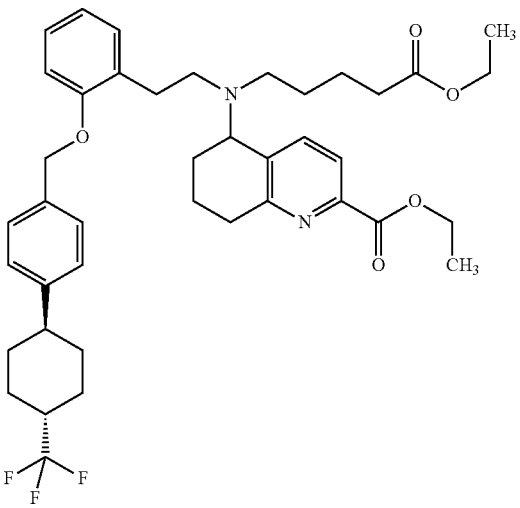 [SMILES: CCOC(=O)CCCCN(CCc1ccccc1OCc1ccc([C@H]2CC[C@H](C(F)(F)F)CC2)cc1)C1CCCc2nc(C(=O)OCC)ccc21]<br>from ethyl 5-({2-[2-({4-[trans-4-(trifluoromethyl)-cyclohexyl]benzyl}oxy)phenyl]ethyl}amino)-5,6,7,8-tetrahydroquinoline-2-carboxylate dihydrochloride and ethyl 5-bromopentanoate | LC-MS (Method 3):<br>$R_t$ = 1.45 min; m/z = 709 $(M + H)^+$. |

Example 43A rac-Ethyl 5-[(2-{2-[(4-tert-butylbenzyl)oxy]phenyl}ethyl){2-[4-(methoxycarbonyl)phenyl]ethyl}-amino]-5,6,7,8-tetrahydroquinoline-2-carboxylate

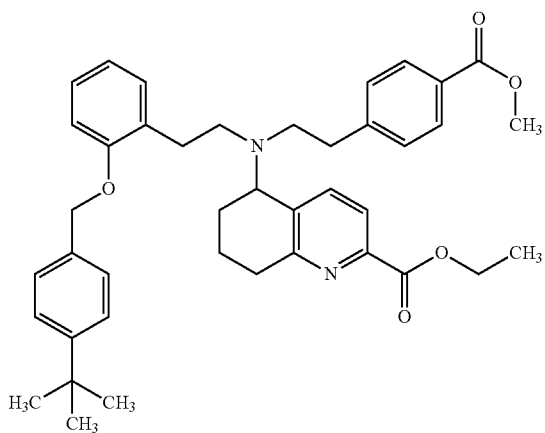 [SMILES: CCOC(=O)c1ccc2c(n1)CCCC2N(CCc1ccc(C(=O)OC)cc1)CCc1ccccc1OCc1ccc(C(C)(C)C)cc1]

129 mg (0.65 mmol) of methyl 4-(2-chloroethyl)benzoate and 91 mg (0.86 mmol) of anhydrous sodium carbonate were added to a solution of 210 mg (0.43 mmol) of ethyl 5-[(2-{2-[(4-tert-butylbenzyl)oxy]phenyl}ethyl)amino]-5,6,7,8-tetrahydroquinoline-2-carboxylate dihydrochloride in 4 ml of dry acetonitrile, and the mixture was initially heated under reflux for 4 hours. A further 0.1 ml of methyl 4-(2-chloroethyl)benzoate was then added, and the mixture was stirred under reflux for 4 hours. Another 0.1 ml of methyl 4-(2-chloroethyl)benzoate was metered in, and the mixture was then heated under reflux overnight. Subsequently, another 0.1 ml of methyl 4-(2-chloroethyl)benzoate and 100 mg of anhydrous sodium carbonate were added, and the mixture was stirred under reflux for a further 5 hours. Finally, another 0.1 ml of methyl 4-(2-chloroethyl)-benzoate and 0.2 ml of methyl 4-(2-iodoethyl)benzoate were added, and the reaction mixture was stirred under reflux for 2 days. The reaction was then concentrated to dryness. The residue obtained was purified by preparative HPLC. This gave 38 mg (0.06 mmol, content 92%, 14% of theory) of the title compound as a colourless oil.

LC-MS (Method 4): $R_t$=1.66 min; m/z=649 (M+H)$^+$.

Example 44A and Example 45A

Ethyl 5-[(2-{2-[(4-tert-butylbenzyl)oxy]phenyl}ethyl)(5-ethoxy-5-oxopentyl)amino]-5,6,7,8-tetrahydroquinoline-2-carboxylate (Enantiomers 1 and 2)

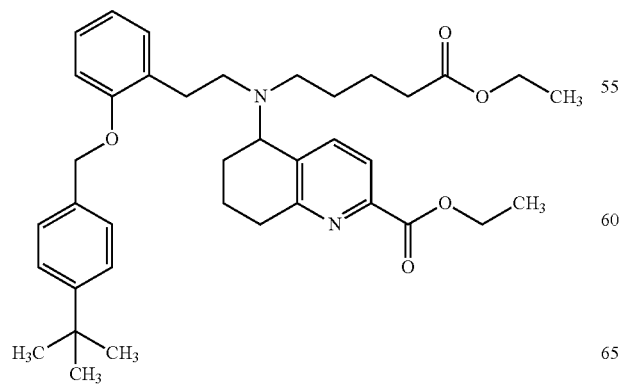

765 mg (1.24 mmol) of the racemic ethyl 5-[(2-{2-[(4-tert-butylbenzyl)oxy]phenyl}ethyl)-(5-ethoxy-5-oxopentyl)amino]-5,6,7,8-tetrahydroquinoline-2-carboxylate (Example 38A) were separated by preparative HPLC on a chiral phase into the enantiomers [column: chiral silica gel phase based on the selector poly(N-methacryloyl-L-phenylalanine-D-neomenthylamide) on spherical SH silica gel, 10 μm, 250 mm×20 mm; mobile phase: ethyl acetate/isohexane 20:80 (v/v); flow rate: 20 ml/min; UV detection: 270 nm; temperature: 25° C.]:

Example 44A (Enantiomer 1)

Yield: 318 mg $R_t$=2.84 min; chemical purity >98%; >99.9% ee
[column: chiral silica gel phase based on the selector poly(N-methacryloyl-L-phenylalanine-D-neomenthylamide) on spherical SH silica gel, 5 μm, 250 mm×4 mm; mobile phase: ethyl acetate/isohexane 20:80 (v/v); flow rate: 1.5 ml/min; UV detection: 260 nm; temperature: 25° C.].

Example 45A (Enantiomer 2)

Yield: 316 mg $R_t$=3.50 min; chemical purity >98%; >99% ee
[column: chiral silica gel phase based on the selector poly(N-methacryloyl-L-phenylalanine-D-neomenthylamide) on spherical SH silica gel, 5 μm, 250 mm×4 mm; mobile phase: ethyl acetate/isohexane 20:80 (v/v); flow rate: 1.5 ml/min; UV detection: 260 nm; temperature: 25° C.].

Example 46A and Example 47A

Ethyl 5-{[2-(2-{[3-chloro-4'-(trifluoromethyl)biphenyl-4-yl]methoxy}phenyl)ethyl](5-ethoxy-5-oxopentyl)amino}-5,6,7,8-tetrahydroquinoline-2-carboxylate (Enantiomers 1 and 2)

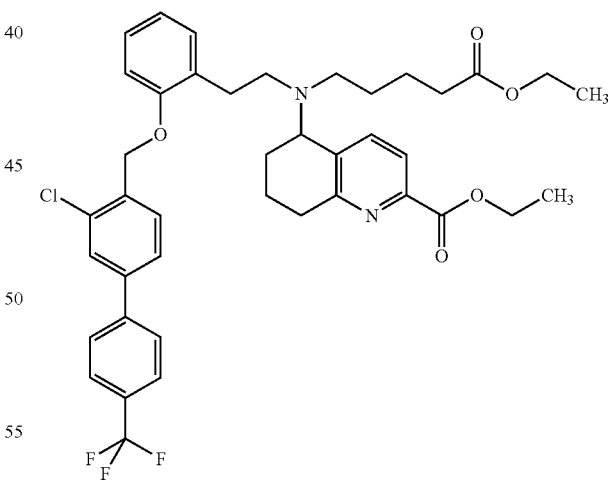

69 mg (0.09 mmol) of the racemic ethyl 5-{[2-(2-{[3-chloro-4'-(trifluoromethyl)biphenyl-4-yl]-methoxy}phenyl)ethyl](5-ethoxy-5-oxopentyl)amino}-5,6,7,8-tetrahydroquinoline-2-carboxylate (Example 40A) were separated by preparative HPLC on a chiral phase into the enantiomers [column: Daicel Chiralcel OZ-H, 5 μm, 250 mm×20 mm; mobile phase: ethanol/isohexane 50:50+0.2% diethylamine (v/v); flow rate: 15 ml/min; UV detection: 220 nm; temperature: 40° C.]:

Example 46A (Enantiomer 1)

Yield: 28 mg $R_t$=4.34 min; chemical purity >99%; >99% ee
[column: Daicel Chiralcel OZ-H, 5 μm, 250 mm×4.6 mm; mobile phase: ethanol/isohexane 50:50+0.2% diethylamine (v/v); flow rate: 1 ml/min; UV detection: 220 nm; temperature: 40° C.].

LC-MS (Method 3): $R_t$=1.51 min; m/z=737 (M+H)$^+$.

$[α]_D^{20}$=+61.09°, c=0.275, methanol.

Example 47A (Enantiomer 2)

Yield: 29 mg $R_t$=5.14 min; chemical purity >99%; >99% ee
[column: Daicel Chiralcel OZ-H, 5 μm, 250 mm×4.6 mm; mobile phase: ethanol/isohexane 50:50+0.2% diethylamine (v/v); flow rate: 1 ml/min; UV detection: 220 nm; temperature: 40° C.].

LC-MS (Method 3): $R_t$=1.50 min; m/z=737 (M+H)$^+$.

$[α]_D^{20}$=−81.21°, c=0.330, methanol.

Example 48A and Example 49A

Ethyl 5-[(5-ethoxy-5-oxopentyl)(2-{2-[(5-phenylpentyl)oxy]phenyl}ethyl)amino]-5,6,7,8-tetrahydroquinoline-2-carboxylate (Enantiomers 1 and 2)

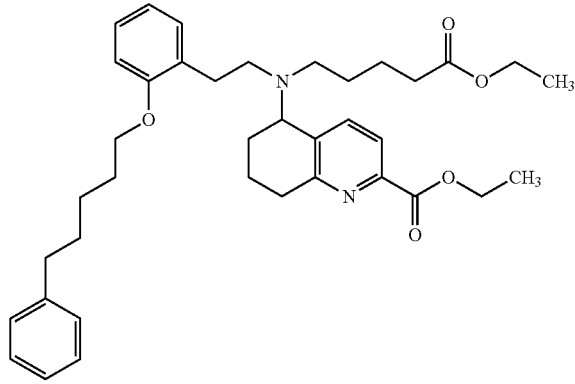 [SMILES: CCOC(=O)CCCCN(CCc1ccccc1OCCCCCc1ccccc1)C1CCCc2nc(C(=O)OCC)ccc21]

67 mg (0.11 mmol) of the racemic ethyl 5-[(5-ethoxy-5-oxopentyl)(2-(2-[(5-phenylpentyl)oxy]phenyl)ethyl)amino]-5,6,7,8-tetrahydroquinoline-2-carboxylate (Example 41A) were separated by preparative HPLC on a chiral phase into the enantiomers [column: Daicel Chiralcel OZ-H, 5 μm, 250 mm×20 mm; mobile phase: ethanol/isohexane 15:85 (v/v); flow rate: 15 ml/min; UV detection: 220 nm; temperature: 40° C.]:

Example 48A (Enantiomer 1)

Yield: 14 mg $R_t$=5.84 min; chemical purity >99%; >99% ee
[column: Daicel Chiralcel OZ-H, 5 μm, 250 mm×4.6 mm; mobile phase: ethanol/isohexane 15:85+0.2% diethylamine (v/v); flow rate: 1 ml/min; UV detection: 220 nm; temperature: 40° C.].

LC-MS (Method 3): $R_t$=1.38 min; m/z=615 (M+H)$^+$.

Example 49A (Enantiomer 2)

Yield: 10 mg $R_t$=7.30 min; chemical purity >99%; >99% ee
[column: Daicel Chiralcel OZ-H, 5 μm, 250 mm×4.6 mm; mobile phase: ethanol/isohexane 15:85+0.2% diethylamine (v/v); flow rate: 1 ml/min; UV detection: 220 nm; temperature: 40° C.].

LC-MS (Method 3): $R_t$=1.39 min; m/z=615 (M+H)$^+$.

Example 50A and Example 51A

Ethyl 5-{(5-ethoxy-5-oxopentyl)[2-(2-{[4-(2-phenylethyl)benzyl]oxy}phenyl)ethyl]amino}-5,6,7,8-tetrahydroquinoline-2-carboxylate (Enantiomers 1 and 2)

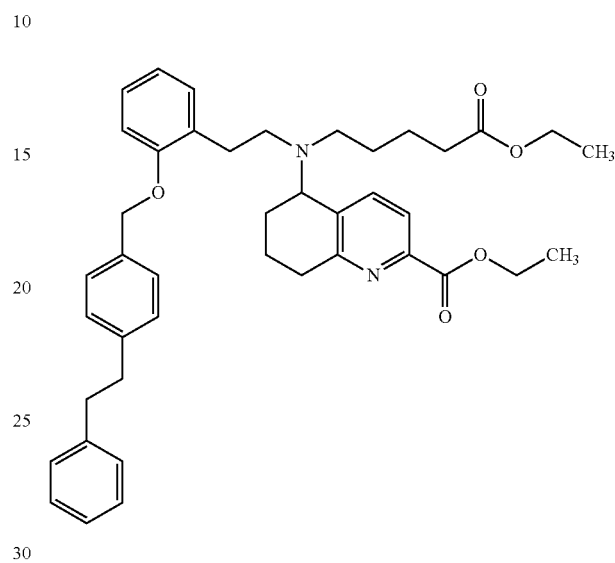

760 mg (1.15 mmol) of the racemic ethyl 5-{(5-ethoxy-5-oxopentyl)[2-(2-{[4-(2-phenylethyl)-benzyl]oxy}phenyl)ethyl]amino}-5,6,7,8-tetrahydroquinoline-2-carboxylate (Example 15A) were separated by preparative HPLC on a chiral phase into the enantiomers [column: Daicel Chiralpak AD-H, 5 μm, 250 mm×20 mm; mobile phase: isopropanol (+0.2% diethylamine)/isohexane 50:50 (v/v); flow rate: 20 ml/min; UV detection: 210 nm; temperature: 20° C.]:

Example 50A (Enantiomer 1)

Yield: 261 mg $R_t$=8.78 min; chemical purity >98%; >99% ee

[column: Daicel Chiralpak AD-H, 5 μm, 250 mm×4.6 mm; mobile phase: isopropanol/isohexane 15:85 (v/v); flow rate: 1 ml/min; UV detection: 230 nm; temperature: 20° C.].

LC-MS (Method 4): $R_t$=1.40 min; m/z=663 (M+H)$^+$.

Example 51A (Enantiomer 2)

Yield: 276 mg $R_t$=9.89 min; chemical purity >86%; >98.5% ee

[column: Daicel Chiralpak AD-H, 5 μm, 250 mm×4.6 mm; mobile phase: isopropanol/isohexane 15:85 (v/v); flow rate: 1 ml/min; UV detection: 230 nm; temperature: 20° C.].

LC-MS (Method 4): $R_t$=1.40 min; m/z=663 (M+H)$^+$.

Example 52A and Example 53A

Ethyl 5-[(5-ethoxy-5-oxopentyl){2-[2-({4-[2-(4-fluorophenyl)ethyl]benzyl}oxy)phenyl]ethyl}amino]-5,6,7,8-tetrahydroquinoline-2-carboxylate (Enantiomers 1 and 2)

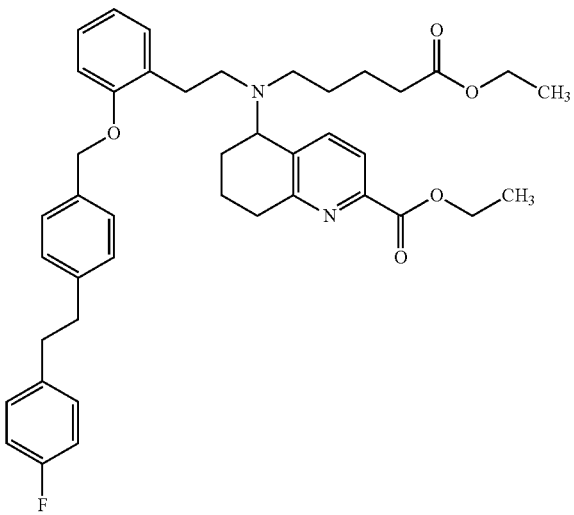 [SMILES: CCOC(=O)CCCCN(CCc1ccccc1OCc1ccc(CCc2ccc(F)cc2)cc1)C1CCCc2nc(C(=O)OCC)ccc21]

603 mg (0.89 mmol) of the racemic ethyl 5-[(5-ethoxy-5-oxopentyl)(2-[2-({4-[2-(4-fluorophenyl)-ethyl]benzyl}oxy)phenyl]ethylamino]-5,6,7,8-tetrahydroquinoline-2-carboxylate (Example 16A) were separated by preparative HPLC on a chiral phase into the enantiomers [column: Daicel Chiralpak AD-H, 5 μm, 250 mm×20 mm; mobile phase: isopropanol/isohexane 10:90 (v/v); flow rate: 20 ml/min; UV detection: 230 nm; temperature: 25° C.]:

Example 52A (Enantiomer 1)

Yield: 70 mg $R_t$=10.83 min; chemical purity >97.5%; >99% ee

[column: Daicel Chiralpak AD-H, 5 μm, 250 mm×4.6 mm; mobile phase: isopropanol (+0.2% di-ethylamine)/isohexane 10:90 (v/v); flow rate: 1 ml/min; UV detection: 230 nm; temperature: 40° C.]

LC-MS (Method 4): $R_t$=1.40 min; m/z=681 (M+H)$^+$.

Example 53A (Enantiomer 2)

Yield: 72 mg $R_t$=12.69 min; chemical purity >93.5%; >98% ee

[column: Daicel Chiralpak AD-H, 5 μm, 250 mm×4.6 mm; mobile phase: isopropanol (+0.2% di-ethylamine)/isohexane 10:90 (v/v); flow rate: 1 ml/min; UV detection: 230 nm; temperature: 40° C.].

LC-MS (Method 4): $R_t$=1.40 min; m/z=681 (M+H)$^+$.

Example 54A and Example 55A

Ethyl 5-{(5-ethoxy-5-oxopentyl)[2-(2-{[4'-(trifluoromethyl)biphenyl-4-yl]methoxy}phenyl)ethyl]amino}-5,6,7,8-tetrahydroquinoline-2-carboxylate (Enantiomers 1 and 2)

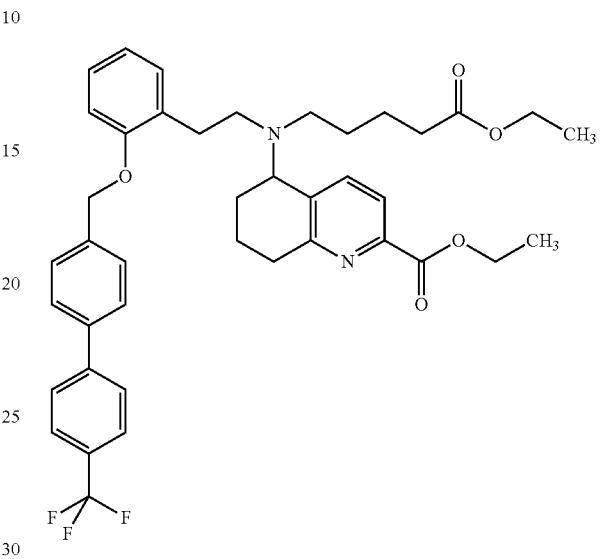

642 mg (0.91 mmol) of the racemic ethyl 5-{(5-ethoxy-5-oxopentyl)[2-(2-{[4'-(trifluoromethyl)-biphenyl-4-yl]methoxy}phenyl)ethyl]amino}-5,6,7,8-tetrahydroquinoline-2-carboxylate (Example 17A) were separated by preparative HPLC on a chiral phase into the enantiomers [column: Daicel Chiralpak AD-H, 5 μm, 250 mm×20 mm; mobile phase: isopropanol/isohexane 20:80 (v/v); flow rate: 15 ml/min; UV detection: 220 nm; temperature: 40° C.]:

Example 54A (Enantiomer 1)

Yield: 161 mg $R_t$=5.50 min; chemical purity >99%; >99% ee

[column: Daicel Chiralpak AD-H, 5 μm, 250 mm×4.6 mm; mobile phase: isopropanol (+0.2% di-ethylamine)/isohexane 20:80 (v/v); flow rate: 1 ml/min; UV detection: 220 nm; temperature: 40° C.].

LC-MS (Method 4): $R_t$=1.44 min; m/z=703 (M+H)$^+$.

Example 55A (Enantiomer 2)

Yield: 168 mg $R_t$=7.01 min; chemical purity >97.5%; >99% ee

[column: Daicel Chiralpak AD-H, 5 μm, 250 mm×4.6 mm; mobile phase: isopropanol (+0.2% di-ethylamine)/isohexane 20:80 (v/v); flow rate: 1 ml/min; UV detection: 220 nm; temperature: 40° C.].

LC-MS (Method 4): $R_t$=1.44 min; m/z=703 (M+H)$^+$.

Analogously to Example 11A, the following compound was prepared from the starting materials stated:

| Example | Name/Structure/Starting materials | Analytical data |
|---|---|---|
| 56A | N-(5-chloro-2-hydroxyphenyl)-4-(chloromethyl)-benzamide 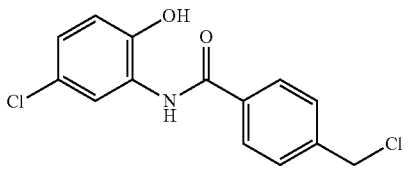 [SMILES: O=C(Nc1cc(Cl)ccc1O)c1ccc(CCl)cc1] from 2-amino-4-chlorophenol and 4-(chloromethyl)benzoyl chloride | LC-MS (Method 3): $R_t$ = 1.05 min; m/z = 296/298 (M + H)$^+$. $^1$H-NMR (400 MHz, DMSO-$d_6$): δ [ppm] = 4.85 (s, 2H), 6.93 (d, 1H), 7.08 (dd, 1H), 7.60 (d, 2H), 7.83 (d, 1H), 7.96 (d, 2H), 9.53 (s, 1H), 10.17 (s, 1H). |

Analogously to Example 12A, the following compound was prepared from the starting material stated:

| Example | Name/Structure/Starting material | Analytical data |
|---|---|---|
| 57A | 5-chloro-2-[4-(chloromethyl)phenyl]-1,3-benzoxazole 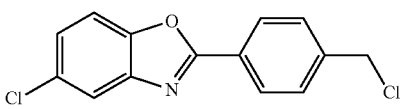 [SMILES: ClCc1ccc(-c2nc3cc(Cl)ccc3o2)cc1] from N-(5-chloro-2-hydroxyphenyl)-4-(chloromethyl)benzamide | LC-MS (Method 3): $R_t$ = 1.34 min; m/z = 278/280 (M + H)$^+$. $^1$H-NMR (400 MHz, DMSO-$d_6$): δ [ppm] = 4.89 (s, 2H), 7.50 (dd, 1H), 7.70 (d, 2H), 7.86 (d, 1H), 7.95 (d, 1H), 8.22 (d, 2H). |

Analogously to Example 18A, the following compound was prepared from the starting materials stated:

| Example | Name/Structure/Starting materials | Analytical data |
|---|---|---|
| 58A | rac-ethyl 5-{(tert-butoxycarbonyl)[2-(2-{[4-(5-chloro-1,3-benzoxazol-2-yl)benzyl]oxy}phenyl)-ethyl]amino}-5,6,7,8-tetrahydroquinoline-2-carboxylate 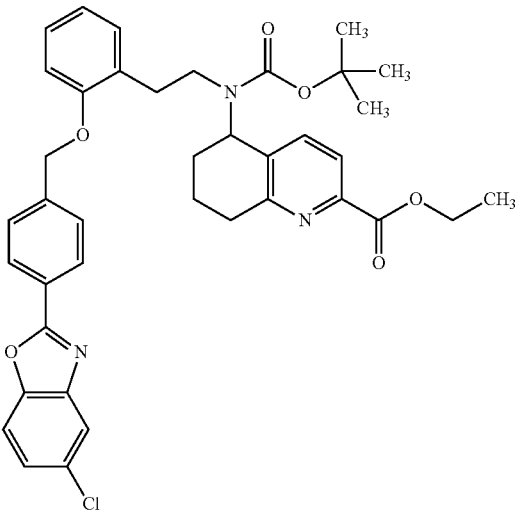 [SMILES: CCOC(=O)c1ccc2c(n1)CCCC2N(CCc1ccccc1OCc1ccc(-c2nc3cc(Cl)ccc3o2)cc1)C(=O)OC(C)(C)C] from ethyl 5-{(tert-butoxycarbonyl)[2-(2-hydroxy-phenyl)ethyl]amino}-5,6,7,8-tetrahydroquinoline-2-carboxylate and 5-chloro-2-[4-(chloromethyl)-phenyl]-1,3-benzoxazole | LC-MS (Method 3): $R_t$ = 1.64 min; m/z = 682/684 (M + H)$^+$. |

Example 59A and Example 60A

Ethyl 5-{(tert-butoxycarbonyl)[2-(2-{[4-(5-chloro-1,3-benzoxazol-2-yl)benzyl]oxy}phenyl)ethyl]-amino}-5,6,7,8-tetrahydroquinoline-2-carboxylate (Enantiomers 1 and 2)

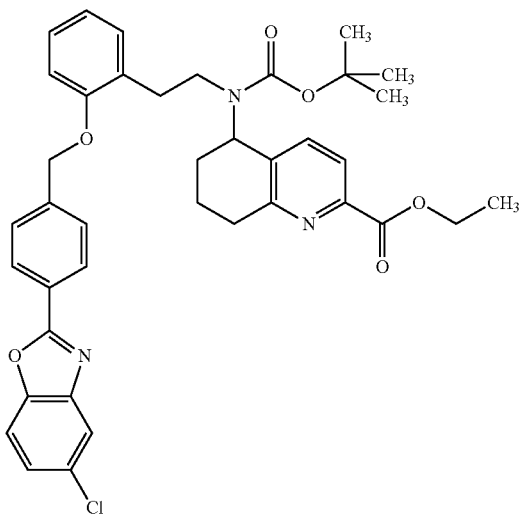 [SMILES: CCOC(=O)c1ccc2c(n1)CCCC2N(CCc1ccccc1OCc1ccc(-c2nc3cc(Cl)ccc3o2)cc1)C(=O)OC(C)(C)C]

494 mg (0.72 mmol) of the racemic ethyl 5-{(tert-butoxycarbonyl)[2-(2-{[4-(5-chloro-1,3-benzoxazol-2-yl)benzyl]oxy}phenyl)ethyl]amino}-5,6,7,8-tetrahydroquinoline-2-carboxylate (Example 58A) were separated by supercritical fluid chromatography (SPC) on a chiral phase into the enantiomers [column: Daicel Chiracel OD-H, 5 μm, 250 mm×20 mm; mobile phase: carbon dioxide/ethanol 70:30 (v/v); flow rate: 100 ml/min; pressure: 100 bar; UV detection: 210 nm; temperature: 40° C.]:

Example 59A (Enantiomer 1)

Yield: 247 mg $R_t$=4.47 min; chemical purity >99.9%; >99% ee

[column: Chiralpak OD-H, 5 μm, 250 mm×4.6 mm; mobile phase: carbon dioxide/ethanol 70:30 (v/v); flow rate: 3 ml/min; UV detection: 210 nm].

LC-MS (Method 3): $R_t$=1.62 min; m/z=682/684 (M+H)$^+$.

Example 60A (Enantiomer 2)

Yield: 213 mg $R_t$=9.22 min; chemical purity >99%; >99% ee

[column: Chiralpak OD-H, 5 μm, 250 mm×4.6 mm; mobile phase: carbon dioxide/ethanol 70:30 (v/v); flow rate: 3 ml/min; UV detection: 210 nm].

LC-MS (Method 3): $R_t$=1.62 min; m/z=682/684 (M+H)$^+$.

Example 61A

Ethyl 5-{[2-(2-{[4-(5-chloro-1,3-benzoxazol-2-yl)benzyl]oxy}phenyl)ethyl]amino}-5,6,7,8-tetrahydroquinoline-2-carboxylate (Enantiomer 1)

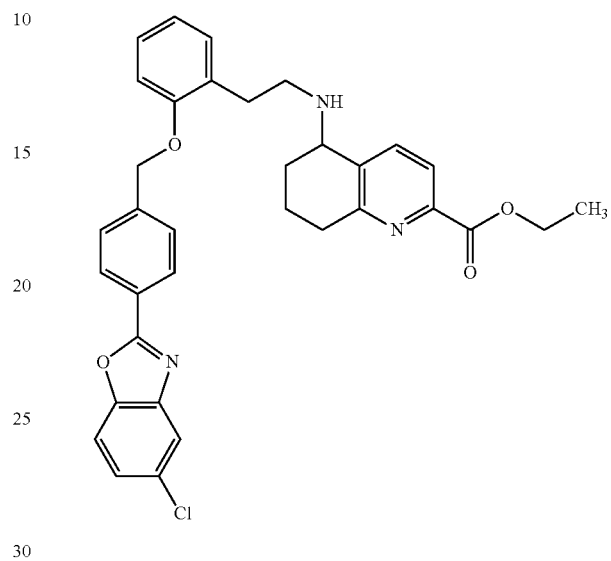

10 ml of a 4 N solution of hydrogen chloride in dioxane were added to 247 mg (0.36 mmol) of ethyl 5-{(tert-butoxycarbonyl)[2-(2-{[4-(5-chloro-1,3-benzoxazol-2-yl)benzyl]oxy}phenyl)ethyl]-amino}-5,6,7,8-tetrahydroquinoline-2-carboxylate (Enantiomer 1, Example 59A), and the mixture was stirred at room temperature for 4 h. The reaction solution was then concentrated to dryness and the residue was dried under high vacuum overnight. This gave 210 mg of the title compound as the hydrochloride in the form of a solid. This solid was taken up in 5 ml of THP, 0.13 ml of triethylamine was added and the mixture was stirred at room temperature for one hour. Water and ethyl acetate were then added to the mixture, and the phases were separated. The aqueous phase was extracted twice with ethyl acetate, and the combined organic phases were then dried over magnesium sulphate, filtered and then concentrated to dryness. This gave 149 mg (0.26 mmol, 72% of theory) of the target compound.

LC-MS (Method 3): $R_t$=1.06 min; m/z=582/584 (M+H)$^+$.

$^1$H-NMR (400 MHz, DMSO-$d_6$, δ/ppm): 1.27 (t, 3H), 1.63-1.77 (m, 2H), 1.81-2.02 (m, 2H), 2.71-2.91 (m, 6H), 3.44-3.54 (m, 0.5H), 3.64-3.74 (m, 0.5H), 3.75-3.84 (br. s, 1H), 4.27 (q, 2H), 5.23 (s, 2H), 6.90 (t, 1H), 7.05 (d, 1H), 7.14-7.24 (m, 2H), 7.49 (dd, 1H), 7.67 (d, 2H), 7.74 (d, 1H), 7.82-7.90 (m, 2H), 7.95 (d, 1H), 8.20 (d, 2H).

Analogously to Example 61A, the following compound was prepared:

| Example | Name/Structure/Starting material | Analytical data |
|---|---|---|
| 62A | ethyl 5-{[2-(2-{[4-(5-chloro-1,3-benzoxazol-2-yl)-benzyl]oxy}phenyl)ethyl]amino}-5,6,7,8-tetra-hydroquinoline-2-carboxylate (Enantiomer 2)<br><br>from ethyl 5-{(tert-butoxycarbonyl)[2-(2-{[4-(5-chloro-1,3-benzoxazol-2-yl)benzyl]oxy}phenyl)-ethyl]amino}-5,6,7,8-tetrahydroquinoline-2-carboxylate (Enantiomer 2, Example 60A) | LC-MS (Method 3):<br>$R_t$ = 1.05 min; m/z = 582/584 (M + H)$^+$. |

Example 63A

Ethyl 5-{[2-(2-[4-(5-chloro-1,3-benzoxazol-2-yl)benzyl]oxy}phenyl)ethyl]{2-[4-(methoxy-carbonyl)phenyl]ethyl}amino)-5,6,7,8-tetrahydroquinoline-2-carboxylate (Enantiomer 1)

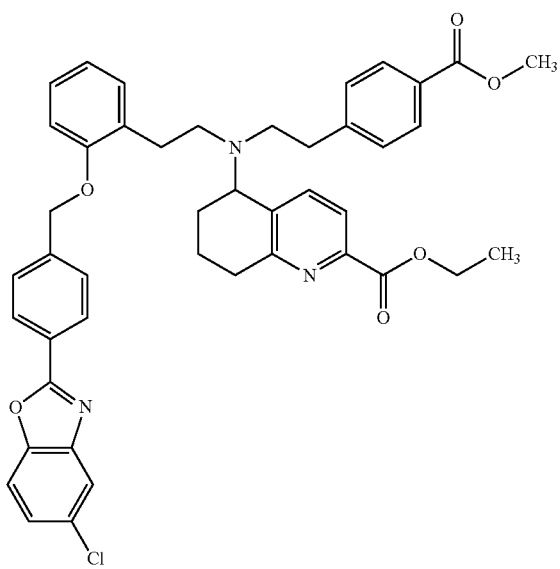

112 mg (0.39 mmol) of methyl 4-(2-iodoethyl)benzoate and 41 mg (0.39 mmol) of anhydrous sodium carbonate were added to a solution of 149 mg (0.26 mmol) of ethyl 5-{[2-(2-{[4-(5-chloro-1,3-benzoxazol-2-yl)benzyl]oxy}phenyl)ethyl]amino}-5,6,7,8-tetrahydroquinoline-2-carboxylate (Enantiomer 1, Example 61A) in 10 ml of dry acetonitrile, and the mixture was heated under reflux overnight. A further 112 mg of methyl 4-(2-iodoethyl)benzoate were then added, and the mixture was once more heated under reflux overnight. The reaction was then evaporated to dryness, the residue was taken up in water and ethyl acetate and the phases were separated. The organic phase was evaporated to dryness and the residue obtained was purified by preparative HPLC. This gave 72 mg (0.10 mmol, 38% of theory) of the title compound.

LC-MS (Method 3): $R_t$=1.60 min; m/z=744/746 (M+H)$^+$.

Analogously to Example 63A, the following compound was prepared:

| Example | Name/Structure/Starting materials | Analytical data |
|---|---|---|
| 64A | ethyl 5-([2-(2-{[4-(5-chloro-1,3-benzoxazol-2-yl)-benzyl]oxy}phenyl)ethyl]{2-[4-(methoxycarbonyl)-phenyl]ethyl}amino)-5,6,7,8-tetrahydroquinoline-2-carboxylate (Enantiomer 2)<br><br>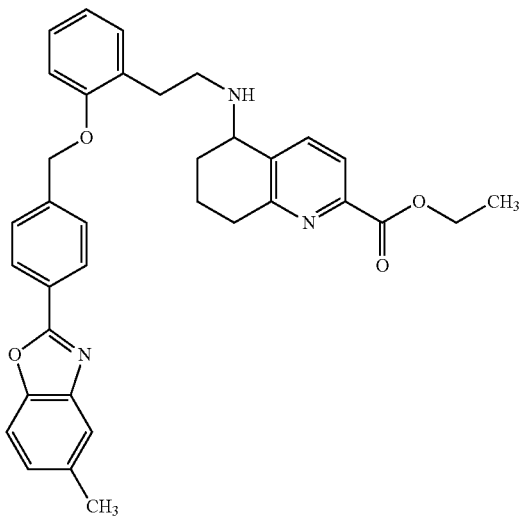<br><br>from ethyl 5-{[2-(2-{[4-(5-chloro-1,3-benzoxazol-2-yl)benzyl]oxy}phenyl)ethyl]amino}-5,6,7,8-tetrahydroquinoline-2-carboxylate (Enantiomer 2, Example 62A) and methyl 4-(2-iodoethyl)benzoate | LC-MS (Method 3): $R_t$ = 1.61 min; m/z = 744/746 (M + H)$^+$.<br>$^1$H-NMR (400 MHz, DMSO-$d_6$, δ/ppm): 1.26 (t, 3H), 1.42-1.55 (m, 1H), 1.55-1.70 (m, 1H), 1.89-2.08 (m, 2H), 2.44-2.84 (m, 10H, partially obscured by DMSO signal), 3.76 (s, 3H), 4.01-4.12 (m, 1H), 4.26 (q, 2H), 5.04-5.15 (m, 2H), 6.86 (t, 1H), 7.02 (d, 1H), 7.05-7.15 (m, 3H), 7.21 (t, 1H), 7.43 (d, 1H), 7.46-7.57 (m, 4H), 7.72 (d, 2H), 7.83 (d, 1H), 7.92 (d, 1H), 8.09 (d, 2H). |

Example 65A

Ethyl 5-{[2-(2-{[4-(5-methyl-1,3-benzoxazol-2-yl)benzyl]oxy}phenyl)ethyl]amino}-5,6,7,8-tetrahydroquinoline-2-carboxylate (Enantiomer 1)

3.8 g (5.99 mmol) of ethyl 5-{[2-(2-{[4-(5-methyl-1,3-benzoxazol-2-yl)benzyl]oxy}phenyl)ethyl]-amino}-5,6,7,8-tetrahydroquinoline-2-carboxylate dihydrochloride (Enantiomer 1, Example 27A) were dissolved in 50 ml of THF, 2.5 ml of triethylamine were added and the mixture was stirred at room temperature for 1 h. Water and ethyl acetate were then added to the mixture, and the phases were separated. The aqueous phase was extracted twice with ethyl acetate, and the combined organic phases were then dried over magnesium sulphate, filtered and concentrated to dryness. This gave 2.48 g (4.42 mmol, 74% of theory) of the target compound.

LC-MS (Method 3): $R_t$=1.06 min; m/z=562 (M+H)$^+$.

$^1$H-NMR (400 MHz, DMSO-$d_6$, δ/ppm): 1.27 (t, 3H), 1.59-1.79 (m, 2H), 1.99 (s, 3H), 2.01-2.16 (m, 1H), 2.69-2.92 (m, 6H), 3.42-3.55 (m, 1H), 3.64-3.87 (m, 1H), 3.98-4.07 (m, 1H), 4.28 (q, 2H), 5.22 (s, 2H), 6.84-6.95 (m, 1H), 7.00-7.09 (m, 1H), 7.20 (s, 3H), 7.58-7.70 (m, 4H), 7.71-7.79 (m, 1H), 7.83-7.94 (m, 1H), 8.18 (d, 2H).

Analogously to Example 65A, the following compound was prepared:

| Example | Name/Structure/Starting material | Analytical data |
|---|---|---|
| 66A | ethyl 5-{[2-(2-{[4-(5-methyl-1,3-benzoxazol-2-yl)-benzyl]oxy}phenyl)ethyl]amino}-5,6,7,8-tetrahydroquinoline-2-carboxylate (Enantiomer 2)<br><br>from ethyl 5-{[2-(2-{[4-(5-methyl-1,3-benzoxazol-2-yl)benzyl]oxy}phenyl)ethyl]amino}-5,6,7,8-tetrahydroquinoline-2-carboxylate dihydrochloride (Enantiomer 2, Example 28A) | LC-MS (Method 6):<br>$R_t$ = 3.24 min; m/z = 562 (M + H)$^+$. |

Analogously to Example 63A, the following compounds were prepared:

| Example | Name/Structure/Starting materials | Analytical data |
|---|---|---|
| 67A | ethyl 5-({2-[4-(methoxycarbonyl)phenyl]ethyl}-[2-(2-{[4-(5-methyl-1,3-benzoxazol-2-yl)-benzyl]oxy}phenyl)ethyl]amino)-5,6,7,8-tetrahydroquinoline-2-carboxylate (Enantiomer 1)<br><br>from ethyl 5-{[2-(2-{[4-(5-methyl-1,3-benzoxazol-2-yl)benzyl]oxy}phenyl)ethyl]amino}-5,6,7,8-tetrahydroquinoline-2-carboxylate (Enantiomer 1, Example 65A) and methyl 4-(2-iodoethyl)benzoate | LC-MS (Method 3):<br>$R_t$ = 1.61 min; m/z = 724 (M + H)$^+$. |

| Example | Name/Structure/Starting materials | Analytical data |
|---|---|---|
| 68A | ethyl 5-({2-[4-(methoxycarbonyl)phenyl]ethyl}-[2-(2-{[4-(5-methyl-1,3-benzoxazol-2-yl)-benzyl]oxy}phenyl)ethyl]amino)-5,6,7,8-tetrahydroquinoline-2-carboxylate (Enantiomer 2)<br><br>from ethyl 5-{[2-(2-{[4-(5-methyl-1,3-benzoxazol-2-yl)benzyl]oxy}phenyl)ethyl]amino}-5,6,7,8-tetrahydroquinoline-2-carboxylate (Enantiomer 2, Example 66A) and methyl 4-(2-iodoethyl)benzoate | LC-MS (Method 3): $R_t$ = 1.58 min; m/z = 724 $(M + H)^+$.<br>$^1$H-NMR (400 MHz, DMSO-$d_6$, δ/ppm): 1.26 (t, 3H), 1.42-1.54 (m, 1H), 1.55-1.71 (m, 1H), 1.89-2.09 (m, 2H), 2.42-2.57 (m, 3H, partially obscured by DMSO signal) 2.57-2.86 (m, 10H), 3.76 (s, 3H), 4.02-4.13 (m, 1H), 4.26 (q, 2H), 5.08 (m, 2H), 6.79-6.92 (m, 1H), 6.98-7.09 (m, 2H), 7.10-7.16 (m, 2H), 7.17-7.29 (m, 2H), 7.42 (d, 1H), 7.48-7.56 (m, 3H), 7.57-7.69 (m, 2H), 7.74 (d, 2H), 8.09 (d, 2H). |

Example 69A

Ethyl 5-{(tert-butoxycarbonyl)[2-(2-hydroxyphenyl)ethyl]amino}-5,6,7,8-tetrahydroquinoline-2-carboxylate (Enantiomer 2)

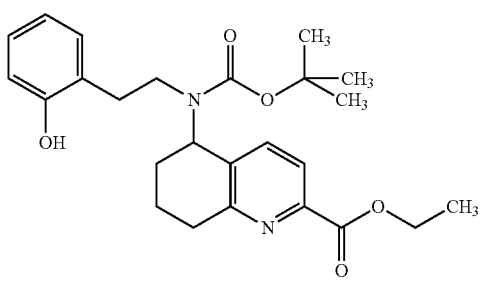 [SMILES: CCOC(=O)c1ccc2c(n1)CCCC2N(CCc1ccccc1O)C(=O)OC(C)(C)C]

10 g (15.11 mmol) of (−)-ethyl 5-{(tert-butoxycarbonyl)[2-(2-{[4-(5-methyl-1,3-benzoxazol-2-yl)-benzyl]oxy}phenyl)ethyl]amino}-5,6,7,8-tetrahydroquinoline-2-carboxylate (Enantiomer 2, Example 26A) were dissolved in 500 ml of ethanol, and 9.53 g (151.10 mmol) of ammonium formate and 161 mg (1.51 mmol) of 10% palladium on activated carbon were added. The reaction mixture was then heated to 80° C. and stirred at this temperature overnight. The mixture was then cooled to room temperature, another 100 mg of the palladium catalyst were added and the mixture was stirred at 80° C. for a further 6 h. The reaction mixture was then once more cooled to room temperature and filtered, and the filtrate was evaporated to dryness. The residue obtained was purified chromatographically on silica gel (mobile phase: cyclohexane/ethyl acetate 20:1-2:1). This gave 6.55 g (14.87 mmol, 98% of theory) of the title compound.

LC-MS (Method 3): $R_t$=1.17 min; m/z=441 $(M+H)^+$.

An alternative preparation route for Example 69A is shown in connection with the description of Example 147A (q.v.).

Analogously to Example 11A, the following compounds were prepared from the starting materials stated:

| Example | Name/Structure/Starting materials | Analytical data |
|---|---|---|
| 70A | 4-(chloromethyl)-N-[2-hydroxy-5-(trifluoromethyl)-phenyl]benzamide 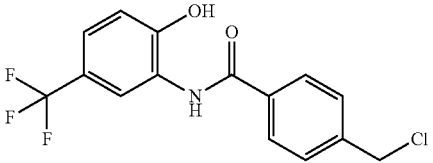 [SMILES: O=C(Nc1cc(C(F)(F)F)ccc1O)c1ccc(CCl)cc1] from 2-amino-4-(trifluoromethyl)phenol and 4-(chloromethyl)benzoyl chloride | LC-MS (Method 3): $R_t$ = 1.12 min; m/z = 330 $(M + H)^+$. $^1$H-NMR (400 MHz, DMSO-$d_6$): δ [ppm] = 4.85 (s, 2H), 7.09 (d, 1H), 7.40 (dd, 1H), 7.60 (d, 2H), 7.98 (d, 2H), 8.12 (d, 1H), 9.62 (s, 1H), 10.81 (s, 1H). |
| 71A | 4-(chloromethyl)-N-[2-hydroxy-5-(trifluoromethoxy)phenyl]benzamide 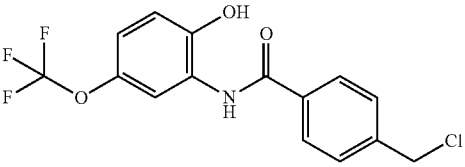 [SMILES: O=C(Nc1cc(OC(F)(F)F)ccc1O)c1ccc(CCl)cc1] from 2-amino-4-(trifluoromethoxy)phenol and 4-(chloromethyl)benzoyl chloride | LC-MS (Method 3): $R_t$ = 1.14 min; m/z = 346 $(M + H)^+$. $^1$H-NMR (400 MHz, DMSO-$d_6$): δ [ppm] = 4.85 (s, 2H), 6.96-7.01 (m, 1H), 7.02-7.08 (m, 1H), 7.60 (d, 2H), 7.78-7.90 (m, 1H), 7.97 (d, 2H), 9.54 (s, 1H), 10.31 (s, 1H). |

Analogously to Example 12A, the following compounds were prepared from the starting material stated:

| Example | Name/Structure/Starting material | Analytical data |
|---|---|---|
| 72A | 2-[4-(chloromethyl)phenyl]-5-(trifluoromethyl)-1,3-benzoxazole 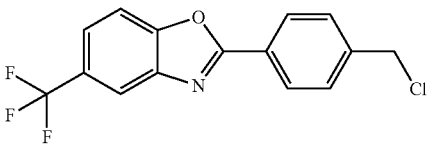 [SMILES: FC(F)(F)c1ccc2oc(-c3ccc(CCl)cc3)nc2c1] from 4-(chloromethyl)-N-[2-hydroxy-5-(trifluoromethyl)phenyl]benzamide | LC-MS (Method 3): $R_t$ = 1.32 min; m/z = 312 $(M + H)^+$. $^1$H-NMR (400 MHz, DMSO-$d_6$): δ [ppm] = 4.90 (s, 2H), 7.71 (d, 2H), 7.82 (dd, 1H), 8.04 (d, 1H), 8.19-8.35 (m, 3H). |
| 73A | 2-[4-(chloromethyl)phenyl]-5-(trifluoromethoxy)-1,3-benzoxazole 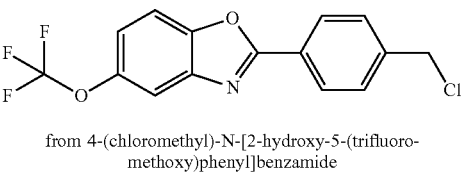 from 4-(chloromethyl)-N-[2-hydroxy-5-(trifluoromethoxy)phenyl]benzamide | LC-MS (Method 3): $R_t$ = 1.37 min; m/z = 328 $(M + H)^+$. $^1$H-NMR (400 MHz, DMSO-$d_6$): δ [ppm] = 4.89 (s, 2H), 7.47 (dd, 1H), 7.70 (d, 2H), 7.87-8.01 (m, 2H), 8.23 (d, 2H). |

Example 74A

Ethyl 5-{(tert-butoxycarbonyl)[2-(2-{[3-chloro-4'-(trifluoromethyl)biphenyl-4-yl]methoxy}-phenyl)ethyl]amino}-5,6,7,8-tetrahydroquinoline-2-carboxylate (Enantiomer 2)

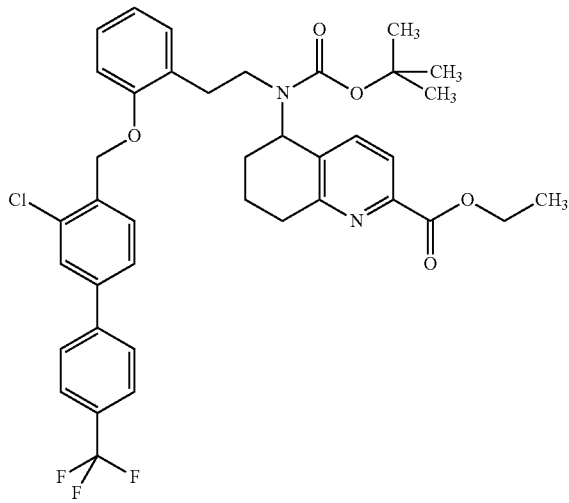 [SMILES: CCOC(=O)c1ccc2c(n1)CCCC2N(CCc1ccccc1OCc1ccc(-c2ccc(C(F)(F)F)cc2)cc1Cl)C(=O)OC(C)(C)C]

A suspension of 51.21 g (116.24 mmol) of ethyl 5-{(tert-butoxycarbonyl)[2-(2-hydroxyphenyl)-ethyl]amino}-5,6,7,8-tetrahydroquinoline-2-carboxylate (Enantiomer 2, Example 69A), 44.70 g (127.86 mmol) of 4-(bromomethyl)-3-chloro-4'-(trifluoromethyl)biphenyl and 40.16 g (290.60 mmol) of potassium carbonate in 1420 ml of acetonitrile was heated to 110° C. and stirred at this temperature overnight. After cooling, the reaction mixture was filtered, the filter cake was washed repeatedly with acetonitrile and the combined filtrates were concentrated to dryness on a rotary evaporator. The residue obtained was purified chromatographically on silica gel (2.5 kg) (mobile phase: petroleum ether/ethyl acetate 4:1). This gave 79 g (111.39 mmol, 96% of theory) of the target compound.

LC-MS (Method 3): $R_t$=1.69 min; m/z=709 (M+H)$^+$.

$^1$H-NMR (400 MHz, DMSO-d$_6$, δ/ppm): 1.05-1.20 (m, 4H), 1.21-1.34 (m, 4H), 1.45 (s, 6H), 1.56-1.74 (m, 2H), 1.75-1.93 (m, 2H), 2.76-2.99 (m, 3H), 4.30 (q, 2H), 5.00-5.24 (m, 3H), 6.86-6.99 (m, 1H), 7.03-7.16 (m, 1.5H), 7.17-7.29 (m, 1.5H), 7.38-7.45 (m, 0.5H), 7.50-7.56 (m, 0.5H), 7.58-7.68 (m, 1H), 7.69-7.78 (m, 1.5H), 7.79-7.93 (m, 5H), 8.01-8.12 (m, 1.5H).

An alternative preparation route for Example 74A is shown in connection with the description of Example 148A (q.v.).

Analogously to Example 74A described above, the following compounds were prepared from the starting materials stated for each case:

| Example | Name/Structure/Starting materials | Analytical data |
|---|---|---|
| 75A | ethyl 5-[(tert-butoxycarbonyl){2-[2-({4-[5-(trifluoromethyl)-1,3-benzoxazol-2-yl]benzyl}oxy)-phenyl]ethyl}amino]-5,6,7,8-tetrahydroquinoline-2-carboxylate (Enantiomer 2)<br><br>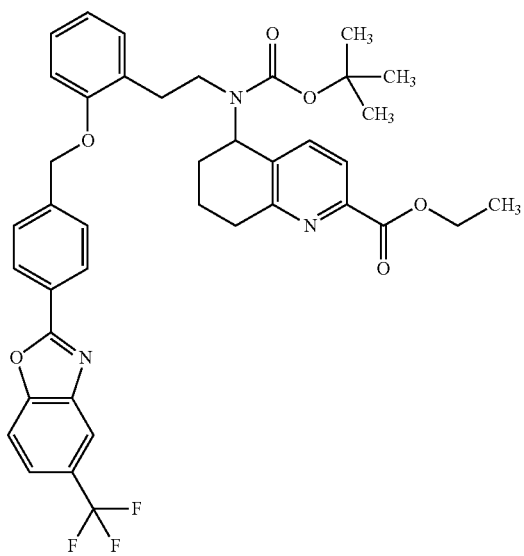 [SMILES: CCOC(=O)c1ccc2c(n1)CCCC2N(CCc1ccccc1OCc1ccc(-c2nc3cc(C(F)(F)F)ccc3o2)cc1)C(=O)OC(C)(C)C]<br><br>from ethyl 5-{(tert-butoxycarbonyl)[2-(2-hydroxyphenyl)ethyl]amino}-5,6,7,8-tetrahydroquinoline-2-carboxylate (Enantiomer 2, Example 69A) and 2-[4-(chloromethyl)phenyl]-5-(trifluoromethyl)-1,3-benzoxazole | LC-MS (Method 3): $R_t$ = 1.62 min; m/z = 716 (M + H)$^+$. |

| Example | Name/Structure/Starting materials | Analytical data |
|---------|-----------------------------------|-----------------|
| 76A | ethyl 5-{[2-(2-{[4-(1,3-benzoxazol-2-yl)benzyl]-oxy}phenyl)ethyl](tert-butoxycarbonyl)amino}-5,6,7,8-tetrahydroquinoline-2-carboxylate (Enantiomer 2)<br><br>from ethyl 5-{(tert-butoxycarbonyl)[2-(2-hydroxyphenyl)ethyl]amino}-5,6,7,8-tetrahydroquinoline-2-carboxylate (Enantiomer 2, Example 69A) and 2-[4-(chloromethyl)phenyl]-1,3-benzoxazole | LC-MS (Method 3): $R_t$ = 1.53 min; m/z = 648 (M + H)⁺. |
| 77A | ethyl 5-[(tert-butoxycarbonyl){2-[2-({4-[5-(trifluoromethoxy)-1,3-benzoxazol-2-yl]benzyl}oxy)-phenyl]ethyl}amino]-5,6,7,8-tetrahydroquinoline-2-carboxylate (Enantiomer 2)<br><br>from ethyl 5-{(tert-butoxycarbonyl)[2-(2-hydroxyphenyl)ethyl]amino}-5,6,7,8-tetrahydroquinoline-2-carboxylate (Enantiomer 2, Example 69A) and 2-[4-(chloromethyl)phenyl]-5-(trifluoromethoxy)-1,3-benzoxazole | LC-MS (Method 3): $R_t$ = 1.63 min; m/z = 732 (M + H)⁺. |

| Example | Name/Structure/Starting materials | Analytical data |
|---|---|---|
| 78A | ethyl 5-{(tert-butoxycarbonyl)[2-(2-{[4-(5-cyano-1,3-benzoxazol-2-yl)benzyl]oxy}phenyl)-ethyl]amino}-5,6,7,8-tetrahydroquinoline-2-carboxylate (Enantiomer 2)<br>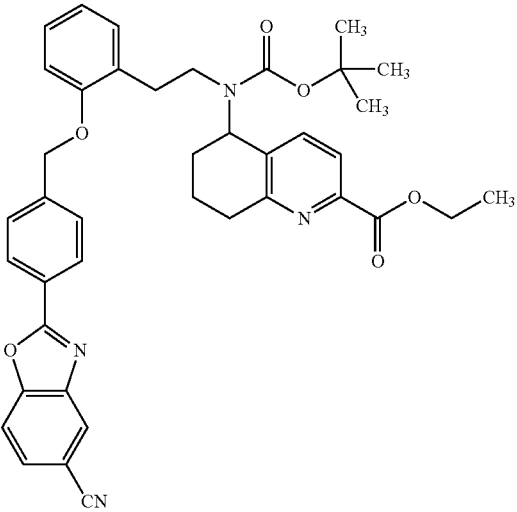 [SMILES: CCOC(=O)c1ccc2c(n1)CCCC2N(CCc1ccccc1OCc1ccc(-c2nc3cc(C#N)ccc3o2)cc1)C(=O)OC(C)(C)C]<br>from ethyl 5-{(tert-butoxycarbonyl)[2-(2-hydroxyphenyl)ethyl]amino}-5,6,7,8-tetrahydroquinoline-2-carboxylate (Enantiomer 2, Example 69A) and 2-[4-(chloromethyl)phenyl]-1,3-benzoxazole-5-carbonitrile [CAS Reg.-Nr. 885050-65-7] | LC-MS (Method 3):<br>$R_t$ = 1.47 min; m/z = 673 (M + H)$^+$. |
| 79A | ethyl 5-{(tert-butoxycarbonyl)[2-(2-{[4-(2-phenylethyl)benzyl]oxy}phenyl)ethyl]amino}-5,6,7,8-tetrahydroquinoline-2-carboxylate (Enantiomer 2)<br>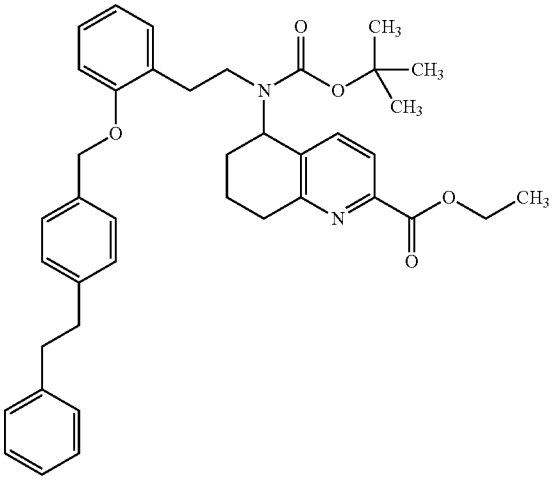 [SMILES: CCOC(=O)c1ccc2c(n1)CCCC2N(CCc1ccccc1OCc1ccc(CCc2ccccc2)cc1)C(=O)OC(C)(C)C]<br>from ethyl 5-{(tert-butoxycarbonyl)[2-(2-hydroxyphenyl)ethyl]amino}-5,6,7,8-tetrahydroquinoline-2-carboxylate (Enantiomer 2, Example 69A) and 1-(chloromethyl)-4-(2-phenylethyl)benzene | LC-MS (Method 3):<br>$R_t$ = 1.58 min; m/z = 635 (M + H)$^+$. |

Example 80A

Ethyl 5-{[2-(2-{[3-chloro-4'-(trifluoromethyl)biphenyl-4-yl]methoxy}phenyl)ethyl]amino}-5,6,7,8-tetrahydroquinoline-2-carboxylate dihydrochloride (Enantiomer 2)

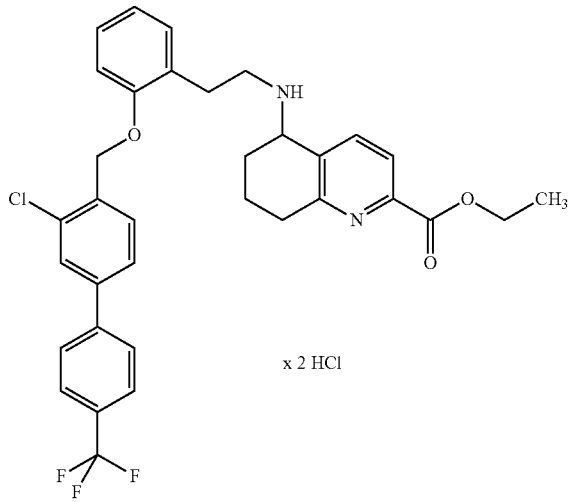 [SMILES: CCOC(=O)c1ccc2c(n1)CCCC2NCCc1ccccc1OCc1ccc(-c2ccc(C(F)(F)F)cc2)cc1Cl]

x 2 HCl 557 ml of a 4 N solution of hydrogen chloride in dioxane, diluted with a further 389 ml of dioxane, were added to 79 g (111.39 mmol) of ethyl 5-{(tert-butoxycarbonyl)[2-(2-{[3-chloro-4'-(trifluoromethyl)biphenyl-4-yl]methoxy}phenyl)ethyl]amino}-5,6,7,8-tetrahydroquinoline-2-carboxylate (Enantiomer 2, Example 74A), and the mixture was stirred at room temperature overnight. The reaction solution was then concentrated to dryness and the residue was dried under high vacuum overnight. This gave 78 g (111.39 mmol, about 100% of theory) of the target product.

LC-MS (Method 3): $R_t$=1.07 min; m/z=609/611 (M+H)$^+$.

Analogously to Example 80A, the following compounds were prepared:

| Example | Name/Structure/Starting material | Analytical data |
|---|---|---|
| 81A | ethyl 5-({2-[2-({4-[5-(trifluoromethyl)-1,3-benzoxazol-2-yl]benzyl}oxy)phenyl]ethyl}amino)-5,6,7,8-tetrahydroquinoline-2-carboxylate dihydrochloride (Enantiomer 2) | LC-MS (Method 3): $R_t$ = 1.01 min; m/z = 616 (M + H)$^+$. |

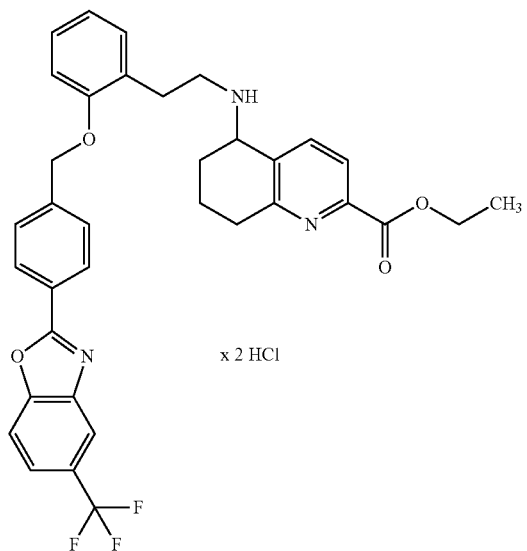 [SMILES: CCOC(=O)c1ccc2c(n1)CCCC2NCCc1ccccc1OCc1ccc(-c2nc3cc(C(F)(F)F)ccc3o2)cc1]

x 2 HCl from ethyl 5-[(tert-butoxycarbonyl){2-[2-({4-[5-(trifluoromethyl)-1,3-benzoxazol-2-yl]benzyl}oxy)phenyl]ethyl}amino]-5,6,7,8-tetrahydroquinoline-2-carboxylate (Enantiomer 2)

| Example | Name/Structure/Starting material | Analytical data |
|---|---|---|
| 82A | ethyl 5-{[2-(2-{[4-(1,3-benzoxazol-2-yl)benzyl]-oxy}phenyl)ethyl]amino}-5,6,7,8-tetrahydro-quinoline-2-carboxylate dihydrochloride (Enantiomer 2)<br>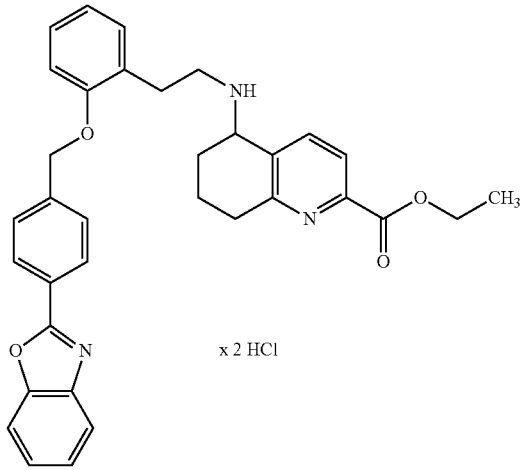 [SMILES: CCOC(=O)c1ccc2c(n1)CCCC2NCCc1ccccc1OCc1ccc(-c2nc3ccccc3o2)cc1]<br>x 2 HCl<br>from ethyl 5-{[2-(2-{[4-(1,3-benzoxazol-2-yl)-benzyl]oxy}phenyl)ethyl](tert-butoxycarbonyl)-amino}-5,6,7,8-tetrahydroquinoline-2-carboxylate (Enantiomer 2) | |
| 83A | ethyl 5-({2-[2-({4-[5-(trifluoromethoxy)-1,3-benzoxazol-2-yl]benzyl}oxy)phenyl]ethyl}amino)-5,6,7,8-tetrahydroquinoline-2-carboxylate dihydrochloride (Enantiomer 2)<br>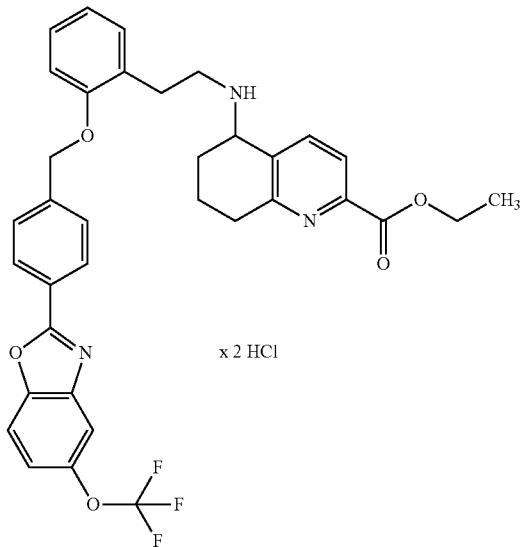 [SMILES: CCOC(=O)c1ccc2c(n1)CCCC2NCCc1ccccc1OCc1ccc(-c2nc3cc(OC(F)(F)F)ccc3o2)cc1]<br>x 2 HCl<br>from ethyl 5-[(tert-butoxycarbonyl){2-[2-({4-[5-(trifluoromethoxy)-1,3-benzoxazol-2-yl]benzyl}-oxy)phenyl]ethyl}amino]-5,6,7,8-tetrahydro-quinoline-2-carboxylate (Enantiomer 2) | LC-MS (Method 3):<br>$R_t$ = 1.01 min; m/z = 632 $(M + H)^+$. |

| Example | Name/Structure/Starting material | Analytical data |
|---|---|---|
| 84A | ethyl 5-{[2-(2-{[4-(5-cyano-1,3-benzoxazol-2-yl)-benzyl]oxy}phenyl)ethyl]amino}-5,6,7,8-tetra-hydroquinoline-2-carboxylate dihydrochloride (Enantiomer 2)<br>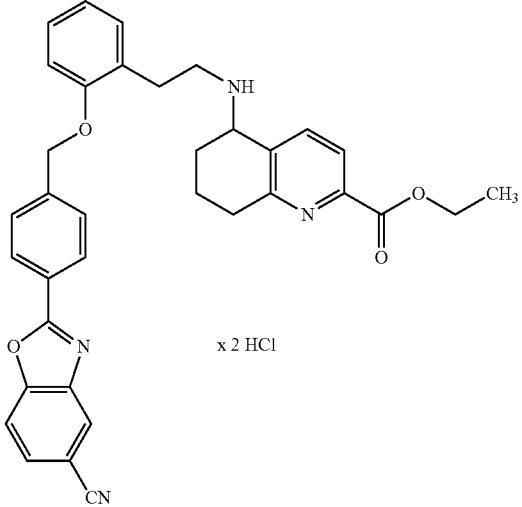 [SMILES: CCOC(=O)c1ccc2c(n1)CCCC2NCCc1ccccc1OCc1ccc(-c2nc3cc(C#N)ccc3o2)cc1]<br>x 2 HCl<br>from ethyl 5-{(tert-butoxycarbonyl)[2-(2-{[4-(5-cyano-1,3-benzoxazol-2-yl)benzyl]oxy}-phenyl)ethyl]amino}-5,6,7,8-tetrahydroquinoline-2-carboxylate (Enantiomer 2) | LC-MS (Method 3):<br>$R_t$ = 0.92 min; m/z = 573 (M + H)$^+$. |
| 85A | ethyl 5-{[2-(2-{[4-(2-phenylethyl)benzyl]oxy}-phenyl)ethyl]amino}-5,6,7,8-tetrahydroquinoline-2-carboxylate dihydrochloride (Enantiomer 2)<br>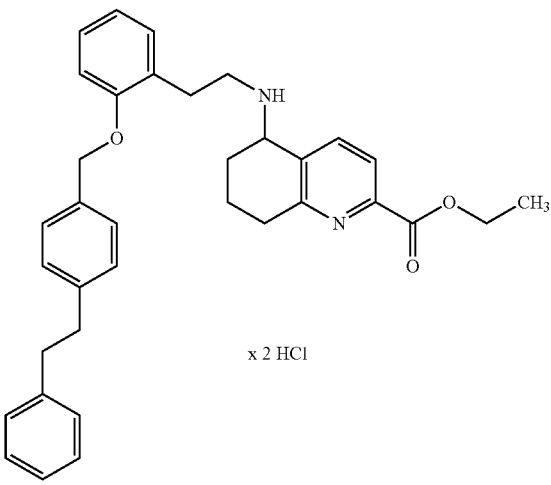 [SMILES: CCOC(=O)c1ccc2c(n1)CCCC2NCCc1ccccc1OCc1ccc(CCc2ccccc2)cc1]<br>x 2 HCl<br>from ethyl 5-{(tert-butoxycarbonyl)[2-(2-{[4-(2-phenylethyl)benzyl]oxy}phenyl)ethyl]amino}-5,6,7,8-tetrahydroquinoline-2-carboxylate (Enantiomer 2) | LC-MS (Method 3):<br>$R_t$ = 1.03 min; m/z = 535 (M + H)$^+$. |

Example 86A

Ethyl 5-{[2-(2-{[3-chloro-4'-(trifluoromethyl)biphenyl-4-yl]methoxy}phenyl)ethyl]amino}-5,6,7,8-tetrahydroquinoline-2-carboxylate (Enantiomer 2)

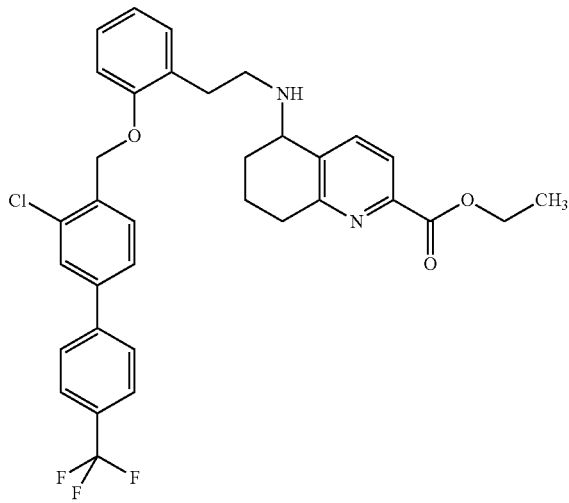 [SMILES: CCOC(=O)c1ccc2c(n1)CCCC2NCCc1ccccc1OCc1ccc(-c2ccc(C(F)(F)F)cc2)cc1Cl]

78 g (111.39 mmol) of ethyl 5-{[2-(2-{[3-chloro-4'-(trifluoromethyl)biphenyl-4-yl]methoxy}-phenyl)ethyl]amino}-5,6,7,8-tetrahydroquinoline-2-carboxylate dihydrochloride (Enantiomer 2, Example 80A) were taken up in 1200 ml of THF, 47 ml of triethylamine were added and the mixture was stirred at room temperature for 1 h. The precipitated triethylammonium chloride crystals were then filtered off and washed with THF. The filtrate obtained was evaporated to dryness. The residue was dissolved in ethyl acetate, washed twice with 10% strength aqueous sodium chloride solution, dried over magnesium sulphate, filtered and once more evaporated to dryness. This gave 69 g (111.24 mmol, 99.9% of theory) of the target compound.

LC-MS (Method 3): $R_t$=1.07 min; m/z=609/611 (M+H)$^+$.

$^1$H-NMR (400 MHz, DMSO-$d_6$, δ/ppm): 1.27 (t, 3H), 1.59-1.71 (m, 2H), 1.76-1.87 (m, 1H), 1.87-1.95 (m, 1H), 1.96-2.06 (m, 1H), 2.66-2.89 (m, 6H), 3.75 (br. s, 1H), 4.27 (q, 2H), 5.19 (s, 2H), 6.91 (t, 1H), 7.07 (d, 1H), 7.16-7.27 (m, 2H), 7.65-7.77 (m, 3H), 7.83 (d, 3H), 7.88 (s, 1H), 7.94 (d, 2H).

Analogously to Example 86A, the following compounds were prepared:

| Example | Name/Structure/Starting material | Analytical data |
|---|---|---|
| 87A | ethyl 5-({2-[2-({4-[5-(trifluoromethyl)-1,3-benzoxazol-2-yl]benzyl}oxy)phenyl]ethyl}amino)-5,6,7,8-tetrahydroquinoline-2-carboxylate (Enantiomer 2)<br>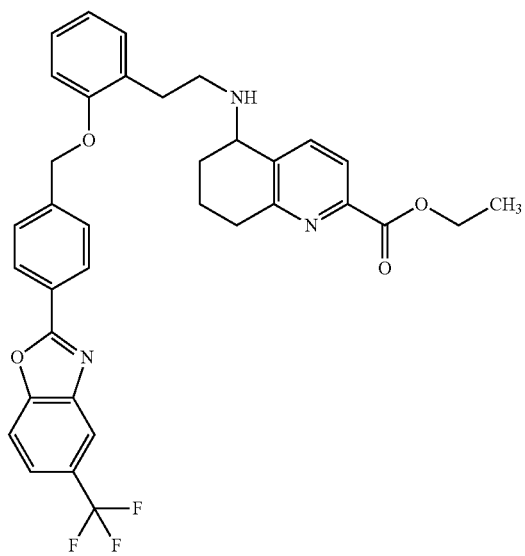 [SMILES: CCOC(=O)c1ccc2c(n1)CCCC2NCCc1ccccc1OCc1ccc(-c2nc3cc(C(F)(F)F)ccc3o2)cc1]<br>from ethyl 5-({2-[2-({4-[5-(trifluoromethyl)-1,3-benzoxazol-2-yl]benzyl}oxy)phenyl]ethyl}amino)-5,6,7,8-tetrahydroquinoline-2-carboxylate dihydrochloride (Enantiomer 2, Example 81A) | LC-MS (Method 3):<br>$R_t$ = 1.06 min; m/z = 616 (M + H)$^+$.<br>$^1$H-NMR (400 MHz, DMSO-$d_6$, δ/ppm): 1.27 (t, 3H), 1.61-1.79 (m, 2H), 1.81-2.03 (m, 3H), 2.72-2.92 (m, 6H), 3.73-3.86 (m, 1H), 4.27 (q, 2H), 5.24 (s, 2H), 6.90 (t, 1H), 7.05 (d, 1H), 7.15-7.27 (m, 2H), 7.69 (d, 1H), 7.73 (d, 1H), 7.82 (d, 1H), 7.87 (d, 1H), 8.04 (d, 1H), 8.18-8.30 (m, 3H). |

| Example | Name/Structure/Starting material | Analytical data |
|---|---|---|
| 88A | ethyl 5-{[2-(2-{[4-(1,3-benzoxazol-2-yl)benzyl]-oxy}phenyl)ethyl]amino}-5,6,7,8-tetrahydro-quinoline-2-carboxylate (Enantiomer 2) 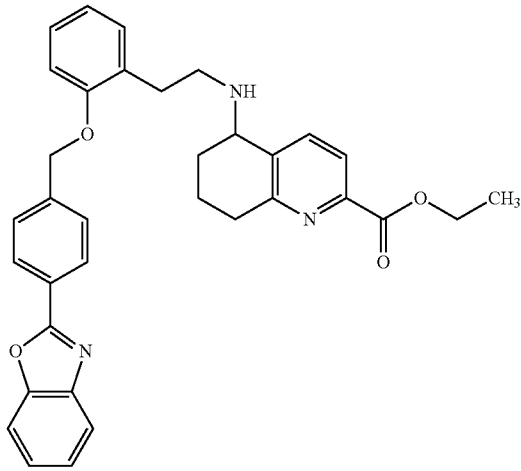 [SMILES: CCOC(=O)c1ccc2c(n1)CCCC2NCCc1ccccc1OCc1ccc(-c2nc3ccccc3o2)cc1] from ethyl 5-{[2-(2-{[4-(1,3-benzoxazol-2-yl)-benzyl]oxy}phenyl)ethyl]amino}-5,6,7,8-tetrahydroquinoline-2-carboxylate dihydrochloride (Enantiomer 2, Example 82A) | |
| 89A | ethyl 5-({2-[2-({4-[5-(trifluoromethoxy)-1,3-benzoxazol-2-yl]benzyl}oxy)phenyl]ethyl}amino)-5,6,7,8-tetrahydroquinoline-2-carboxylate (Enantiomer 2) 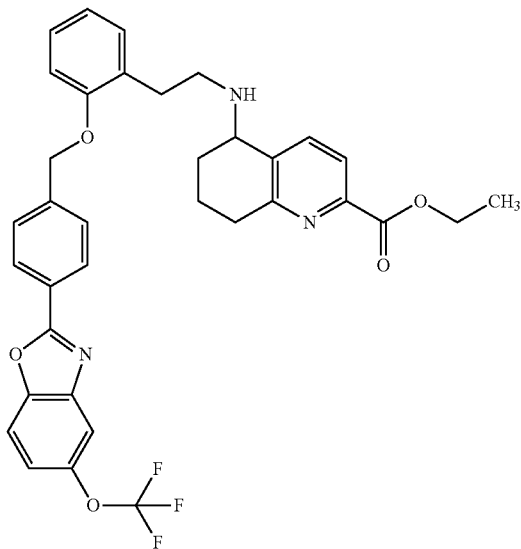 [SMILES: CCOC(=O)c1ccc2c(n1)CCCC2NCCc1ccccc1OCc1ccc(-c2nc3cc(OC(F)(F)F)ccc3o2)cc1] from ethyl 5-({2-[2-({4-[5-(trifluoromethoxy)-1,3-benzoxazol-2-yl]benzyl}oxy)phenyl]ethyl}amino)-5,6,7,8-tetrahydroquinoline-2-carboxylate dihydrochloride (Enantiomer 2, Example 83A) | LC-MS (Method 3): $R_t$ = 1.09 min; m/z = 632 $(M + H)^+$. |

| Example | Name/Structure/Starting material | Analytical data |
|---|---|---|
| 90A | ethyl 5-{[2-(2-{[4-(5-cyano-1,3-benzoxazol-2-yl)-benzyl]oxy}phenyl)ethyl]amino}-5,6,7,8-tetrahydroquinoline-2-carboxylate (Enantiomer 2)<br>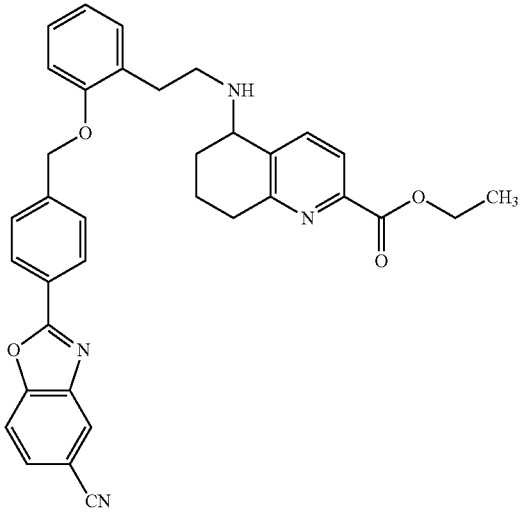 [SMILES: CCOC(=O)c1ccc2c(n1)CCCC2NCCc1ccccc1OCc1ccc(-c2nc3cc(C#N)ccc3o2)cc1]<br>from ethyl 5-{[2-(2-{[4-(5-cyano-1,3-benzoxazol-2-yl)benzyl]oxy}phenyl)ethyl]amino}-5,6,7,8-tetrahydroquinoline-2-carboxylate dihydrochloride (Enantiomer 2, Example 84A) | LC-MS (Method 3):<br>$R_t$ = 0.93 min; m/z = 573 $(M + H)^+$.<br>$^1$H-NMR (400 MHz, DMSO-$d_6$, δ/ppm): 1.27 (t, 3H), 1.62-1.76 (m, 2H), 1.81-2.02 (m, 2H), 2.02-2.13 (m, 1H), 2.69-2.91 (m, 6H), 3.78 (br. s, 1H), 4.27 (q, 2H), 5.24 (s, 2H), 6.90 (t, 1H), 7.05 (d, 1H), 7.14-7.26 (m, 2H), 7.65-7.77 (m, 3H), 7.83-7.95 (m, 2H), 8.03 (d, 1H), 8.22 (d, 2H), 8.43 (d, 1H). |
| 91A | ethyl 5-{[2-(2-{[4-(2-phenylethyl)benzyl]oxy}-phenyl)ethyl]amino}-5,6,7,8-tetrahydroquinoline-2-carboxylate (Enantiomer 2)<br>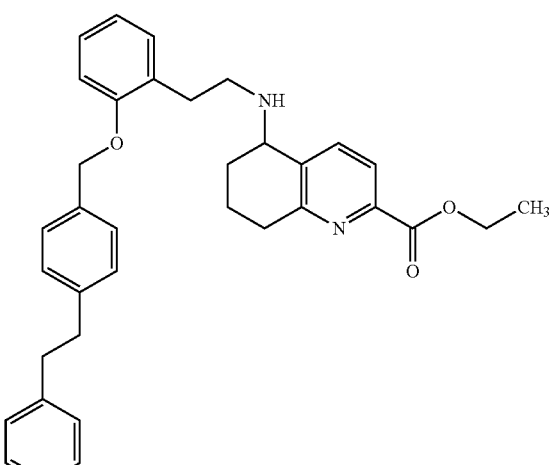<br>from ethyl 5-{[2-(2-{[4-(2-phenylethyl)benzyl]oxy}-phenyl)ethyl]amino}-5,6,7,8-tetrahydroquinoline-2-carboxylate dihydrochloride (Enantiomer 2, Example 85A) | LC-MS (Method 3):<br>$R_t$ = 1.02 min; m/z = 535 $(M + H)^+$. |

Example 92A

Ethyl 5-([2-(2-{[3-chloro-4'-(trifluoromethyl)biphenyl-4-yl]methoxy}phenyl)ethyl]{2-[4-(methoxycarbonyl)phenyl]ethyl}amino)-5,6,7,8-tetrahydroquinoline-2-carboxylate (Enantiomer 2)

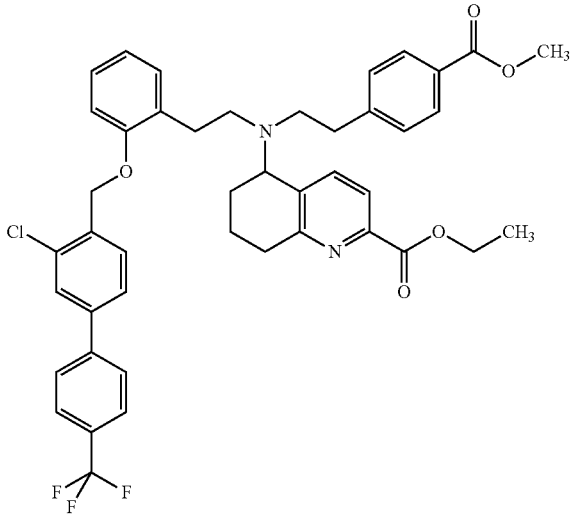 [SMILES: CCOC(=O)c1ccc2c(n1)CCCC2N(CCc1ccc(C(=O)OC)cc1)CCc1ccccc1OCc1ccc(-c2ccc(C(F)(F)F)cc2)cc1Cl]

A suspension of 69 g (111.24 mmol) of ethyl 5-{[2-(2-{[3-chloro-4'-(trifluoromethyl)biphenyl-4-yl]methoxy}phenyl)ethyl]amino}-5,6,7,8-tetrahydroquinoline-2-carboxylate (Enantiomer 2, Example 86A), 129 g (444.98 mmol) of methyl 4-(2-iodoethyl)benzoate and 17.68 g (166.87 mmol) of anhydrous sodium carbonate in 1500 ml of dry acetonitrile was stirred at a bath temperature of 110° C. overnight. A further 65.54 g of methyl 4-(2-iodoethyl)benzoate and 23.06 g (166.87 mmol) of powdered potassium carbonate were then added, and the mixture was heated under reflux for another 48 h. After cooling of the reaction mixture, the inorganic salts were filtered off and the filtrate obtained was evaporated to dryness. The resulting residue was taken up in ethyl acetate, washed twice with 10% strength aqueous sodium chloride solution, dried over magnesium sulphate, filtered and then once more evaporated to dryness. The residue obtained was purified chromatographically on silica gel (3 kg) (mobile phase: petroleum ether/ethyl acetate 8:2→7:3).

This gave 42 g (54.45 mmol, 49% of theory) of the target compound.

LC-MS (Method 3): $R_t$=1.69 min; m/z=771/773 $(M+H)^+$.
$^1$H-NMR (400 MHz, DMSO-$d_6$, δ/ppm): 1.27 (t, 3H), 1.37-1.52 (m, 1H), 1.52-1.67 (m, 1H), 1.85-1.95 (m, 1H), 1.96-2.05 (m, 1H), 2.56-2.79 (m, 10H), 3.80 (s, 3H), 3.97-4.09 (m, 1H), 4.26 (q, 2H), 5.07 (m, 2H), 6.88 (t, 1H), 7.01-7.16 (m, 4H), 7.24 (t, 1H), 7.36-7.48 (m, 2H), 7.53 (d, 1H), 7.61 (d, 1H), 7.74 (d, 2H), 7.77-7.88 (m, 5H).

Analogously to Example 92A, the following compounds were prepared:

| Example | Name/Structure/Starting materials | Analytical data |
|---|---|---|
| 93A | ethyl 5-({2-[4-(methoxycarbonyl)phenyl]ethyl}-{2-[2-({4-[5-(trifluoromethyl)-1,3-benzoxazol-2-yl]benzyl}oxy)phenyl]ethyl}amino)-5,6,7,8-tetrahydroquinoline-2-carboxylate (Enantiomer 2)<br><br>from ethyl 5-({2-[2-({4-[5-(trifluoromethyl)-1,3-benzoxazol-2-yl]benzyl}oxy)phenyl]ethyl}-amino)-5,6,7,8-tetrahydroquinoline-2-carboxylate (Enantiomer 2, Example 87A) and methyl 4-(2-iodoethyl)benzoate | LC-MS (Method 3): $R_t$ = 1.63 min; m/z = 778 $(M + H)^+$.<br>$^1$H-NMR (400 MHz, DMSO-$d_6$, δ/ppm): 1.26 (t, 3H), 1.43-1.55 (m, 1H), 1.56-1.69 (m, 1H), 1.89-2.09 (m, 2H), 2.58-2.86 (m, 10H), 3.74 (s, 3H), 4.03-4.12 (m, 1H), 4.26 (q, 2H), 5.02-5.20 (m, 2H), 6.86 (t, 1H), 7.00-7.14 (m, 4H), 7.16-7.26 (m, 1H), 7.44 (d, 1H), 7.49-7.60 (m, 3H), 7.72 (d, 2H), 7.82 (d, 1H), 8.01 (d, 1H), 8.13 (d, 2H), 8.23 (s, 1H). |

| Example | Name/Structure/Starting materials | Analytical data |
|---|---|---|
| 94A | ethyl 5-([2-(2-{[4-(1,3-benzoxazol-2-yl)benzyl]-oxy}phenyl)ethyl]{2-[4-(methoxycarbonyl)-phenyl]ethyl}amino)-5,6,7,8-tetrahydroquinoline-2-carboxylate (Enantiomer 2)<br>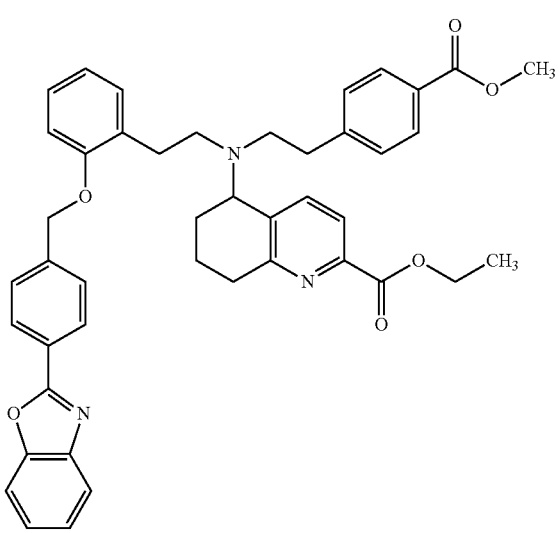<br>from ethyl 5-{[2-(2-{[4-(1,3-benzoxazol-2-yl)-benzyl]oxy}phenyl)ethyl]amino}-5,6,7,8-tetra-hydroquinoline-2-carboxylate (Enantiomer 2, Example 88A) and methyl 4-(2-iodoethyl)benzoate | LC-MS (Method 3):<br>$R_t$ = 1.55 min; m/z = 710 $(M + H)^+$.<br>$^1$H-NMR (400 MHz, DMSO-$d_6$, δ/ppm): 1.26 (t, 3H), 1.41-1.55 (m, 1H), 1.55-1.71 (m, 1H), 1.89-2.08 (m, 2H), 2.58-2.84 (m, 10H), 3.76 (s, 3H), 4.03-4.13 (m, 1H), 4.26 (q, 2H), 5.03-5.16 (m, 2H), 6.86 (t, 1H), 6.99-7.09 (m, 2H), 7.13 (d, 2H), 7.21 (t, 1H), 7.38-7.46 (m, 3H), 7.49-7.57 (m, 3H), 7.73 (d, 2H), 7.77-7.85 (m, 2H), 8.11 (d, 2H). |
| 95A | ethyl 5-({2-[4-(methoxycarbonyl)phenyl]ethyl}-{2-[2-({4-[5-(trifluoromethoxy)-1,3-benzoxazol-2-yl]benzyl}oxy)phenyl]ethyl}amino)-5,6,7,8-tetrahydroquinoline-2-carboxylate (Enantiomer 2)<br>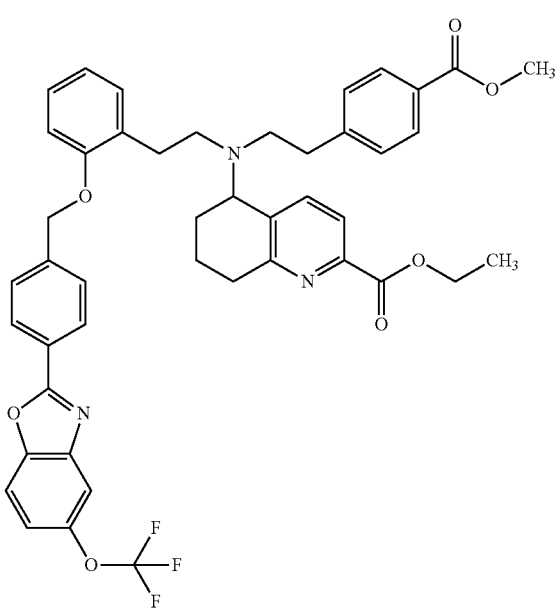<br>from ethyl 5-({2-[2-({4-[5-(trifluoromethoxy)-1,3-benzoxazol-2-yl]benzyl}oxy)phenyl]ethyl}-amino)-5,6,7,8-tetrahydroquinoline-2-carboxylate (Enantiomer 2, Example 89A) and methyl 4-(2-iodoethyl)benzoate | LC-MS (Method 3):<br>$R_t$ = 1.66 min; m/z = 794 $(M + H)^+$.<br>$^1$H-NMR (400 MHz, DMSO-$d_6$, δ/ppm): 1.26 (t, 3H), 1.42-1.55 (m, 1H), 1.55-1.70 (m, 1H), 1.89-2.08 (m, 2H), 2.57-2.85 (m, 10H), 3.75 (s, 3H), 4.02-4.12 (m, 1H), 4.25 (q, 2H), 5.05-5.15 (m, 2H), 6.86 (t, 1H), 7.03 (d, 1H), 7.06-7.15 (m, 3H), 7.21 (t, 1H), 7.40-7.50 (m, 2H), 7.50-7.58 (m, 3H), 7.73 (d, 2H), 7.87-7.95 (m, 2H), 8.10 (d, 2H). |

| Example | Name/Structure/Starting materials | Analytical data |
|---|---|---|
| 96A | ethyl 5-([2-(2-{[4-(5-cyano-1,3-benzoxazol-2-yl)-benzyl]oxy}phenyl)ethyl]{2-[4-(methoxycarbonyl)-phenyl]ethyl}amino)-5,6,7,8-tetrahydroquinoline-2-carboxylate (Enantiomer 2)<br>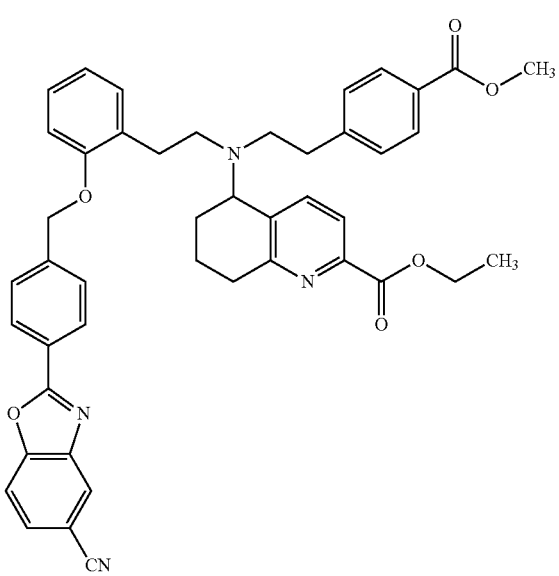<br>from ethyl 5-{[2-(2-{[4-(5-cyano-1,3-benzoxazol-2-yl)benzyl]oxy}phenyl)ethyl]amino}-5,6,7,8-tetrahydroquinoline-2-carboxylate (Enantiomer 2, Example 90A) and methyl 4-(2-iodoethyl)benzoate | LC-MS (Method 3):<br>$R_t$ = 1.50 min; m/z = 735 $(M + H)^+$.<br>$^1$H-NMR (400 MHz, DMSO-$d_6$, δ/ppm): 1.26 (t, 3H), 1.41-1.55 (m, 1H), 1.55-1.71 (m, 1H), 1.89-2.10 (m, 2H), 2.58-2.86 (m, 10H), 3.75 (s, 3H), 4.00-4.13 (m, 1H), 4.25 (q, 2H), 5.03-5.17 (m, 2H), 6.87 (t, 1H), 6.99-7.14 (m, 4H), 7.21 (t, 1H), 7.44 (d, 1H), 7.49-7.60 (m, 3H), 7.71 (d, 2H), 7.92 (d, 1H), 8.00 (d, 1H), 8.12 (d, 2H), 8.42 (s, 1H). |
| 97A | ethyl 5-({2-[4-(methoxycarbonyl)phenyl]ethyl}-[2-(2-{[4-(2-phenylethyl)benzyl]oxy}phenyl)ethyl]-amino)-5,6,7,8-tetrahydroquinoline-2-carboxylate (Enantiomer 2)<br>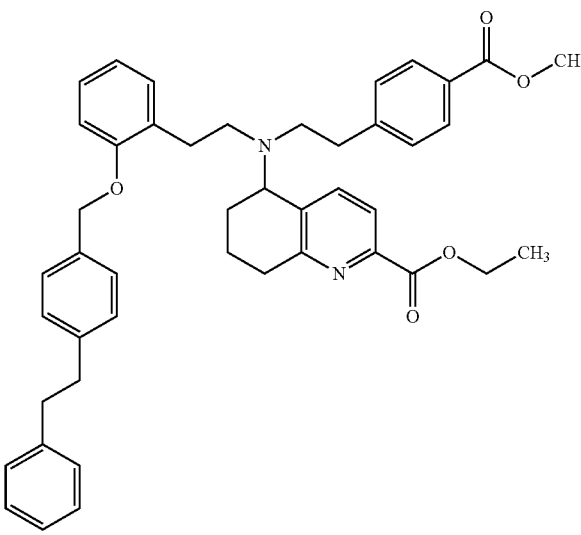<br>from ethyl 5-{[2-(2-{[4-(2-phenylethyl)benzyl]oxy}-phenyl)ethyl]amino}-5,6,7,8-tetrahydroquinoline-2-carboxylate (Enantiomer 2, Example 91A) and methyl 4-(2-iodoethyl)benzoate | LC-MS (Method 3):<br>$R_t$ = 1.58 min; m/z = 697 $(M + H)^+$.<br>$^1$H-NMR (400MHz, DMSO-$d_6$, δ/ppm): 1.29 (t, 3H), 1.40-1.53 (m, 1H), 1.53-1.68 (m, 1H), 1.88-2.06 (m, 2H), 2.57-2.87 (m, 14H), 3.83 (s, 3H), 4.01-4.10 (m, 1H), 4.29 (q, 2H), 4.91 (q, 2H), 6.83 (t, 1H), 6.95-7.07 (m, 2H), 7.10-7.22 (m, 10H), 7.23-7.29 (m, 2H), 7.40 (d, 1H), 7.46 (d, 1H), 7.80 (d, 2H). |

Analogously to Examples 35A and 36A, the following compounds were prepared:

| Example | Name/Structure/Starting materials | Analytical data |
|---|---|---|
| 98A | ethyl 5-[(5-ethoxy-5-oxopentyl){2-[2-({4-[5-(trifluoromethyl)-1,3-benzoxazol-2-yl]benzyl}oxy)-phenyl]ethyl}amino]-5,6,7,8-tetrahydroquinoline-2-carboxylate (Enantiomer 2)<br><br>from ethyl 5-({2-[2-({4-[5-(trifluoromethyl)-1,3-benzoxazol-2-yl]benzyl}oxy)phenyl]ethyl}amino)-5,6,7,8-tetrahydroquinoline-2-carboxylate (Enantiomer 2, Example 87A) and ethyl 5-bromopentanoate | LC-MS (Method 3): $R_t$ = 1.39 min; m/z = 7.44 $(M + H)^+$.<br>$^1$H-NMR (400 MHz, DMSO-$d_6$, δ/ppm): 1.09 (t, 3H), 1.25 (t, 4H), 1.30-1.56 (m, 5H), 1.56-1.70 (m, 1H), 1.90-2.05 (m, 2H), 2.08-2.20 (m, 2H), 2.35-2.64 (m, 3H, partially obscured by DMSO signal), 2.65-2.89 (m, 4H), 3.90-4.03 (m, 3H), 4.26 (q, 2H), 5.05-5.18 (m, 2H), 6.87 (t, 1H), 7.00 (d, 1H), 7.10-7.22 (m, 2H), 7.57 (d, 2H), 7.66 (d, 1H), 7.79-7.91 (m, 2H), 8.04 (d, 1H), 8.20 (d, 2H), 8.26 (s, 1H). |
| 99A | ethyl 5-{[2-(2-{[4-(1,3-benzoxazol-2-yl)benzyl]-oxy}phenyl)ethyl](5-ethoxy-5-oxopentyl)amino}-5,6,7,8-tetrahydroquinoline-2-carboxylate (Enantiomer 2)<br><br>from ethyl 5-{[2-(2-{[4-(1,3-benzoxazol-2-yl)-benzyl]oxy}phenyl)ethyl]amino}-5,6,7,8-tetrahydro-quinoline-2-carboxylate (Enantiomer 2, Example 88A) and ethyl 5-bromopentanoate | LC-MS (Method 3): $R_t$ = 1.27 min; m/z = 676 $(M + H)^+$.<br>$^1$H-NMR (400 MHz, DMSO-$d_6$, δ/ppm): 1.10 (t, 3H), 1.26 (t, 4H), 1.31-1.57 (m, 5H), 1.58-1.71 (m, 1H), 1.90-2.05 (m, 2H), 2.10-2.20 (m, 2H), 2.35-2.64 (m, 3H, partially obscured by DMSO signal), 2.64-2.88 (m, 4H), 3.92-4.02 (m, 3H), 4.26 (q, 2H), 5.02-5.18 (m, 2H), 6.86 (t, 1H), 7.00 (d, 1H), 7.10-7.23 (m, 2H), 7.39-7.49 (m, 2H), 7.53 (d, 2H), 7.66 (d, 1H), 7.78-7.92 (m, 3H), 8.18 (d, 2H). |

-continued

| Example | Name/Structure/Starting materials | Analytical data |
|---|---|---|
| 100A | ethyl 5-[(5-ethoxy-5-oxopentyl){2-[2-({4-[5-(trifluoromethoxy)-1,3-benzoxazol-2-yl]benzyl}oxy)phenyl]ethyl}amino]-5,6,7,8-tetrahydroquinoline-2-carboxylate (Enantiomer 2) 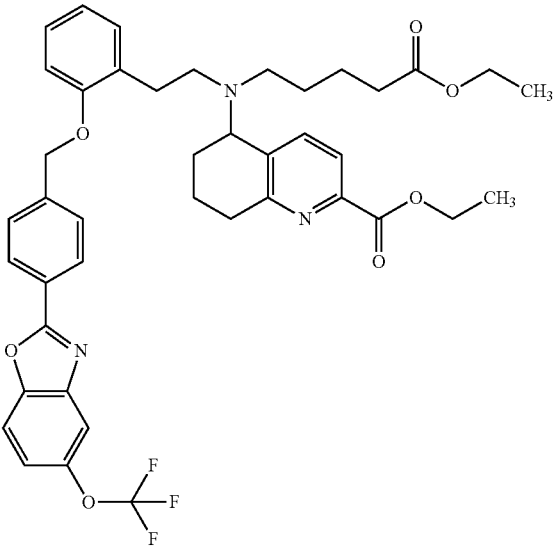 from ethyl 5-({2-[2-({4-[5-(trifluoromethoxy)-1,3-benzoxazol-2-yl]benzyl}oxy)phenyl]ethyl}amino)-5,6,7,8-tetrahydroquinoline-2-carboxylate (Enantiomer 2, Example 89A) and ethyl 5-bromopentanoate | LC-MS (Method 3): $R_t$ = 1.43 min; m/z = 760 $(M + H)^+$. $^1$H-NMR (400 MHz, DMSO-$d_6$, δ/ppm): 1.09 (t, 3H), 1.25 (t, 3H), 1.30-1.56 (m, 6H), 1.56-1.71 (m, 1H), 1.89-2.05 (m, 2H), 2.09-2.20 (m, 2H), 2.35-2.64 (m, 3H, partially obscured by DMSO signal), 2.65-2.88 (m, 4H), 3.90-4.03 (m, 3H), 4.27 (q, 2H), 5.04-5.18 (m, 2H), 6.88 (br. t, 1H), 7.00 (d, 1H), 7.09-7.23 (m, 2H), 7.47 (dd, 1H), 7.56 (d, 2H), 7.65 (d, 1H), 7.86 (d, 1H), 7.90-7.98 (m, 2H), 8.19 (d, 2H). |
| 101A | ethyl 5-{[2-(2-{[4-(5-cyano-1,3-benzoxazol-2-yl)benzyl]oxy}phenyl)ethyl](5-ethoxy-5-oxopentyl)amino}-5,6,7,8-tetrahydroquinoline-2-carboxylate (Enantiomer 2) 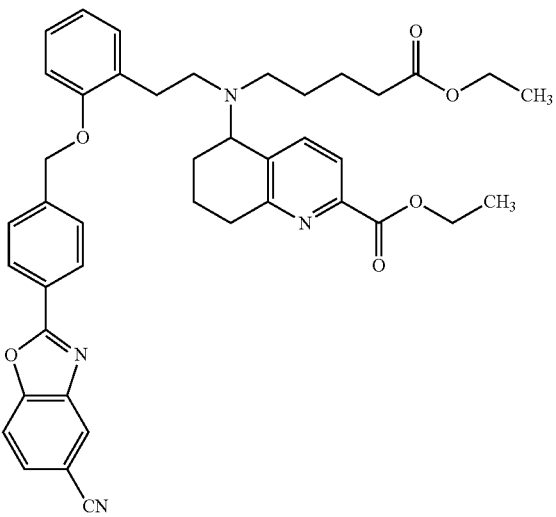 from ethyl 5-{[2-(2-{[4-(5-cyano-1,3-benzoxazol-2-yl)benzyl]oxy}phenyl)ethyl]amino}-5,6,7,8-tetrahydroquinoline-2-carboxylate (Enantiomer 2, Example 90A) and ethyl 5-bromopentanoate | LC-MS (Method 3): $R_t$ = 1.24 min; m/z = 701 $(M + H)^+$. $^1$H-NMR (400 MHz, DMSO-$d_6$, δ/ppm): 1.10 (t, 3H), 1.26 (t, 3H), 1.30-1.72 (m, 7H), 1.90-2.05 (m, 2H), 2.09-2.20 (m, 2H), 2.35-2.64 (m, 3H, partially obscured by DMSO signal), 2.65-2.88 (m, 4H), 3.91-4.02 (m, 3H), 4.26 (q, 2H), 5.11 (m, 2H), 6.87 (t, 1H), 6.99 (d, 1H), 7.10-7.24 (m, 2H), 7.56 (d, 2H), 7.65 (d, 1H), 7.87 (d, 1H), 7.93 (m, 1H), 8.04 (d, 1H), 8.19 (d, 2H), 8.44 (s, 1H). |

-continued

| Example | Name/Structure/Starting materials | Analytical data |
|---|---|---|
| 102A | ethyl 5-{[2-(2-{[4-(5-chloro-1,3-benzoxazol-2-yl)-benzyl]oxy}phenyl)ethyl](5-ethoxy-5-oxopentyl)-amino}-5,6,7,8-tetrahydroquinoline-2-carboxylate (Enantiomer 2)<br>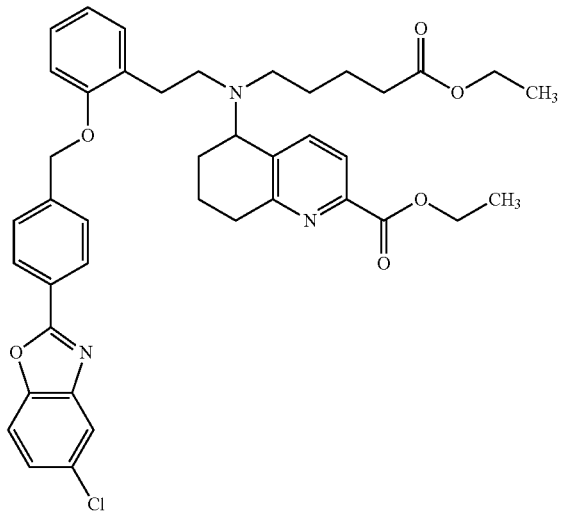<br>from ethyl 5-{[2-(2-{[4-(5-chloro-1,3-benzoxazol-2-yl)benzyl]oxy}phenyl)ethyl]amino}-5,6,7,8-tetrahydroquinoline-2-carboxylate (Enantiomer 2, Example 62A) and ethyl 5-bromopentanoate | LC-MS (Method 3):<br>$R_t$ = 1.39 min; m/z = 710/712 $(M + H)^+$. |

Example 103A rac-5-{[2-(5-Fluoro-2-methoxyphenyl)ethyl]amino}-5,6,7,8-tetrahydroquinoline-2-carbonitrile

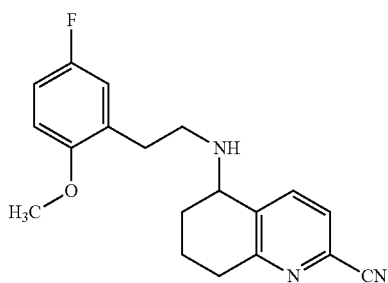 [SMILES: COc1ccc(F)cc1CCNC1CCCc2nc(C#N)ccc21]

21.98 g (127.66 mmol) of 5-oxo-5,6,7,8-tetrahydroquinoline-2-carbonitrile, 21.6 g (127.66 mmol) of 2-(5-fluoro-2-methoxyphenyl)ethanamine [CAS Reg.-No. 1000533-03-8] and 3.64 g (19.15 mmol) of p-toluenesulphonic acid monohydrate were dissolved in 511 ml of toluene, and the solution was stirred under reflux overnight using a water separator. 200 ml of toluene were then distilled off and, after cooling, replaced by fresh toluene. The reaction solution was then evaporated to dryness and the resulting residue was taken up in 511 ml of anhydrous ethanol and 511 ml of anhydrous THF. With stirring at a temperature of from 15° to 20° C., 9.66 g (255.32 mmol) of sodium borohydride were added a little at a time to the solution (careful: reaction mixture foams). The reaction solution was then stirred at the same temperature overnight. 10% strength aqueous sodium chloride solution was then added carefully, and the reaction mixture was extracted twice with ethyl acetate. The combined organic phases were dried over sodium sulphate, filtered and then concentrated to dryness. The residue obtained in this manner was purified by column chromatography on silica gel (mobile phase: cyclohexane/ethyl acetate 2:1). This gave 19.5 g (59.93 mmol, 46% of theory) of the target compound.

LC-MS (Method 2): $R_t$=1.55 min; m/z=326 $(M+H)^+$.

$^1$H-NMR (400 MHz, DMSO-$d_6$, δ/ppm): 1.63-1.81 (m, 2H), 1.84-2.04 (m, 2H), 2.12 (br. s, 1H), 2.63-2.93 (m, 6H), 3.74 (s, 3H), 3.80 (br. s, 1H), 6.87-7.08 (m, 3H), 7.78 (d, 1H), 7.94 (d, 1H).

Example 104A rac-5-{[2-(5-Fluoro-2-hydroxyphenyl)ethyl]amino}-5,6,7,8-tetrahydroquinoline-2-carboxylic acid

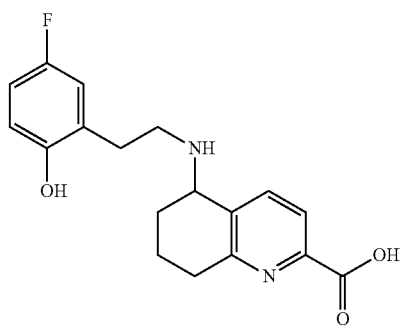 [SMILES: O=C(O)c1ccc2c(n1)CCCC2NCCc1cc(F)ccc1O]

72.8 g (223.73 mmol) of rac-5-{[2-(5-fluoro-2-methoxyphenyl)ethyl]amino}-5,6,7,8-tetrahydroquinoline-2-carbonitrile were taken up in 360 ml of hydrobromic acid (48% in water) and initially stirred at boiling point for 12 h, then cooled to room temperature and allowed to stand at this temperature overnight. The reaction solution was then diluted with 400 ml of water and adjusted to pH 6 using saturated sodium bicarbonate solution. The crystals formed were filtered off with suction, washed with water and dried under reduced pressure at 50° C. This gave 59 g (178.59 mmol, 80% of theory) of the target compound.

LC-MS (Method 2): $R_t$=1.30 min; m/z=331 (M+H)$^+$.

Example 105A rac-Ethyl 5-{[2-(5-fluoro-2-hydroxyphenyl)ethyl]amino}-5,6,7,8-tetrahydroquinoline-2-carboxylate

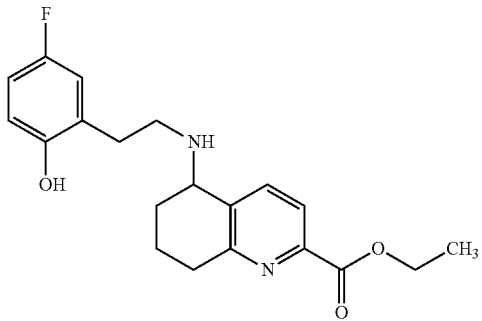 [SMILES: CCOC(=O)c1ccc2c(n1)CCCC2NCCc1cc(F)ccc1O]

40 ml of anhydrous ethanol and 4 ml of a 4 N solution of hydrogen chloride in dioxane were added to 1.93 g (5.84 mmol) of rac-5-{[2-(5-fluoro-2-hydroxyphenyl)ethyl]amino}-5,6,7,8-tetrahydroquinoline-2-carboxylic acid, and the mixture was stirred under reflux overnight. The reaction solution was then cooled to room temperature, and first ethyl acetate and then, slowly, saturated aqueous sodium bicarbonate solution were added. The organic phase was separated off, dried over magnesium sulphate, filtered and concentrated to dryness. This gave 1.67 g (4.66 mmol, 80% of theory) of the target compound.

LC-MS (Method 3): $R_t$=0.60 min; m/z=359 (M+H)$^+$.

$^1$H-NMR (400 MHz, DMSO-d$_6$, δ/ppm): 1.32 (t, 3H), 1.69-1.82 (m, 2H), 1.83-1.93 (m, 1H), 1.94-2.08 (m, 1H), 2.64-2.77 (m, 4H), 2.79-2.91 (m, 2H), 3.81-3.90 (m, 1H), 4.33 (q, 2H), 6.68-6.75 (m, 1H), 6.77-6.85 (m, 1H), 6.87-6.94 (m, 1H), 7.83 (d, 1H), 7.91 (d, 1H), 10.56-10.73 (m, 1H).

Example 106A rac-Ethyl 5-{(tert-butoxycarbonyl)[2-(5-fluoro-2-hydroxyphenyl)ethyl]amino}-5,6,7,8-tetrahydroquinoline-2-carboxylate

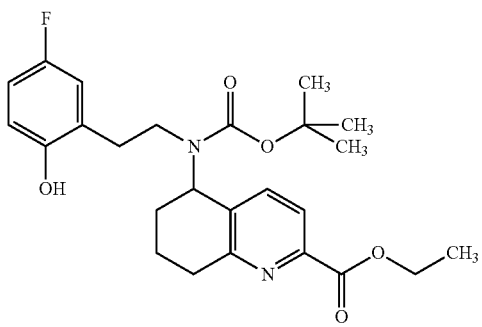 [SMILES: CCOC(=O)c1ccc2c(n1)CCCC2N(CCc1cc(F)ccc1O)C(=O)OC(C)(C)C]

3.73 g (10.41 mmol) of rac-ethyl 5-{[2-(5-fluoro-2-hydroxyphenyl)ethyl]amino}-5,6,7,8-tetrahydroquinoline-2-carboxylate were dissolved in 30 ml of dichloromethane and, with stirring, cooled to 0° C. A solution of 2.95 g (13.53 mmol) of di-tert-butyl dicarbonate in 10 ml of dichloromethane was then slowly added dropwise, and the reaction mixture was stirred at room temperature overnight. The reaction solution was then concentrated to dryness and the residue was triturated with diethyl ether. After filtration, the filter cake was washed repeatedly with diethyl ether and then air-dried. This gave 4.17 g (9.09 mmol, 87% of theory) of the target compound.

LC-MS (Method 3): $R_t$=1.18 min; m/z=459 (M+H)$^+$.

$^1$H-NMR (400 MHz, CDCl$_3$, δ/ppm): 1.12 (br. s, 4H), 1.31 (t, 3H), 1.47 (s, 5H), 1.67-1.90 (m, 1H), 1.91-2.11 (m, 3H), 2.63-2.98 (m, 5H), 3.20-3.55 (m, 1H, partially obscured by H$_2$O signal), 4.32 (q, 2H), 4.64-4.87 (m, 0.5H), 5.08-5.27 (m, 0.5H), 6.65-7.00 (m, 3H), 7.43-7.63 (m, 1H), 7.83 (d, 1H), 9.37 (s, 1H).

Example 107A rac-Ethyl 5-{(tert-butoxycarbonyl)[2-(2-{[4-(5-chloro-1,3-benzoxazol-2-yl)benzyl]oxy}-5-fluorophenyl)ethyl]amino}-5,6,7,8-tetrahydroquinoline-2-carboxylate

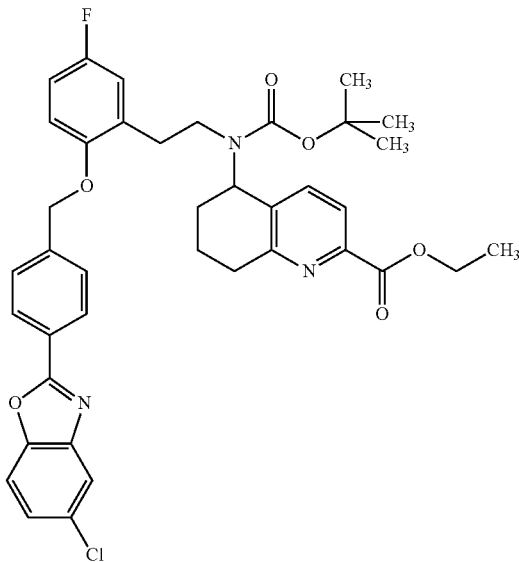 [SMILES: CCOC(=O)c1ccc2c(n1)CCCC2N(CCc1cc(F)ccc1OCc1ccc(-c2nc3cc(Cl)ccc3o2)cc1)C(=O)OC(C)(C)C]

4.17 g (9.09 mmol) of rac-ethyl 5-{(tert-butoxycarbonyl)[2-(5-fluoro-2-hydroxyphenyl)ethyl]-amino}-5,6,7,8-tetrahydroquinoline-2-carboxylate, 3.04 g (10.91 mmol) of 5-chloro-2-[4-(chloromethyl)phenyl]-1,3-benzoxazole and 3.14 g (22.74 mmol) of potassium carbonate in 120 ml of acetonitrile were heated to 110° C. and stirred at this temperature overnight. After cooling, the reaction mixture was filtered, the filter cake was washed repeatedly with acetonitrile and the combined filtrates were concentrated to dryness on a rotary evaporator. The residue obtained was purified chromatographically on silica gel (mobile phase: cyclohexane/ethyl acetate 10:1→4:1). This gave 5.43 g (7.75 mmol, 85% of theory) of the target compound.

LC-MS (Method 3): $R_t$=1.60 min; m/z=700/702 (M+H)$^+$.

Example 108A and Example 109A

Ethyl 5-{(tert-butoxycarbonyl)[2-(2-{[4-(5-chloro-1,3-benzoxazol-2-yl)benzyl]oxy}-5-fluoro-phenyl)ethyl]amino}-5,6,7,8-tetrahydroquinoline-2-carboxylate (Enantiomers 1 and 2)

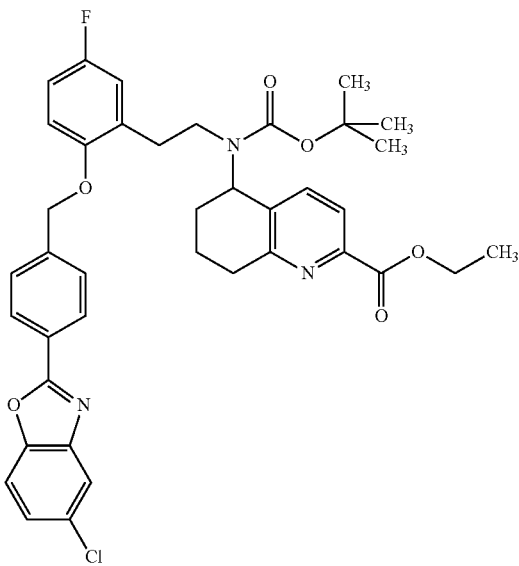 [SMILES: CCOC(=O)c1ccc2c(n1)CCCC2N(CCc1cc(F)ccc1OCc1ccc(-c2nc3cc(Cl)ccc3o2)cc1)C(=O)OC(C)(C)C]

2.5 g (3.57 mmol) of the racemic ethyl 5-{(tert-butoxycarbonyl)[2-(2-{[4-(5-chloro-1,3-benzoxazol-2-yl)benzyl]oxy}-5-fluorophenyl)ethyl]amino}-5,6,7,8-tetrahydroquinoline-2-carboxylate (Example 107A) were separated by supercritical fluid chromatography (SFC) on a chiral phase into the enantiomers [column: Daicel Chiracel OD-H, 5 μm, 250 mm×20 mm; mobile phase: carbon dioxide/ethanol 75:25 (v/v); flow rate: 100 ml/min; pressure: 80 bar; UV detection: 220 nm; temperature: 40° C.]:

Example 108A (Enantiomer 1)

Yield: 1020 mg
$R_t$=3.497 min; chemical purity >99.9%; >99% ee [column: Chiralpak OD-H, 5 μm, 250 mm×4.6 mm; mobile phase: carbon dioxide/ethanol 70:30 (v/v); flow rate: 3 ml/min; UV detection: 210 nm].
LC-MS (Method 3): $R_t$=1.60 min; m/z=700/702 $(M+H)^+$.

Example 109A (Enantiomer 2)

Yield: 1040 mg
$R_t$=4.97 min; chemical purity >99%; >95% ee [column: Chiralpak OD-H, 5 μm, 250 mm×4.6 mm; mobile phase: carbon dioxide/ethanol 70:30 (v/v); flow rate: 3 ml/min; UV detection: 210 nm].
LC-MS (Method 3): $R_t$=1.60 min; m/z=700/702 $(M+H)^+$.
$^1$H-NMR (400 MHz, DMSO-$d_6$, δ/ppm): 1.09 (br. s, 4H), 1.27 (m, 3H), 1.43 (s, 5H), 1.50-1.62 (m, 0.5H), 1.63-1.75 (m, 0.5H), 1.76-1.97 (m, 3H), 2.59-2.80 (m, 2H), 2.81-3.04 (m, 3H), 3.20-3.40 (m, 0.5H, partially obscured by H$_2$O signal), 3.42-3.57 (m, 0.5H), 4.27 (q, 2H), 4.39-4.60 (m, 0.5H), 5.00-5.11 (m, 0.5H), 5.11-5.26 (m, 2H), 6.90-6.98 (m, 0.5H), 6.99-7.17 (m, 2.5H), 7.44 (d, 0.5H), 7.51 (d, 1.5H), 7.59 (d, 1H), 7.69 (d, 1H), 7.76-7.89 (m, 2H), 7.93 (d, 1H), 8.06 (d, 1H), 8.16 (d, 1H).

Analogously to Example 107A, the following compound was prepared:

| Example | Name/Structure/Starting materials | Analytical data |
|---|---|---|
| 110A | rac-ethyl 5-{(tert-butoxycarbonyl)[2-(2-{[3-chloro-4'-(trifluoromethyl)biphenyl-4-yl]methoxy}-5-fluorophenyl)ethyl]amino}-5,6,7,8-tetrahydroquinoline-2-carboxylate<br><br>aus rac-ethyl 5-{(tert-butoxycarbonyl)[2-(5-fluoro-2-hydroxyphenyl)ethyl]amino}-5,6,7,8-tetrahydroquinoline-2-carboxylate and 4-(bromomethyl)-3-chloro-4'-(trifluoromethyl)biphenyl | $^1$H-NMR (400 MHz, DMSO-$d_6$, δ/ppm): 1.10 (br. s, 4H), 1.21-1.34 (m, 3H), 1.43 (s, 5H), 1.56-1.76 (m, 2H), 1.76-1.94 (m, 2H), 2.31-2.45 (m, 0.5H), 2.58-2.73 (m, 2H), 2.74-2.99 (m, 2.5H), 3.16-3.29 (m, 0.5H), 3.38-3.53 (m, 0.5H), 4.30 (q, 2H), 4.39-4.65 (m, 0.5H), 5.00-5.22 (m, 2.5H), 6.93 (d, 1H), 7.01-7.19 (m, 2H), 7.41 (d, 0.5H), 7.52 (d, 0.5H), 7.64 (t, 1H), 7.73 (br. s, 2H), 7.79-7.93 (m, 4H), 7.99-8.12 (m, 1H). |

Example 111A and Example 112A

Ethyl 5-{(tert-butoxycarbonyl)[2-(2-{[3-chloro-4'-(trifluoromethyl)biphenyl-4-yl]methoxy}-5-fluorophenyl)ethyl]amino}-5,6,7,8-tetrahydroquinoline-2-carboxylate (Enantiomers 1 and 2)

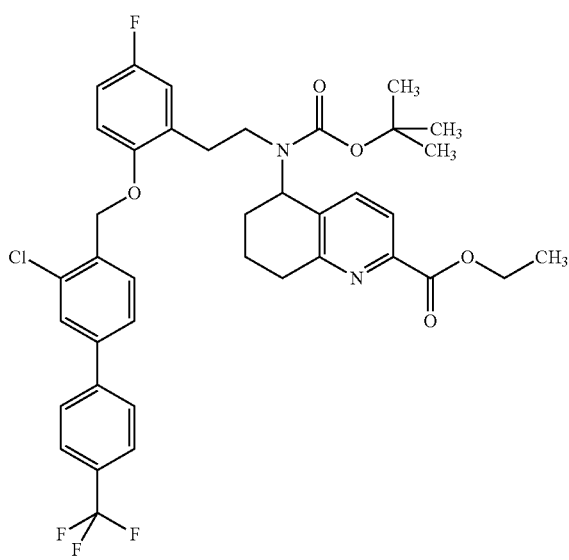 [SMILES: CCOC(=O)c1ccc2c(n1)CCCC2N(CCc1cc(F)ccc1OCc1ccc(-c2ccc(C(F)(F)F)cc2)cc1Cl)C(=O)OC(C)(C)C]

2.59 g (3.56 mmol) of the racemic ethyl 5-{(tert-butoxycarbonyl)[2-(2-{[3-chloro-4'-(trifluoro-methyl)biphenyl-4-yl]methoxy}-5-fluorophenyl)ethyl]amino}-5,6,7,8-tetrahydroquinoline-2-carboxylate (Example 110A) were separated by supercritical fluid chromatography (SFC) on a chiral phase into the enantiomers [column: Daicel Chiracel OD, 20 μm, 250 mm×30 mm; mobile phase: carbon dioxide/ethanol 80:20 (v/v); flow rate: 175 ml/min; pressure: 135 bar; UV detection: 210 nm; temperature: 40° C.]:

Example 111A (Enantiomer 1)

Yield: 1130 mg $R_t$=2.24 min; chemical purity >85%; >99% ee [column: Chiralpak OD-H, 5 μm, 250 mm×4.6 mm; mobile phase: carbon dioxide/ethanol 70:30 (v/v); flow rate: 3 ml/min; UV detection: 210 nm].

LC-MS (Method 3): $R_t$=1.65 min; m/z=727/129 (M+H)$^+$.

Example 112A (Enantiomer 2)

Yield: 1170 mg $R_t$=3.33 min; chemical purity >99%; >90% ee [column: Chiralpak OD-H, 5 μm, 250 mm×4.6 mm; mobile phase: carbon dioxide/ethanol 70:30 (v/v); flow rate: 3 ml/min; UV detection: 210 nm].

LC-MS (Method 3): $R_t$=1.65 min; m/z=727/729 (M+H)$^+$.

Example 113A

Ethyl 5-{[2-(2-{[4-(5-chloro-1,3-benzoxazol-2-yl)benzyl]oxy}-5-fluorophenyl)ethyl]amino}-5,6,7,8-tetrahydroquinoline-2-carboxylate dihydrochloride (Enantiomer 2)

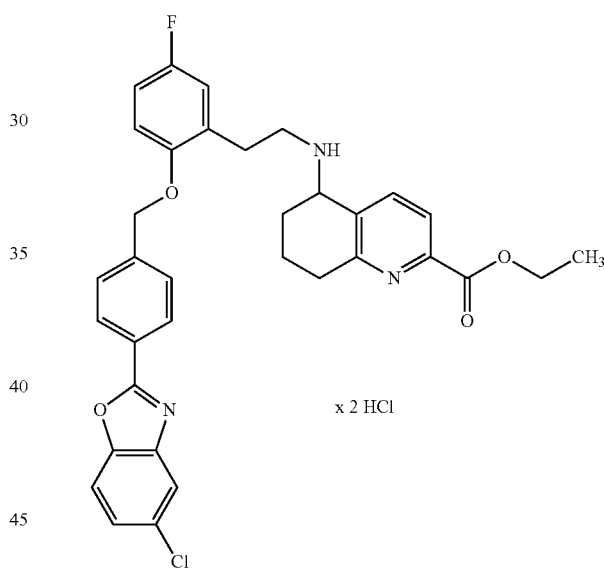

11 ml of a 4 N solution of hydrogen chloride in dioxane were added to 1025 mg (1.46 mmol) of ethyl 5-{(tert-butoxycarbonyl)[2-(2-{[4-(5-chloro-1,3-benzoxazol-2-yl)benzyl]oxy}-5-fluorophenyl)ethyl]amino}-5,6,7,8-tetrahydroquinoline-2-carboxylate (Enantiomer 2, Example 109A), and the mixture was stirred at room temperature for 2 h. The precipitated solid was filtered off, washed repeatedly with diethyl ether and then dried under high vacuum at 40° C. overnight. This gave 980 mg (1.46 mmol, about 99% of theory) of the target product.

LC-MS (Method 3): $R_t$=1.01 min; m/z=600/602 (M+H)$^+$.

Analogously to Example 113A, the following compounds were prepared:

| Example | Name/Structure/Starting material | Analytical data |
|---|---|---|
| 114A | ethyl 5-{[2-(2-{[4-(5-chloro-1,3-benzoxazol-2-yl)-benzyl]oxy}-5-fluorophenyl)ethyl]amino}-5,6,7,8-tetrahydroquinoline-2-carboxylate dihydrochloride (Enantiomer 1)<br>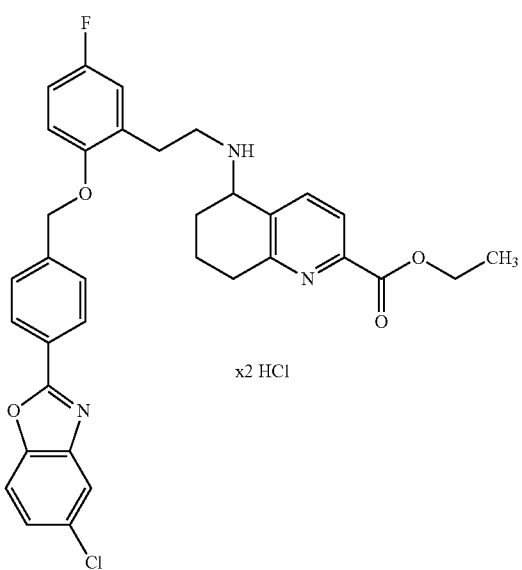<br>x2 HCl<br>from ethyl 5-{(tert-butoxycarbonyl)[2-(2-{[4-(5-chloro-1,3-benzoxazol-2-yl)benzyl]oxy}-5-fluoro-phenyl)ethyl]amino}-5,6,7,8-tetrahydroquinoline-2-carboxylate (Enantiomer 1, Example 108A) | LC-MS (Method 3):<br>$R_t$ = 1.01 min; m/z = 600/602 (M + H)$^+$. |
| 115A | ethyl 5-{[2-(2-{[3-chloro-4'-(trifluoromethyl)-biphenyl-4-yl]methoxy}-5-fluorophenyl)ethyl]amino}-5,6,7,8-tetrahydroquinoline-2-carboxylate dihydrochloride (Enantiomer 1)<br>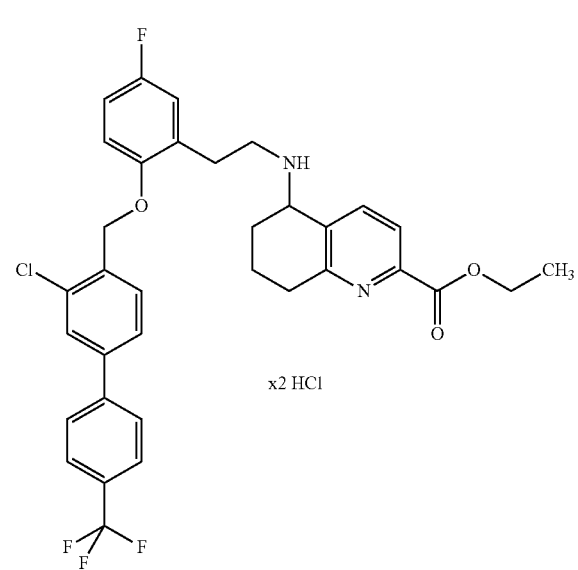<br>x2 HCl<br>from ethyl 5-[(tert-butoxycarbonyl)[2-(2-{[3-chloro-4'-(trifluoromethyl)biphenyl-4-yl]methoxy}-5-fluorophenyl)ethyl]amino}-5,6,7,8-tetrahydroquinoline-2-carboxylate (Enantiomer 1, Example 111A) | |

| Example | Name/Structure/Starting material | Analytical data |
|---|---|---|
| 116A | ethyl 5-{[2-(2-{[3-chloro-4'-(trifluoromethyl)-biphenyl-4-yl]methoxy}-5-fluorophenyl)ethyl]amino}-5,6,7,8-tetrahydroquinoline-2-carboxylate dihydrochloride (Enantiomer 2)<br>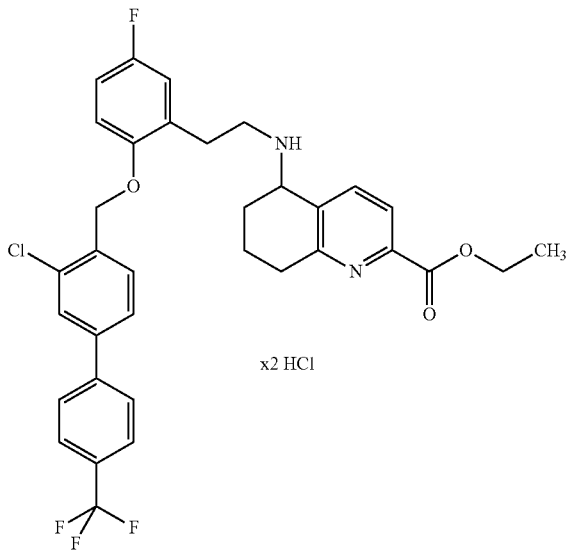<br>from ethyl 5-{(tert-butoxycarbonyl)[2-(2-{[3-chloro-4'-(trifluoromethyl)biphenyl-4-yl]methoxy}-5-fluorophenyl)ethyl]amino}-5,6,7,8-tetrahydroquinoline-2-carboxylate (Enantiomer 2, Example 112A) | |

Example 117A

Ethyl 5-{[2-(2-{[4-(5-chloro-1,3-benzoxazol-2-yl)benzyl]oxy}-5-fluorophenyl)ethyl]amino}-5,6,7,8-tetrahydroquinoline-2-carboxylate (Enantiomer 2)

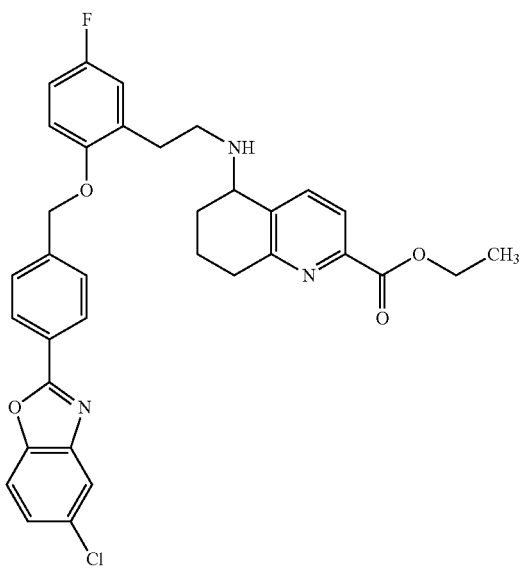 [SMILES: CCOC(=O)c1ccc2c(n1)CCCC2NCCc1cc(F)ccc1OCc1ccc(-c2nc3cc(Cl)ccc3o2)cc1]

980 mg (1.46 mmol) of ethyl 5-{[2-(2-{[3-chloro-4'-(trifluoromethyl)biphenyl-4-yl]methoxy}-phenyl)ethyl]amino}-5,6,7,8-tetrahydroquinoline-2-carboxylate dihydrochloride (Enantiomer 2, Example 113A) were taken up in 20 ml of THF, 0.81 ml of triethylamine was added and the mixture was stirred at room temperature for 1 h. Ethyl acetate and water were then added to the reaction solution, the phases were separated and the organic phase was extracted once more with ethyl acetate. The combined organic phases were washed with water, dried over magnesium sulphate, filtered and then evaporated to dryness. This gave 760 mg (1.27 mmol, 87% of theory) of the target compound.

LC-MS (Method 3): $R_t$=1.03 min; m/z=600/602 (M+H)$^+$.
$^1$H-NMR (400 MHz, DMSO-$d_6$, δ/ppm): 1.28 (t, 3H), 1.62-1.78 (m, 2H), 1.80-2.01 (m, 2H), 2.03-2.17 (m, 1H), 2.70-2.92 (m, 6H), 3.65-3.89 (m, 1H), 4.28 (q, 2H), 5.21 (s, 2H), 6.94-7.15 (m, 3H), 7.48 (dd, 1H), 7.66 (d, 2H), 7.71-7.79 (m, 1H), 7.85 (d, 2H), 7.94 (d, 1H), 8.19 (d, 2H).

Analogously to Example 117A, the following compound was prepared:

| Example | Name/Structure/Starting material | Analytical data |
|---|---|---|
| 118A | ethyl 5-{[2-(2-{[4-(5-chloro-1,3-benzoxazol-2-yl)-benzyl]oxy}-5-fluorophenyl)ethyl]amino}-5,6,7,8-tetrahydroquinoline-2-carboxylate (Enantiomer 1)<br>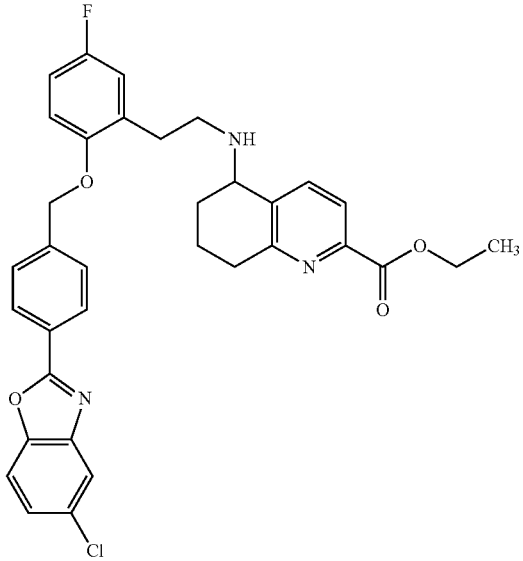 [SMILES: CCOC(=O)c1ccc2c(n1)CCCC2NCCc1cc(F)ccc1OCc1ccc(-c2nc3cc(Cl)ccc3o2)cc1]<br>from ethyl 5-{[2-(2-{[3-chloro-4'-(trifluoromethyl)-biphenyl-4-yl]methoxy}phenyl)ethyl]amino}-5,6,7,8-tetrahydroquinoline-2-carboxylate dihydrochloride (Enantiomer 1, Example 114A) | LC-MS (Method 3): $R_t$ = 1.05 min; m/z = 600/602 (M + H)$^+$.<br>$^1$H-NMR (400 MHz, DMSO-$d_6$, δ/ppm): 1.28 (t, 3H), 1.62-1.77 (m, 2H), 1.81-2.02 (m, 2H), 2.04-2.17 (m, 1H), 2.72-2.91 (m, 6H), 3.71-3.87 (m, 1H), 4.28 (q, 2H), 5.21 (s, 2H), 6.95-7.15 (m, 3H), 7.49 (dd, 1H), 7.66 (d, 2H), 7.74 (d, 1H), 7.82-7.91 (m, 2H), 7.94 (d, 1H), 8.19 (d, 2H). |

Analogously to Examples 35A and 36A, the following compounds were prepared:

| Example | Name/Structure/Starting materials | Analytical data |
|---|---|---|
| 119A | ethyl 5-{[2-(2-{[4-(5-chloro-1,3-benzoxazol-2-yl)-benzyl]oxy}-5-fluorophenyl)ethyl](5-ethoxy-5-oxopentyl)amino}-5,6,7,8-tetrahydroquinoline-2-carboxylate (Enantiomer 1)<br>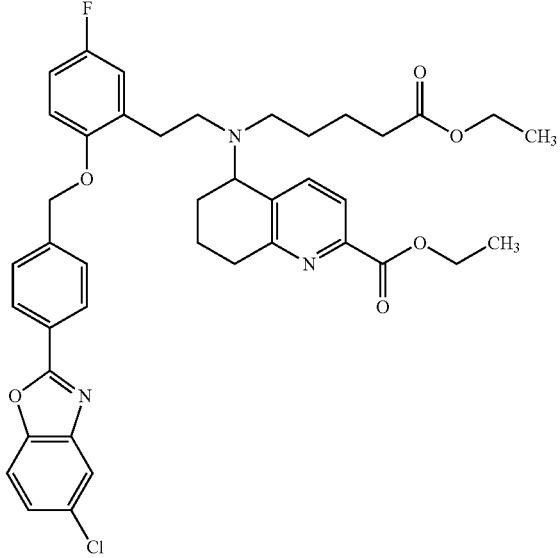<br>from ethyl 5-{[2-(2-{[4-(5-chloro-1,3-benzoxazol-2-yl)benzyl]oxy}-5-fluorophenyl)ethyl]amino}-5,6,7,8-tetrahydroquinoline-2-carboxylate (Enantiomer 1, Example 118A) and ethyl 5-bromopentanoate | LC-MS (Method 3): $R_t$ = 1.48 min; m/z = 728/730 (M + H)$^+$.<br>$^1$H-NMR (400 MHz, DMSO-$d_6$, δ/ppm): 1.10 (t, 3H), 1.26 (t, 3H), 1.30-1.70 (m, 6H), 1.90-2.05 (m, 2H), 2.08-2.18 (m, 2H), 2.35-2.45 (m, 2H), 2.57-2.64 (m, 2H), 2.72-2.83 (m, 4H), 3.91-4.02 (m, 3H), 4.26 (q, 2H), 5.02-5.15 (m, 2H), 6.96-7.08 (m, 3H), 7.46-7.57 (m, 3H), 7.65 (d, 1H), 7.78-7.88 (m, 2H), 7.95 (d, 1H), 8.17 (d, 2H). |

| Example | Name/Structure/Starting materials | Analytical data |
|---|---|---|
| 120A | ethyl 5-{[2-(2-{[4-(5-chloro-1,3-benzoxazol-2-yl)-benzyl]oxy}-5-fluorophenyl)ethyl](5-ethoxy-5-oxo-pentyl)amino}-5,6,7,8-tetrahydroquinoline-2-carboxylate (Enantiomer 2)<br>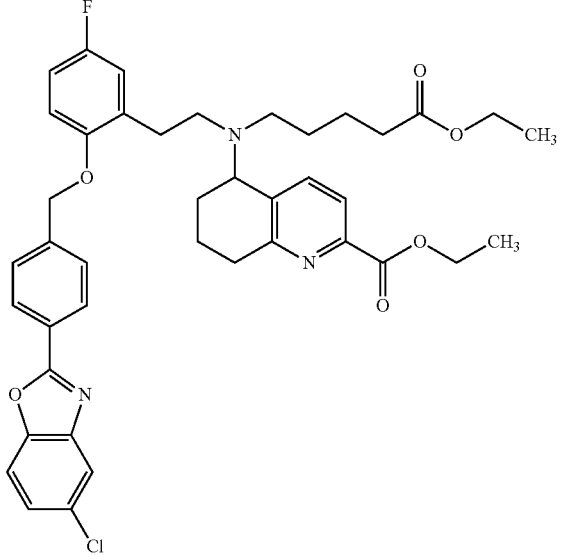<br>from ethyl 5-{[2-(2-[4-(5-chloro-1,3-benzoxazol-2-yl)benzyl]oxy}-5-fluorophenyl)ethyl]amino}-5,6,7,8-tetrahydroquinoline-2-carboxylate (Enantiomer 2, Example 117A) and ethyl 5-bromopentanoate | LC-MS (Method 3): Rt = 1.49 min; m/z = 728/730 (M + H)$^+$.<br>$^1$H-NMR (400 MHz, DMSO-$d_6$, δ/ppm): 1.10 (t, 3H), 1.26 (t, 3H), 1.30-1.69 (m, 6H), 1.90-2.03 (m, 2H), 2.10-2.17 (m, 2H), 2.35-2.46 (m, 2H), 2.56-2.64 (m, 2H), 2.72-2.83 (m, 4H), 3.91-4.01 (m, 3H), 4.26 (q, 2H), 5.02-5.16 (m, 2H), 6.95-7.07 (m, 3H), 7.46-7.57 (m, 3H), 7.65 (d, 1H), 7.79-7.88 (m, 2H), 7.94 (d, 1H), 8.17 (d, 2H). |

Example 121A

Ethyl 5-([2-(2-{[4-(5-chloro-1,3-benzoxazol-2-yl)benzyl]oxy}-5-fluorophenyl)ethyl]{2-[4-(methoxycarbonyl)phenyl]ethyl}amino)-5,6,7,8-tetrahydroquinoline-2-carboxylate (Enantiomer 2)

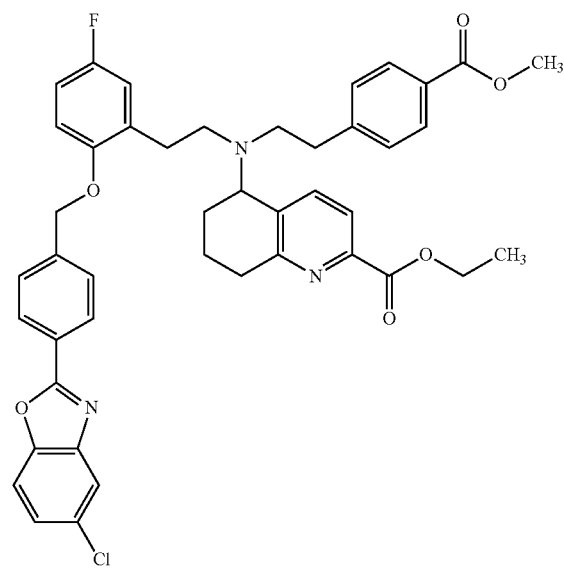 [SMILES: CCOC(=O)c1ccc2c(n1)CCCC2N(CCc1ccc(C(=O)OC)cc1)CCc1cc(F)ccc1OCc1ccc(-c2nc3cc(Cl)ccc3o2)cc1]

A suspension of 375 mg (0.63 mmol) of ethyl 5-{[2-(2-{[4-(5-chloro-1,3-benzoxazol-2-yl)benzyl]-oxy}-5-fluorophenyl)ethyl]amino}-5,6,7,8-tetrahydroquinoline-2-carboxylate (Enantiomer 2, Example 117A), 272 mg (0.94 mmol) of methyl 4-(2-iodoethyl)benzoate and 99 mg (0.94 mmol) of anhydrous sodium carbonate in 10 ml of dry acetonitrile was stirred overnight at a bath temperature of 110° C. A further 272 mg of methyl 4-(2-iodoethyl)benzoate and 99 mg of sodium carbonate were then added, and the mixture was once more heated under reflux overnight. Another 272 mg of methyl 4-(2-iodoethyl)benzoate and 99 mg of sodium carbonate were then added, and the mixture was again heated under reflux overnight. After cooling of the reaction mixture, ethyl acetate and water were added, the organic phase was separated off and the aqueous phase was extracted three more times with ethyl acetate. The combined organic phases were dried over magnesium sulphate, filtered and evaporated to dryness. The residue obtained was purified chromatographically on silica gel (mobile phase: petroleum ether/ethyl acetate 4:1→2:1). This gave 324 mg (0.42 mmol, 68% of theory) of the target compound.

LC-MS (Method 3): $R_t$=1.63 min; m/z=762/764 (M+H)$^+$.

$^1$H-NMR (400 MHz, DMSO-$d_6$, δ/ppm): 1.26 (t, 3H), 1.41-1.55 (m, 1H), 1.55-1.69 (m, 1H), 1.89-2.08 (m, 2H), 2.57-2.83 (m, 10H), 3.76 (s, 3H), 4.02-4.12 (m, 1H), 4.26 (q, 2H), 5.02-5.12 (m, 2H), 6.95 (d, 1H), 7.03 (d, 2H), 7.11 (d, 2H), 7.41 (d, 1H), 7.45-7.56 (m, 4H), 7.72 (d, 2H), 7.82 (d, 1H), 7.92 (d, 1H), 8.09 (d, 2H).

Analogously to Example 121A, the following compound was prepared:

| Example | Name/Structure/Starting materials | Analytical data |
|---|---|---|
| 122A | ethyl 5-([2-(2-{[4-(5-chloro-1,3-benzoxazol-2-yl)-benzyl]oxy}-5-fluorophenyl)ethyl]{2-[4-(methoxy-carbonyl)phenyl]ethyl}amino)-5,6,7,8-tetrahydro-quinoline-2-carboxylate (Enantiomer 1)<br>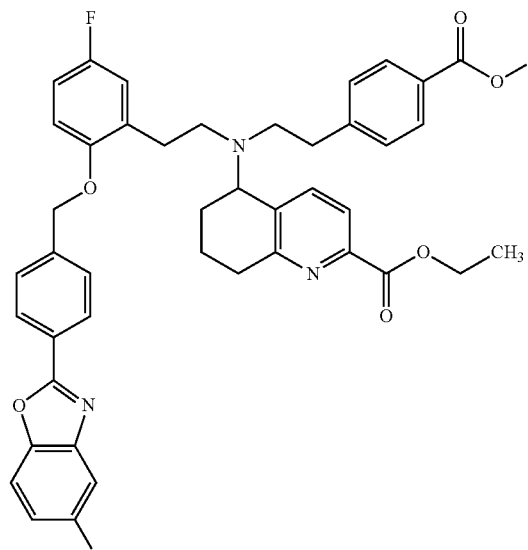<br>from ethyl 5-{[2-(2-{[4-(5-chloro-1,3-benzoxazol-2-yl)benzyl]oxy}-5-fluorophenyl)ethyl]amino}-5,6,7,8-tetrahydroquinoline-2-carboxylate (Enantiomer 1, Example 118A) and methyl 4-(2-iodoethyl)-benzoate | LC-MS (Method 3):<br>$R_t$ = 1.63 min; m/z = 762/764 (M + H)$^+$.<br>$^1$H-NMR (400 MHz, DMSO-$d_6$, δ/ppm): 1.26 (t, 3H), 1.41-1.55 (m, 1H), 1.55-1.69 (m, 1H), 1.89-2.08 (m, 2H), 2.57-2.81 (m, 10H), 3.76 (s, 3H), 4.02-4.11 (m, 1H), 4.26 (q, 2H), 5.02-5.12 (m, 2H), 6.95 (d, 1H), 7.02 (d, 2H), 7.11 (d, 2H), 7.41 (d, 1H), 7.45-7.56 (m, 4H), 7.72 (d, 2H), 7.82 (d, 1H), 7.92 (d, 1H), 8.09 (d, 2H). |

Example 123A

Ethyl 5-{[2-(2-[3-chloro-4'-(trifluoromethyl)biphenyl-4-yl]methoxy}-5-fluorophenyl)ethyl]{2-[4-(methoxycarbonyl)phenyl]ethyl}amino)-5,6,7,8-tetrahydroquinoline-2-carboxylate (Enantiomer 2)

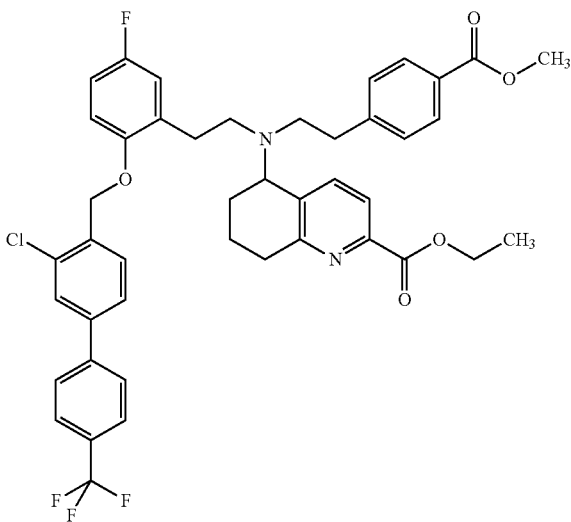 [SMILES: CCOC(=O)c1ccc2c(n1)CCCC2N(CCc1ccc(C(=O)OC)cc1)CCc1cc(F)ccc1OCc1ccc(-c2ccc(C(F)(F)F)cc2)cc1Cl]

685 mg (2.36 mmol) of methyl 4-(2-iodoethyl)benzoate and 188 mg (1.77 mmol) of anhydrous sodium carbonate were added to a solution of 740 mg (1.18 mmol) of ethyl 5-{[2-(2-{[3-chloro-4'-(trifluoromethyl)biphenyl-4-yl]methoxy}-5-fluorophenyl)ethyl]amino}-5,6,7,8-tetrahydroquinoline-2-carboxylate dihydrochloride (Enantiomer 2, Example 116A) in 20 ml of dry acetonitrile, and the mixture was heated under reflux overnight. A further 342 mg of methyl 4-(2-iodoethyl)benzoate were then added, and the mixture was stirred under reflux overnight. This procedure was repeated two more times on the subsequent days. Then, another 342 mg of methyl 4-(2-iodoethyl)benzoate and 188 mg of anhydrous sodium carbonate were added and the mixture was again stirred under reflux overnight. Another 342 mg of methyl 4-(2-iodoethyl)benzoate were then added to the reaction solution, and the mixture was heated under reflux overnight and then cooled to room temperature. The reaction was filtered, the filter cake was washed with acetonitrile and the filtrate was concentrated to dryness. The residue was taken up in ethyl acetate, and water was added. The organic phase was separated, dried over magnesium sulphate, filtered and evaporated to dryness. The residue obtained was purified chromatographically on silica gel (mobile phase: cyclohexane/ethyl acetate 10:1→4:1). This gave 588 mg (0.40 mmol, 63% of theory) of the title compound.

LC-MS (Method 3): $R_t$=1.68 min; m/z=789/791 (M+H)$^+$.
$^1$H-NMR (400 MHz, DMSO-$d_6$, δ/ppm): 1.27 (t, 3H), 1.38-1.51 (m, 1H), 1.51-1.68 (m, 1H), 1.87-2.05 (m, 2H), 2.57-2.80 (m, 10H), 3.81 (s, 3H), 4.00-4.08 (m, 1H), 4.26 (q, 2H), 5.00-5.10 (m, 2H), 6.92-6.98 (m, 1H), 7.01-7.15 (m, 4H), 7.35-7.42 (m, 2H), 7.53 (d, 1H), 7.61 (d, 1H), 7.74 (d, 2H), 7.77-7.88 (m, 5H).

Analogously to Example 123A, the following compound was prepared:

| Example | Name/Structure/Starting materials | Analytical data |
|---|---|---|
| 124A | ethyl 5-([2-(2-{[3-chloro-4'-(trifluoromethyl)biphenyl-4-yl]methoxy}-5-fluorophenyl)ethyl]{2-[4-(methoxycarbonyl)phenyl]ethyl}amino)-5,6,7,8-tetrahydroquinoline-2-carboxylate (Enantiomer 1)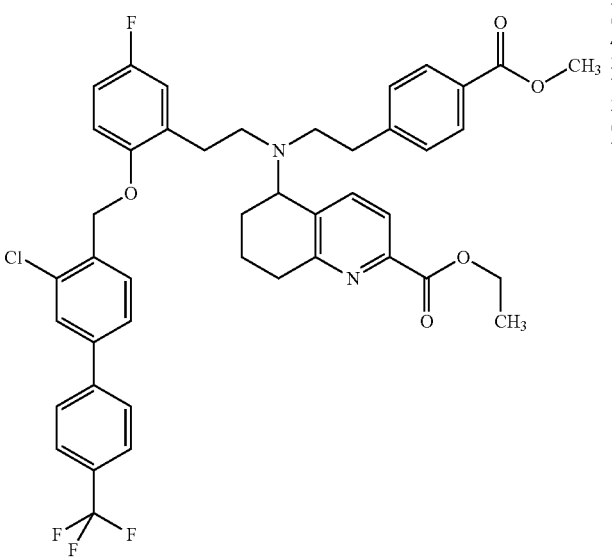from ethyl 5-{[2-(2-{[3-chloro-4'-(trifluoromethyl)-biphenyl-4-yl]methoxy}-5-fluorophenyl)ethyl]-amino}-5,6,7,8-tetrahydroquinoline-2-carboxylate dihydrochloride (Enantiomer 1, Example 115A) and methyl 4-(2-iodoethyl)benzoate | LC-MS (Method 3): $R_t$ = 1.68 min; m/z = 789/791 (M + H)$^+$. $^1$H-NMR (400 MHz, DMSO-$d_6$, δ/ppm): 1.27 (t, 3H), 1.42-1.69 (m, 2H), 1.86-2.05 (m, 2H), 2.58-2.79 (m, 10H), 3.81 (s, 3H), 3.99-4.08 (m, 1H), 4.26 (q, 2H), 5.00-5.10 (m, 2H), 6.91-6.99 (m, 1H), 7.03-7.15 (m, 4H), 7.35-7.42 (m, 2H), 7.53 (d, 1H), 7.58-7.64 (m, 1H), 7.74 (d, 2H), 7.77-7.89 (m, 5H). |

Example 125A

Methyl 4-[(E/Z)-2-(4-fluorophenyl)vinyl]benzoate

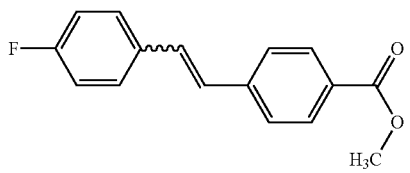 [SMILES: COC(=O)c1ccc(C=Cc2ccc(F)cc2)cc1]

79.75 g (176.70 mmol) of (4-fluorobenzyl)(triphenyl)phosphonium bromide and 29.59 g (180.24 mmol) of methyl 4-formylbenzoate were dissolved in 250 ml of methanol, the solution was cooled to 0° C. and 10.98 g (203.21 mmol) of sodium methoxide were added a little at a time. The reaction mixture was then slowly warmed to room temperature and stirred at this temperature overnight. The reaction solution was then once more cooled to 0° C., a further 4.77 g (88.35 mmol) of sodium methoxide were added in portions and, after warming to room temperature, the mixture was once more stirred overnight. The precipitated solid was filtered off, washed with methanol and dried in a drying cabinet at 40° C. and under reduced pressure overnight. This gave 21.08 g (82.25 mmol, 46.5% of theory) of the target compound. The filtrate was evaporated to dryness and the residue obtained was purified chromatographically on silica gel (mobile phase: cyclohexane/ethyl acetate 10:1). This gave a further 23.75 g (92.67 mmol, 52% of theory) of the title compound.

LC-MS (Method 2): $R_t$=2.80 min; m/z=257 (M+H)$^+$ (fraction 1); $R_t$=2.82 min; m/z=257 (M+H)$^+$ (fraction 2).

Example 126A

Methyl 4-[2-(4-fluorophenyl)ethyl]benzoate

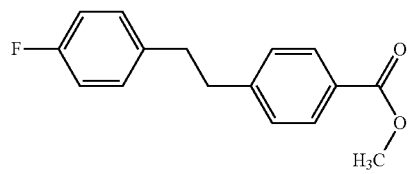 [SMILES: COC(=O)c1ccc(CCc2ccc(F)cc2)cc1]

2 g of 10% palladium on carbon were added to 44 g (171.70 mmol) of methyl 4-[(F/Z)-2-(4-fluorophenyl)vinyl]benzoate in 500 ml of THF, and the mixture was stirred at room temperature overnight under a hydrogen atmosphere under standard pressure. Another 1 g of 10% palladium on carbon was then added, and the mixture was once more stirred at room temperature overnight under a hydrogen atmosphere under standard pressure. The reaction mixture was then filtered and the resulting filtrate was concentrated to dryness. This gave 35 g (135.5 mmol, 79% of theory) of the title compound.

LC-MS (Method 2): $R_t$=2.76 min; m/z=259 (M+H)$^+$.

Example 127A

{4-[2-(4-Fluorophenyl)ethyl]phenyl}methanol

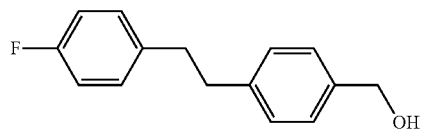

Under reflux, 45 ml of a 3.5 M solution of lithium aluminium hydride in toluene were slowly added dropwise to a solution of 35.4 g (136.98 mmol) of methyl 4-[2-(4-fluorophenyl)ethyl]benzoate in 500 ml of dry THF. After the addition had ended, the reaction mixture was stirred under reflux for one hour. The reaction mixture was then cooled to 0° C., and 500 ml of ice-cooled 1 M hydrochloric acid were added slowly and carefully. 750 ml of ethyl acetate were then added, the aqueous phase was removed and the organic phase was washed successively in each case once with 1 M hydrochloric acid and saturated sodium chloride solution. The organic phase was then dried over magnesium sulphate, filtered and concentrated to dryness. This gave 31.5 g (136.7 mmol, 99.9% of theory) of the title compound.

LC-MS (Method 3): $R_t$=1.05 min; m/z=213 (M+H-H$_2$O)$^+$.

$^1$H-NMR (400 MHz, DMSO-d$_6$, δ/ppm): 2.84 (s, 4H), 4.44 (d, 2H), 5.09 (t, 1H), 7.08 (t, 2H), 7.13-7.27 (m, 6H).

Example 128A 1-(Chloromethyl)-4-[2-(4-fluorophenyl)ethyl]benzene

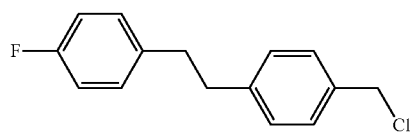 [SMILES: Fc1ccc(CCc2ccc(CCl)cc2)cc1]

At 0° C., 14.96 ml of thionyl chloride in 100 ml of dichloromethane were slowly added dropwise to a solution of 31.5 g (136.7 mmol) of {4-[2-(4-fluorophenyl)ethyl]phenyl}methanol in 400 ml of dichloromethane. After the addition had ended, the reaction mixture was warmed to room temperature and stirred at this temperature for another 2 hours. The reaction mixture was then once more cooled to 0° C., and 200 ml of saturated aqueous sodium bicarbonate solution were added slowly and carefully, with vigorous stirring. Subsequently, small portions of solid sodium bicarbonate were added to the solution until the pH had been adjusted to 6. The phases were then separated, and the organic phase was dried over magnesium sulphate, filtered and concentrated to dryness. This gave 28.5 g (114.5 mmol, 84% of theory) of the title compound.

$^1$H-NMR (400 MHz, DMSO-d$_6$, δ/ppm): 2.86 (s, 4H), 4.72 (s, 2H), 7.08 (t, 2H), 7.19-7.28 (m, 4H), 7.33 (d, 2H).

Example 129A rac-Ethyl 5-[(tert-butoxycarbonyl){2-[2-({4-[2-(4-fluorophenyl)ethyl]benzyl}oxy)phenyl]ethyl}-amino]-5,6,7,8-tetrahydroquinoline-2-carboxylate

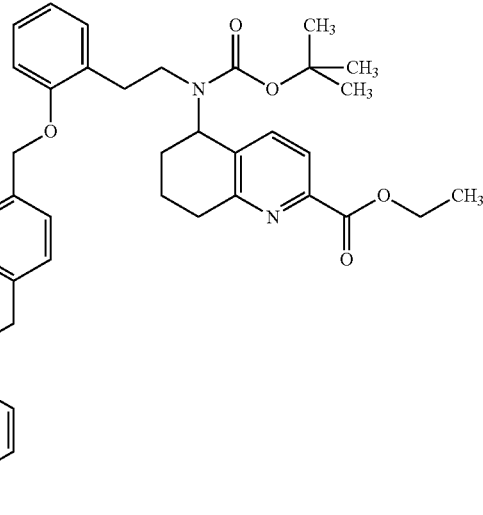

5.60 g (12.71 mmol) of rac-ethyl 5-{(tert-butoxycarbonyl)[2-(2-hydroxyphenyl)ethyl]amino}-5,6,7,8-tetrahydroquinoline-2-carboxylate, 3.79 g (15.25 mmol) of 1-(chloromethyl)-4-[2-(4-fluorophenyl)ethyl]benzene and 2.64 g (19.07 mmol) of potassium carbonate in 200 ml of acetonitrile were heated to 110° C. and stirred at this temperature overnight. After cooling, the reaction mixture was filtered, the filter cake was washed repeatedly with acetonitrile and the combined filtrates were concentrated to dryness on a rotary evaporator. The residue obtained was purified chromatographically on silica gel (mobile phase: cyclohexane/ethyl acetate 10:1→4:1). This gave 6.8 g (10.42 mmol, 82% of theory) of the target compound.

LC-MS (Method 3): $R_t$=1.62 min; m/z=653 (M+H)$^+$.

Example 130A and Example 131A

Ethyl 5-[(tert-butoxycarbonyl){2-[2-({4-[2-(4-fluorophenyl)ethyl]benzyl}oxy)phenyl]ethyl}-amino]-5,6,7,8-tetrahydroquinoline-2-carboxylate (Enantiomers 1 and 2)

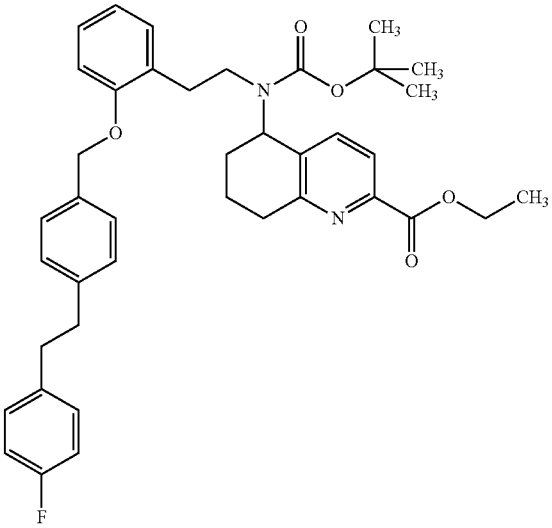 [SMILES: CCOC(=O)c1ccc2c(n1)CCCC2N(CCc1ccccc1OCc1ccc(CCc2ccc(F)cc2)cc1)C(=O)OC(C)(C)C]

6.8 g (10.42 mmol) of the racemic ethyl 5-[(tert-butoxycarbonyl){2-[2-({4-[2-(4-fluorophenyl)-ethyl]benzyl}oxy)phenyl]ethyl}amino]-5,6,7,8-tetrahydroquinoline-2-carboxylate (Example 129A) were separated by supercritical fluid chromatography (SFC) on a chiral phase into the enantiomers [column: Chiracel OD-H, 20 μm, 250 mm×30 mm; mobile phase: carbon dioxide/ethanol 83:17 (v/v); flow rate: 185 ml/min; pressure: 135 bar; UV detection: 210 nm; temperature: 38° C.]:

Example 130A (Enantiomer 1)

Yield: 3240 mg $R_t$=2.83 min; chemical purity >99.9%; >99% ee

[column: Chiralpak OD-H, 5 μm, 250 mm×4.6 mm; mobile phase: carbon dioxide/ethanol 70:30 (v/v); flow rate: 3 ml/min; UV detection: 210 nm].

LC-MS (Method 3): $R_t$=1.57 min; m/z=653 (M+H)$^+$.

Example 131A (Enantiomer 2)

Yield: 3180 mg $R_t$=4.12 min; chemical purity >99%; >99% ee

[column: Chiralpak OD-H, 5 μm, 250 mm×4.6 mm; mobile phase: carbon dioxide/ethanol 70:30 (v/v); flow rate: 3 ml/min; UV detection: 210 nm].

LC-MS (Method 3): $R_t$=1.57 min; m/z=653 (M+H)$^+$.

Example 132A
Ethyl 5-({2-[2-({4-[2-(4-fluorophenyl)ethyl]benzyl}oxy)phenyl]ethyl}amino)-5,6,7,8-tetrahydroquinoline-2-carboxylate dihydrochloride
(Enantiomer 2)

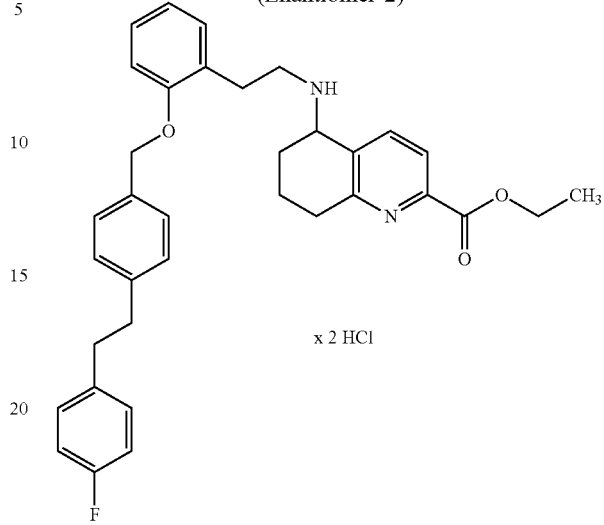

x 2 HCl 12 ml of a 4 N solution of hydrogen chloride in dioxane were added to 3180 mg (4.87 mmol) of ethyl 5-[(tert-butoxycarbonyl){2-[2-({4-[2-(4-fluorophenyl)ethyl]benzyl}oxy)phenyl]ethyl}-amino]-5,6,7,8-tetrahydroquinoline-2-carboxylate (Enantiomer 2, Example 131A), and the mixture was stirred at room temperature for 2 h. The reaction mixture was then concentrated to dryness. This gave 3290 mg of the target product which was reacted further without further analytical characterization.

Analogously to Example 132A, the following compound was prepared:

| Example | Name/Structure/Starting material | Analytical data |
| --- | --- | --- |
| 133A | ethyl 5-({2-[2-({4-[2-(4-fluorophenyl)ethyl]benzyl}-oxy)phenyl]ethyl}amino)-5,6,7,8-tetrahydroquinoline-2-carboxylate dihydrochloride (Enantiomer 1)<br><br>x2 HCl<br><br>from ethyl 5-[(tert-butoxycarbonyl){2-[2-({4-[2-(4-fluorophenyl)ethyl]benzyl}oxy)phenyl]ethyl}-amino]-5,6,7,8-tetrahydroquinoline-2-carboxylate (Enantiomer 1, Example 130A) | |

Example 134A

Ethyl 5-({2-[2-({4-[2-(4-fluorophenyl)ethyl]benzyl}oxy)phenyl]ethyl}amino)-5,6,7,8-tetrahydroquinoline-2-carboxylate (Enantiomer 2)

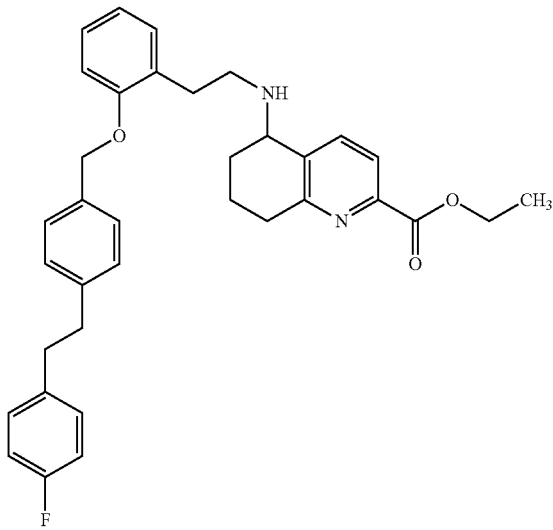 [SMILES: CCOC(=O)c1ccc2c(n1)CCCC2NCCc1ccccc1OCc1ccc(CCc2ccc(F)cc2)cc1]

3290 mg (5.58 mmol) of ethyl 5-({2-[2-(4-[2-(4-fluorophenyl)ethyl]benzyl oxy)phenyl]ethyl}-amino)-5,6,7,8-tetrahydroquinoline-2-carboxylate dihydrochloride (Enantiomer 2, Example 132A) were taken up in 50 ml of THF, 3.11 ml of triethylamine were added and the mixture was stirred at room temperature for one hour. Ethyl acetate and water were then added to the reaction solution, the phases were separated and the aqueous phase was extracted once more with ethyl acetate. The combined organic phases were again washed with water, dried over magnesium sulphate, filtered and then evaporated to dryness. This gave 2150 mg (3.89 mmol, 70% of theory) of the target compound.

LC-MS (Method 3): $R_t$=1.06 min; m/z=553 (M+H)$^+$.

$^1$H-NMR (400 MHz, DMSO-$d_6$, δ/ppm): 1.30 (t, 3H), 1.60-1.74 (m, 2H), 1.78-1.89 (m, 1H), 1.89-2.06 (m, 2H), 2.65-2.92 (m, 10H), 3.76 (br. s, 1H), 4.31 (q, 2H), 5.04 (s, 2H), 6.86 (t, 1H), 6.99-7.11 (m, 3H), 7.13-7.27 (m, 6H), 7.31 (d, 2H), 7.76 (d, 1H), 7.85 (d, 1H).

Analogously to Example 134A, the following compound was prepared:

| Example | Name/Structure/Starting material | Analytical data |
|---|---|---|
| 135A | ethyl 5-({2-[2-({4-[2-(4-fluorophenyl)ethyl]benzyl}-oxy)phenyl]ethyl}amino)-5,6,7,8-tetrahydroquinoline-2-carboxylate (Enantiomer 1)<br><br>from ethyl 5-({2-[2-({4-[2-(4-fluorophenyl)ethyl]-benzyl}oxy)phenyl]ethyl}amino)-5,6,7,8-tetrahydroquinoline-2-carboxylate dihydrochloride (Enantiomer 1, Example 133A) | LC-MS (Method 3): $R_t$ = 1.02 min; m/z = 553 (M + H)$^+$.<br>$^1$H-NMR (400 MHz, DMSO-$d_6$, δ/ppm): 1.30 (t, 3H), 1.60-1.75 (m, 2H), 1.79-1.89 (m, 1H), 1.90-2.05 (m, 2H), 2.65-2.91 (m, 10H), 3.76 (br. s, 1H), 4.31 (q, 2H), 5.04 (s, 2H), 6.87 (t, 1H), 6.98-7.11 (m, 3H), 7.13-7.27 (m, 6H), 7.31 (d, 2H), 7.76 (d, 1H), 7.85 (d, 1H). |

Example 136A

Ethyl 5-({2-[2-({4-[2-(4-fluorophenyl)ethyl]benzyl)oxy)phenyl]ethyl}2-[4-(methoxycarbonyl)-phenyl]ethyl}amino)-5,6,7,8-tetrahydroquinoline-2-carboxylate (Enantiomer 2)

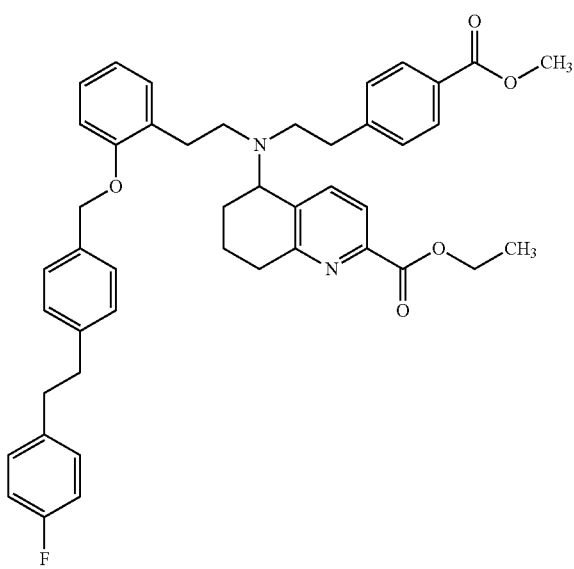 [SMILES: CCOC(=O)c1ccc2c(n1)CCCC2N(CCc1ccc(C(=O)OC)cc1)CCc1ccccc1OCc1ccc(CCc2ccc(F)cc2)cc1]

3118 mg (10.75 mmol) of methyl 4-(2-iodoethyl)benzoate and 570 mg (5.37 mmol) of anhydrous sodium carbonate were added to a solution of 1980 mg (3.58 mmol) of ethyl 5-({2-[2-({4-[2-(4-fluorophenyl)ethyl]benzyl}oxy)phenyl]ethyl}amino)-5,6,7,8-tetrahydroquinoline-2-carboxylate (Enantiomer 2, Example 134A) in 30 ml of dry acetonitrile, and the mixture was heated under reflux overnight. A further 379 mg of methyl 4-(2-iodoethyl)benzoate were then added, and the mixture was once more stirred under reflux overnight. Subsequently, another 379 mg of methyl 4-(2-iodoethyl)benzoate were added. The mixture was then stirred under reflux for a further three days and finally cooled to room temperature. The reaction was filtered, the filter cake was washed with acetonitrile and the filtrate was concentrated to dryness. The residue obtained was purified chromatographically on silica gel (mobile phase: cyclohexane/ethyl acetate 10:1→4:1→2:1). This gave 715 mg (2.40 mmol, content 97%, 67% of theory) of the title compound.

LC-MS (Method 3): $R_t$=1.57 min; m/z=715 (M+H)$^+$.

$[\alpha]_D^{20}$=+60.75°, c=0.40, methanol.

Analogously to Example 136A, the following compound was prepared:

| Example | Name/Structure/Starting materials | Analytical data |
|---|---|---|
| 137A | ethyl 5-({2-[2-({4-[2-(4-fluorophenyl)ethyl]benzyl}-oxy)phenyl]ethyl}{2-[4-(methoxycarbonyl)-phenyl]ethyl}amino)-5,6,7,8-tetrahydroquinoline-2-carboxylate (Enantiomer 1)<br><br>from ethyl 5-({2-[2-({4-[2-(4-fluorophenyl)ethyl]-benzyl}oxy)phenyl]ethyl}amino)-5,6,7,8-tetrahydroquinoline-2-carboxylate (Enantiomer 1, Example 135A) and methyl 4-(2-iodoethyl)benzoate | LC-MS (Method 3):<br>$R_t$ = 1.57 min; m/z = 715 (M + H)$^+$.<br>$[\alpha]_D^{20}$ = −52.1°, c = 0.325, methanol. |

Example 138A rac-Ethyl 5-[(tert-butoxycarbonyl){2-[5-fluoro-2-({4-[2-(4-fluorophenyl)ethyl]benzyl}oxy)-phenyl]ethyl}amino]-5,6,7,8-tetrahydroquinoline-2-carboxylate

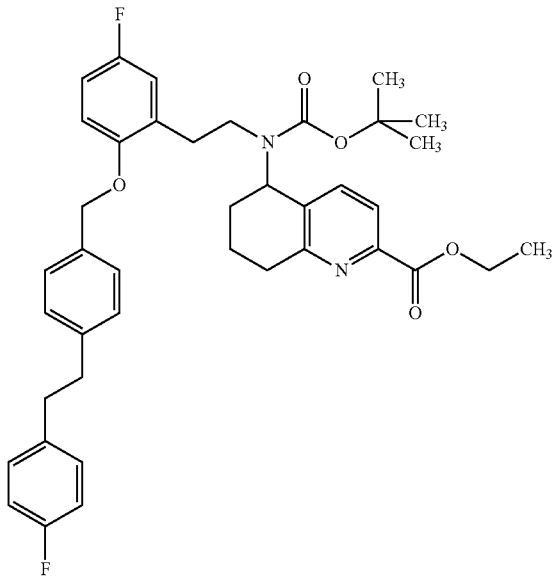 [SMILES: CCOC(=O)c1ccc2c(n1)CCCC2N(CCc1cc(F)ccc1OCc1ccc(CCc2ccc(F)cc2)cc1)C(=O)OC(C)(C)C]

10 g (21.81 mmol) of rac-ethyl 5-{(tert-butoxycarbonyl)[2-(5-fluoro-2-hydroxyphenyl)ethyl]-amino}-5,6,7,8-tetrahydroquinoline-2-carboxylate (Example 106A), 5.98 g (23.99 mmol) of 1-(chloromethyl)-4-[2-(4-fluorophenyl)ethyl]benzene and 4.52 g (32.71 mmol) of potassium carbonate in 240 ml of acetonitrile were heated to 110° C. and stirred at this temperature overnight. After cooling, the reaction mixture was filtered, the filter cake was washed repeatedly with acetonitrile and the combined filtrates were concentrated to dryness on a rotary evaporator. The residue obtained was purified chromatographically on silica gel (mobile phase: cyclohexane/ethyl acetate 10:1→4:1). This gave 14.11 g (21.03 mmol, 96% of theory) of the target compound.

LC-MS (Method 3): $R_t$=1.57 min; m/z=671 (M+H)$^+$.

Example 139A and Example 140A

Ethyl 5-[(tert-butoxycarbonyl){2-[5-fluoro-2-({4-[2-(4-fluorophenyl)ethyl]benzyl}oxy)phenyl]-ethyl}amino]-5,6,7,8-tetrahydroquinoline-2-carboxylate (Enantiomers 1 and 2)

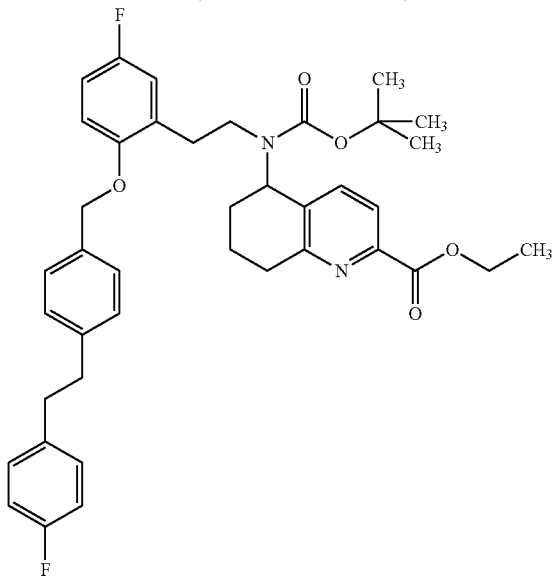 [SMILES: CCOC(=O)c1ccc2c(n1)CCCC2N(CCc1cc(F)ccc1OCc1ccc(CCc2ccc(F)cc2)cc1)C(=O)OC(C)(C)C]

14.11 g (21.03 mmol) of the racemic ethyl 5-[(tert-butoxycarbonyl){2-[5-fluoro-2-({4-[2-(4-fluorophenyl)ethyl]benzyl}oxy)phenyl]ethyl}amino]-5,6,7,8-tetrahydroquinoline-2-carboxylate (Example 138A) were separated by supercritical fluid chromatography (SFC) on a chiral phase into the enantiomers [column: Daicel Chiralpak AZ-H, 5 µm, 250 mm×50 mm; mobile phase: carbon dioxide/ethanol 70:30 (v/v); flow rate: 200 ml/min; pressure: 80 bar; UV detection: 220 nm; temperature: 15° C.]:

Example 139A (Enantiomer 1)

Yield: 5690 mg $R_t$=3.98 min; chemical purity >99.9%; >99% ee [column: Daicel Chiralpak AZ-H, 5 µm, 250 mm×4.6 mm; mobile phase: carbon dioxide/ethanol 70:30 (v/v); flow rate: 3 ml/min; UV detection: 220 nm].

LC-MS (Method 3): $R_t$=1.61 min; m/z=671 (M+H)$^+$.

Example 140A (Enantiomer 2)

Yield: 6080 mg $R_t$=6.41 min; chemical purity >99%; >99% ee [column: Daicel Chiralpak AZ-H, 5 µm, 250 mm×4.6 mm; mobile phase: carbon dioxide/ethanol 70:30 (v/v); flow rate: 3 ml/min; UV detection: 220 nm].

LC-MS (Method 3): $R_t$=1.61 min; m/z=671 (M+H)$^+$.

Example 141A

Ethyl 5-({2-[5-fluoro-2-({4-[2-(4-fluorophenyl)ethyl]benzyl}oxy)phenyl]ethyl}amino)-5,6,7,8-tetrahydroquinoline-2-carboxylate dihydrochloride (Enantiomer 2)

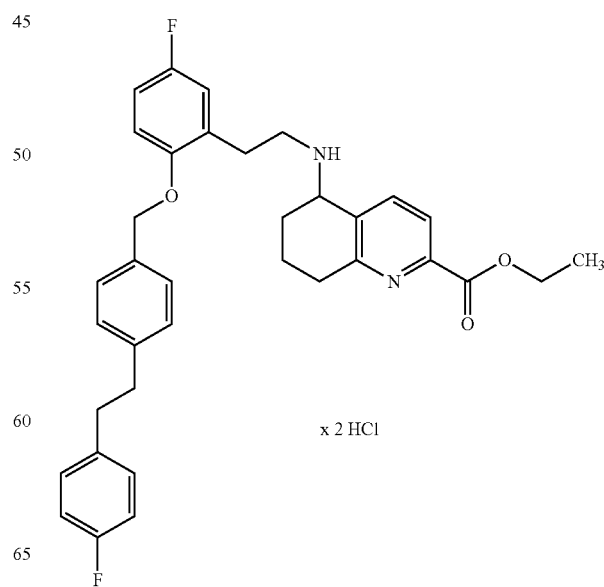

23 ml of a 4 N solution of hydrogen chloride in dioxane were added to 6080 mg (9.06 mmol) of ethyl 5-[(tert-butoxycarbonyl){2-[5-fluoro-2-({4-[2-(4-fluorophenyl)ethyl]benzyl}oxy)phenyl]-ethyl}amino]-5,6,7,8-tetrahydroquinoline-2-carboxylate (Enantiomer 2, Example 140A), and the mixture was stirred at room temperature for 2 h. The reaction mixture was then concentrated to dryness. This gave 6240 mg of the target product which was reacted further without further analytical characterization.

Analogously to Example 141A, the following compound was prepared:

| Example | Name/Structure/Starting material | Analytical data |
|---|---|---|
| 142A | ethyl 5-({2-[5-fluoro-2-({4-[2-(4-fluorophenyl-ethyl]benzyl}oxy)phenyl]ethyl}amino)-5,6,7,8-tetrahydroquinoline-2-carboxylate dihydrochloride (Enantiomer 1) | |

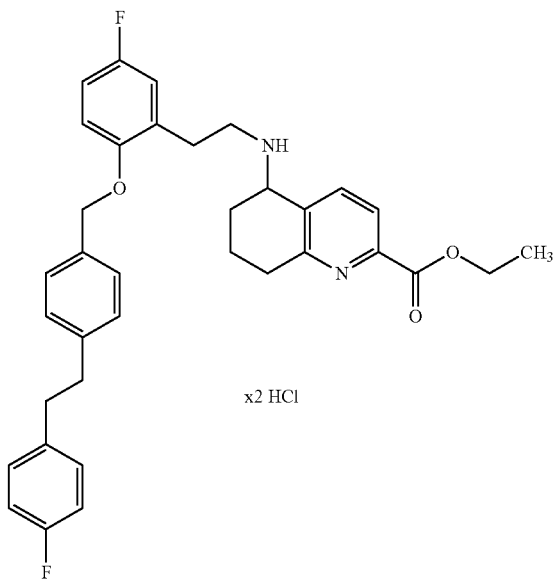 [SMILES: CCOC(=O)c1ccc2c(n1)CCCC2NCCc1cc(F)ccc1OCc1ccc(CCc2ccc(F)cc2)cc1]

x2 HCl from ethyl 5-[(tert-butoxycarbonyl){2-[5-fluoro-2-({4-[2-(4-fluorophenyl)ethyl]benzyl}oxy)phenyl]-ethyl}amino]-5,6,7,8-tetrahydroquinoline-2-carboxylate (Enantiomer 1, Example 139A)

Example 143A

Ethyl 5-({2-[5-fluoro-2-({4-[2-(4-fluorophenyl)ethyl]benzyl}oxy)phenyl]ethyl}amino)-5,6,7,8-tetrahydroquinoline-2-carboxylate (Enantiomer 2)

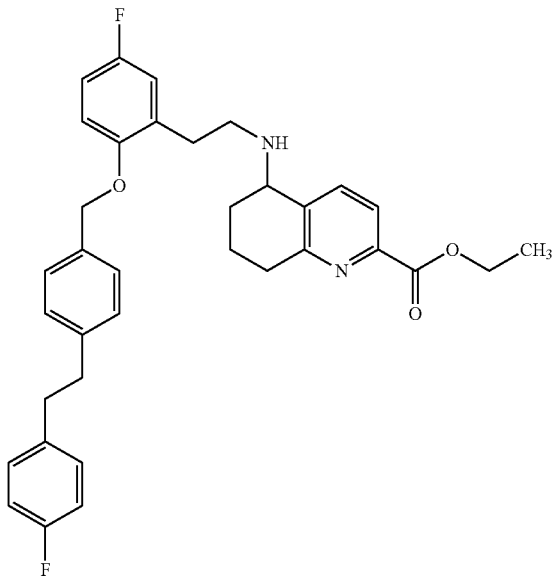 [SMILES: CCOC(=O)c1ccc2c(n1)CCCC2NCCc1cc(F)ccc1OCc1ccc(CCc2ccc(F)cc2)cc1]

6240 mg (10.28 mmol) of ethyl 5-({2-[5-fluoro-2-({4-[2-(4-fluorophenyl)ethyl]benzyl}-oxy)phenyl]ethyl}amino)-5,6,7,8-tetrahydroquinoline-2-carboxylate dihydrochloride (Enantiomer 2, Example 141A) were taken up in 103 ml of THF, 5.7 ml of triethylamine were added and the mixture was stirred at room temperature for one hour. Ethyl acetate and water were then added to the reaction solution, the phases were separated and the aqueous phase was extracted once more with ethyl acetate. The combined organic phases were again washed with water, dried over magnesium sulphate, filtered and finally evaporated to dryness. This gave 3600 mg (6.31 mmol, 61% of theory) of the target compound which was reacted further without further analytical characterization.

Analogously to Example 143A, the following compound was prepared:

| Example | Name/Structure/Starting material | Analytical data |
|---|---|---|
| 144A | ethyl 5-({2-[5-fluoro-2-({4-[2-(4-fluorophenyl)-ethyl]benzyl}oxy)phenyl]ethyl}amino)-5,6,7,8-tetrahydroquinoline-2-carboxylate (Enantiomer 1)<br><br>from ethyl 5-({2-[5-fluoro-2-({4-[2-(4-fluorophenyl)ethyl]benzyl}oxy)phenyl]ethyl}amino)-5,6,7,8-tetrahydroquinoline-2-carboxylate dihydrochloride (Enantiomer 1, Example 142A) | |

Example 145A

Ethyl 5-({2-[5-fluoro-2-({4-[2-(4-fluorophenyl)ethyl]benzyl}oxy)phenyl]ethyl}{2-[4-(methoxycarbonyl)phenyl]ethyl}amino)-5,6,7,8-tetrahydroquinoline-2-carboxylate (Enantiomer 2)

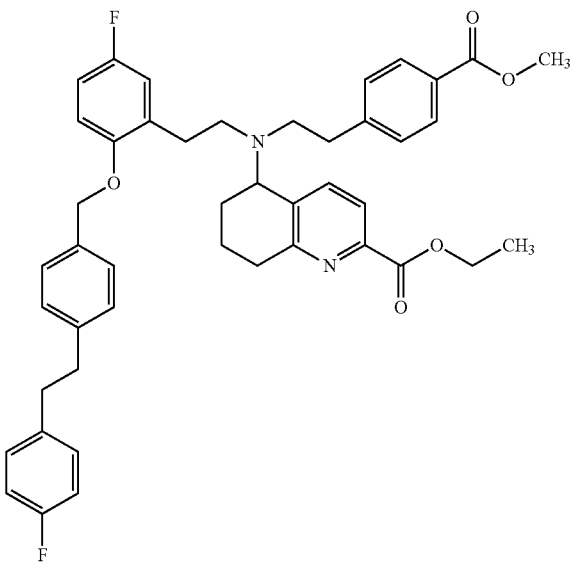 [SMILES: CCOC(=O)c1ccc2c(n1)CCCC2N(CCc1ccc(C(=O)OC)cc1)CCc1cc(F)ccc1OCc1ccc(CCc2ccc(F)cc2)cc1]

305 mg (1.05 mmol) of methyl 4-(2-iodoethyl)benzoate and 56 mg (0.53 mmol) of anhydrous sodium carbonate were added to a solution of 200 mg (0.35 mmol) of ethyl 5-({2-[5-fluoro-2-({4-[2-(4-fluorophenyl)ethyl]benzyl}oxy)phenyl]ethyl}amino)-5,6,7,8-tetrahydroquinoline-2-carboxylate (Enantiomer 2, Example 143A) in 3 ml of dry acetonitrile, and the mixture was stirred in a microwave apparatus (Biotage Initiator) at 140° C. for 4 hours. The reaction solution was then cooled and purified directly by preparative HPLC (mobile phase: acetonitrile/water 9:1). This gave 75 mg (0.10 mmol, 29% of theory) of the title compound.

LC-MS (Method 3): $R_t$=1.58 min; m/z=733 (M+H)$^+$.

$^1$H-NMR (400 MHz, DMSO-d$_6$, δ/ppm): 1.29 (t, 3H), 1.40-1.53 (m, 1H), 1.53-1.67 (m, 1H), 1.87-2.06 (m, 2H), 2.56-2.86 (m, 14H), 3.83 (s, 3H), 4.00-4.09 (m, 1H), 4.29 (q, 2H), 4.82-4.94 (m, 2H), 6.91 (d, 1H), 6.96-7.02 (m, 2H), 7.03-7.26 (m, 10H), 7.34-7.44 (m, 2H), 7.80 (d, 2H).

Analogously to Example 145A, the following compound was prepared:

| Example | Name/Structure/Starting materials | Analytical data |
|---|---|---|
| 146A | ethyl 5-({2-[5-fluoro-2-({4-[2-(4-fluorophenyl)ethyl]benzyl}oxy)phenyl]ethyl}{2-[4-(methoxycarbonyl)phenyl]ethyl}amino)-5,6,7,8-tetrahydroquinoline-2-carboxylate (Enantiomer 1)<br><br>from ethyl 5-({2-[5-fluoro-2-({4-[2-(4-fluorophenyl)ethyl]benzyl}oxy)phenyl]ethyl}amino)-5,6,7,8-tetrahydroquinoline-2-carboxylate (Enantiomer 1, Example 144A) and methyl 4-(2-iodoethyl)benzoate | LC-MS (Method 3): $R_t$ = 1.59 min; m/z = 733 (M + H)$^+$.<br>$^1$H-NMR (400 MHz, DMSO-d$_6$, δ/ppm): 1.29 (t, 3H), 1.39-1.52 (m, 1H), 1.53-1.68 (m, 1H), 1.88-2.07 (m, 2H), 2.57-2.85 (m, 14H), 3.83 (s, 3H), 4.00-4.10 (m, 1H), 4.29 (q, 2H), 4.81-4.94 (m, 2H), 6.86-6.94 (m, 1H), 6.99 (d, 2H), 7.03-7.26 (m, 10H), 7.39 (m, 2H), 7.80 (d, 2H). |

Example 147A and Example 69A

Ethyl 5-{(tert-butoxycarbonyl)[2-(2-hydroxyphenyl)ethyl]amino}-5,6,7,8-tetrahydroquinoline-2-carboxylate (Enantiomers 1 and 2)

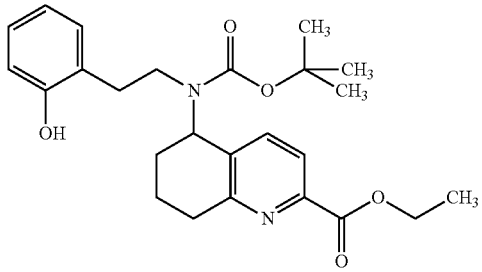 [SMILES: CCOC(=O)c1ccc2c(n1)CCCC2N(CCc1ccccc1O)C(=O)OC(C)(C)C]

25 g (56.74 mmol) of the racemic ethyl 5-{(tert-butoxycarbonyl)[2-(2-hydroxyphenyl)ethyl]-amino}-5,6,7,8-tetrahydroquinoline-2-carboxylate (Example 10A) were separated by supercritical fluid chromatography (SFC) on a chiral phase into the enantiomers [column: Daicel Chiralpak AZ-H, 5 µm, 250 mm×50 mm; mobile phase: carbon dioxide/isopropanol 85:15 (v/v); flow rate: 400 ml/min; pressure: 80 bar; UV detection: 220 nm; temperature: 37° C.]:

Example 147A (Enantiomer 1)

Yield: 11.3 g
$R_t$=5.98 min; chemical purity >99.9%; >99% ee
[column: Daicel Chiralpak OZ-H, 5 µm, 250 mm×4.6 mm; mobile phase: isohexane/ethanol 80:20 (v/v); flow rate: 1 ml/min; UV detection: 220 nm].

Example 69A (Enantiomer 2)

Yield: 11.9 g
$R_t$=4.36 min; chemical purity >99%; >92% ee
[column: Daicel Chiralpak OZ-H, 5 µm, 250 mm×4.6 mm; mobile phase: isohexane/ethanol 80:20 (v/v); flow rate: 1 ml/min; UV detection: 220 nm].

Example 148A and Example 74A

Ethyl 5-{(tert-butoxycarbonyl)[2-(2-{[3-chloro-4'-(trifluoromethyl)biphenyl-4-yl]methoxy}-phenyl)ethyl]amino}-5,6,7,8-tetrahydroquinoline-2-carboxylate (Enantiomers 1 and 2)

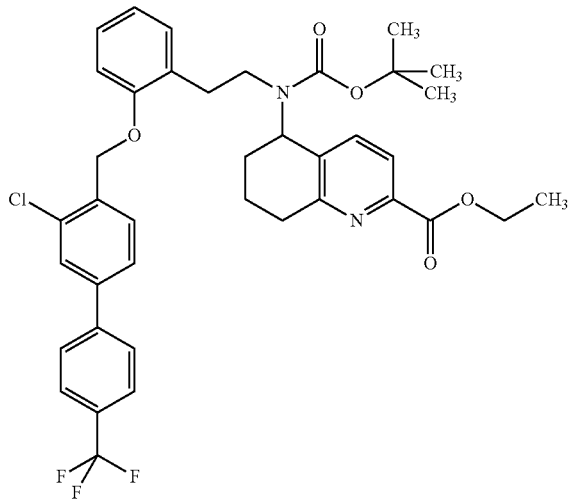 [SMILES: CCOC(=O)c1ccc2c(n1)CCCC2N(CCc1ccccc1OCc1ccc(-c2ccc(C(F)(F)F)cc2)cc1Cl)C(=O)OC(C)(C)C]

15 g (21.42 mmol) of the racemic ethyl 5-{(tert-butoxycarbonyl)[2-(2-{[3-chloro-4'-(trifluoromethyl)biphenyl-4-yl]methoxy}phenyl)ethyl]amino}-5,6,7,8-tetrahydroquinoline-2-carboxylate (Example 22A) were separated by supercritical fluid chromatography (SFC) on a chiral phase into the enantiomers [column: Chiralpak OD-H, 20 µm, 400 mm×50 mm; mobile phase: carbon dioxide/isopropanol 70:30 (v/v); flow rate: 400 ml/min; pressure: 80 bar, UV detection: 220 nm; temperature: 37° C.]:

Example 148A (Enantiomer 1)

Yield: 5830 mg
$R_t$=2.83 min; chemical purity >99.9%; >99% ee
[column: Chiralpak OD-H, 5 µm, 250 mm×4.6 mm; mobile phase: carbon dioxide/isopropanol 70:30 (v/v); flow rate: 3 ml/min; UV detection: 210 nm].

Example 74A (Enantiomer 2)

Yield: 6330 mg
$R_t$=5.30 min; chemical purity >99%; >98% ee
[column: Chiralpak OD-H, 5 µm, 250 mm×4.6 mm; mobile phase: carbon dioxide/isopropanol 70:30 (v/v); flow rate: 3 ml/min; UV detection: 210 nm].

Example 149A

Methyl 4-{(E/Z)-2-[4-(trifluoromethyl)phenyl]vinyl}benzoate

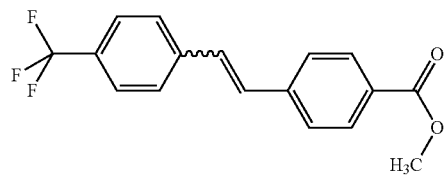

59.13 g (94.36 mmol) of [4-(trifluoromethyl)benzyl](triphenyl)phosphonium bromide and 15.80 g (96.24 mmol) of methyl 4-formylbenzoate were dissolved in 160 ml of methanol, the mixture was cooled to 0° C. and 5.86 g (108.51 mmol) of sodium methoxide were added a little at a time. The reaction mixture was then slowly warmed to room temperature and stirred at this temperature overnight. The reaction solution was then once more cooled to 0° C., a further 2.55 g (47.18 mmol) of sodium methoxide were added in portions and the mixture was, after warming to room temperature, once more stirred overnight. The reaction mixture was then concentrated to dryness and the residue was purified chromatographically on silica gel (mobile phase: cyclohexane/ethyl acetate 10:1). This gave 12.39 g (40.45 mmol, 43% of theory) of the title compound.

LC-MS (Method 2): $R_t$=2.87 min; m/z=307 (M+H)⁺.

Example 150A

Methyl 4-{2-[4-(trifluoromethyl)phenyl]ethyl}benzoate

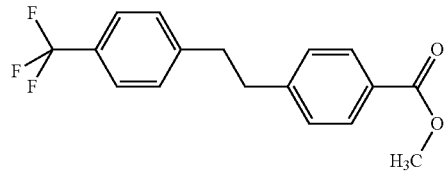

427 mg of 10% palladium on carbon were added to 12.3 g (40.16 mmol) of methyl 4-{(E/Z)-2-[4-(trifluoromethyl)

phenyl]vinyl}benzoate in 150 ml of THF and 150 ml of ethanol, and the mixture was stirred overnight at room temperature under a hydrogen atmosphere at standard pressure. The reaction mixture was then filtered and the resulting filtrate was concentrated to dryness. This gave 11.52 g (37.37 mmol, 93% of theory) of the title compound.

LC-MS (Method 2): $R_t$=2.86 min; m/z=309 (M+H)$^+$.

$^1$H-NMR (400 MHz, DMSO-d$_6$, δ/ppm): 2.93-3.05 (m, 4H), 3.83 (s, 3H), 7.38 (d, 2H), 7.45 (d, 2H), 7.63 (d, 2H), 7.87 (d, 2H).

Example 151A (4-{2-[4-(Trifluoromethyl)phenyl]ethyl}phenyl)methanol

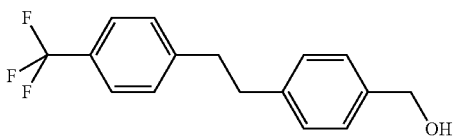 [SMILES: OCc1ccc(CCc2ccc(C(F)(F)F)cc2)cc1]

At room temperature and under argon, 12.3 ml of a M solution of lithium aluminium hydride in THF were slowly added dropwise to a solution of 11.5 g (37.30 mmol) of methyl 4-{2-[4-(trifluoromethyl)phenyl]ethyl}benzoate in 150 ml of dry THF. After the addition had ended, the reaction mixture was stirred at room temperature for another hour. The reaction mixture was then cooled to 0° C., and 150 ml of ice-cooled 1 M hydrochloric acid were added slowly and carefully. About 250 ml of ethyl acetate were then added, the aqueous phase was separated off and the organic phase was washed successively in each case once with 1 M hydrochloric acid and saturated sodium chloride solution. The organic phase was then dried over magnesium sulphate, filtered and concentrated to dryness. This gave 9.69 g (34.57 mmol, 93% of theory) of the title compound.

LC-MS (Method 2): $R_t$=2.55 min; m/z=263 (M+H-H$_2$O)$^+$.

$^1$H-NMR (400 MHz, DMSO-d$_6$, δ/ppm): 2.85-2.93 (m, 2H), 2.93-3.02 (m, 2H), 4.45 (d, 2H), 5.09 (t, 1H), 7.19 (q, 4H), 7.45 (d, 2H), 7.62 (d, 2H).

Example 152A 1-(Chloromethyl)-4-{2-[4-(trifluoromethyl)phenyl]ethyl}benzene

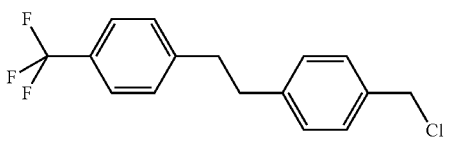 [SMILES: FC(F)(F)c1ccc(CCc2ccc(CCl)cc2)cc1]

At 0° C., 3.78 ml of thionyl chloride in 30 ml of dichloromethane were slowly added dropwise to a solution of 9.69 g (34.57 mmol) of (4-{2-[4-(trifluoromethyl)phenyl]ethyl}phenyl)methanol in 100 ml of dichloromethane. After the addition had ended, the reaction mixture was warmed to room temperature and stirred at this temperature for two hours. The reaction mixture was then once more cooled to 0° C., and 100 ml of saturated aqueous sodium bicarbonate solution were added slowly and carefully with vigorous stirring until a pH of 6 had been reached. The phases were then separated, and the organic phase was dried over magnesium sulphate, filtered and concentrated to dryness. This gave 8.64 g (28.92 mmol, 84% of theory) of the title compound.

GC-MS (Method 5): $R_t$=5.96 min; m/z=298/300 (M+H)$^+$.

Example 153A

Ethyl 5-[(tert-butoxycarbonyl)(2-{2-[(4-{2-[4-(trifluoromethyl)phenyl]ethyl}benzyl)oxy]phenyl}-ethyl)amino]-5,6,7,8-tetrahydroquinoline-2-carboxylate (Enantiomer 2)

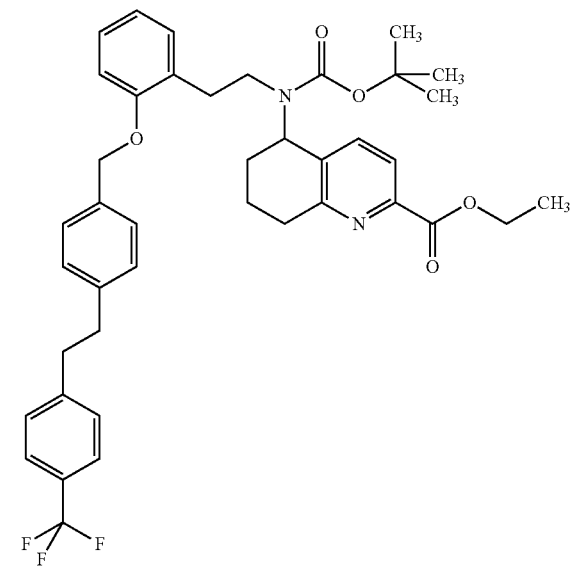 [SMILES: CCOC(=O)c1ccc2c(n1)CCCC2N(CCc1ccccc1OCc1ccc(CCc2ccc(C(F)(F)F)cc2)cc1)C(=O)OC(C)(C)C]

1 g (2.27 mmol) of ethyl 5-{(tert-butoxycarbonyl)[2-(2-hydroxyphenyl)ethyl]amino}-5,6,7,8-tetrahydroquinoline-2-carboxylate (Enantiomer 2, Example 69A), 746 mg (2.50 mmol) of 1-(chloromethyl)-4-{2-[4-(trifluoromethyl)phenyl]ethyl}benzene and 784 mg (5.68 mmol) of potassium carbonate in 25 ml of acetonitrile were heated to 110° C. and stirred at this temperature overnight. After cooling, the reaction mixture was filtered, the filter cake was washed repeatedly with acetonitrile and the combined filtrates were concentrated to dryness on a rotary evaporator. The residue obtained was purified chromatographically on silica gel (mobile phase: cyclohexane/ethyl acetate 20:1→10:1). This gave 1110 mg (1.48 mmol, 65% of theory) of the target compound.

LC-MS (Method 3): $R_t$=1.66 min; m/z=703 (M+H)$^+$.

Example 154A

Ethyl 5-[(2-{2-[(4-{2-[4-(trifluoromethyl)phenyl]ethyl}benzyl)oxy]phenyl}ethyl)amino]-5,6,7,8-tetrahydroquinoline-2-carboxylate dihydrochloride (Enantiomer 2)

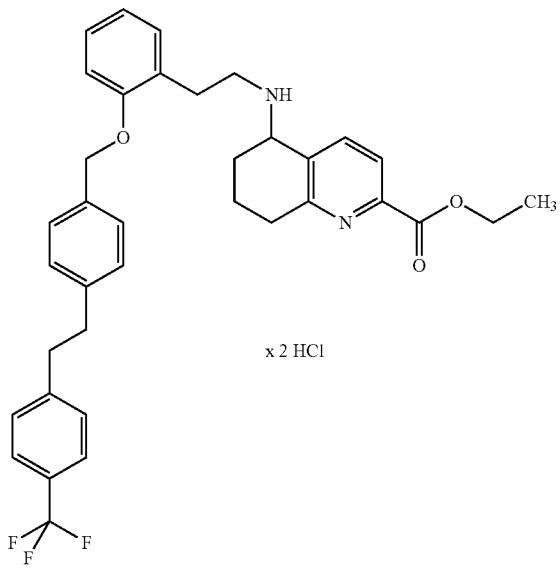 [SMILES: CCOC(=O)c1ccc2c(n1)CCCC2NCCc1ccccc1OCc1ccc(CCc2ccc(C(F)(F)F)cc2)cc1]

x 2 HCl 12 ml of a 4 N solution of hydrogen chloride in dioxane were added to 1100 mg (1.57 mmol) of ethyl 5-[(tert-butoxycarbonyl)(2-{2-[(4-{2-[4-(trifluoromethyl)phenyl]ethyl}benzyl)oxy]phenyl}-ethyl)amino]-5,6,7,8-tetrahydroquinoline-2-carboxylate (Enantiomer 2, Example 153A), and the mixture was stirred at room temperature for 2 h. The reaction mixture was then concentrated to dryness. This gave 1045 mg of the target product which was reacted further without further analytical characterization.

Example 155A

Ethyl 5-[(2-{2-[(4-{2-[4-(trifluoromethyl)phenyl]ethyl}benzyl)oxy]phenyl}ethyl)amino]-5,6,7,8-tetrahydroquinoline-2-carboxylate (Enantiomer 2)

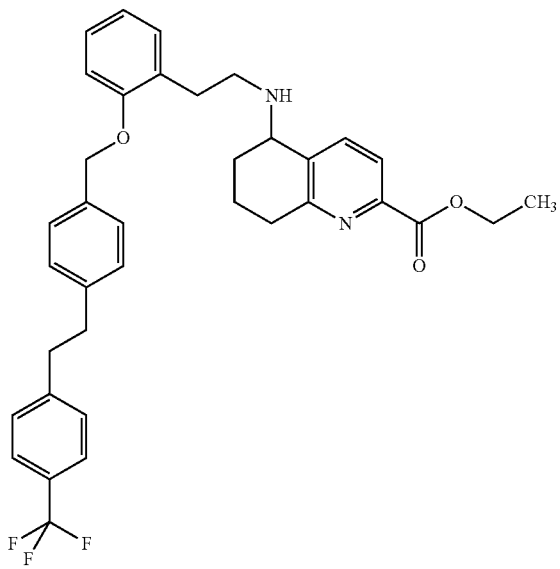 [SMILES: CCOC(=O)c1ccc2c(n1)CCCC2NCCc1ccccc1OCc1ccc(CCc2ccc(C(F)(F)F)cc2)cc1]

1045 mg (1.55 mmol) of ethyl 5-[(2-{2-[(4-{2-[4-(trifluoromethyl)phenyl]ethyl}benzyl)oxy]-phenyl}ethyl)amino]-5,6,7,8-tetrahydroquinoline-2-carboxylate dihydrochloride (Enantiomer 2, Example 154A) were taken up in 15 ml of THF, 0.65 ml of triethylamine were added and the mixture was stirred at room temperature for one hour. Ethyl acetate and water were then added to the reaction solution, the phases were separated and the aqueous phase was extracted once more with ethyl acetate. The combined organic phases were again washed with water, dried over magnesium sulphate, filtered and then concentrated to dryness. This gave 800 mg (1.33 mmol, 86% of theory) of the target compound.

LC-MS (Method 3): $R_t$=1.03 min; m/z=603 (M+H)$^+$.

Example 156A

Ethyl 5-[{2-[4-(methoxycarbonyl)phenyl]ethyl}(2-{2-[(4-{2-[4-(trifluoromethyl)phenyl]ethyl}-benzyl)oxy]phenyl}ethyl)amino]-5,6,7,8-tetrahydroquinoline-2-carboxylate (Enantiomer 2)

300 mg (1.04 mmol) of methyl 4-(2-iodoethyl)benzoate and 55 mg (0.52 mmol) of anhydrous sodium carbonate were added to a solution of 208 mg (0.35 mmol) of ethyl 5-[(2-{2-[(4-{2-[4-(trifluoromethyl)phenyl]ethyl}benzyl)oxy]phenyl}ethyl)amino]-5,6,7,8-tetrahydroquinoline-2-carboxylate (Enantiomer 2, Example 155A) in 3 ml of dry acetonitrile, and the mixture was stirred in a microwave apparatus (Biotage Initiator) at 140° C. for 4 h. The reaction solution was then cooled and purified directly by preparative HPLC (mobile phase: acetonitrile/water 9:1). This gave 102 mg (0.13 mmol, 39% of theory) of the title compound.

LC-MS (Method 3): $R_t$=1.64 min; m/z=765 (M+H)$^+$.

Example 157A rac-Ethyl 5-[(tert-butoxycarbonyl)(2-{5-fluoro-2-[(4-{2-[4-(trifluoromethyl)phenyl]ethyl}benzyl)-oxy]phenyl}ethyl)amino]-5,6,7,8-tetrahydroquinoline-2-carboxylate

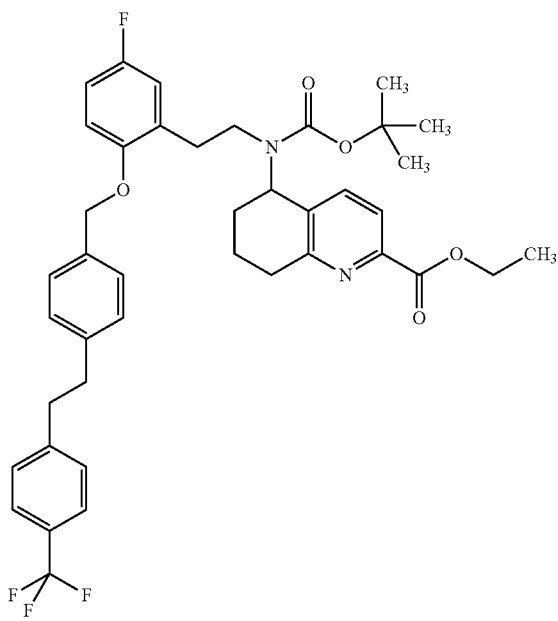 [SMILES: CCOC(=O)c1ccc2c(n1)CCCC2N(CCc1cc(F)ccc1OCc1ccc(CCc2ccc(C(F)(F)F)cc2)cc1)C(=O)OC(C)(C)C]

2 g (4.36 mmol) of rac-ethyl 5-{(tert-butoxycarbonyl)[2-(5-fluoro-2-hydroxyphenyl)ethyl]amino}-5,6,7,8-tetrahydroquinoline-2-carboxylate (Example 106A), 1433 mg (4.80 mmol) of 1-(chloromethyl)-4-{2-[4-(trifluoromethyl)phenyl]ethyl}benzene and 1507 mg (10.90 mmol) of potassium carbonate in 50 ml of acetonitrile were heated to 110° C. and stirred at this temperature overnight. After cooling, the reaction mixture was filtered, the filter cake was washed repeatedly with acetonitrile and the combined filtrates were concentrated to dryness on a rotary evaporator. The residue obtained was purified chromatographically on silica gel (mobile phase: cyclohexane/ethyl acetate 20:1→10:1). This gave 2490 mg (3.29 mmol, 95% of theory) of the target compound.

LC-MS (Method 3): $R_t$=1.60 min; m/z=721 (M+H)$^+$.

Example 158A rac-Ethyl 5-[(2-{5-fluoro-2-[(4-{2-[4-(trifluoromethyl)phenyl]ethyl}benzyl)oxy]phenyl}ethyl)-amino]-5,6,7,8-tetrahydroquinoline-2-carboxylate dihydrochloride

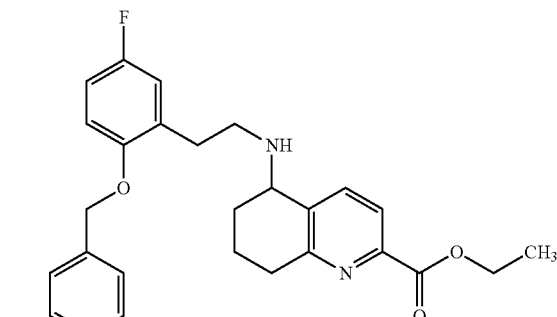

x 2 HCl 5.2 ml of a 4 N solution of hydrogen chloride in dioxane were added to 500 mg (0.69 mmol) of rac-ethyl 5-[(tert-butoxycarbonyl)(2-{5-fluoro-2-[(4-{2-[4-(trifluoromethyl)phenyl]-ethyl}benzyl)oxy]phenyl}ethyl)amino]-5,6,7,8-tetrahydroquinoline-2-carboxylate (Example 157A), and the mixture was stirred at room temperature for 2 h. The reaction mixture was then concentrated to dryness. This gave 479 mg of the target product which was reacted further without further analytical characterization.

Example 159A rac-Ethyl 5-[(2-{5-fluoro-2-[(4-{2-[4-(trifluoromethyl)phenyl]ethyl}benzyl)oxy]phenyl}ethyl)-amino]-5,6,7,8-tetrahydroquinoline-2-carboxylate

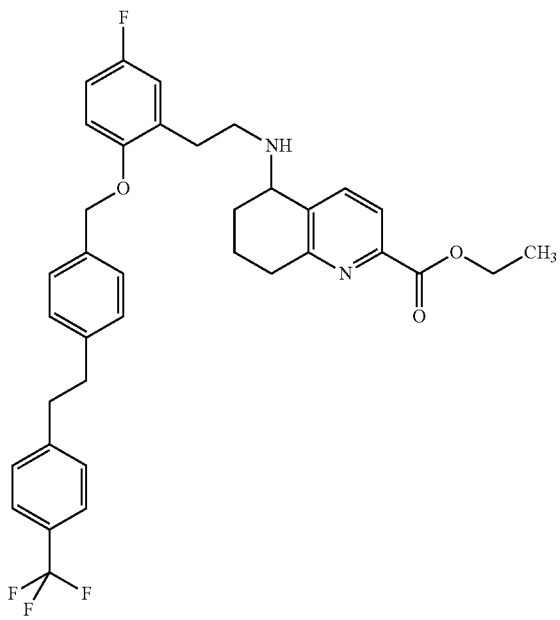 [SMILES: CCOC(=O)c1ccc2c(n1)CCCC2NCCc1cc(F)ccc1OCc1ccc(CCc2ccc(C(F)(F)F)cc2)cc1]

479 mg (0.64 mmol) of rac-ethyl 5-[(2-{5-fluoro-2-[(4-{2-[4-(trifluoromethyl)phenyl]ethyl}-benzyl)oxy]phenyl}ethyl)amino]-5,6,7,8-tetrahydroquinoline-2-carboxylate dihydrochloride (Example 158A) were taken up in 4.7 ml of THF, 0.27 ml of triethylamine was added and the mixture was stirred at room temperature for one hour. Ethyl acetate and water were then added to the reaction solution, the phases were separated and the aqueous phase was extracted once more with ethyl acetate. The combined organic phases were again washed with water, dried over magnesium sulphate, filtered and then concentrated to dryness. This gave 383 mg (0.62 mmol, 96% of theory) of the target compound.

LC-MS (Method 3): $R_t$=1.04 min; m/z=621 (M+H)$^+$.

Example 160A rac-Ethyl 5-[(2-{5-fluoro-2-[(4-{2-[4-(trifluoromethyl)phenyl]ethyl}benzyl)oxy]phenyl}ethyl)-{2-[4-(methoxycarbonyl)phenyl]ethyl}amino]-5,6,7,8-tetrahydroquinoline-2-carboxylate

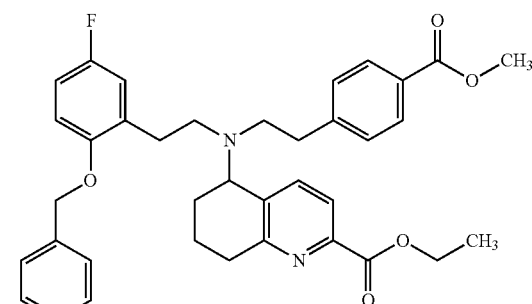

533 mg (1.84 mmol) of methyl 4-(2-iodoethyl)benzoate and 97 mg (0.92 mmol) of anhydrous sodium carbonate were added to a solution of 380 mg (0.61 mmol) of rac-ethyl 5-[(2-{5-fluoro-2-[(4-{2-[4-(trifluoromethyl)phenyl]ethyl}benzyl)oxy]phenyl}ethyl)amino]-5,6,7,8-tetrahydroquinoline-2-carboxylate (Example 159A) in 5 ml of dry acetonitrile, and the mixture was stirred in a microwave apparatus (Biotage Initiator) at 140° C. for 4 h. The reaction solution was then cooled and purified directly by preparative HPLC (mobile phase: acetonitrile/water 9:1). This gave 178 mg (0.23 mmol, 37% of theory) of the title compound.

LC-MS (Method 3): $R_t$=1.62 min; m/z=783 (M+H)$^+$.

Working Examples

Example 1

(−)-5-{(4-Carboxybutyl)[2-(2-{[4-(5-methyl-1,3-benzoxazol-2-yl)benzyl]oxy}phenyl)ethyl]-amino}-5,6,7,8-tetrahydroquinoline-2-carboxylic acid
(Enantiomer 1)

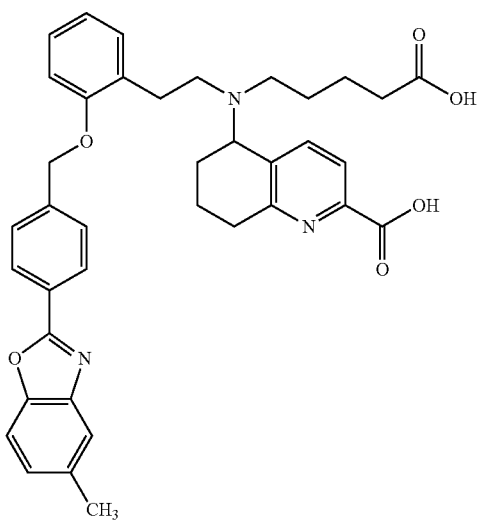 [SMILES: Cc1ccc2oc(-c3ccc(COc4ccccc4CCN(CCCCC(=O)O)C4CCCc5nc(C(=O)O)ccc54)cc3)nc2c1]

752 mg (1.09 mmol) of (−)-ethyl 5-{(5-ethoxy-5-oxopentyl)[2-(2-{[4-(5-methyl-1,3-benzoxazol-2-yl)benzyl]oxy}phenyl)ethyl]amino}-5,6,7,8-tetrahydroquinoline-2-carboxylate (Enantiomer 1, Example 35A) were taken up in 9 ml of THF and 4.6 ml of water, and 137 mg (3.27 mmol) of lithium hydroxide monohydrate were added. The reaction was stirred at 60° C. overnight. After the reaction had gone to completion, the THF was removed on a rotary evaporator and the mixture that remained was diluted with water. The mixture was then acidified with acetic acid to pH 4-5 and extracted repeatedly with ethyl acetate. The combined organic phases were dried over magnesium sulphate, filtered and concentrated to dryness. This gave 590 mg (0.93 mmol, 86% of theory) of the title compound as a yellowish foam.

LC-MS (Method 3): $R_t$=1.03 min; m/z=634 (M+H)$^+$.

$^1$H-NMR (400 MHz, DMSO-d$_6$): δ [ppm]=1.10-1.71 (m, 7H), 1.89-2.04 (m, 2H), 2.05-2.17 (m, 2H), 2.35-2.64 (m, 3H, partially obscured by DMSO signal), 2.45 (s, 3H), 2.65-2.88 (m, 4H), 3.94-4.05 (m, 1H), 5.08 (q, 2H), 6.87 (t, 1H), 6.99 (d, 1H), 7.13 (d, 1H), 7.18 (t, 1H), 7.25 (d, 1H), 7.52 (d, 2H), 7.61 (s, 1H), 7.68 (d, 2H), 7.85 (d, 1H), 8.16 (d, 2H), 11.31-12.96 (br. s, 2H).

$[α]_D^{20}$=−61.61°, c=0.455, methanol.

Example 2

(+)-5-{(4-Carboxybutyl)[2-(2-{[4-(5-methyl-1,3-benzoxazol-2-yl)benzyl]oxy}phenyl)ethyl]-amino}-5,6,7,8-tetrahydroquinoline-2-carboxylic acid
(Enantiomer 2)

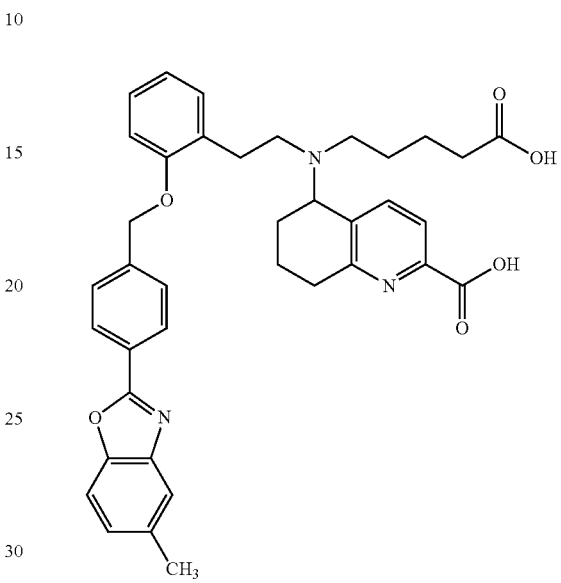

735 mg (1.07 mmol) of (+)-ethyl 5-{(5-ethoxy-5-oxopentyl)[2-(2-{[4-(5-methyl-1,3-benzoxazol-2-yl)benzyl]oxy}phenyl)ethyl]amino}-5,6,7,8-tetrahydroquinoline-2-carboxylate (Enantiomer 2, Example 36A) were taken up in 9 ml of THF and 4.5 ml of water, and 134 mg (3.20 mmol) of lithium hydroxide monohydrate were added. The reaction was stirred at 60° C. overnight. After the reaction had gone to completion, the THF was removed on a rotary evaporator and the mixture that remained was diluted with water. The mixture was then acidified with acetic acid to pH 4-5 and extracted repeatedly with ethyl acetate. The combined organic phases were dried over magnesium sulphate, filtered and concentrated to dryness. This gave 617 mg (0.97 mmol, 91% of theory) of the title compound as a yellowish foam.

LC-MS (Method 3): $R_t$=1.03 min; m/z=634 (M+H)$^+$.

$^1$H-NMR (400 MHz, DMSO-d$_6$): δ [ppm]=1.32-1.70 (m, 7H), 1.89-2.03 (m, 2H), 2.07-2.16 (m, 2H), 2.39-2.64 (m, 3H, partially obscured by DMSO signal), 2.46 (s, 3H), 2.65-2.87 (m, 4H), 3.95-4.03 (m, 1H), 5.08 (q, 2H), 6.87 (t, 1H), 6.99 (d, 1H), 7.13 (d, 1H), 7.18 (t, 1H), 7.25 (d, 1H), 7.52 (d, 2H), 7.61 (s, 1H), 7.67 (d, 2H), 7.85 (d, 1H), 8.16 (d, 2H), 11.30-12.97 (br. s, 2H).

$[α]_D^{20}$=+62.89°, c=0.380, methanol.

Analogously to Examples 1 and 2, the following compounds were prepared:

| Example | Name/Structure/Starting material | Analytical data |
|---|---|---|
| 3 | 5-[(2-{2-[(4-tert-butylbenzyl)oxy]phenyl}ethyl)-(4-carboxybutyl)amino]-5,6,7,8-tetrahydro-quinoline-2-carboxylic acid (Enantiomer 1)<br>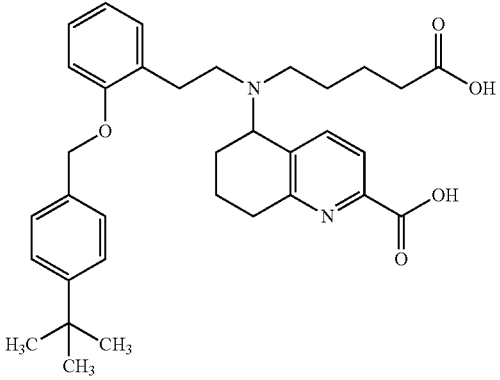<br>from ethyl 5-[(2-{2-[(4-tert-butylbenzyl)oxy]-phenyl}ethyl)(5-ethoxy-5-oxopentyl)amino]-5,6,7,8-tetrahydroquinoline-2-carboxylate (Enantiomer 1) | LC-MS (Method 4):<br>$R_t$ = 1.00 min; m/z = 559 (M + H)$^+$.<br>$^1$H-NMR (400 MHz, DMSO-d$_6$):<br>δ [ppm] = 1.20-1.31 (m, 1H), 1.27 (s, 9H), 1.33-1.67 (m, 6H), 1.88-2.02 (m, 2H), 2.06-2.16 (m, 2H), 2.35-2.59 (m, 3H, partially obscured by DMSO signal), 2.59-2.84 (m, 4H), 3.91-4.01 (m, 1H), 4.85-4.98 (m, 2H), 6.84 (t, 1H), 6.98 (d, 1H), 7.10 (d, 1H), 7.16 (t, 1H), 7.22 (d, 1H), 7.35 (d, 2H), 7.67 (d, 1H), 7.85 (d, 1H), 11.35-13.30 (br. s, about 2H). |
| 4 | 5-[(2-{2-[(4-tert-butylbenzyl)oxy]phenyl}ethyl)-(4-carboxybutyl)amino]-5,6,7,8-tetrahydro-quinoline-2-carboxylic acid (Enantiomer 2)<br>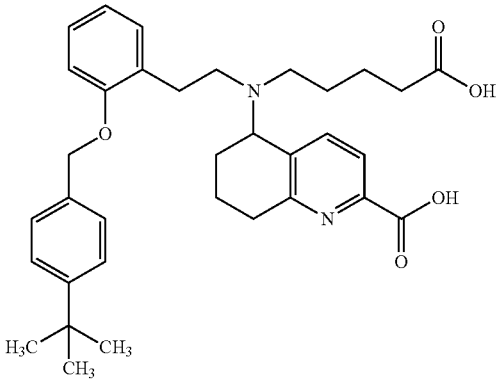<br>from ethyl 5-[(2-{2-[(4-tert-butylbenzyl)oxy]-phenyl}ethyl)(5-ethoxy-5-oxopentyl)amino]-5,6,7,8-tetrahydroquinoline-2-carboxylate (Enantiomer 2) | LC-MS (Method 3):<br>$R_t$ = 1.00 min; m/z = 559 (M + H)$^+$.<br>$^1$H-NMR (400 MHz, DMSO-d$_6$):<br>δ [ppm] = 1.22-1.31 (m, 1H), 1.27 (s, 9H), 1.32-1.67 (m, 6H), 1.89-2.02 (m, 2H), 2.07-2.17 (m, 2H), 2.35-2.59 (m, 3H, partially obscured by DMSO signal), 2.59-2.84 (m, 4H), 3.93-4.01 (m, 1H), 4.85-4.98 (m, 2H), 6.84 (t, 1H), 6.98 (d, 1H), 7.10 (d, 1H), 7.16 (t, 1H), 7.22 (d, 1H), 7.35 (d, 2H), 7.67 (d, 1H), 7.85 (d, 1H), 11.16-12.92 (br. s, about 2H). |

| Example | Name/Structure/Starting material | Analytical data |
|---|---|---|
| 5 | rac-5-{(4-carboxybutyl)[2-(2-{[4-(1-propionyl-piperidin-4-yl)benzyl]oxy}phenyl)ethyl]amino}-5,6,7,8-tetrahydroquinoline-2-carboxylic acid<br>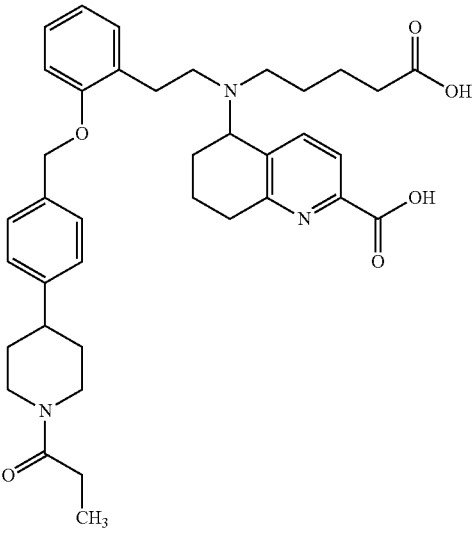<br>from ethyl 5-{(5-ethoxy-5-oxopentyl)[2-(2-{[4-(1-propionylpiperidin-4-yl)benzyl]oxy}phenyl)-ethyl]amino}-5,6,7,8-tetrahydroquinoline-2-carboxylate | LC-MS (Method 3):<br>$R_t$ = 0.86 min; m/z = 642 (M + H)$^+$.<br>$^1$H-NMR (400 MHz, DMSO-$d_6$):<br>δ [ppm] = 1.01 (t, 3H), 1.31-1.66 (m, 8H), 1.70-1.84 (m, 2H), 1.88-2.02 (m, 2H), 2.06-2.16 (m, 2H), 2.29-2.39 (m, 2H), 2.39-2.47 (m, 2H), 2.47-2.84 (m, 8H, partially obscured by DMSO signal), 3.01-3.14 (m, 1H), 3.88-4.02 (m, 2H), 4.48-4.60 (m, 1H), 4.84-4.99 (m, 2H), 6.80-6.88 (m, 1H), 6.94-7.01 (m, 1H), 7.07-7.30 (m, 6H), 7.62-7.69 (m, 1H), 7.78-7.87 (m, 1H), 11.51-13.13 (br. s, about 2H). |
| 6 | rac-5-[(4-carboxybutyl)(2-{2-[(4-cyclohexyl-benzyl)oxy]phenyl}ethyl)amino]-5,6,7,8-tetrahydroquinoline-2-carboxylic acid<br>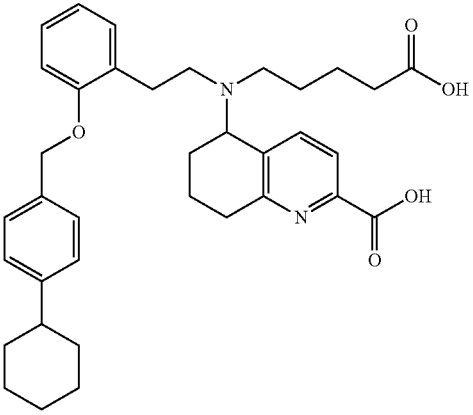<br>from ethyl 5-[2-{4-[(4-cyclohexylbenzyl)oxy]-phenyl}ethyl)(5-ethoxy-5-oxopentyl)amino]-5,6,7,8-tetrahydroquinoline-2-carboxylate | $^1$H-NMR (400 MHz, DMSO-$d_6$):<br>δ [ppm] = 1.14-1.65 (m, 13H), 1.65-1.83 (m, 5H), 1.87-2.02 (m, 2H), 2.07-2.16 (m, 2H), 2.35-2.84 (m, 7H, partially obscured by DMSO signal), 3.92-4.01 (m, 1H), 4.83-4.96 (m, 2H), 6.84 (t, 1H), 6.98 (d, 1H), 7.10 (d, 1H), 7.13-7.22 (m, 5H), 7.66 (d, 1H), 7.84 (d, 1H), 11.06-13.55 (br. s, about 2H). |

| Example | Name/Structure/Starting material | Analytical data |
|---|---|---|
| 7 | 5-{(4-carboxybutyl)[2-(2-{[3-chloro-4'-(trifluoromethyl)biphenyl-4-yl]methoxy}phenyl)ethyl]amino}-5,6,7,8-tetrahydroquinoline-2-carboxylic acid (Enanitomer 1)<br>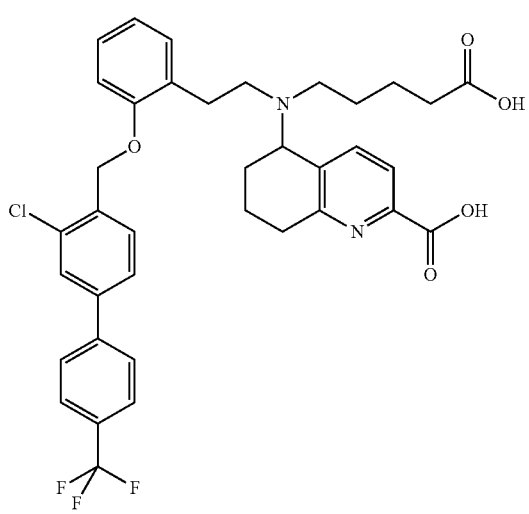<br>from ethyl 5-{[2-(2-{[3-chloro-4'-(trifluoromethyl)biphenyl-4-yl]methoxy}phenyl)ethyl](5-ethoxy-5-oxopentyl)amino}-5,6,7,8-tetrahydroquinoline-2-carboxylate (Enantiomer 1) | LC-MS (Method 3): $R_t$ = 1.18 min; m/z = 681 (M + H)$^+$.<br>$^1$H-NMR (400 MHz, DMSO-d$_6$):<br>δ [ppm] = 1.20-1.30 (m, 1H), 1.31-1.62 (m, 6H), 1.86-1.99 (m, 2H), 2.06-2.16 (m, 2H), 2.35-2.46 (m, 2H), 2.46-2.60 (m, 1H, partially obscured by DMSO signal), 2.60-2.83 (m, 4H), 3.90-3.99 (m, 1H), 5.00-5.14 (m, 2H), 6.89 (t, 1H), 7.03 (d, 1H), 7.14 (d, 1H), 7.21 (t, 1H), 7.54 (d, 1H), 7.65 (d, 1H), 7.70 (dd, 1H), 7.78-7.89 (m, 4H), 7.95 (d, 2H), 11.29-12.89 (br. s, about 2H). |
| 8 | 5-{(4-carboxybutyl)[2-(2-{[3-chloro-4'-(trifluoromethyl)biphenyl-4-yl]methoxy}phenyl)ethyl]amino}-5,6,7,8-tetrahydroquinoline-2-carboxylic acid (Enanitomer 2)<br>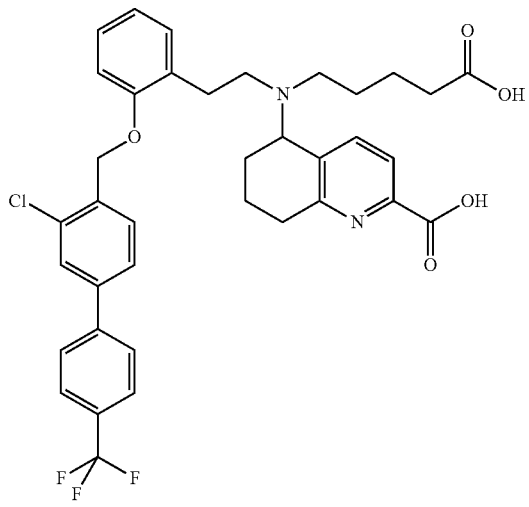<br>from ethyl 5-{[2-(2-{[3-chloro-4'-(trifluoromethyl)biphenyl-4-yl]methoxy}phenyl)phenyl](5-ethoxy-5-oxopentyl)amino}-5,6,7,8-tetrahydroquinoline-2-carboxylate (Enantiomer 2) | LC-MS (Method 3): $R_t$ = 1.17 min; m/z = 681 (M + H)$^+$.<br>$^1$H-NMR (400 MHz, DMSO-d$_6$):<br>δ [ppm] = 1.21-1.29 (m, 1H), 1.32-1.64 (m, 6H), 1.86-2.00 (m, 2H), 2.06-2.15 (m, 2H), 2.36-2.47 (m, 2H), 2.47-2.60 (m, 1H, partially obscured by DMSO signal), 2.60-2.84 (m, 4H), 3.90-4.00 (m, 1H), 5.01-5.14 (m, 2H), 6.89 (t, 1H), 7.03 (d, 1H), 7.14 (d, 1H), 7.21 (t, 1H), 7.54 (d, 1H), 7.65 (d, 1H), 7.70 (dd, 1H), 7.79-7.89 (m, 4H), 7.95 (d, 2H), 11.35-12.90 (br. s, 2H). |

| Example | Name/Structure/Starting material | Analytical data |
|---------|----------------------------------|-----------------|
| 9 | 5-[(4-carboxybutyl)(2-{2-[(5-phenylpentyl)oxy]-phenyl}ethyl)amino]-5,6,7,8-tetrahydro-quinoline-2-carboxylic acid (Enantiomer 1)<br>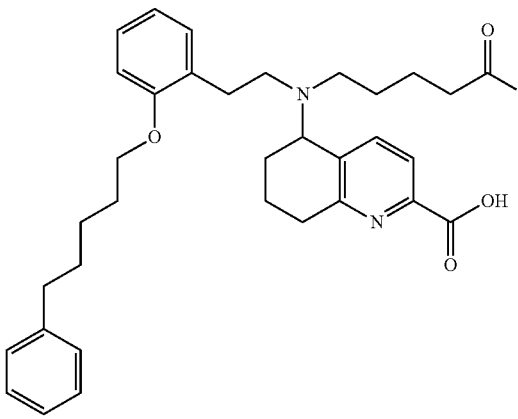<br>from ethyl 5-[(5-ethoxy-5-oxopentyl)(2-{2-[(5-phenylpentyl)oxy]phenyl}ethyl)amino]-5,6,7,8-tetrahydroquinoline-2-carboxylate (Enantiomer 1) | LC-MS (Method 3):<br>$R_t$ = 1.03 min; m/z = 559 (M + H)$^+$.<br>$^1$H-NMR (400 MHz, DMSO-$d_6$):<br>δ [ppm] = 1.09-1.77 (m, 16H), 1.94-2.08 (m, 2H), 2.12-2.22 (m, 2H), 2.38-2.64 (m, 3H, partially obscured by DMSO signal), 2.65-2.76 (m, 1H), 2.78-2.88 (m, 2H), 3.69-3.79 (m, 1H), 3.79-3.88 (m, 1H), 3.95-4.05 (m, 1H), 6.76-6.88 (m, 2H), 7.07 (d, 1H), 7.10-7.20 (m, 4H), 7.22-7.29 (m, 2H), 7.68 (d, 1H), 7.82 (d, 1H), 11.05-13.54 (br. s, about 2H). |
| 10 | 5-[(4-carboxybutyl)(2-{2-[(5-phenylpentyl)oxy]-phenyl}ethyl)amino]-5,6,7,8-tetrahydro-quinoline-2-carboxylic acid (Enantiomer 2)<br>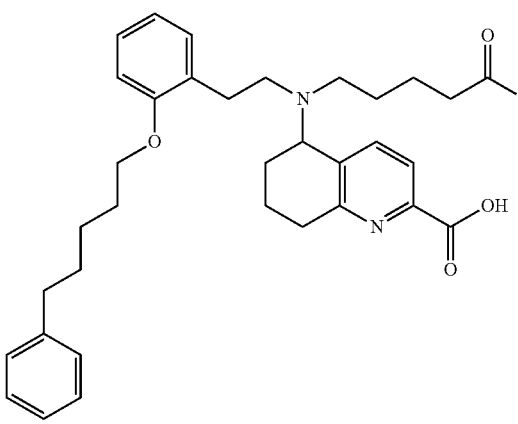<br>from ethyl 5-[(5-ethoxy-5-oxopentyl)(2-{2-[(5-phenylpentyl)oxy]phenyl}ethyl)amino]-5,6,7,8-tetrahydroquinoline-2-carboxylate (Enantiomer 2) | LC-MS (Method 3):<br>$R_t$ = 1.02 min; m/z = 559 (M + H)$^+$.<br>$^1$H-NMR (400 MHz, DMSO-$d_6$):<br>δ [ppm] = 1.08-1.78 (m, 16H), 1.94-2.07 (m, 2H), 2.11-2.23 (m, 2H), 2.39-2.65 (m, 3H, partially obscured by DMSO signal), 2.65-2.76 (m, 1H), 2.77-2.89 (m, 2H), 3.69-3.80 (m, 1H), 3.80-3.89 (m, 1H), 3.95-4.05 (m, 1H), 6.75-6.89 (m, 2H), 7.07 (d, 1H), 7.10-7.20 (m, 4H), 7.21-7.30 (m, 2H), 7.68 (d, 1H), 7.82 (d, 1H), 11.03-12.99 (br. s, about 2H). |

| Example | Name/Structure/Starting material | Analytical data |
|---|---|---|
| 11 | rac-5-[(4-carboxybutyl){2-[2-({4-[trans-4-(trifluoromethyl)cyclohexyl]benzyl}oxy)phenyl]-ethyl}amino]-5,6,7,8-tetrahydroquinoline-2-carboxylic acid<br>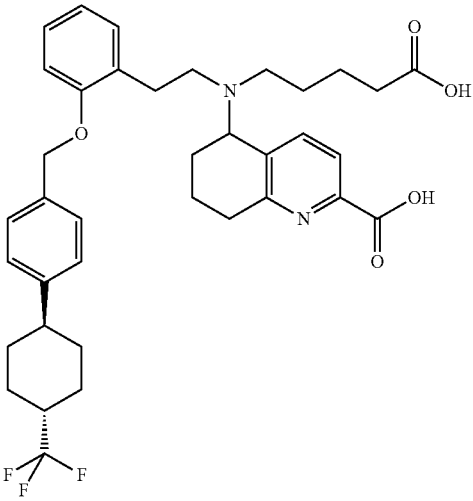<br>from ethyl 5-[(5-ethoxy-5-oxopentyl){2-[2-({4-[trans-4-(trifluoromethyl)cyclohexyl]benzyl}-oxy)phenyl]ethyl}amino]-5,6,7,8-tetrahydro-quinoline-2-carboxylate | LC-MS (Method 3):<br>$R_t$ = 1.12 min; m/z = 653 (M + H)$^+$.<br>$^1$H-NMR (400 MHz, DMSO-d$_6$):<br>δ [ppm] = 1.14-1.65 (m, 12H), 1.79-2.02 (m, 6H), 2.05-2.16 (m, 2H), 2.28-2.59 (m, 4H, partially obscured by DMSO signal), 2.59-2.70 (m, 1H), 2.70-2.84 (m, 3H), 3.91-3.99 (m, 1H), 4.83-4.98 (m, 2H), 6.84 (t, 1H), 6.98 (d, 1H), 7.10 (d, 1H), 7.12-7.25 (m, 5H), 7.66 (d, 1H), 7.84 (d, 1H), 11.39-13.00 (br. s, 2H). |

Example 12 rac-5-{(2-{2-[(4-tert-Butylbenzyl)oxy]phenyl}ethyl) [2-(4-carboxyphenyl)ethyl]amino}-5,6,7,8-tetrahydroquinoline-2-carboxylic acid

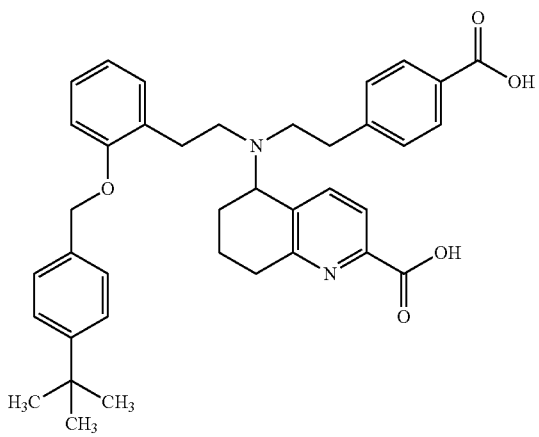 [SMILES: CC(C)(C)c1ccc(COc2ccccc2CCN(CCc2ccc(C(=O)O)cc2)C2CCCc3nc(C(=O)O)ccc32)cc1]

35 mg (0.05 mmol) of ethyl 5-[(2-{2-[(4-tert-butylbenzyl) oxy]phenylethyl)2-[4-(methoxycarbonyl)phenyl] ethyl}amino]-5,6,7,8-tetrahydroquinoline-2-carboxylate (Example 43A) were taken up in 1 ml of THF and 1 ml of water, and 7 mg (0.16 mmol) of lithium hydroxide monohydrate were added. The reaction was stirred at 50° C. overnight. After the reaction had gone to completion, the THF was removed on a rotary evaporator and the mixture that remained was diluted with water. The mixture was then acidified with 1 M hydrochloric acid and extracted repeatedly using a 1:1 mixture of ethyl acetate and dichloromethane. The combined organic phases were dried over magnesium sulphate, filtered and concentrated to dryness. This gave 29 mg (0.04 mmol, content 91%, 81% of theory) of the title compound as a yellowish solid.

LC-MS (Method 4): $R_t$=1.29 min; m/z=607 (M+H)$^+$.
$^1$H-NMR (400 MHz, DMSO-d$_6$): δ [ppm]=0.77-0.90 (m, 0.5H), 1.12-1.31 (m, 10H), 1.42-1.87 (m, 2H), 1.88-2.14 (m, 2H), 2.22-2.34 (m, 0.5H), 2.41-3.07 (m, 7H, partially obscured by DMSO signal), 3.98-4.11 (m, 0.5H), 4.84-5.13 (m, 2H), 5.13-5.26 (m, 0.5H), 6.79-6.89 (m, 0.5H), 6.95-7.52 (m, 11H), 7.55-7.62 (m, 0.5H), 7.74-7.88 (m, 2H), 7.90-8.00 (m, 1H), 8.54-8.68 (m, 0.5H), 10.39-10.58 (m, 0.5H), 11.69-14.09 (br. s, about 1H).

Example 13

5-{(4-Carboxybutyl)[2-(2-{[4-(2-phenylethyl)benzyl]oxy}phenyl)ethyl]amino}-5,6,7,8-tetrahydroquinoline-2-carboxylic acid (Enantiomer 1)

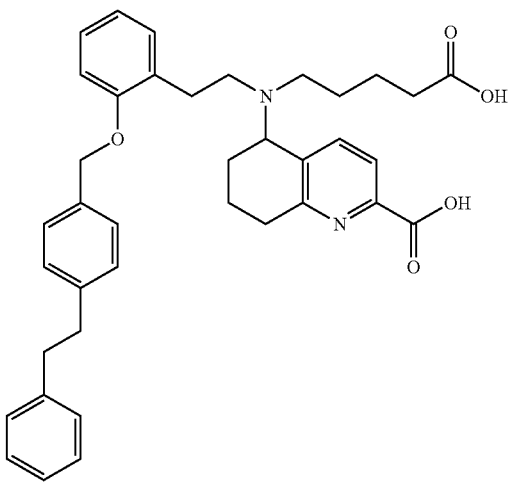 [SMILES: O=C(O)CCCCN(CCc1ccccc1OCc1ccc(CCc2ccccc2)cc1)C1CCCc2nc(C(=O)O)ccc21]

259 mg (0.39 mmol) of ethyl 5-{(5-ethoxy-5-oxopentyl)[2-(2-{[4-(2-phenylethyl)benzyl]oxy}phenyl)ethyl]amino}-5,6,7,8-tetrahydroquinoline-2-carboxylate (Enantiomer 1, Example 50A) were taken up in 4 ml of dioxane, 2 ml of a 2 M solution of potassium hydroxide in water were added and the mixture was stirred at room temperature overnight. After the reaction had gone to completion, the reaction mixture was acidified slightly using 0.75 ml of acetic acid and 1 N of hydrochloric acid and then concentrated to dryness. The residue obtained was purified by preparative HPLC. This gave 183 mg (0.30 mmol, 77% of theory) of the title compound.

LC-MS (Method 4): $R_t$=1.02 min; m/z=607 (M+H)$^+$.

$^1$H-NMR (400 MHz, DMSO-d$_6$): δ [ppm]=1.30-1.68 (m, 6H), 1.89-2.04 (m, 2H), 2.08-2.18 (m, 2H), 2.39-2.47 (m, 2H), 2.47-2.58 (m, 1H, obscured by DMSO signal), 2.58-2.84 (m, 5H), 2.86 (s, 4H), 3.92-4.01 (m, 1H), 4.82-4.97 (m, 2H), 6.84 (t, 1H), 6.97 (d, 1H), 7.10 (d, 1H), 7.13-7.21 (m, 6H), 7.21-7.30 (m, 4H), 7.66 (d, 1H), 7.83 (d, 1H), 11.20-13.00 (br. s, about 2H).

Analogously to Example 13, the following compounds were prepared:

| Example | Name/Structure/Starting material | Analytical data |
|---|---|---|
| 14 | 5-{(4-carboxybutyl)[2-(2-{[4-(2-phenylethyl)benzyl]oxy}phenyl)ethyl]amino}-5,6,7,8-tetrahydroquinoline-2-carboxylic acid (Enantiomer 2)<br><br>from ethyl 5-{(5-ethoxy-5-oxopentyl)[2-(2-{[4-(2-phenylethyl)benzyl]oxy}phenyl)ethyl]amino}-5,6,7,8-tetrahydroquinoline-2-carboxylate (Enantiomer 2) | LC-MS (Method 1):<br>$R_t$ = 1.08 min; m/z = 607 (M + H)$^+$.<br>$^1$H-NMR (400 MHz, DMSO-d$_6$):<br>δ [ppm] = 1.31-1.69 (m, 6H), 1.90-2.02 (m, 2H), 2.08-2.17 (m, 2H), 2.39-2.46 (m, 2H), 2.46-2.58 (m, 1H, obscured by DMSO signal), 2.58-2.83 (m, 5H), 2.86 (s, 4H), 3.92-4.01 (m, 1H), 4.83-4.97 (m, 2H), 6.84 (t, 1H), 6.97 (d, 1H), 7.10 (d, 1H), 7.13-7.21 (m, 6H), 72.1-7.30 (m, 4H), 7.66 (d, 1H), 7.82 (d, 1H), 11.36-12.90 (br. s, about 2H). |

| Example | Name/Structure/Starting material | Analytical data |
| --- | --- | --- |
| 15 | 5-[(4-carboxybutyl){2-[2-({4-[2-(4-fluorophenyl)-ethyl]benzyl}oxy)phenyl]ethyl}amino]-5,6,7,8-tetrahydroquinoline-2-carboxylic acid (Enantiomer 1)<br>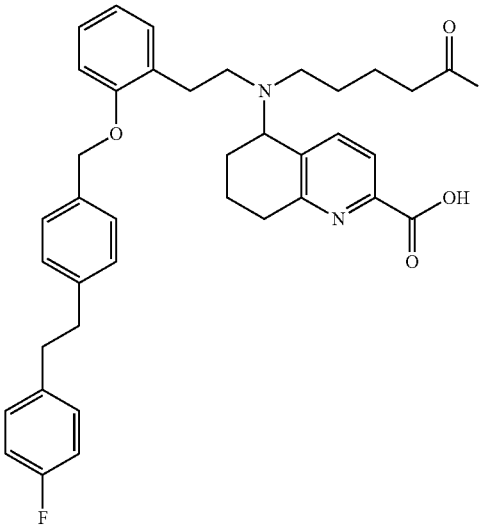<br>from ethyl 5-[(5-ethoxy-5-oxopentyl){2-[2-({4-[2-(4-fluorophenyl)ethyl]benzyl}oxy)phenyl]-ethyl}amino]-5,6,7,8-tetrahydroquinoline-2-carboxylate (Enantiomer 1) | LC-MS (Method 4):<br>$R_t$ = 1.03 min; m/z = 625 (M + H)$^+$.<br>$^1$H-NMR (400 MHz, DMSO-$d_6$):<br>δ [ppm] = 1.31-1.54 (m, 5H), 1.54-1.69 (m, 1H), 1.89-2.02 (m, 2H), 2.08-2.17 (m, 2H), 2.37 (s, 2H), 2.40-2.70 (m, 2H, partially obscured by DMSO signal), 2.71 (s, 2H), 2.77-2.83 (m, 2H), 2.85 (s, 4H), 3.92-4.00 (m, 1H), 4.82-4.97 (m, 2H), 6.84 (t, 1H), 6.97 (d, 1H), 7.04-7.12 (m, 3H), 7.13-7.21 (m, 5H), 7.22-7.29 (m, 2H), 7.66 (d, 1H), 7.82 (d, 1H). |
| 16 | 5-[(4-carboxybutyl){2-[2-({4-[2-(4-fluorophenyl)-ethyl]benzyl}oxy)phenyl]ethyl}amino]-5,6,7,8-tetrahydroquinoline-2-carboxylic acid (Enantiomer 2)<br>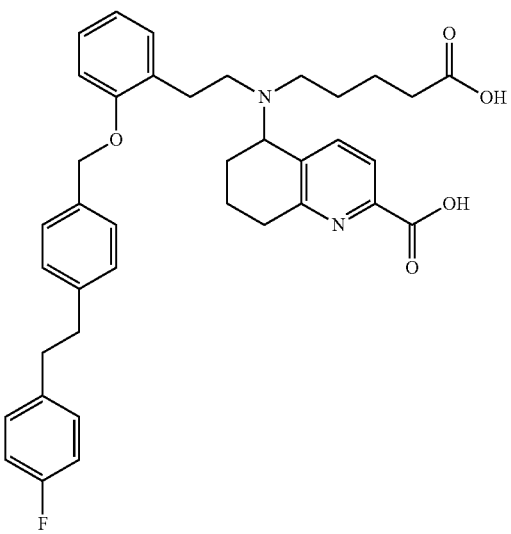<br>from ethyl 5-[(5-ethoxy-5-oxopentyl){2-[2-({4-[2-(4-fluorophenyl)ethyl]benzyl}oxy)phenyl]-ethyl}amino]-5,6,7,8-tetrahydroquinoline-2-carboxylate (Enantiomer 2) | LC-MS (Method 4):<br>$R_t$ = 1.03 min; m/z = 625 (M + H)$^+$. |

| Example | Name/Structure/Starting material | Analytical data |
|---|---|---|
| 17 | 5-{(4-carboxybutyl)[2-(2-{[4'-(trifluoromethyl)-biphenyl-4-yl]methoxy}phenyl)ethyl]amino}-5,6,7,8-tetrahydroquinoline-2-carboxylic acid (Enantiomer 1)<br>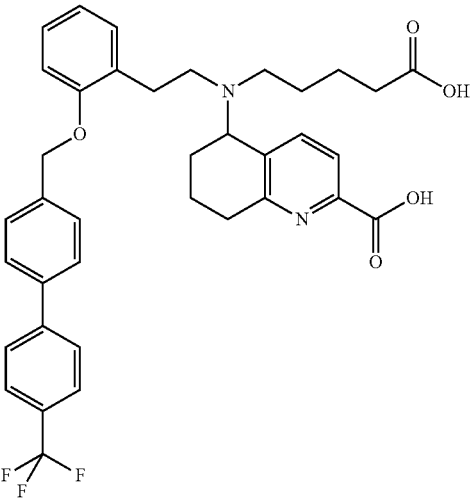<br>from ethyl 5-{(5-ethoxy-5-oxopentyl)[2-(2-{[4'-(trifluoromethyl)biphenyl-4-yl]methoxy}phenyl)-ethyl]amino}-5,6,7,8-tetrahydroquinoline-2-carboxylate (Enantiomer 1) | LC-MS (Method 1):<br>$R_t$ = 1.04 min; m/z = 647 (M + H)$^+$.<br>$^1$H-NMR (400 MHz, DMSO-$d_6$):<br>δ [ppm] = 1.34-1.68 (m, 6H), 1.88-2.03 (m, 2H), 2.08-2.18 (m, 2H), 2.41-2.63 (m, 4H, partially obscured by DMSO signal), 2.64-2.74 (m, 1H), 2.74-2.85 (m, 3H), 3.94-4.02 (m, 1H), 4.97-5.11 (m, 2H), 6.86 (t, 1H), 7.00 (d, 1H), 7.13 (d, 1H), 7.18 (t, 1H), 7.42 (d, 2H), 7.64-7.73 (m, 3H), 7.79-7.93 (m, 5H), 11.26-12.64 (br. s, about 2H). |
| 18 | 5-{(4-carboxybutyl)[2-(2-{[4'-(trifluoromethyl)-biphenyl-4-yl]methoxy}phenyl)ethyl]amino}-5,6,7,8-tetrahydroquinoline-2-carboxylic acid (Enantiomer 2)<br>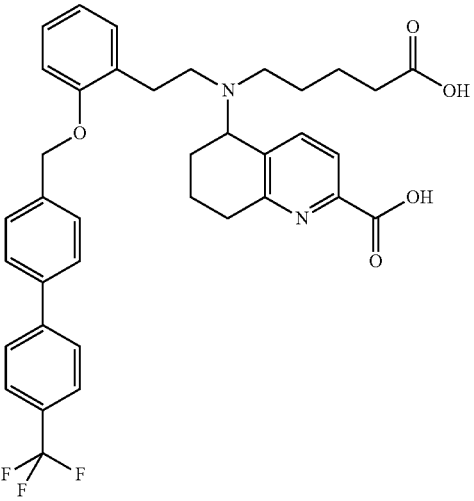<br>from ethyl 5-{(5-ethoxy-5-oxopentyl)[2-(2-{[4'-(trifluoromethyl)biphenyl-4-yl]methoxy}phenyl)-ethyl]amino}-5,6,7,8-tetrahydroquinoline-2-carboxylate (Enantiomer 2) | LC-MS (Method 4):<br>$R_t$ = 1.05 min; m/z = 647 (M + H)$^+$.<br>$^1$H-NMR (400 MHz, DMSO-$d_6$):<br>δ [ppm] = 1.33-1.68 (m, 6H), 1.88-2.03 (m, 2H), 2.09-2.18 (m, 2H), 2.40-2.63 (m, 4H, partially obscured by DMSO signal), 2.64-2.74 (m, 1H), 2.74-2.85 (m, 3H), 3.94-4.03 (m, 1H), 4.96-5.10 (m, 2H), 6.86 (t, 1H), 7.00 (d, 1H), 7.13 (d, 1H), 7.18 (t, 1H), 7.42 (d, 2H), 7.64-7.74 (m, 3H), 7.78-7.93 (m, 5H), 11.20-12.71 (br. s, about 2H). |

Example 19

5-{[2-(4-Carboxyphenyl)ethyl][2-(2-{[4-(5-chloro-1,3-benzoxazol-2-yl)benzyl]oxy}phenyl)ethyl]-amino}-5,6,7,8-tetrahydroquinoline-2-carboxylic acid (Enantiomer 1)

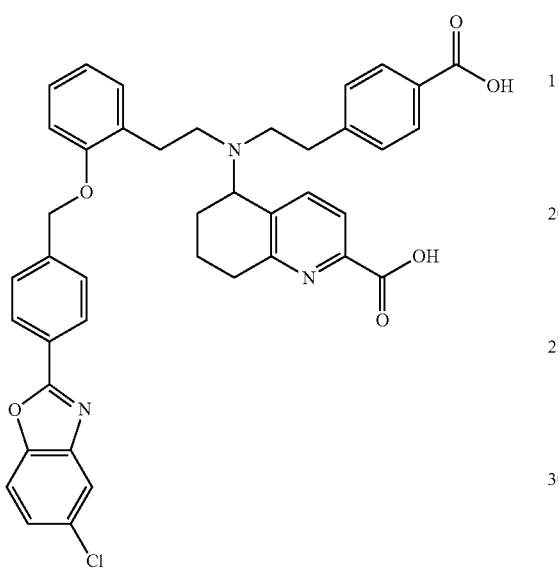

68 mg (0.09 mmol) of ethyl 5-([2-(2-{[4-(5-chloro-1,3-benzoxazol-2-yl)benzyl]oxy}phenyl)ethyl]-{2-[4-(methoxycarbonyl)phenyl]ethyl}amino)-5,6,7,8-tetrahydroquinoline-2-carboxylate (Enantiomer 1, Example 63A) were taken up in 4 ml of THF and 2 ml of water, and 12 mg (0.27 mmol) of lithium hydroxide monohydrate were added. The reaction was stirred at 60° C. overnight. After the reaction had gone to completion, the THF was removed on a rotary evaporator and the mixture that remained was diluted with water. The mixture was then acidified to pH 4-5 using acetic acid and extracted repeatedly with ethyl acetate. The combined organic phases were dried over magnesium sulphate, filtered and concentrated to dryness. This gave 33 mg (0.04 mmol, 48% of theory) of the title compound.

LC-MS (Method 3): $R_t$=1.26 min; m/z=702/704 (M+H)$^+$.

$^1$H-NMR (400 MHz, DMSO-d$_6$): δ [ppm]=1.41-1.55 (m, 1H), 1.55-1.70 (m, 1H), 1.89-2.08 (m, 2H), 2.59-2.87 (m, 10H), 4.01-4.14 (m, 1H), 5.01-5.15 (m, 2H), 6.86 (t, 1H), 7.01 (d, 1H), 7.06 (d, 1H), 7.14 (d, 2H), 7.20 (t, 1H), 7.42-7.57 (m, 5H), 7.76 (d, 2H), 7.83 (d, 1H), 7.93 (d, 1H), 8.11 (d, 2H), 12.03-13.45 (br. s, about 2H).

Example 20

5-{[2-(4-Carboxyphenyl)ethyl][2-(2-{[4-(5-chloro-1,3-benzoxazol-2-yl)benzyl]oxy}phenyl)ethyl]-amino}-5,6,7,8-tetrahydroquinoline-2-carboxylic acid (Enantiomer 2)

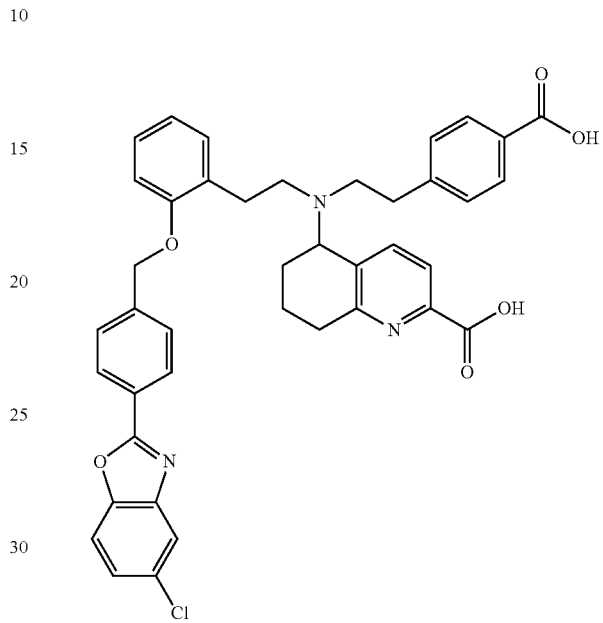

45 mg (0.06 mmol) of ethyl 5-([2-(2-{[4-(5-chloro-1,3-benzoxazol-2-yl)benzyl]oxy}phenyl)ethyl]-{2-[4-(methoxycarbonyl)phenyl]ethyl}amino)-5,6,7,8-tetrahydroquinoline-2-carboxylate (Enantiomer 2, Example 64A) were taken up in 4 ml of THF and 2 ml of water, and 8 mg (0.18 mmol) of lithium hydroxide monohydrate were added. The reaction was stirred at 60° C. overnight. After the reaction had gone to completion, the THF was removed on a rotary evaporator and the mixture that remained was diluted with water. The mixture was then acidified to pH 4-5 using acetic acid and extracted repeatedly with ethyl acetate. The combined organic phases were dried over magnesium sulphate, filtered and concentrated to dryness. This gave 13 mg (0.02 mmol, 32% of theory) of the title compound.

LC-MS (Method 3): $R_t$=1.26 min; m/z=702/704 (M+H)$^+$.

$^1$H-NMR (400 MHz, DMSO-d$_6$): δ [ppm]=1.40-1.55 (m, 1H), 1.55-1.70 (m, 1H), 1.88-2.08 (m, 2H), 2.58-2.87 (m, 10H), 4.02-4.13 (m, 1H), 5.01-5.15 (m, 2H), 6.86 (t, 1H), 7.02 (d, 1H), 7.06 (d, 1H), 7.14 (d, 2H), 7.20 (t, 1H), 7.42-7.57 (m, 5H), 7.76 (d, 2H), 7.84 (d, 1H), 7.93 (d, 1H), 8.11 (d, 2H), 11.69-13.84 (br. s, about 2H).

Analogously to Example 20, the following compounds were prepared:

| Example | Name/Structure/Starting material | Analytical data |
|---|---|---|
| 21 | 5-{[2-(4-carboxyphenyl)ethyl][2-(2-{[4-(5-methyl-1,3-benzoxazol-2-yl)benzyl]oxy}phenyl)ethyl]-amino}-5,6,7,8-tetrahydroquinoline-2-carboxylic acid (Enantiomer 1)<br>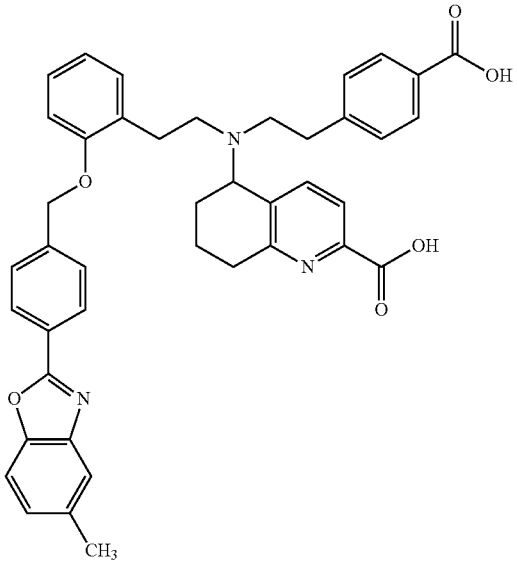<br>from ethyl 5-({2-[4-(methoxycarbonyl)phenyl]-ethyl}[2-(2-{[4-(5-methyl-1,3-benzoxazol-2-yl)benzyl]oxy}phenyl)ethyl]amino)-5,6,7,8-tetrahydroquinoline-2-carboxylate (Enantiomer 1, Example 67A) | LC-MS (Method 3):<br>$R_t$ = 1.25 min; m/z = 682 (M + H)$^+$.<br>$^1$H-NMR (400 MHz, DMSO-$d_6$): δ [ppm] = 1.40-1.70 (m, 2H), 1.87-2.11 (m, 2H), 2.45 (s, 3H), 2.59-2.87 (m, 10H), 4.02-4.16 (m, 1H), 5.07 (m, 2H), 6.86 (t, 1H), 7.02 (m, 2H), 7.15 (m, 4H), 7.42-7.55 (m, 4H), 7.61 (s, 1H), 7.66 (d, 1H), 7.77 (d, 2H), 8.11 (d, 2H), 12.01-13.58 (br. s, about 2H).<br>$[α]_D^{20}$ = −38.06°, c = 0.310, methanol. |
| 22 | 5-{[2-(4-carboxyphenyl)ethyl][2-(2-{[4-(5-methyl-1,3-benzoxazol-2-yl)benzyl]oxy}phenyl)ethyl]-amino}-5,6,7,8-tetrahydroquinoline-2-carboxylic acid (Enantiomer 2)<br>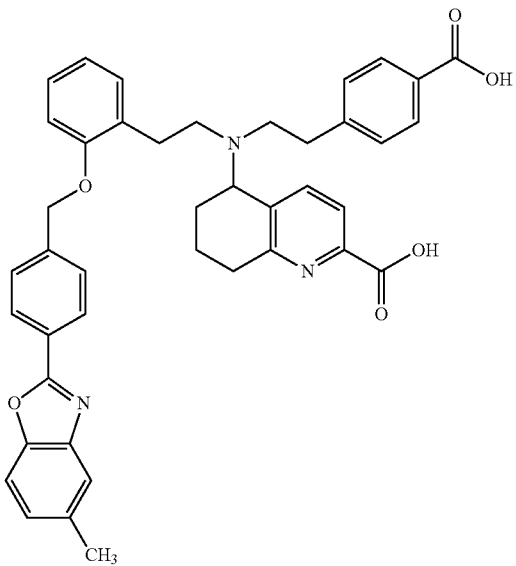 [SMILES: O=C(O)c1ccc(CCN(CCc2ccccc2OCc2ccc(-c3nc4cc(Cl)ccc4o3)cc2)C2CCCc3nc(C(=O)O)ccc32)cc1]<br>from ethyl 5-({2-[4-(methoxycarbonyl)phenyl]-ethyl}[2-(2-{[4-(5-methyl-1,3-benzoxazol-2-yl)benzyl]oxy}phenyl)ethyl]amino)-5,6,7,8-tetrahydroquinoline-2-carboxylate (Enantiomer 2, Example 68A) | LC-MS (Method 3):<br>$R_t$ = 1.25 min; m/z = 682 (M + H)$^+$.<br>$^1$H-NMR (400 MHz, DMSO-$d_6$): δ [ppm] = 1.41-1.70 (m, 2H), 1.87-2.10 (m, 2H), 2.45 (s, 3H), 2.59-2.88 (m, 10H), 4.03-4.14 (m, 1H), 5.07 (m, 2H), 6.86 (t, 1H), 6.97-7.10 (m, 2H), 7.11-7.29 (m, 4H), 7.42-7.55 (m, 4H), 7.61 (s, 1H), 7.66 (d, 1H), 7.78 (d, 2H), 8.11 (d, 2H), 11.78-13.52 (br. s, about 2H). |

Example 23

5-{[2-(4-Carboxyphenyl)ethyl][2-(2-{[3-chloro-4'-(trifluoromethyl)biphenyl-4-yl]methoxy}-phenyl)ethyl]amino}-5,6,7,8-tetrahydroquinoline-2-carboxylic acid (Enantiomer 2)

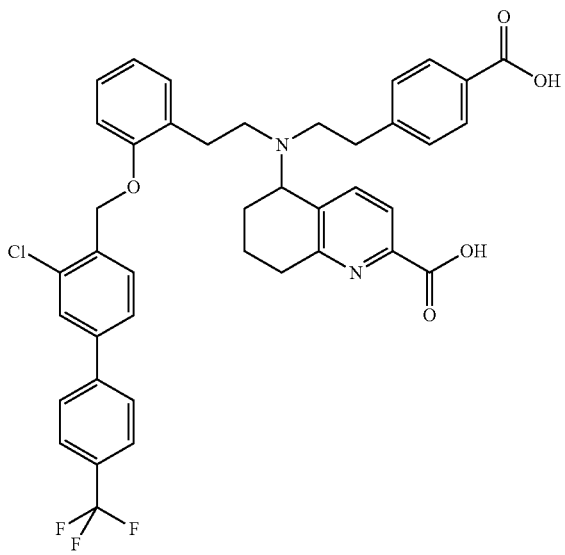

42 g (54.46 mmol) of ethyl 5-{[2-(2-([3-chloro-4'-(trifluoromethyl)biphenyl-4-yl]methoxy}-phenyl)ethyl]{2-[4-(methoxycarbonyl)phenyl]ethyl}amino)-5,6,7,8-tetrahydroquinoline-2-carboxylate (Enantiomer 2, Example 92A) were dissolved in 429 ml of dioxane, 163 ml of 1 N aqueous sodium hydroxide solution were added and the mixture was then stirred at room temperature overnight. After the reaction had gone to completion, the dioxane was removed on a rotary evaporator and the mixture that remained was diluted with about 750 ml of water. The mixture was then acidified to pH 4-5 using acetic acid. The precipitated solid was filtered off with suction and washed repeatedly with water (about 250 ml of water in total). The solid was then taken up in 750 ml of water and stirred at room temperature overnight. After another filtration with suction, the solid was again washed with water and then dried under high vacuum overnight using the drying agent phosphorus pentoxide. The drying agent was then removed and the solid was dried at 40° C. for a further 24 h. In this manner, 35 g (48 mmol, 88% of theory) of the title compound were obtained.

LC-MS (Method 3): $R_t$=1.39 min; m/z=729/731 (M+H)$^+$.
$^1$H-NMR (400 MHz, DMSO-$d_6$): δ [ppm]=1.37-1.68 (m, 2H), 1.85-2.06 (m, 2H), 2.59-2.83 (m, 10H), 3.98-4.10 (m, 1H), 4.99-5.15 (m, 2H), 6.87 (t, 1H), 7.05 (d, 2H), 7.12 (d, 2H), 7.23 (t, 1H), 7.38-7.48 (m, 2H), 7.54 (d, 1H), 7.62 (d, 1H), 7.71-7.91 (m, 7H), 11.60-13.85 (br. s, about 2H).
$[α]_D^{20}$=+61.75°, c=0.420, methanol.

Analogously to Example 20 and Example 23, the following compounds were prepared:

| Example | Name/Structure/Starting material | Analytical data |
| --- | --- | --- |
| 24 | 5-([2-(4-carboxyphenyl)ethyl]{2-[2-({4-[5-(trifluoromethyl)-1,3-benzoxazol-2-yl]benzyl}oxy)phenyl]ethyl}amino)-5,6,7,8-tetrahydroquinoline-2-carboxylic acid (Enantiomer 2)<br><br>from ethyl 5-({2-[4-(methoxycarbonyl)phenyl]-ethyl}{2-[2-({4-[5-(trifluoromethyl)-1,3-benzoxazol-2-yl]benzyl}oxy)phenyl]ethyl}amino)-5,6,7,8-tetrahydroquinoline-2-carboxylate (Enantiomer 2, Example 93A) | LC-MS (Method 3): $R_t$ = 1.32 min; m/z = 736 (M + H)$^+$.<br>$^1$H-NMR (400 MHz, DMSO-$d_6$): δ [ppm] = 1.41-1.55 (m, 1H), 1.55-1.71 (m, 1H), 1.88-2.10 (m, 2H), 2.58-2.89 (m, 10H), 4.01-4.14 (m, 1H), 5.03-5.16 (m, 2H), 6.86 (t, 1H), 6.99-7.10 (m, 2H), 7.14 (d, 2H), 7.21 (t, 1H), 7.46 (d, 1H), 7.49-7.60 (m, 3H), 7.72-7.86 (m, 3H), 8.03 (d, 1H), 8.14 (d, 2H), 8.24 (s, 1H), 12.01-13.42 (br. s, about 2H). |

| Example | Name/Structure/Starting material | Analytical data |
|---|---|---|
| 25 | 5-[(4-carboxybutyl){2-[2-({4-[5-(trifluoromethyl)-1,3-benzoxazol-2-yl]benzyl}oxy)phenyl]ethyl}-amino]-5,6,7,8-tetrahydroquinolin-2-carboxylic acid (Enantiomer 2)<br>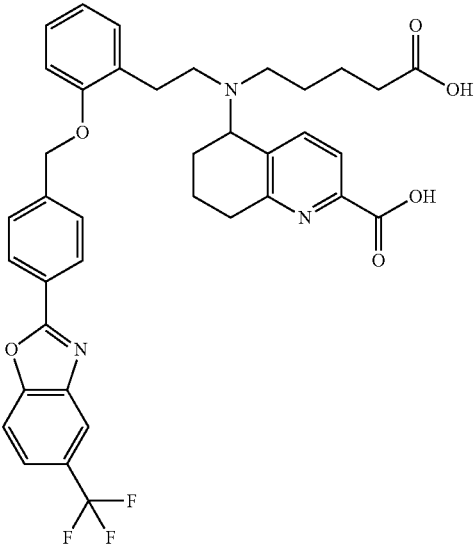<br>from ethyl 5-[(5-ethoxy-5-oxopentyl){2-[2-({4-[5-(trifluoromethyl)-1,3-benzoxazol-2-yl]benzyl}oxy)-phenyl]ethyl}amino]-5,6,7,8-tetrahydroquinoline-2-carboxylate (Enantiomer 2, Example 98A) | LC-MS (Method 3): $R_t$ = 1.07 min; m/z = 688 $(M + H)^+$.<br>$^1$H-NMR (400 MHz, DMSO-$d_6$): δ [ppm] = 1.30-1.71 (m, 6H), 1.90-2.04 (m, 2H), 2.07-2.18 (m, 2H), 2.39-2.65 (m, 4H, partially obscured by DMSO signal), 2.65-2.91 (m, 4H), 3.87-4.07 (m, 1H), 5.10 (q, 2H), 6.87 (t, 1H), 7.00 (d, 1H), 7.10-7.23 (m, 2H), 7.56 (d, 2H), 7.66 (d, 1H), 7.85 (d, 2H), 8.04 (d, 1H), 8.16-8.30 (m, 3H), 11.10-13.31 (br. s, about 2H). |
| 26 | 5-{[2-(2-{[4-(1,3-benzoxazol-2-yl)benzyl]oxy}-phenyl)ethyl][2-(4-carboxyphenyl)ethyl]amino}-5,6,7,8-tetrahydroquinoline-2-carboxylic acid (Enantiomer 2)<br>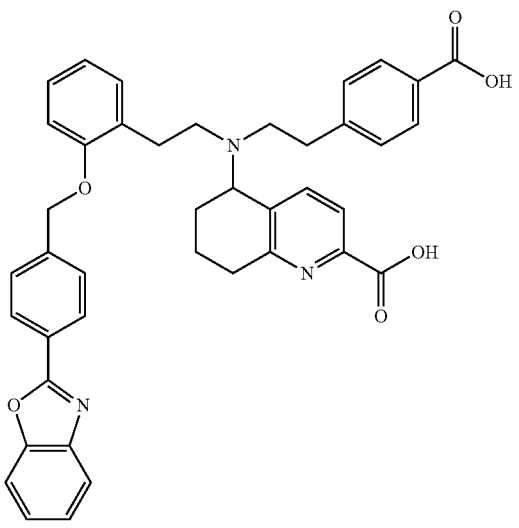<br>from ethyl 5-([2-(2-{[4-(1,3-benzoxazol-2-yl)-benzyl]oxy}phenyl)ethyl]{2-[4-(methoxycarbonyl)-phenyl]ethyl}amino)-5,6,7,8-tetrahydroquinoline-2-carboxylate (Enantiomer 2, Example 94A) | LC-MS (Method 3): $R_t$ = 1.17 min; m/z = 668 $(M + H)^+$.<br>$^1$H-NMR (400 MHz, DMSO-$d_6$): δ [ppm] = 1.41-1.54 (m, 1H), 1.55-1.69 (m, 1H), 1.86-2.09 (m, 2H), 2.58-2.86 (m, 10H), 4.05-4.13 (m, 1H), 5.00-5.15 (m, 2H), 6.86 (t, 1H), 6.97-7.10 (m, 2H), 7.12-7.26 (m, 3H), 7.37-7.56 (m, 6H), 7.72-7.88 (m, 4H), 8.13 (d, 2H), 11.90-13.36 (br. s, about 2H). |

| Example | Name/Structure/Starting material | Analytical data |
|---|---|---|
| 27 | 5-{[2-(2-{[4-(1,3-benzoxazol-2-yl)benzyl]oxy}-phenyl)ethyl](4-carboxybutyl)amino}-5,6,7,8-tetrahydroquinoline-2-carboxylic acid (Enantiomer 2)<br>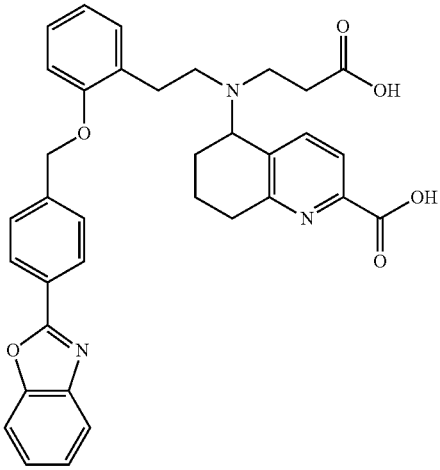<br>from ethyl 5-{[2-(2-{[4-(1,3-benzoxazol-2-yl)-benzyl]oxy}phenyl)ethyl](5-ethoxy-5-oxopentyl)-amino}-5,6,7,8-tetrahydroquinolin-2-carboxylate (Enantiomer 2, Example 99A) | LC-MS (Method 3): $R_t$ = 0.95 min; m/z = 620 $(M + H)^+$.<br>$^1$H-NMR (400 MHz, DMSO-$d_6$): δ [ppm] = 1.34-1.70 (m, 6H), 1.90-2.04 (m, 2H), 2.12 (t, 2H), 2.39-2.64 (m, 4H, partially obscured by DMSO signal), 2.65-2.87 (m, 4H), 3.90-4.06 (m, 1H), 5.09 (q, 2H), 6.87 (t, 1H), 6.99 (d, 1H), 7.09-7.23 (m, 2H), 7.37-7.49 (m, 2H), 7.53 (d, 2H), 7.67 (d, 1H), 7.77-7.89 (m, 3H), 8.18 (d, 2H), 11.00-13.58 (br. s, about 2H). |
| 28 | 5-[(4-carboxybutyl){2-[2-({4-[5-(trifluoromethoxy)-1,3-benzoxazol-2-yl]benzyl}oxy)phenyl]ethyl}-amino]-5,6,7,8-tetrahydroquinoline-2-carboxylic acid (Enantiomer 2)<br>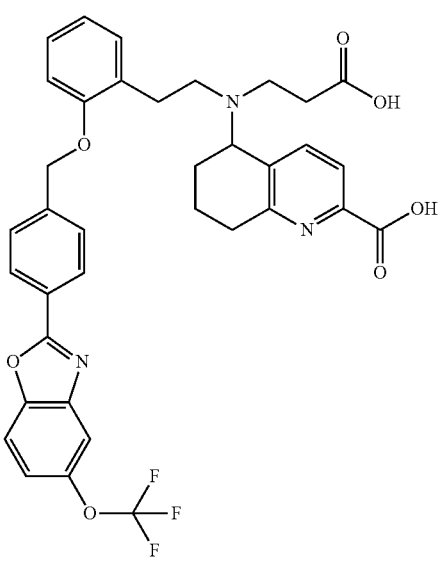<br>from ethyl 5-[(5-ethoxy-5-oxopentyl){2-[2-({4-[5-(trifluoromethoxy)-1,3-benzoxazol-2-yl]benzyl}-oxy)phenyl]ethyl}amino]-5,6,7,8-tetrahydroquinoline-2-carboxylate (Enantiomer 2, Example 100A) | LC-MS (Method 3): $R_t$ = 1.09 min; m/z = 704 $(M + H)^+$.<br>$^1$H-NMR (400 MHz, DMSO-$d_6$): δ [ppm] = 1.32-1.71 (m, 6H), 1.88-2.05 (m, 2H), 2.07-2.17 (m, 2H), 2.39-2.64 (m, 4H, partially obscured by DMSO signal), 2.64-2.88 (m, 4H), 3.93-4.05 (m, 1H), 5.10 (q, 2H), 6.87 (t, 1H), 6.99 (d, 1H), 7.09-7.23 (m, 2H), 7.46 (dd, 1H), 7.54 (d, 2H), 7.66 (d, 1H), 7.85 (d, 1H), 7.89-7.98 (m, 2H), 8.18 (d, 2H), 11.10-13.04 (br. s, about 2H). |

-continued

| Example | Name/Structure/Starting material | Analytical data |
|---|---|---|
| 29 | 5-([2-(4-carboxyphenyl)ethyl]{2-[2-({4-[5-(tri-fluoromethoxy)-1,3-benzoxazol-2-yl]benzyl}oxy)-phenyl]ethyl}amino)-5,6,7,8-tetrahydroquinoline-2-carboxylic acid (Enantiomer 2)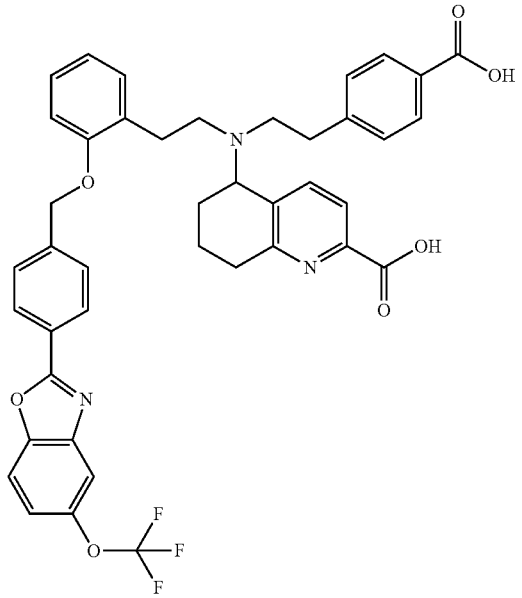from ethyl 5-({2-[4-(methoxycarbonyl)phenyl]-ethyl}{2-[2-({4-[5-(trifluoromethoxy)-1,3-benz-oxazol-2-yl]benzyl}oxy)phenyl]ethyl}amino)-5,6,7,8-tetrahydroquinoline-2-carboxylate (Enantiomer 2, Example 95A) | LC-MS (Method 3): $R_t$ = 1.34 min; m/z = 752 $(M + H)^+$. $^1$H-NMR (400 MHz, DMSO-$d_6$): δ [ppm] = 1.42-1.55 (m, 1H), 1.55-1.71 (m, 1H), 1.88-2.11 (m, 2H), 2.59-2.87 (m, 10H), 3.99-4.13 (m, 1H), 5.09 (q, 2H), 6.88 (t, 1H), 6.98-7.09 (m, 2H), 7.15 (d, 2H), 7.20 (t, 1H), 7.41-7.58 (m, 5H), 7.77 (d, 2H), 7.87-7.96 (m, 2H), 8.12 (d, 2H), 11.89-13.63 (br. s, about 2H). |
| 30 | 5-{[2-(4-carboxyphenyl)ethyl][2-(2-{[4-(5-cyano-1,3-benzoxazol-2-yl)benzyl]oxy}phenyl)ethyl]-amino}-5,6,7,8-tetrahydroquinoline-2-carboxylic acid (Enantiomer 2)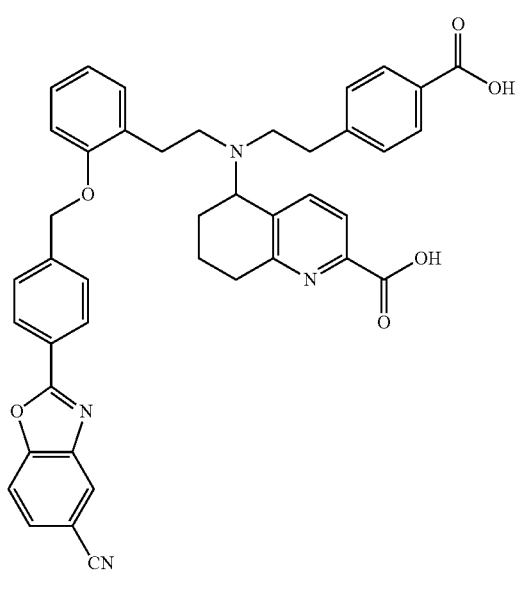 [SMILES: O=C(O)c1ccc(CCN(CCc2ccccc2OCc2ccc(-c3nc4cc(Cl)ccc4o3)cc2)C2CCCc3nc(C(=O)O)ccc32)cc1]from ethyl 5-({2-(2-{[4-(5-cyano-1,3-benzoxazol-2-yl)benzyl]oxy}phenyl)ethyl]{2-[4-(methoxy-carbonyl)phenyl]ethyl}amino)-5,6,7,8-tetrahydro-quinoline-2-carboxylate (Enantiomer 2, Example 96A) | LC-MS (Method 3): $R_t$ = 1.14 min; m/z = 693 $(M + H)^+$. $^1$H-NMR (400 MHz, DMSO-$d_6$): δ [ppm] = 1.42-1.55 (m, 1H), 1.56-1.70 (m, 1H), 1.89-2.10 (m, 2H), 2.59-2.90 (m, 10H), 4.02-4.13 (m, 1H), 5.10 (m, 2H), 6.86 (t, 1H), 6.99-7.09 (m, 2H), 7.13 (d, 2H), 7.21 (t, 1H), 7.47 (d, 1H), 7.50-7.60 (m, 3H), 7.74 (d, 2H), 7.91 (dd, 1H), 8.01 (d, 1H), 8.13 (d, 2H), 8.41 (s, 1H), 11.96-13.51 (br. s, about 2H). |

| Example | Name/Structure/Starting material | Analytical data |
|---|---|---|
| 31 | 5-{(4-carboxybutyl)[2-(2-{[4-(5-cyano-1,3-benz-oxazol-2-yl)benzyl]oxy}phenyl)ethyl]amino}-5,6,7,8-tetrahydroquinoline-2-carboxylic acid (Enantiomer 2)<br />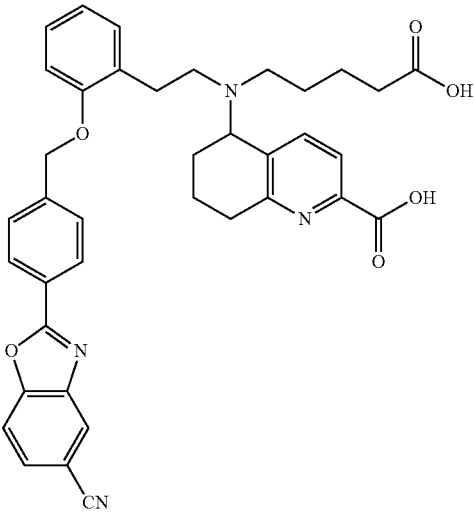<br />from ethyl 5-{[2-(2-{[4-(5-cyano-1,3-benzoxazol-2-yl)benzyl]oxy}phenyl)ethyl](5-ethoxy-5-oxo-pentyl)amino}-5,6,7,8-tetrahydroquinoline-2-carboxylate (Enantiomer 2, Example 101A) | LC-MS (Method 3): $R_t$ = 0.93 min; m/z = 645 $(M + H)^+$.<br />$^1$H-NMR (400 MHz, DMSO-$d_6$): δ [ppm] = 1.31-1.77 (m, 6H), 1.90-2.05 (m, 2H), 2.05-2.18 (m, 2H), 2.39-2.64 (m, 4H, partially obscured by DMSO signal), 2.65-2.88 (m, 4H), 3.92-4.05 (m, 1H), 5.10 (q, 2H), 6.87 (t, 1H), 6.99 (d, 1H), 7.10-7.22 (m, 2H), 7.55 (d, 2H), 7.67 (d, 1H), 7.85 (d, 1H), 7.93 (d, 1H), 8.04 (d, 1H), 8.19 (d, 2H), 8.44 (s, 1H), 11.38-12.79 (br. s, about 2H). |
| 32 | 5-{(4-carboxybutyl)[2-(2-{[4-(5-chloro-1,3-benz-oxazol-2-yl)benzyl]oxy}phenyl)ethyl]amino}-5,6,7,8-tetrahydroquinoline-2-carboxylic acid (Enantiomer 2)<br />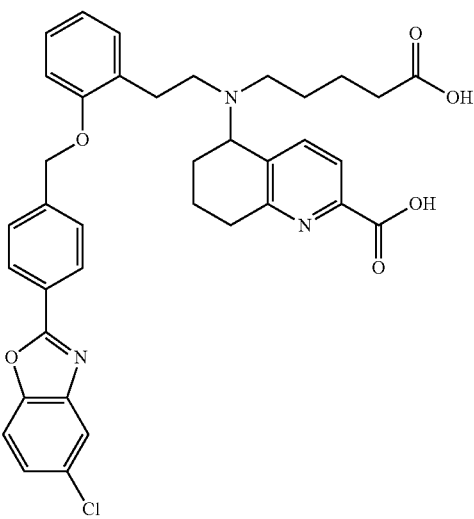<br />from ethyl 5-{[2-(2-{[4-(5-chloro-1,3-benzoxazol-2-yl)benzyl]oxy}phenyl)ethyl](5-ethoxy-5-oxo-pentyl)amino}-5,6,7,8-tetrahydroquinoline-2-carboxylate (Enantiomer 2, Example 102A) | LC-MS (Method 3): $R_t$ = 1.04 min; m/z = 654/656 $(M + H)^+$.<br />$^1$H-NMR (400 MHz, DMSO-$d_6$): δ [ppm] = 1.32-1.70 (m, 6H), 1.89-2.04 (m, 2H), 2.12 (t, 2H), 2.39-2.65 (m, 4H, partially obscured by DMSO signal), 2.65-2.88 (m, 4H), 3.92-4.04 (m, 1H), 5.09 (q, 2H), 6.88 (t, 1H), 6.99 (d, 1H), 7.09-7.24 (m, 2H), 7.44-7.57 (m, 3H), 7.66 (d, 1H), 7.85 (d, 2H), 7.94 (d, 1H), 8.17 (d, 2H), 11.71-13.29 (br. s, about 2H). |

| Example | Name/Structure/Starting material | Analytical data |
|---|---|---|
| 33 | 5-{[2-(4-carboxyphenyl)ethyl][2-(2-{[3-chloro-4'-(trifluoromethyl)biphenyl-4-yl]methoxy}-5-fluorophenyl)ethyl]amino}-5,6,7,8-tetrahydroquinoline-2-carboxylic acid (Enantiomer 1)<br>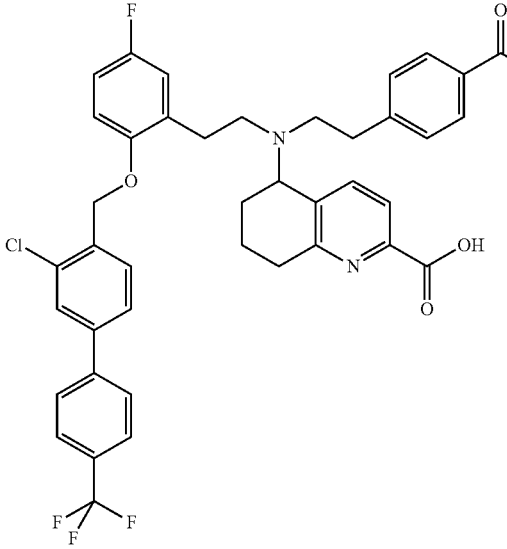<br>from ethyl 5-([2-(2-{[3-chloro-4'-(trifluoromethyl)-biphenyl-4-yl]methoxy}-5-fluorophenyl)ethyl]{2-[4-(methoxycarbonyl)phenyl]ethyl}amino)-5,6,7,8-tetrahydroquinoline-2-carboxylate (Enantiomer 1, Example 124A) | LC-MS (Method 3): $R_t$ = 1.39 min; m/z = 747/749 $(M + H)^+$.<br>$^1$H-NMR (400 MHz, DMSO-$d_6$): δ [ppm] = 1.38-1.67 (m, 2H), 1.84-2.05 (m, 2H), 2.57-2.80 (m, 10H), 3.98-4.08 (m, 1H), 5.00-5.11 (m, 2H), 6.90-7.00 (m, 1H), 7.01-7.15 (m, 4H), 7.41 (s, 2H), 7.54 (d, 1H), 7.63 (dd, 1H), 7.72-7.89 (m, 7H), 12.07-13.44 (br. s, about 2H). |
| 34 | 5-{[2-(4-carboxyphenyl)ethyl][2-(2-{[3-chloro-4'-(trifluoromethyl)biphenyl-4-yl]methoxy}-5-fluorophenyl)ethyl]amino}-5,6,7,8-tetrahydroquinoline-2-carboxylic acid (Enantiomer 2)<br>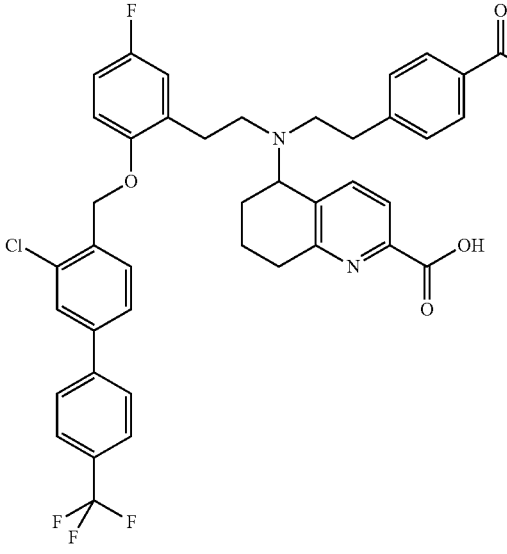<br>from ethyl 5-([2-(2-{[3-chloro-4'-(trifluoromethyl)-biphenyl-4-yl]methoxy}-5-fluorophenyl)ethyl]{2-[4-(methoxycarbonyl)phenyl]ethyl}amino)-5,6,7,8-tetrahydroquinoline-2-carboxylate (Enantiomer 2, Example 123A) | LC-MS (Method 3): $R_t$ = 1.39 min; m/z = 747/749 $(M + H)^+$.<br>$^1$H-NMR (400 MHz, DMSO-$d_6$): δ [ppm] = 1.38-1.66 (m, 2H), 1.85-2.06 (m, 2H), 2.57-2.79 (m, 10H), 3.99-4.08 (m, 1H), 5.00-5.11 (m, 2H), 6.92-7.00 (m, 1H), 7.01-7.16 (m, 4H), 7.41 (s, 2H), 7.54 (d, 1H), 7.63 (dd, 1H), 7.72-7.90 (m, 7H), 12.21-13.18 (br. s, about 2H). |

-continued

| Example | Name/Structure/Starting material | Analytical data |
|---|---|---|
| 35 | 5-{[2-(4-carboxyphenyl)ethyl][2-(2-{[4-(5-chloro-1,3-benzoxazol-2-yl)benzyl]oxy}-5-fluorophenyl)-ethyl]amino}-5,6,7,8-tetrahydroquinoline-2-carboxylic acid (Enantiomer 1)<br>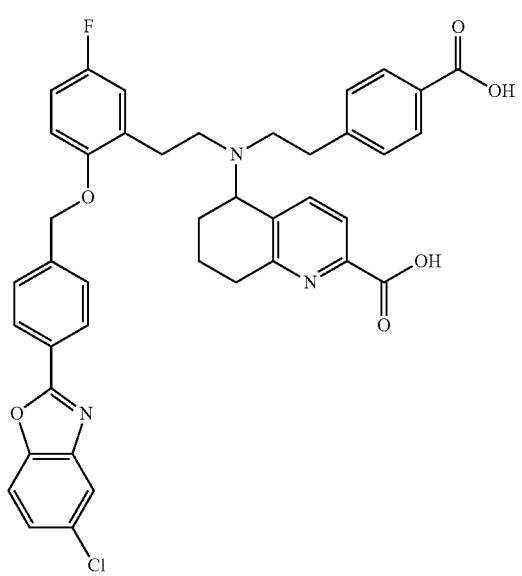<br>from ethyl 5-([2-(2-{[4-(5-chloro-1,3-benzoxazol-2-yl)benzyl]oxy}-5-fluorophenyl)ethyl]{2-[4-(methoxycarbonyl)phenyl]ethyl}amino)-5,6,7,8-tetrahydroquinoline-2-carboxylate (Enantiomer 1, Example 122A) | LC-MS (Method 3):<br>$R_t$ = 1.27 min; m/z = 720/722 (M + H)$^+$.<br>$^1$H-NMR (400 MHz, DMSO-$d_6$): δ [ppm] = 1.41-1.70 (m, 2H), 1.88-2.08 (m, 2H), 2.57-2.85 (m, 10H), 4.01-4.12 (m, 1H), 5.00-5.12 (m, 2H), 6.96 (d, 1H), 7.02 (d, 2H), 7.13 (d, 2H), 7.40-7.57 (m, 5H), 7.75 (d, 2H), 7.83 (d, 1H), 7.93 (d, 1H), 8.11 (d, 2H), 11.88-13.55 (br. s, about 2H). |
| 36 | 5-{(4-carboxybutyl)[2-(2-{[4-(5-chloro-1,3-benzoxazol-2-yl)benzyl]oxy}-5-fluorophenyl)ethyl]-amino}-5,6,7,8-tetrahydroquinoline-2-carboxylic acid (Enantiomer 1)<br>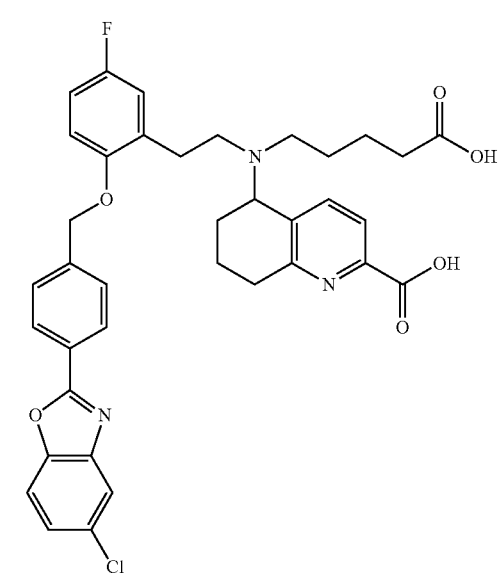<br>from ethyl 5-{[2-(2-{[4-(5-chloro-1,3-benzoxazol-2-yl)benzyl]oxy}-5-fluorophenyl)ethyl](5-ethoxy-5-oxopentyl)amino}-5,6,7,8-tetrahydroquinoline-2-carboxylate (Enantiomer 1, Example 119A) | LC-MS (Method 3):<br>$R_t$ = 1.10 min; m/z = 672/674 (M + H)$^+$. |

| Example | Name/Structure/Starting material | Analytical data |
|---|---|---|
| 37 | 5-{(4-carboxybutyl)[2-(2-{[4-(5-chloro-1,3-benz-oxazol-2-yl)benzyl]oxy}-5-fluorophenyl)ethyl]-amino}-5,6,7,8-tetrahydroquinoline-2-carboxylic acid (Enantiomer 2)<br><br>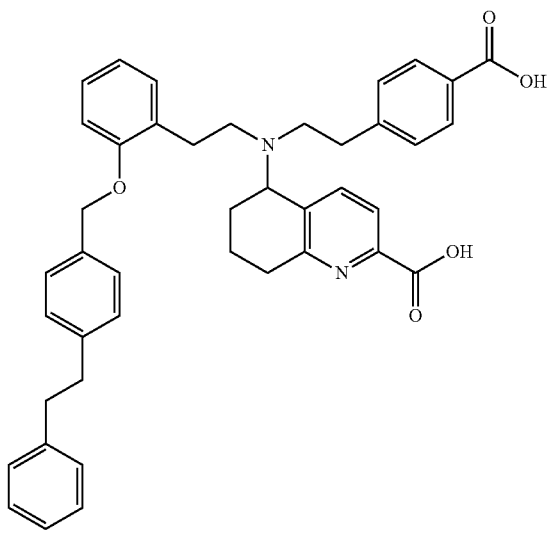 [SMILES: O=C(O)c1ccc(CCN(CCc2ccccc2OCc2ccc(CCc3ccccc3)cc2)C2CCCc3nc(C(=O)O)ccc32)cc1]<br><br>from ethyl 5-{[2-(2-{[4-(5-chloro-1,3-benzoxazol-2-yl)benzyl]oxy}-5-fluorophenyl)ethyl](5-ethoxy-5-oxopentyl)amino}-5,6,7,8-tetrahydroquinoline-2-carboxylate (Enantiomer 2, Example 120A) | LC-MS (Method 3):<br>$R_t$ = 1.10 min; m/z = 672/674 (M + H)$^+$. |

Example 38

5-{[2-(4-Carboxyphenyl)ethyl][2-(2-{[4-(2-phenyl-ethyl)benzyl]oxy}phenyl)ethyl]amino}-5,6,7,8-tetra-hydroquinoline-2-carboxylic acid (Enantiomer 2)

3.64 g (5.22 mmol) of ethyl 5-({2-[4-(methoxycarbonyl) phenyl]ethyl}[2-(2-{[4-(2-phenylethyl)-benzyl] oxy}phenyl)ethyl]amino)-5,6,7,8-tetrahydroquinoline-2-carboxylate (Enantiomer 2, Example 97A) were taken up in 40 ml of dioxane and 20 ml of water, 658 mg (15.67 mmol) of lithium hydroxide monohydrate were added and the mixture was then stirred at room temperature overnight. After the reaction had gone to completion, the dioxane was removed on a rotary evaporator and the mixture that remained was diluted with water. The mixture was then acidified with acetic acid to pH 4-5. The precipitated solid was filtered off with suction and washed repeatedly with water. The solid was then taken up in water and stirred at room temperature. After another filtration with suction, the solid was again washed with water and then dried under high vacuum at 40° C. overnight. This gave 3.24 g (4.95 mmol, 95% of theory) of the title compound.

LC-MS (Method 3): $R_t$=1.27 min; m/z=655 (M+H)$^+$.

$^1$H-NMR (400 MHz, DMSO-d$_6$): δ [ppm]=1.38-1.53 (m, 1H), 1.54-1.68 (m, 1H), 1.89-2.08 (m, 2H), 2.57-2.87 (m, 14H), 4.01-4.10 (m, 1H), 4.90 (q, 2H), 6.83 (t, 1H), 6.93-7.06 (m, 2H), 7.09-7.30 (m, 12H), 7.39-7.50 (m, 2H), 7.80 (d, 2H), 12.03-13.45 (br. s, about 2H).

[α]$_D^{20}$=+64.36°, c=0.380, methanol.

Example 39

5-{[2-(4-Carboxyphenyl)ethyl][2-(2-{[4-(5-chloro-1,3-benzoxazol-2-yl)benzyl]oxy}-5-fluorophenyl)ethyl]amino}-5,6,7,8-tetrahydroquinoline-2-carboxylic acid (Enantiomer 2)

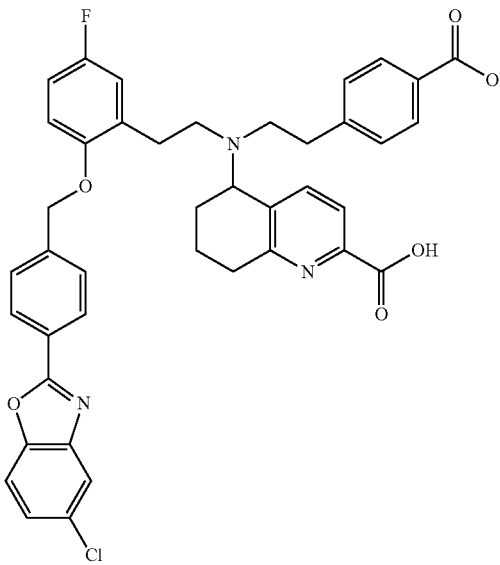

5.4 g (7.08 mmol) of ethyl 5-([2-(2-{[4-(5-chloro-1,3-benzoxazol-2-yl)benzyl]oxy}-5-fluorophenyl)ethyl]{2-[4-(methoxycarbonyl)phenyl]ethyl}amino)-5,6,7,8-tetrahydroquinoline-2-carboxylate (Enantiomer 2, Example 121A) were dissolved in 50 ml of dioxane, 21 ml of 1 N aqueous sodium hydroxide solution were added and the mixture was then stirred at room temperature overnight. After the reaction had gone to completion, the dioxane was removed on a rotary evaporator and the mixture that remained was diluted with water. The mixture was then acidified with acetic acid to pH 4-5. The precipitated solid was filtered off with suction, washed repeatedly with water and then air-dried overnight. This gave 4.8 g (6.66 mmol, 94% of theory) of the title compound.

LC-MS (Method 3): $R_t$=1.28 min; m/z=720/722 (M+H)$^+$.

$^1$H-NMR (400 MHz, DMSO-d$_6$): δ [ppm]=1.40-1.72 (m, 2H), 1.88-2.11 (m, 2H), 2.59-2.84 (m, 10H), 4.02-4.13 (m, 1H), 5.00-5.14 (m, 2H), 6.96 (d, 1H), 7.02 (d, 2H), 7.13 (d, 2H), 7.41-7.57 (m, 5H), 7.75 (d, 2H), 7.83 (d, 1H), 7.93 (d, 1H), 8.11 (d, 2H), 12.05-13.41 (br. s, about 2H).

$[α]_D^{20}$=+58.77°, c=0.405, DMSO.

Example 40

5-([2-(4-Carboxyphenyl)ethyl]{2-[2-({4-[2-(4-fluorophenyl)ethyl]benzyl}oxy)phenyl]ethyl}-amino)-5,6,7,8-tetrahydroquinoline-2-carboxylic acid (Enantiomer 2)

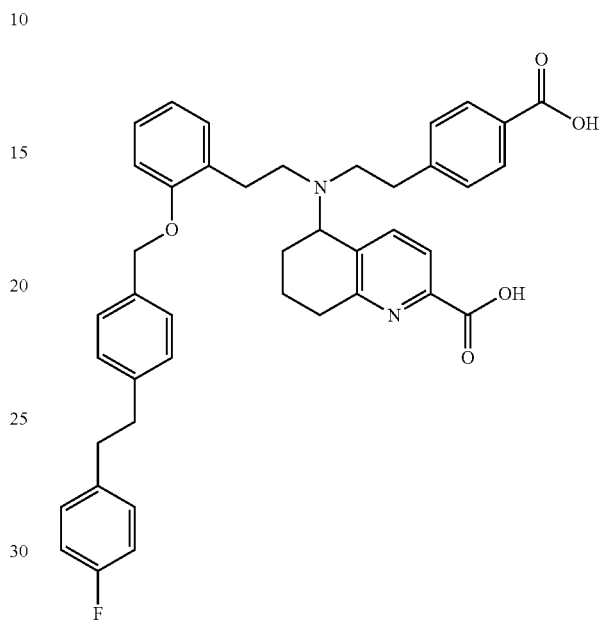

1.76 g (2.46 mmol) of ethyl 5-({2-[2-({4-[2-(4-fluorophenyl)ethyl]benzyl}oxy)phenyl]ethyl}{2-[4-(methoxycarbonyl)phenyl]ethyl}amino)-5,6,7,8-tetrahydroquinoline-2-carboxylate (Enantiomer 2, Example 136A) were dissolved in 50 ml of dioxane, 7.4 ml of 1 N aqueous sodium hydroxide solution were added and the mixture was stirred at room temperature overnight. A further 0.2 ml of 1 M aqueous sodium hydroxide solution was then metered in, and the mixture was stirred at room temperature for two hours. After the reaction had gone to completion, the dioxane was removed on a rotary evaporator and the mixture that remained was diluted with water. The mixture was then acidified with acetic acid to pH 4-5. The precipitated solid was filtered off with suction, washed repeatedly with water and then dried in a drying cabinet under reduced pressure at 40° C. for three days. This gave 673 mg (2.31 mmol, 94% of theory) of the title compound.

LC-MS (Method 3): $R_t$=1.33 min; m/z=673 (M+H)$^+$.

$^1$H-NMR (400 MHz, DMSO-d$_6$): δ [ppm]=1.39-1.53 (m, 1H), 1.54-1.70 (m, 1H), 1.87-2.07 (m, 2H), 2.57-2.89 (m, 14H), 3.98-4.11 (m, 1H), 4.90 (q, 2H), 6.84 (t, 1H), 6.96-7.28 (m, 13H), 7.38-7.50 (m, 2H), 7.79 (d, 2H), 11.79-13.60 (br. s, about 2H).

$[α]_D^{20}$=+85.73°, c=0.285, DMSO.

Analogously to Example 40, the following compounds were prepared:

| Example | Name/Structure/Starting material | Analytical data |
|---|---|---|
| 41 | 5-([2-(4-carboxyphenyl)ethyl]{2-[2-({4-[2-(4-fluorophenyl)ethyl]benzyl}oxy)phenyl]ethyl}amino)-5,6,7,8-tetrahydroquinoline-2-carboxylic acid (Enantiomer 1)<br>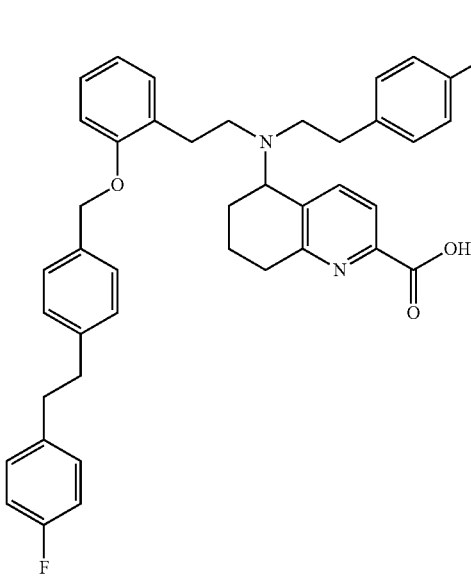<br>from ethyl 5-({2-[2-({4-[2-(4-fluorophenyl)ethyl]benzyl}oxy)phenyl]ethyl}{2-[4-(methoxycarbonyl)phenyl]ethyl}amino)-5,6,7,8-tetrahydroquinoline-2-carboxylate (Enantiomer 1, Example 137A) | LC-MS (Method 3):<br>$R_t$ = 1.33 min; m/z = 673 $(M + H)^+$.<br>$^1$H-NMR (400 MHz, DMSO-$d_6$): δ [ppm] = 1.40-1.53 (m, 1H), 1.53-1.69 (m, 1H), 1.88-2.08 (m, 2H), 2.57-2.88 (m, 14H), 4.00-4.10 (m, 1H), 4.90 (q, 2H), 6.83 (t, 1H), 6.94-7.28 (m, 13H), 7.39-7.50 (m, 2H), 7.80 (d, 2H), 12.08-13.73 (br. s, about 2H).<br>$[α]_D^{20}$ = -84.29°, c = 0.305, DMSO. |
| 42 | 5-([2-(4-carboxyphenyl)ethyl]{2-[5-fluoro-2-({4-[2-(4-fluorophenyl)ethyl]benzyl}oxy)phenyl]ethyl}-amino)-5,6,7,8-tetrahydroquinoline-2-carboxylic acid (Enantiomer 1)<br>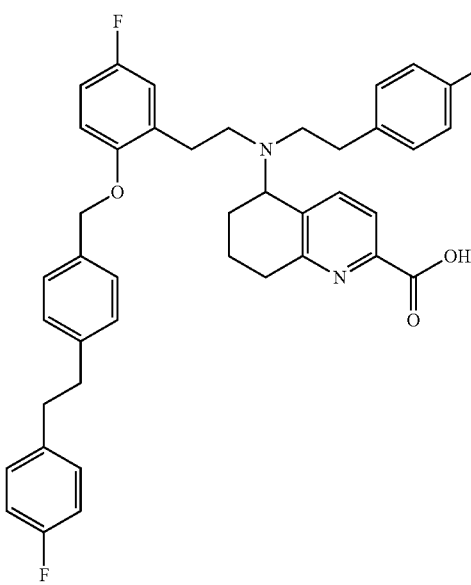<br>from ethyl 5-({2-[5-fluoro-2-({4-[2-(4-fluorophenyl)ethyl]benzyl}oxy)phenyl]ethyl}{2-[4-(methoxycarbonyl)phenyl]ethyl}amino)-5,6,7,8-tetrahydroquinoline-2-carboxylate (Enantiomer 1, Example 146A) | LC-MS (Method 3):<br>$R_t$ = 1.29 min; m/z = 691 $(M + H)^+$.<br>$^1$H-NMR (400 MHz, DMSO-$d_6$): δ [ppm] = 1.40-1.53 (m, 1H), 1.54-1.68 (m, 1H), 1.87-2.08 (m, 2H), 2.57-2.88 (m, 14H), 3.97-4.11 (m, 1H), 4.88 (q, 2H), 6.92 (d, 1H), 6.99 (d, 2H), 7.03-7.29 (m, 10H), 7.42 (s, 2H), 7.79 (d, 2H), 11.93-13.43 (br. s, about 2H).<br>$[α]_D^{20}$ = -79.32°, c = 0.295, DMSO. |

Example 43

5-([2-(4-Carboxyphenyl)ethyl]{2-[5-fluoro-2-({4-[2-(4-fluorophenyl)ethyl]benzyl}oxy)phenyl]-ethyl}amino)-5,6,7,8-tetrahydroquinoline-2-carboxylic acid (Enantiomer 2)

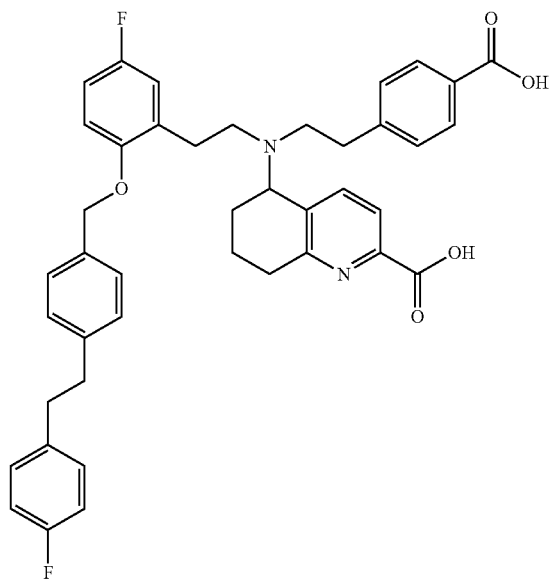 [SMILES: O=C(O)c1ccc(CCN(CCc2cc(F)ccc2OCc2ccc(CCc3ccc(F)cc3)cc2)C2CCCc3nc(C(=O)O)ccc32)cc1]

75 mg (0.10 mmol) of ethyl 5-({2-[5-fluoro-2-({4-[2-(4-fluorophenyl)ethyl]benzyl}oxy)phenyl]-ethyl}{2-[4-(methoxycarbonyl)phenyl]ethyl}amino)-5,6,7,8-tetrahydroquinoline-2-carboxylate (Enantiomer 2, Example 145A) were dissolved in 2 ml of dioxane, 0.3 ml of 1 N aqueous sodium hydroxide solution was added and the mixture was stirred at room temperature overnight. After the reaction had gone to completion, the dioxane was removed on a rotary evaporator and the mixture that remained was diluted with water. The mixture was then acidified with acetic acid to pH 4-5. The precipitated solid was filtered off with suction, washed repeatedly with water and then dried in a drying cabinet under reduced pressure at 40° C. for three days. This gave 58 mg (0.08 mmol, 78% of theory) of the title compound.

LC-MS (Method 3): $R_t$=1.29 min; m/z=691 (M+H)$^+$.

$^1$H-NMR (400 MHz, DMSO-d$_6$): δ [ppm]=1.41-1.53 (m, 1H), 1.54-1.69 (m, 1H), 1.88-2.07 (m, 2H), 2.58-2.88 (m, 14H), 3.99-4.10 (m, 1H), 4.88 (q, 2H), 6.92 (d, 1H), 6.99 (d, 2H), 7.03-7.27 (m, 10H), 7.41 (s, 2H), 7.79 (d, 2H), 12.25-13.34 (br. s, about 2H).

$[α]_D^{20}$=+77.21°, c=0.335, DMSO.

Example 44

5-{[2-(4-Carboxyphenyl)ethyl](2-{2-[(4-{2-[4-(trifluoromethyl)phenyl]ethyl}benzyl)oxy]phenyl}-ethyl)amino}-5,6,7,8-tetrahydroquinoline-2-carboxylic acid (Enantiomer 2)

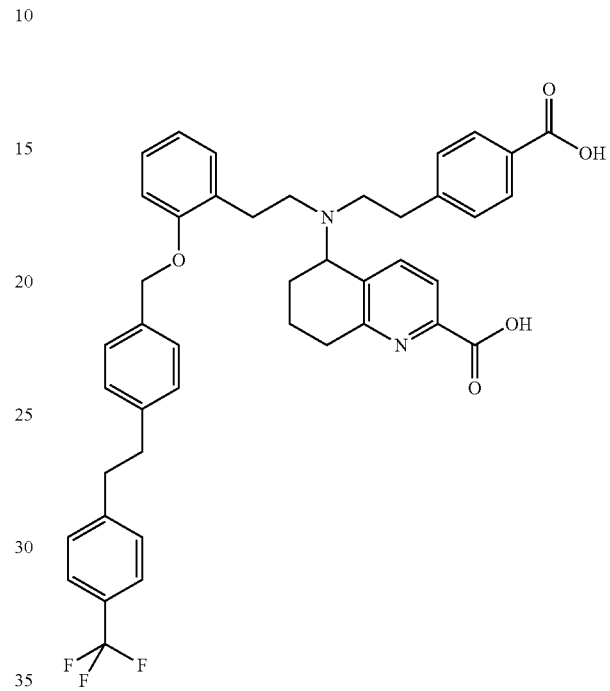

98 mg (0.13 mmol) of ethyl 5-[{2-[4-(methoxycarbonyl)phenyl]ethyl}(2-{2-[(4-{2-[4-(trifluoromethyl)phenyl]ethyl}benzyl)oxy]phenyl}ethyl)amino]-5,6,7,8-tetrahydroquinoline-2-carboxylate (Enantiomer 2, Example 156A) were dissolved in 2.5 ml of dioxane, 0.4 ml of 1 N aqueous sodium hydroxide solution was added and the mixture was then stirred at room temperature overnight. After the reaction had gone to completion, the dioxane was removed on a rotary evaporator and the mixture that remained was diluted with water. The mixture was then acidified with acetic acid to pH 4-5. The precipitated solid was filtered off with suction, washed repeatedly with water and then dried in a drying cabinet under reduced pressure at 40° C. for three days. This gave 71 mg (73% of theory) of the title compound.

LC-MS (Method 3): $R_t$=1.33 min; m/z=723 (M+H)$^+$.

$^1$H-NMR (400 MHz, DMSO-d$_6$): δ [ppm]=1.40-1.43 (m, 1H), 1.54-1.69 (m, 1H), 1.88-2.09 (m, 2H), 2.57-2.99 (m, 14H), 3.97-4.11 (m, 1H), 4.90 (q, 2H), 6.83 (t, 1H), 7.00 (dd, 2H), 7.09-7.27 (m, 7H), 7.37-7.52 (m, 4H), 7.61 (d, 2H), 7.80 (d, 2H), 11.77-13.56 (br. s, about 2H).

Example 45 rac-5-{[2-(4-Carboxyphenyl)ethyl](2-{5-fluoro-2-[(4-{2-[4-(trifluoromethyl)phenyl]ethyl}benzyl)-oxy]phenyl}ethyl)amino}-5,6,7,8-tetrahydroquinoline-2-carboxylic acid

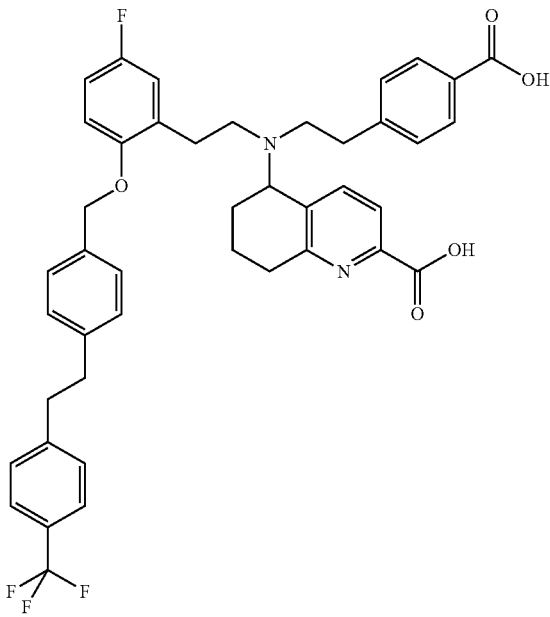 [SMILES: O=C(O)c1ccc(CCN(CCc2cc(F)ccc2OCc2ccc(CCc3ccc(C(F)(F)F)cc3)cc2)C2CCCc3nc(C(=O)O)ccc32)cc1]

173 mg (0.22 mmol) of rac-ethyl 5-[(2-{5-fluoro-2-[(4-{2-[4-(trifluoromethyl)phenyl]ethyl}-benzyl)oxy]phenyl}ethyl){2-[4-(methoxycarbonyl)phenyl]ethyl}amino]-5,6,7,8-tetrahydroquinoline-2-carboxylate (Example 160A) were dissolved in 4 ml of dioxane, 0.7 ml of 1 N aqueous sodium hydroxide solution was added and the mixture was then stirred at room temperature overnight. After the reaction had gone to completion, the dioxane was removed on a rotary evaporator and the mixture that remained was diluted with water. The mixture was then acidified with acetic acid to pH 4-5. The precipitated solid was filtered off with suction, washed repeatedly with water and then dried in a drying cabinet under reduced pressure at 40° C. for three days. This gave 134 mg (75% of theory) of the title compound.

LC-MS (Method 3): $R_t$=1.34 min; m/z=741 (M+H)$^+$.

$^1$H-NMR (400 MHz, DMSO-$d_6$): δ [ppm]=1.37-1.70 (m, 2H), 1.85-2.09 (m, 2H), 2.57-2.98 (m, 14H), 3.96-4.15 (m, 1H), 4.80-4.99 (m, 2H), 6.85-7.05 (m, 3H), 7.16 (br. s, 6H), 7.42 (br. s, 4H), 7.61 (d, 2H), 7.79 (d, 2H).

B. ASSESSMENT OF THE PHARMACOLOGICAL ACTIVITY

The pharmacological effect of the compounds according to the invention can be shown in the following assays:

B-1. Stimulation of Recombinant Soluble Guanylate Cyclase (sGC) In Vitro

Investigations on the stimulation of recombinant soluble guanylate cyclase (sGC) by the compounds according to the invention with and without sodium nitroprusside, and with and without the haem-dependent sGC inhibitor 1H-1,2,4-oxadiazolo[4,3a]quinoxalin-1-one (ODQ), are carried out by the method described in detail in the following reference: M. Hoenicka, E. M. Becker, H. Apeler, T. Sirichoke, H. Schroeder, R. Gerzer and J.-P. Stasch, "Purified soluble guanylyl cyclase expressed in a baculovirus/Sf9 system: Stimulation by YC-1, nitric oxide, and carbon oxide", *J. Mol. Med.* 77 (1999), 14-23. The haem-free guanylate cyclase is obtained by adding Tween 20 to the sample buffer (0.5% in the final concentration).

The activation of sGC by a test substance is reported as x-fold stimulation of the basal activity. The result for Example 2 is shown in Table 1A, that for Example 23 in Table 1B and that for Example 39 in Table 1C:

TABLE 1A

Stimulation (x-fold) of recombinant soluble guanylate cyclase (sGC) in vitro by Example 2

| | Haem-containing sGC | | | |
|---|---|---|---|---|
| Concentration Example 2 [µM] | Basal (n = 7) | +0.01 µM DEA/NO (n = 5) | +10 µM ODQ (n = 6) | Haem-free sGC Basal (n = 6) |
| 0 | 1.0 ± 0.0 | 7.0 ± 1.3 | 2.8 ± 0.3 | 1.0 ± 0.0 |
| 0.01 | 13.7 ± 1.9 | 20.2 ± 3.8 | 63.9 ± 12.2 | 5.2 ± 0.6 |
| 0.1 | 31.2 ± 3.5 | 42.7 ± 7.2 | 129.2 ± 18.9 | 19.9 ± 2.2 |
| 1.0 | 40.2 ± 4.0 | 56.5 ± 10.5 | 172.2 ± 26.3 | 82.7 ± 10.5 |
| 10 | 51.6 ± 6.4 | 62.7 ± 11.0 | 189.5 ± 28.2 | 169.5 ± 23.6 |

TABLE 1B

Stimulation (x-fold) of recombinant soluble guanylate cyclase (sGC) in vitro by Example 23

| | Haem-containing sGC | | | |
|---|---|---|---|---|
| Concentration Example 23 [µM] | Basal (n = 7) | +0.1 µM DEA/NO (n = 5) | +10 µM ODQ (n = 6) | Haem-free sGC Basal (n = 7) |
| 0 | 1.0 ± 0.0 | 14.4 ± 3.0 | 2.0 ± 0.8 | 1.0 ± 0.0 |
| 0.01 | 8.3 ± 1.1 | 24.5 ± 4.4 | 16.9 ± 3.3 | 52.5 ± 3.8 |
| 0.1 | 54.2 ± 11.9 | 77.1 ± 9.2 | 105.4 ± 18.0 | 184.3 ± 15.4 |
| 1.0 | 108.7 ± 16.3 | 155.2 ± 20.7 | 216.1 ± 28.9 | 284.7 ± 18.8 |
| 10 | 135.7 ± 20.0 | 180.4 ± 22.9 | 227.0 ± 31.7 | 310.4 ± 22.6 |
| 100 | 180.5 ± 21.2 | 241.0 ± 34.4 | 261.7 ± 32.1 | 342.0 ± 27.6 |

TABLE 1C

Stimulation (x-fold) of recombinant soluble guanylate cyclase (sGC) in vitro by Example 39

| | Haem-containing sGC | | | |
|---|---|---|---|---|
| Concentration Example 39 [µM] | Basal (n = 6) | +0.1 µM DEA/NO (n = 5) | +10 µM ODQ (n = 6) | Haem-free sGC Basal (n = 6) |
| 0 | 1.0 ± 0.0 | 33.4 ± 2.1 | 1.7 ± 0.2 | 1.0 ± 0.0 |
| 0.01 | 17.4 ± 2.4 | 46.5 ± 2.8 | 42.0 ± 4.9 | 39.0 ± 5.8 |
| 0.1 | 73.0 ± 7.7 | 115.5 ± 11.9 | 145.6 ± 14.7 | 176.9 ± 29.9 |
| 1.0 | 96.6 ± 8.5 | 145.2 ± 15.9 | 182.5 ± 17.6 | 284.9 ± 54.5 |
| 10 | 108.6 ± 9.0 | 159.4 ± 17.9 | 188.7 ± 16.5 | 311.5 ± 55.9 |
| 100 | 143.6 ± 13.4 | 192.1 ± 24.6 | 208.5 ± 19.0 | 309.4 ± 54.8 |

[DEA/NO=2-(N,N-diethylamino)diazenolate 2-oxide; ODQ=1H-1,2,4-oxadiazolo-[4,3a]quinoxalin-1-one].

It is evident from Tables 1A, 1 B and 1C that stimulation both of the haem-containing and of the haem-free enzyme is achieved. Furthermore, combination of Example 2, Example 23 or Example 39 and 2-(N,N-diethylamino)diazenolate 2-oxide (DEA/NO), an NO donor, shows no synergistic effect, i.e. the effect of DEA/NO is not potentiated as would be expected with an sGC activator acting via a haem-dependent mechanism. In addition, the effect of the sGC activator according to the invention is not blocked by 1H-1,2,4-oxadiazolo[4,3a]quinoxalin-1-one (ODQ), a haem-dependent inhibitor of soluble guanylate cyclase, but is in fact increased. The results in Tables 1A, 1B and 1C thus confirm the mechanism of action of the compounds according to the invention as activators of soluble guanylate cyclase.

B-2. Action at a Recombinant Guanylate Cyclase Reporter Cell Line

The cellular action of the compounds according to the invention is determined at a recombinant guanylate cyclase reporter cell line, as described in F. Wunder et al., *Anal. Biochem.* 32, 104-112 (2005).

Representative results for the compounds according to the invention are listed in Table 2:

TABLE 2 sGC-activating activity in the CHO reporter cell in vitro

| Example No. | MEC [nM] |
|---|---|
| 1 | 160 |
| 2 | 1.1 |
| 3 | 100 |
| 4 | 0.5 |
| 5 | 100 |
| 7 | 0.3 |
| 8 | 3 |
| 9 | 10 |
| 10 | 300 |
| 11 | 0.3 |
| 12 | 0.3 |
| 13 | 0.3 |
| 14 | 30 |
| 15 | 0.3 |
| 16 | 3 |
| 17 | 1000 |
| 18 | 0.3 |
| 19 | 30 |
| 20 | 3 |
| 21 | 100 |
| 22 | 1 |
| 23 | 0.7 |
| 24 | 1 |
| 25 | 0.3 |
| 26 | 1 |
| 27 | 1 |
| 28 | 1 |
| 29 | 3 |
| 30 | 1 |
| 31 | 10 |
| 32 | 0.3 |
| 33 | 10 |
| 34 | 1 |
| 35 | 3 |
| 36 | 30 |
| 37 | 1 |
| 38 | 0.3 |
| 39 | 1 |
| 42 | 3 |
| 43 | 0.3 |

(MEC = minimum effective concentration).

B-3. Vasorelaxant Effect In Vitro

Rabbits are anaesthetized and sacrificed by intravenous injection of thiopental sodium (about 50 mg/kg) and exsanguinated. The saphenous artery is removed and divided into rings 3 mm wide. The rings are mounted singly on in each case a pair of triangular hooks open at the end and made of 0.3 mm-thick special wire (Remanium®). Each ring is placed under an initial tension in 5 ml organ baths with Krebs-Henseleit solution which is at 37° C., is gassed with carbogen and has the following composition: NaCl 119 mM; KCl 4.8 mM; $CaCl_2 \times 2\, H_2O$ 1 mM; $MgSO_4 \times 7H_2O$ 1.4 mM; $KH_2PO_4$ 1.2 mM; $NaHCO_3$ 25 mM; glucose 10 mM; bovine serum albumin 0.001%. The force of contraction is detected with Statham UC2 cells, amplified and digitized via A/D converters (DAS-1802 HC, Keithley Instruments, Munich) and recorded in parallel on chart recorders. Contractions are induced by addition of phenylephrine.

After several (generally 4) control cycles, the substance to be investigated is added in each further run in increasing dosage, and the level of the contraction achieved under the influence of the test substance is compared with the level of the contraction reached in the last preceding run. The concentration necessary to reduce the contraction reached in the preceding control by 50% is calculated from this ($IC_{50}$). The standard application volume is 5 µl. The proportion of DMSO in the bath solution corresponds to 0.1%.

Representative results for the compounds according to the invention are listed in Table 3:

TABLE 3

Vasorelaxant effect in vitro

| Example No. | $IC_{50}$ [nM] |
|---|---|
| 1 | 571 |
| 2 | 3.6 |
| 4 | 0.3 |
| 13 | 0.1 |
| 14 | 41.8 |
| 15 | 0.2 |
| 16 | 15.5 |
| 18 | 0.4 |

B-4. Bronchodilatory Effect In Vitro and In Vivo

B-4.1 Bronchorelaxation In Vitro

Bronchial rings (2-3 segments) are removed from rat, mouse or guinea pig and individually mounted on a triangular pair of hooks, made from special wire of a diameter of 0.3 mm (Remanium®), which is open at the end. With pretension applied, each ring is introduced into 5 ml organ baths containing carbogen-gassed buffer solution of a temperature of 37° C. (for example Krebs-Henseleit solution). The bronchial rings are precontracted with methacholine (1 µM) to examine bronchorelaxation by addition of increasing concentrations ($10^{-9}$ to $10^{-6}$ M) of the respective test substance. The results are evaluated as percent relaxation with reference to the preconstriction by methacholine.

B-4.2 Animal Experiment Examining the Effect on Bronchoconstriction in the Asthma Model Prior to the provocation test, all animals (rats, mice) are treated intragastrally with a stomach tube or inhalatively. Here, the animals of the treatment groups receive the test substance, the control animals correspondingly receive a vehicle solution. After the waiting period, the animals are anaesthetized and intubated. Once an oesophagus catheter has been placed and a steady state of respiration has been reached, the lung function is initially measured prior to provocation. Measured parameters are, among others, lung resistance (RL) and dynamic compliance (Cdyn), and also tidal volume (VT) and respiratory frequency (f). Data storage and statistical evaluation are carried out using calculation programs specifically developed for the lung function tests (Notocord HEM).

This is followed by defined inhalative exposure of the test animals to a methacholine (MCh) aerosol (model of an unspecifically induced asthmatic bronchoconstriction).

Recording of lung function parameters is continued during and 3 minutes after the exposure. MCh concentration and dose in the inhalation air are controlled and monitored using a developed feedback dose control system (via measuring aerosol concentration and minute volume). The test is stopped when the target dose is achieved. The inhibitory effect of the test substances is determined by the increase in resistance in comparison with the sham-treated positive control.

Study in the Allergic Asthma Model:

All animals except for the negative control are systemically sensitized with the allergen ovalbumin and adjuvans (alum). Instead, the negative control group receives physiological saline (NaCl). All groups are then provoked with ovalbumin. The study employs 6 treatment groups—2 test substances in 3 dose groups each—; in addition, there is a reference group treated with dexamethasone i.p., a sham-treated and -challenged negative control group and a sham-treated and ovalbumin-provoked positive control group. Sensitization, treatment and challenge protocol: On day 0, 14 and 21, all animals are sensitized with ovalbumin and adjuvans i.p., the negative control is treated with NaCl. On day 28 and 29, the animals are provoked by intratracheal administration of ovalbumin solution. The test substances are administered intragastrally or inhalatively 1 h prior to each intratracheal allergen challenge. 18 h and 1 h prior to each intratracheal allergen provocation, a reference group is treated with dexamethasone i.p. The positive and the negative control group are treated correspondingly with the vehicle.

Airway Hyperreactivity and Inflammatory Response:

The animals are initially examined for airway hyperreactivity to unspecific stimuli. To this end, a hyperreactivity test in the form of a gradually increasing inhalative methacholine provocation is carried out about 24 h after ovalbumine challenge.

The animals are anaesthetized and orotracheally intubated, and prior to the provocation the lung function is measured body-plethysmographically (incl. parameters such as tidal volume, respiratory frequency, dynamic compliance and lung resistance). Once the measurements have been concluded, the dose/activity curve is plotted for each animal and the hyperreactivity of the positive control is evaluated with respect to the negative control or its inhibition in the treatment groups.

The animals are then sacrificed painlessly, blood samples are talen and the lungs are subjected to lavage (BAL). The lavage fluid is used to determined total cell number and differential blood count including the number of eosinophiles in the BAL. The remaining BAL fluid is initially frozen. This allows additional parameters (e.g. cytokines) to be determined at a later stage, if required. The lung tissue is stored for an optional histopathological examination.

B-5. Isolated Perfused Heart According to Langendorff

Male Wistar rats (strain HsdCpb:WU) of a body weight of 200-250 g are anaesthetized with Narcoren® (100 mg/kg). The thorax is opened and the heart is then exposed, excised and connected to a Langendorff apparatus by placing a cannula into the aorta. The heart is perfused retrogradely at 9 ml/min at constant flow with a Krebs-Henseleit buffer solution (gassed with 95% $O_2$ and 5% $CO_2$, pH 7.4, 35° C.; composition in mmol/l: NaCl 118; KCl 3; $NaHCO_3$ 22; $KH_2PO_4$ 1.2; $MgSO_4$ 1.2; $CaCl_2$ 1.8; Glucose 10; Na pyruvate 2). To measure the contractility of the heart, a balloon, made of thin plastic film, which is attached to a PE tube and filled with water is introduced via an opening in the left auricle of the heart into the left ventricle. The balloon is connected to a pressure transducer. The end-diastolic pressure is adjusted to 5-10 mmHg via the balloon volume. The perfusion pressure is detected with the aid of a second pressure transducer. The data are sent via a bridge amplifier to a computer and registered.

Following an equilibration time of 40 min, the test substance in question is added in a final concentration of $10^{-7}$ mol/l of the perfusion solution for 20 min, which, as symptom of coronary dilation, leads to a reduction of the perfusion pressure. The hearts are then perfused without test substance for a further 120 min (wash-out phase). To determine the reversibility of the lowering of the perfusion pressure (wash-out score), the value of the perfusion pressure after 60 min of the wash-out phase is based on the maximum reduction of perfusion pressure by the test substance and expressed in percent. The wash-out score obtained in this manner is taken as a measure for the residence time of the test substance at the site of action.

B-6. Haemodynamics in the Anesthetized Piglet

Healthy Göttingen Minipigs® Ellegaard (Ellegaard, Denmark) of both sexes and having a weight of 2-6 kg are used. The animals are sedated by i.m. administration of about 25 mg/kg ketamine and about 10 mg/kg azaperone. Anaesthesia is initiated by i.v. administration of about 2 mg/kg ketamine and about 0.3 mg/kg midazolam. Maintenance of anaesthesia is by i.v. administration of about 7.5-30 mg/kg/h ketamine and about 1-4 mg/kg/h midazolam (rate of infusion 1-4 ml/kg/h) and about 150 µg/kg/h pancuronium bromide (for example Pancuronium-Actavis). After intubation, the animals are ventilated by the ventilator at a constant respiratory volume (10-12 ml/kg, 35 breaths/min; Avea®, Viasys Healthcare, USA, or Engström Carestation, GE Healthcare, Preiburg, Germany) such that an end-tidal $CO_2$ concentration of about 5% is achieved. Ventilation is performed with room air, enriched with about 40% oxygen (normoxia). For the measurement of the hemodynamic parameters such as pulmonary arterial pressure (PAP), blood pressure (BP) and heart rate (HR), catheters are inserted into the carotid artery to measure the blood pressure, and a Swan-Ganz® catheter is introduced in a flow-directed manner via the jugular vein into the pulmonary artery. The haemodynamic signals are recorded and evaluated by means of pressure transducers (Combitransducer, B. Braun, Melsungen, Germany)/amplifiers and Ponemah® as data acquisition software.

After the instruments have been placed into the animals, continuous infusion of a thromboxane $A_2$ analog is initiated to increase the pulmonary arterial pressure. About 0.3-0.75 µg/kg/min of 9,11-didesoxy-9α,11α-epoxymethanoprostaglandine $F_{2\alpha}$ (U-44069; Sigma, cat. no. D0400, or Cayman Chemical Company, cat. no. 16440), dissolved in physiological saline, are infused to achieve an increase of the mean pulmonary arterial pressure to values of over 25 mmHg. 30 minutes after the start of the infusion, a plateau is reached, and the experiment is started.

The test substances are administered as i.v. infusion or by inhalation. For the preparation of the solution for inhalation, the following procedure is adopted: For an animal having a weight of 4 kg, to prepare the stock solution (300 µg/kg), 1.2 mg of the test compound are weighed out and dissolved in a total volume of 3 ml (1% DMSO, 99% 0.2% strength citric acid solution, 1 N aqueous sodium hydroxide solution to adjust the pH to 8). The solution is then diluted to the concentration employed using 0.2% strength citric acid which had been adjusted to pH 8 beforehand with aqueous sodium hydroxide solution. In each test, 3 ml of the solution of test compound per 4 kg animal are nebulized in the inhalation arm of the respiratory circuit using the Aeroneb®

Pro nebulizer system. The mean nebulization time is about 7 min from the start of the nebulization.

B-7. Inhalative Administration of sGC Activators in PAH Animal Models

The experiments are carried out in anesthetized Göttingen minipigs, anesthetized rats and conscious, telemetrically instrumented dogs. Acute pulmonary hypertension is induced for example by infusion of a thromboxane $A_2$ analogon, by acute hypoxia treatment or hypoxia treatment over a number of weeks and/or by administration of monocrotaline. The test substances are nebulized using the Nebutec® or Aeroneb® Pro nebulizer system, by means of powder and/or solution applicators for experimental intratracheal administration (liquid MicroSprayer®, Dry Powder Insufflator™, MicroSprayer®, Penn-Century Inc., Wyndmoor, Pa., USA) or after solid nebulization inserted into the inspiration arm of the ventilation. The substances are employed as solids or solutions depending on the molecular structure. The haemodynamic signals are recorded and evaluated by means of pressure transducers/amplifiers (Combitransducer B. Braun, Melsungen, Germany or CardioMEMS Inc., Atlanta, Ga., USA) and Ponemah® or CardioMems® as data acquisition software. After long-term experiments (for example monocrotaline rat), is it also possible to carry out a histological evaluation.

B-8. Radiotelemetric Measurement of Blood Pressure and Heart Rate on Conscious Rats A commercially available telemetry system from Data Sciences International DSI, USA, is employed for the measurements on conscious rats described below. The system consists of 3 main components: (1) implantable transmitters (Physiotel® telemetry transmitter), (2) receivers (Physiotel® receiver), which are linked via a multiplexer (DSI Data Exchange Matrix) to a (3) data acquisition computer. The telemetry system allows continuous recording of blood pressure, heart rate and body movements of conscious animals in their usual habitat.

The investigations are carried out on adult female Wistar rats with a body weight of >200 g. After transmitter implantation, the experimental animals are housed singly in type 3 Makrolon cages. They have free access to standard feed and water. The day/night rhythm in the experimental laboratory is changed by the room lighting at 6.00 am and at 7.00 pm.

Transmitter Implantation:

The telemetry transmitters (TA11 PA-C40, DSI) employed are surgically implanted under aseptic conditions in the experimental animals at least 14 days before the first experimental use. The animals instrumented in this way can be employed repeatedly after the wound has healed and the implant has settled.

For the implantation, the fasted animals are anaesthetized with pentobarbital (Nembutal®, Sanofi, 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and layered closure of the wound is performed. An antibiotic (Oxytetracyclin® 10%, 60 mg/kg s.c., 0.06 ml/100 g of body weight, BetaPharma GmbH, Germany) and an analgetic (Rimadyl®, 4 mg/kg s.c., Pfizer, Germany) are administered postoperatively for prophylaxis of infection.

Substances and Solutions:

Unless described otherwise, the substances to be investigated are administered orally by gavage in each case to a group of animals (n=6). The test substances are dissolved in suitable solvent mixtures, or suspended in 0.5% strength Tylose, appropriate for an administration volume of 5 ml/kg of body weight. A solvent-treated group of animals is employed as control.

Experimental Procedure:

The telemetry measuring unit is configured for 24 animals. Each experiment is recorded under an experiment number.

Each of the instrumented rats living in the system is assigned a separate receiving antenna (1010 Receiver, DSI). The implanted transmitters can be activated externally by means of an incorporated magnetic switch and are switched to transmission in the run-up to the experiment. The emitted signals can be detected online by a data acquisition system (Dataquest™ A.R.T. for Windows, DSI) and be appropriately processed. The data are stored in each case in a file created for this purpose and bearing the experiment number.

In the standard procedure, the following are measured for 10-second periods in each case: (1) systolic blood pressure (SBP), (2) diastolic blood pressure (DBP), (3) mean arterial pressure (MAP), (4) heart rate (HR) and (5) activity (ACT).

The acquisition of measured values is repeated under computer control at 5-minute intervals. The source data obtained as absolute value are corrected in the diagram with the currently measured barometric pressure (Ambient Pressure Reference Monitor, APR-1) and stored as individual data. Further technical details are given in the documentation from the manufacturing company (DSI).

Unless described otherwise, the test substances are administered at 9.00 am on the day of the experiment. Following the administration, the parameters described above are measured over 24 hours.

Evaluation:

After the end of the experiment, the acquired individual data are sorted using the analysis software (Dataquest™ A.R.T. 4.1 Analysis). The void value is assumed to be the time 2 hours before administration of the substance, so that the selected data set includes the period from 7.00 am on the day of the experiment to 9.00 am on the following day.

The data are smoothed over a presettable time by determination of the average (15-minute average) and transferred as a text file to a storage medium. The measured values presorted and compressed in this way are transferred into Excel templates and tabulated. For each day of the experiment, the data recorded are stored in a separate file labelled with the number of the experiment. Results and test protocols are stored in numerical order in files.

LITERATURE

K. Witte, K. Hu, J. Swiatek, C. Miissig, G. Ertl and B. Lemmer, *Experimental heart failure in rats: effects on cardiovascular circadian rhythms and on myocardial β-adrenergic signaling*, Cardio-vasc. Res. 47 (2), 350-358 (2000).

B-9. Test of the Desaturation Potential of Substances (Ventilation/Perfusion Mismatch)

Healthy Göttingen Minipigs® Ellegaard (Ellegaard, Denmark) of both sexes and having a weight of 4-5 kg are used. The animals are sedated by i.m. administration of about 25 mg/kg ketamine and about 10 mg/kg azaperone. Anaesthesia is initiated by i.v. administration of about 2 mg/kg ketamine and about 0.3 mg/kg midazolam. Maintenance of anaesthesia is by i.v. administration of about 7.5-30 mg/kg/h ketamine and about 1-4 mg/kg/h midazolam (rate of infusion 1-4 ml/kg/h) and about 150 µg/kg/h pancuronium bromide (for example Pancuronium-Actavis). After intubation, the animals are ventilated by the ventilator at a constant respiratory volume (50-60 ml, 35 breaths/min; Avea®, Viasys Healthcare, USA, or Engström Carestation, GE Healthcare, Freiburg, Germany) such that an end-tidal $CO_2$ concentration of about 5% is achieved. Ventilation is performed with room air, enriched with about 40% oxygen (normoxia), and is adjusted such that a positive end-expiratory pressure of a water column of 5 cm is achieved. For the measurement of the haemodynamic parameters such as pulmonary arterial pressure (PAP), blood pressure (BP) and heart rate (HR), catheters are inserted into the carotid artery to measure the blood pressure, and a Swan-Ganz® catheter is introduced in a flow-directed manner via the jugular vein into the pulmonary artery. The haemodynamic signals are recorded and evaluated by means of pressure transducers (Combitransducer, B. Braun, Melsungen, Germany)/amplifiers and Ponemah® as data acquisition software. A 4 French oximetry catheter (Edwards Lifesciences, Irvine, Calif., USA) is placed in the left femoral artery and connected to a Vigilance monitor (Edwards Lifesciences, Irvine, Calif., USA) for measuring arterial oxygen saturation ($SaO_2$).

All haemodynamic parameters are measured continuously; for evaluation, the means of stable intervals of at least 1 min (in the case of extreme values, for example maximum PAP increase) and/or 3 min (for basal conditions) are formed. Blood gases (Stat Profile pHOx plus L; Nova Biomedical, Waltham, Mass., USA) are determined 3 min after the start of each unilateral broncho-occlusion cycle. Univentilation of the right lung is achieved by advancing the tracheal tube into the right main bronchus and cutting the left side of the lung off from ventilation by inflation of a balloon. Placement of the tube is confirmed by auscultation. Each animal is subjected to several 10-min-cycles of univentilation, in each case interrupted by 30 min of biventilation. The first cycles are used as control cycles to ensure the reproducibility of the cycles. Subsequently, the effect of solvent (vehicle) and the test substance dissolved therein after intravenous and/oder inhalative administration is measured for the following main parameters: blood pressure (BP), pulmonary pressure (PAP) and arterial oxygen saturation ($SaO_2$). This animal model is used to identify a substance which causes a relatively large reduction of the PAP or the hypoxia-induced PAP increase (desired effect) without increasing oxygen desaturation by dilation of pulmonary arteries in non-ventilated regions of the lung (unwanted effect).

LITERATURE

E. M. Becker et al., "V/Q mismatch" bei sekundärer pulmonaler Hypertonie—Riociguat im Vergleich, Pneumologie 65 (Suppl. 2), S122-S123 (2011).

C. EXEMPLARY EMBODIMENTS OF PHARMACEUTICAL COMPOSITIONS

The compounds according to the invention can be converted into pharmaceutical preparations in the following ways:
Tablet:
Composition:
100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.
Production:
The mixture of compound according to the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.
Suspension which can be Administered Orally:
Composition:
1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.
Production:
The Rhodigel is suspended in ethanol, and the compound according to the invention is added to the suspension. The water is added while stirring. The mixture is stirred for about 6 h until the swelling of the Rhodigel is complete.
Solution which can be Administered Orally:
Composition:
500 mg of the compound according to the invention, 2.5 g of polysorbate and 97 g of polyethylene glycol 400. 20 g of oral solution correspond to a single dose of 100 mg of the compound according to the invention.
Production:
The compound according to the invention is suspended in the mixture of polyethylene glycol and polysorbate with stirring. The stirring process is continued until the compound according to the invention has completely dissolved.
i.v. Solution:
The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:
1. A method for the treatment of primary and secondary forms of pulmonary hypertension, heart failure, angina pectoris, hypertension, ischaemias, vascular disorders, impaired microcirculation, renal insufficiency, acute respiratory distress syndrome, acute lung injury, chronic-obstructive pulmonary diseases, asthmatic disorders, fibrotic disorders, thromboembolic disorders, and arteriosclerosis comprising administering an effective amount of a compound of formula (I) to a human or animal in need thereof, wherein formula (I) is

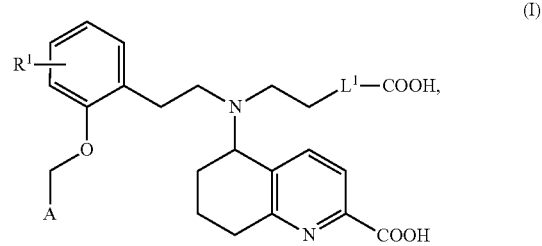

in which
R¹ represents hydrogen or fluorine,
L¹ represents ethane-1,2-diyl or 1,4-phenylene,
and
A represents a group of the formula

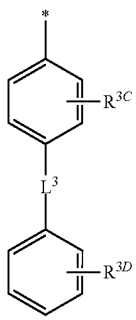

in which
* denotes the respective point of attachment to the remainder of the molecule,
L³ represents a bond, —O—, —CH$_2$—, —CH$_2$—CH$_2$— or —CH═CH—,
R$^{3C}$ represents a substituent selected from the group consisting of fluorine, chlorine, bromine, cyano, (C$_1$-C$_4$)-alkyl, difluoromethyl, trifluoromethyl, (C$_1$-C$_4$)-alkoxy, difluoromethoxy and trifluoromethoxy,
and R$^{3D}$ represents a substituent selected from the group consisting of hydrogen, fluorine, chlorine, bromine, cyano, (C$_1$-C$_4$)-alkyl, difluoromethyl, trifluoromethyl, (C$_1$-C$_4$)-alkoxy, difluoromethoxy and trifluoromethoxy,
or a salt, solvate or solvate of a salt thereof.

2. The method of claim 1, in which
R¹ represents hydrogen or fluorine,
L¹ represents ethane-1,2-diyl or 1,4-phenylene,
and
A represents a group of the formula

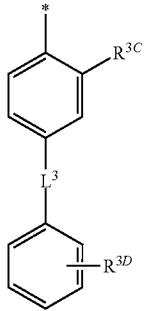

in which
* denotes the respective point of attachment to the remainder of the molecule,
L³ represents a bond, —CH$_2$—CH$_2$— or —CH═CH—,
R$^{3C}$ represents fluorine, chlorine, methyl or trifluoromethyl,
and
R$^{3D}$ represents hydrogen, fluorine, chlorine, cyano, methyl, trifluoromethyl, methoxy or trifluoromethoxy.

3. The method of claim 1, in which
R¹ represents hydrogen or fluorine,
L¹ represents ethane-1,2-diyl or 1,4-phenylene,
and
A represents a group of the formula

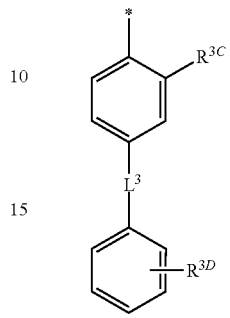

in which
* denotes the respective point of attachment to the remainder of the molecule,
L³ represents a bond, —CH$_2$—CH$_2$— or —CH═CH—,
R$^{3C}$ represents fluorine, chlorine, methyl or trifluoromethyl,
and
R$^{3D}$ represents hydrogen, fluorine, chlorine, cyano, methyl, trifluoromethyl or trifluoromethoxy.

4. The method of claim 1, in which
R¹ represents hydrogen or fluorine,
L¹ represents ethane-1,2-diyl or 1,4-phenylene,
and
A represents a group of the formula

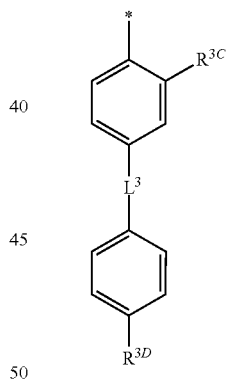

in which
* denotes the respective point of attachment to the remainder of the molecule,
L³ represents a bond or —CH$_2$—CH$_2$—,
R$^{3C}$ represents chlorine,
and
R$^{3D}$ represents hydrogen, fluorine or trifluoromethyl.

5. The method of claim 1, wherein the compound is administered by inhalation.

6. The method of claim 1, wherein the method is for the treatment of acute respiratory distress syndrome.

7. A method for the treatment of primary and secondary forms of pulmonary hypertension, heart failure, angina pectoris, hypertension, ischaemias, vascular disorders, impaired microcirculation, renal insufficiency, acute respiratory distress syndrome, acute lung injury, chronic-obstructive pulmonary diseases, asthmatic disorders, fibrotic disorders and arteriosclerosis comprising administering an effective amount of a compound to a human or animal in need thereof, wherein the compound is a compound having the formula

[Structure: chemical diagram of compound with phenyl, chloro, trifluoromethyl biphenyl, and tetrahydroquinoline-2-carboxylic acid substituents]

or a salt, solvate or solvate of the salt thereof.

8. The method of claim 7, wherein the compound is administered by inhalation.

9. The method of claim 7, wherein the method is for the treatment of acute respiratory distress syndrome.

10. A method for activating soluble guanylate cyclase in a human or animal comprising administering an effective amount of a compound of formula (I) to the human or animal, wherein formula (I) is

[Structure (I): general formula with $R^1$, $L^1$—COOH, A, and tetrahydroquinoline-COOH core]

in which
$R^1$ represents hydrogen or fluorine,
$L^1$ represents ethane-1,2-diyl or 1,4-phenylene,
and
A represents a group of the formula

[Structure: biphenyl group with $R^{3C}$, $L^3$, and $R^{3D}$ substituents, * denotes attachment]

in which
* denotes the respective point of attachment to the remainder of the molecule, $L^3$ represents a bond, —O—, —CH$_2$—, —CH$_2$—CH$_2$— or —CH=CH—,
and
$R^{3C}$ represents a substituent selected from the group consisting of fluorine, chlorine, bromine, cyano, (C$_1$-C$_4$)-alkyl, difluoromethyl, trifluoromethyl, (C$_1$-C$_4$)-alkoxy, difluoromethoxy and trifluoromethoxy,
and $R^{3D}$ represents a substituent selected from the group consisting of hydrogen, fluorine, chlorine, bromine, cyano, (C$_1$-C$_4$)-alkyl, difluoromethyl, trifluoromethyl, (C$_1$-C$_4$)-alkoxy, difluoromethoxy and trifluoromethoxy,
or a salt, solvate or solvate of a salt thereof.

11. The method of claim 10, in which
$R^1$ represents hydrogen or fluorine,
$L^1$ represents ethane-1,2-diyl or 1,4-phenylene,
and
A represents a group of the formula

[Structure: ortho-substituted phenyl with $R^{3C}$ and $L^3$ to phenyl with $R^{3D}$]

in which
* denotes the respective point of attachment to the remainder of the molecule,
$L^3$ represents a bond, —CH$_2$—CH$_2$— or —CH=CH—,
$R^{3C}$ represents fluorine, chlorine, methyl or trifluoromethyl,
and
$R^{3D}$ represents hydrogen, fluorine, chlorine, cyano, methyl, trifluoromethyl, methoxy or trifluoromethoxy.

12. The method of claim 10, in which
$R^1$ represents hydrogen or fluorine,
$L^1$ represents ethane-1,2-diyl or 1,4-phenylene,
and
A represents a group of the formula

[Structure: ortho-substituted phenyl with $R^{3C}$ and $L^3$ to phenyl with $R^{3D}$]

in which
* denotes the respective point of attachment to the remainder of the molecule, L³ represents a bond, —CH₂—CH₂— or —CH═CH—, R³ᶜ represents fluorine, chlorine, methyl or trifluoromethyl, and R³ᴰ represents hydrogen, fluorine, chlorine, cyano, methyl, trifluoromethyl or trifluoromethoxy.

13. The method of claim 10, in which

R¹ represents hydrogen or fluorine,

L¹ represents ethane-1,2-diyl or 1,4-phenylene, and

A represents a group of the formula

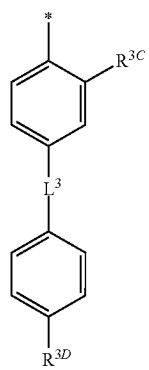

in which

* denotes the respective point of attachment to the remainder of the molecule,

L³ represents a bond or —CH₂—CH₂—,

R³ᶜ represents chlorine, and

R³ᴰ represents hydrogen, fluorine or trifluoromethyl.

14. The method of claim 10, wherein the compound is a compound having the formula

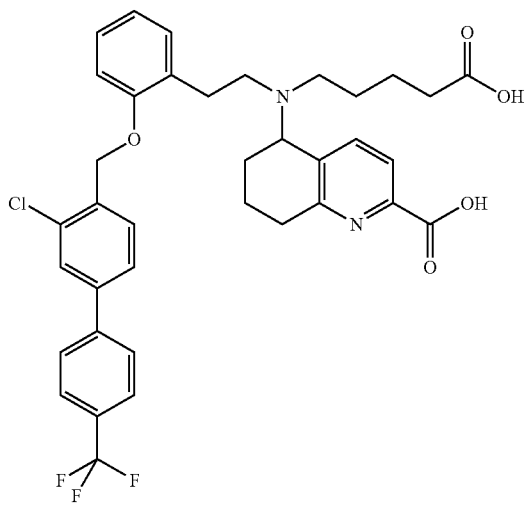 [SMILES: O=C(O)CCCCN(CCc1ccccc1OCc1ccc(-c2ccc(C(F)(F)F)cc2)cc1Cl)C1CCCc2nc(C(=O)O)ccc21]

or a salt, solvate or solvate of the salt thereof.

15. A pharmaceutical composition comprising a compound of formula (I)

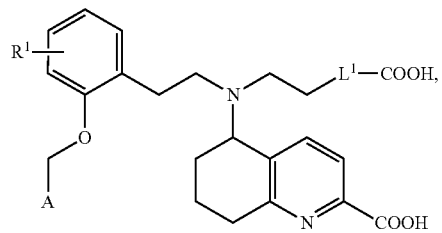

(I)

in which

R¹ represents hydrogen or fluorine,

L¹ represents ethane-1,2-diyl or 1,4-phenylene, and

A represents a group of the formula

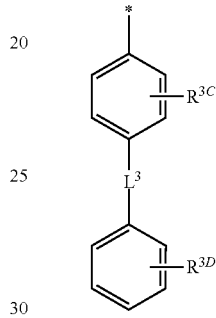

in which

* denotes the respective point of attachment to the remainder of the molecule,

L³ represents a bond, —O—, —CH₂—, —CH₂—CH₂— or —CH═CH—, and

R³ᶜ represents a substituent selected from the group consisting of fluorine, chlorine, bromine, cyano, (C₁-C₄)-alkyl, difluoromethyl, trifluoromethyl, (C₁-C₄)-alkoxy, difluoromethoxy and trifluoromethoxy, and R³ᴰ represents a substituent selected from the group consisting of hydrogen, fluorine, chlorine, bromine, cyano, (C₁-C₄)-alkyl, difluoromethyl, trifluoromethyl, (C₁-C₄)-alkoxy, difluoromethoxy and trifluoromethoxy, or a salt, solvate or solvate of a salt thereof, and one or more pharmaceutically suitable excipients.

16. The pharmaceutical composition of claim 15, in which

R¹ represents hydrogen or fluorine,

L¹ represents ethane-1,2-diyl or 1,4-phenylene, and

A represents a group of the formula

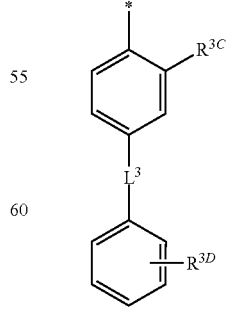

in which

* denotes the respective point of attachment to the remainder of the molecule, $L^3$ represents a bond, —CH$_2$—CH$_2$— or —CH=CH—,
$R^{3C}$ represents fluorine, chlorine, methyl or trifluoromethyl,
and
$R^{3D}$ represents hydrogen, fluorine, chlorine, cyano, methyl, trifluoromethyl, methoxy or trifluoromethoxy.

17. The pharmaceutical composition of claim 15, in which
$R^1$ represents hydrogen or fluorine,
$L^1$ represents ethane-1,2-diyl or 1,4-phenylene,
and
A represents a group of the formula

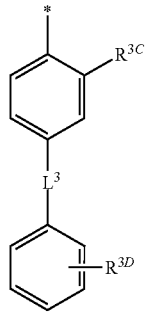

in which
* denotes the respective point of attachment to the remainder of the molecule,
$L^3$ represents a bond, —CH$_2$—CH$_2$— or —CH=CH—,
$R^{3C}$ represents fluorine, chlorine, methyl or trifluoromethyl,
and
$R^{3D}$ represents hydrogen, fluorine, chlorine, cyano, methyl, trifluoromethyl or trifluoromethoxy.

18. The pharmaceutical composition of claim 15, in which
$R^1$ represents hydrogen or fluorine,
$L^1$ represents ethane-1,2-diyl or 1,4-phenylene,
and
A represents a group of the formula

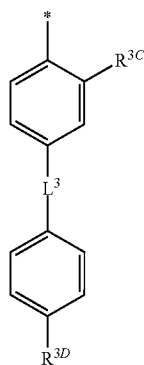

in which
* denotes the respective point of attachment to the remainder of the molecule,
$L^3$ represents a bond or —CH$_2$—CH$_2$—,
$R^{3C}$ represents chlorine,
and
$R^{3D}$ represents hydrogen, fluorine or trifluoromethyl.

19. The pharmaceutical composition of claim 15 that is a pharmaceutical form suitable for inhalation.

20. The pharmaceutical composition of claim 15 that is suitable for administration by a powder inhaler, nebulizer, or aerosol.

21. The pharmaceutical composition of claim 16 that is a pharmaceutical form suitable for inhalation.

22. The pharmaceutical composition of claim 16 that is suitable for administration by a powder inhaler, nebulizer, or aerosol.

23. The pharmaceutical composition of claim 17 that is a pharmaceutical form suitable for inhalation.

24. The pharmaceutical composition of claim 17 that is suitable for administration by a powder inhaler, nebulizer, or aerosol.

25. The pharmaceutical composition of claim 18 that is a pharmaceutical form suitable for inhalation.

26. The pharmaceutical composition of claim 18 that is suitable for administration by a powder inhaler, nebulizer, or aerosol.

27. A pharmaceutical composition comprising a compound having the formula

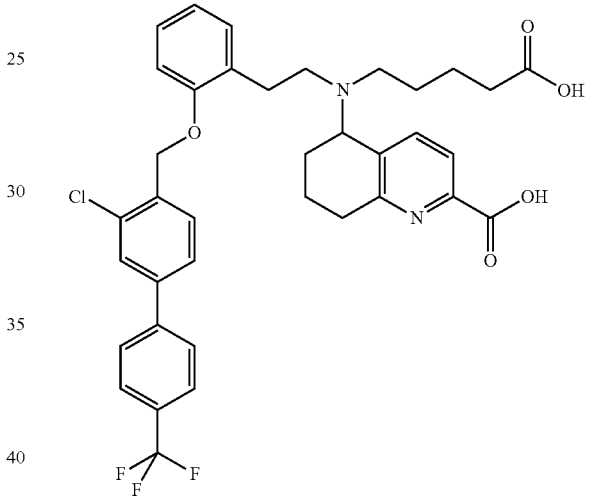

or a salt, solvate or sovate of the salt thereof and one or more pharmaceutically suitable excipients.

28. The pharmaceutical composition of claim 27 that is a pharmaceutical form suitable for inhalation.

29. The pharmaceutical composition of claim 27 that is suitable for administration by a powder inhaler, nebulizer, or aerosol.

30. A method for the prevention of thromboembolic disorders comprising administering an effective amount of a compound of formula (I) or a salt, solvate or solvate of the salt thereof to a human or animal in need thereof, wherein formula (I) is

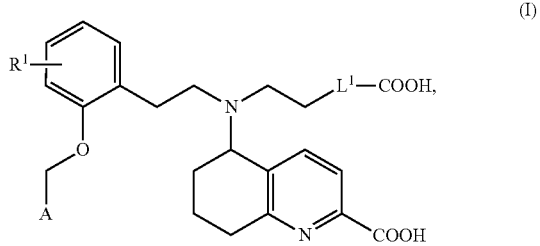

in which
R¹ represents hydrogen or fluorine,
L¹ represents ethane-1,2-diyl or 1,4-phenylene,
and
A represents a group of the formula

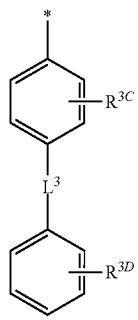

in which
* denotes the respective point of attachment to the remainder of the molecule,
L³ represents a bond, —O—, —CH₂—, —CH₂—CH₂— or —CH=CH—,
and
R³ᶜ represents a substituent selected from the group consisting of fluorine, chlorine, bromine, cyano, (C₁-C₄)-alkyl, difluoromethyl, trifluoromethyl, (C₁-C₄)-alkoxy, difluoromethoxy and trifluoromethoxy,
and R³ᴰ represents a substituent selected from the group consisting of hydrogen, fluorine, chlorine, bromine, cyano, (C₁-C₄)-alkyl, difluoromethyl, trifluoromethyl, (C₁-C₄)-alkoxy, difluoromethoxy and trifluoromethoxy.

31. The method of claim 30, in which
R¹ represents hydrogen or fluorine,
L¹ represents ethane-1,2-diyl or 1,4-phenylene,
and
A represents a group of the formula

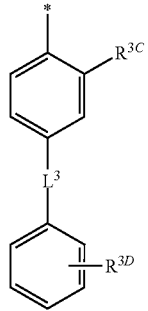

in which
* denotes the respective point of attachment to the remainder of the molecule,
L³ represents a bond, —CH₂—CH₂— or —CH=CH—,
R³ᶜ represents fluorine, chlorine, methyl or trifluoromethyl,
and
R³ᴰ represents hydrogen, fluorine, chlorine, cyano, methyl, trifluoromethyl, methoxy or trifluoromethoxy.

32. The method of claim 30, in which
R¹ represents hydrogen or fluorine,
L¹ represents ethane-1,2-diyl or 1,4-phenylene,
and
A represents a group of the formula

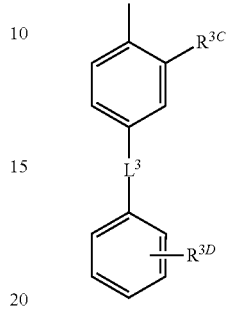

in which
* denotes the respective point of attachment to the remainder of the molecule,
L³ represents a bond, —CH₂—CH₂— or —CH=CH—,
R³ᶜ represents fluorine, chlorine, methyl or trifluoromethyl,
and
R³ᴰ represents hydrogen, fluorine, chlorine, cyano, methyl, trifluoromethyl or trifluoromethoxy.

33. The method of claim 30, in which
R¹ represents hydrogen or fluorine,
L¹ represents ethane-1,2-diyl or 1,4-phenylene,
and
A represents a group of the formula

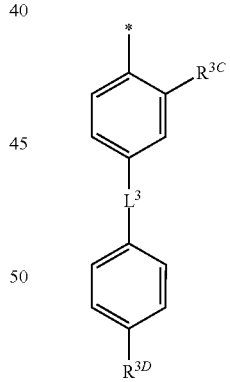

in which
* denotes the respective point of attachment to the remainder of the molecule,
L³ represents a bond or —CH₂—CH₂—,
R³ᶜ represents chlorine,
and
R³ᴰ represents hydrogen, fluorine or trifluoromethyl.

34. A method for the prevention of thromboembolic disorders comprising administering to a human or animal in need thereof an effective amount of a compound of formula

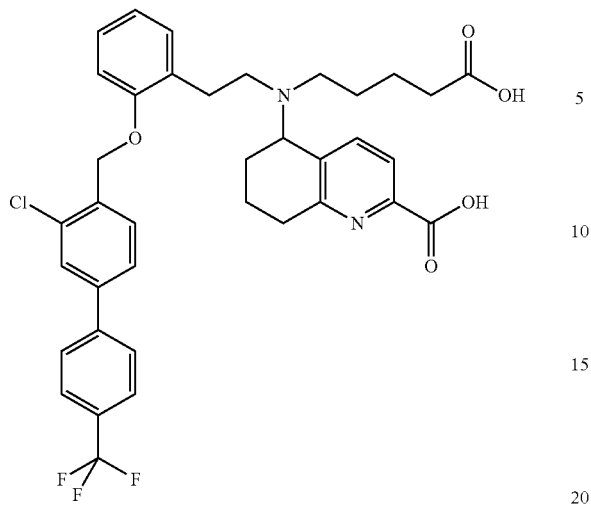
or a salt, solvate or solvate of the salt thereof.
* * * * *